(12) United States Patent
Johnson et al.

(10) Patent No.: US 6,380,201 B1
(45) Date of Patent: *Apr. 30, 2002

(54) METHODS OF TREATING OR AMELIORATING THE SYMPTOMS OF COMMON COLD OR ALLERGIC RHINITIS WITH SEROTONIN 5-$HT_{1F}$ AGONISTS

(75) Inventors: Kirk Willis Johnson, Camby; Lee Alan Phebus, Fountaintown, both of IN (US)

(73) Assignee: Eli Lilly and Company, Indianapolis, IN (US)

(*) Notice: Subject to any disclaimer, the term of this patent is extended or adjusted under 35 U.S.C. 154(b) by 0 days.

This patent is subject to a terminal disclaimer.

(21) Appl. No.: 09/262,726

(22) Filed: Mar. 4, 1999

Related U.S. Application Data

(62) Division of application No. 08/906,770, filed on Aug. 5, 1997, now Pat. No. 5,962,473.

(51) Int. Cl.$^7$ .................. A61K 31/495; A61K 31/505; A61K 31/445

(52) U.S. Cl. .................. 514/255.05; 514/256; 514/318

(58) Field of Search .................. 514/255, 256, 514/318

(56) References Cited

U.S. PATENT DOCUMENTS

| | | | |
|---|---|---|---|
| 4,443,451 A | 4/1984 | Kennis et al. | 424/251 |
| 5,521,196 A | 5/1996 | Audia et al. | 514/323 |
| 5,521,197 A | 5/1996 | Audia et al. | 514/323 |
| 5,708,008 A | 1/1998 | Audia et al. | 514/323 |

OTHER PUBLICATIONS

CA 126:157395 (1997).
CA 125:275668 (1996).
CA 123:169499 (1994).
CA 122:314450 (1994).
CA 120:124110 (1993).

*Primary Examiner*—Russell Travers
(74) *Attorney, Agent, or Firm*—R. Craig Tucker; Robert D. Titus

(57) ABSTRACT

This invention provides methods for the treatment or amelioration of the symptoms of the common cold or allergic rhinitis which comprises administering to a mammal in need thereof a serotonin 5-$HT_{1F}$ agonist.

3 Claims, No Drawings

METHODS OF TREATING OR AMELIORATING THE SYMPTOMS OF COMMON COLD OR ALLERGIC RHINITIS WITH SEROTONIN 5-HT$_{1F}$ AGONISTS

This is a divisional application of application Ser. No. 08/906,770, filed Aug. 5, 1997, now U.S. Pat. No. 5,962,473.

BACKGROUND OF THE INVENTION

Since the discovery of serotonin (5-hydroxytryptamine, 5-HT) over four decades ago, the cumulative results of many diverse studies have indicated that serotonin plays a significant role in the functioning of the mammalian body, both in the central nervous system and in peripheral systems as well. Morphological studies of the central nervous system have shown that serotonergic neurons, which originate in the brain stem, form a very diffuse system that projects to most areas of the brain and spinal cord. R. A. O'Brien, *Serotonin in Mental Abnormalities*, 1:41 (1978); H. W. M. Steinbusch, Handbook of Chemical Neuroanatomy, Volume 3, Part II, 68 (1984); N. E. Anden, et al., *Acta Physiologica Scandinavia*, 67:313 (1966). These studies have been complemented by biochemical evidence that indicates large concentrations of 5-HT exist in the brain and spinal cord. H. W. M. Steinbusch, supra.

With such a diffuse system, it is not surprising that 5-HT has been implicated as being involved in the expression of a number of behaviors, physiological responses, and diseases which originate in the central nervous system. These include such diverse areas as sleeping, eating, perceiving pain, controlling body temperature, controlling blood pressure, depression, schizophrenia, and other bodily states. R. W. Fuller, Biology of Serotonergic Transmission, 221 (1982); D. J. Boullin, Serotonin in Mental Abnormalities 1:316 (1978); J. Barchas, et al., *Serotonin and Behavior*, (1973).

Serotonin plays an important role in peripheral systems as well. For example, approximately 90% of the body's serotonin is synthesized in the gastrointestinal system, and serotonin has been found to mediate a variety of contractile, secretory, and electrophysiologic effects in this system. Serotonin may be taken up by the platelets and, upon platelet aggregation, be released such that the cardiovascular system provides another example of a peripheral network that is very sensitive to serotonin. Given the broad distribution of serotonin within the body, it is understandable that tremendous interest in drugs that affect serotonergic systems exists. In particular, receptor-specific agonists and antagonists are of interest for the treatment of a wide range of disorders, including anxiety, depression, hypertension, migraine, compulsive disorders, schizophhrenia, autism, neurodegenerative disorders, such as Alzheimer's disease, Parkinsonism, and Huntington's chorea, and cancer chemotherapy-induced vomiting. M. D. Gershon, et al., The Peripheral Actions of 5-Hydroxytryptamine, 246 (1989); P. R. Saxena, et al., *Journal of Cardiovascular Pharmacology*, 15:Supplement 7 (1990).

Serotonin produces its effects on cellular physiology by binding to specialized receptors on the cell surface. It is now recognized that multiple types of receptors exist for many neurotransmitters and hormones, including serotonin. The existence of multiple, structurally distinct serotonin receptors has provided the possibility that subtype-selective pharmacologic agents can be produced. The development of such compounds could result in new and increasingly selective therapeutic agents with fewer side effects, since activation of individual receptor subtypes may function to affect specific actions of the different parts of the central and/or peripheral serotonergic systems.

An example of such specificity can be demonstrated by using the vascular system as an example. In certain blood vessels, stimulation of 5-HT$_1$-like receptors on the endothelial cells produces vasodilation while stimulation of 5-HT$_2$ receptors on the smooth muscle cells produces vasoconstriction.

Currently, the major classes of serotonin receptors (5-HT$_1$, 5-HT$_2$, 5-HT$_3$, 5-HT$_4$, 5-HT$_5$, 5-HT$_6$, and 5-HT$_7$) contain some fourteen to eighteen separate receptors that have been formally classified based on their pharmacological or structural differences. [For an excellent review of the pharmacological effects and clinical implications of the various 5-HT receptor types, see Glennon, et al., *Neuroscience and Behavioral Reviews*, 14:35 (1990).]

Pollen has long been recognized as a cause of allergic rhinitis commonly called "hay fever". Pollen contains proteases which induce the release of mediators from mast cells, thereby stimulating IgE biosynthesis. The granulation of mast cells by IgE results in the release of histamines which leads to an inflammatory response which causes congestion, itching, and swelling of sinuses. Many eosinophils are present in allergic patients with nasal mucus and neutrophils are present in patients with infected mucus.

Antihistamines are drugs commonly utilized which, when taken orally, frequently have a sedative effect. Alternatively, nasal sprays containing cromolyn sodium have been effective as cromolyn acts by clocking the reaction of the allergen with tissue mast cells. Cromolyn is not entirely effective, however, as it apparently does not bind to some of the mediators of inflammation or the activators of IgE biosynthesis that stimulate the degranulation of mast cells and the production of histamines from the mast cells.

Inflammation is a non-specific response of tissues to diverse stimuli or insults and results in the release of materials at the site of inflammation that induce pain. It is now recognized that mast cells, neutrophils, and T-cells are implicated in the pathophysiology of inflammatory skin conditions as well as in other physiological disorders. Mast cells provide the greatest source of histamines in acute inflammation, as well as chymases, after degranulation by IgE.

The "common cold" is a time honored phrase used by both physicians and lay persons alike for the identification of acute minor respiratory illness. Since the identification of rhinovirus in 1956, a considerable body of knowledge has been acquired on the etiology and epidemiology of common colds. It is known that the common cold is not a single entity, but rather is a group of diseases caused by members of several families of viruses, including parainfluenza viruses, rhinoviruses, respiratory syncytial viruses, enteroviruses, and coronaviruses. Much work has been performed in characterizing viruses which cause the common cold. In addition, the molecular biology of rhinoviruses, the most important common cold viruses, is understood in great detail. In contrast, progress on the treatment of common colds has been slow despite these advances. While there are now large numbers of compounds that have been found to exhibit antiviral activity against cold viruses in cell culture, antiviral compounds have had limited effectiveness in patients.

Because of the widespread dissatisfaction with the currently marketed treatments for the common cold and allergic rhinitis within the affected population, there exists a need for a more efficacious and safe treatment.

SUMMARY OF THE INVENTION

This invention provides methods for the treatment or amelioration of the symptoms of the common cold or allergic rhinitis in a mammal which comprise administering to a mammal in need thereof an effective amount of a composition having serotonin 5-$HT_{1F}$ agonist activity.

DETAILED DESCRIPTION AND PREFERRED EMBODIMENTS

The term "allergic rhinitis" as employed herein is understood to include rhinitis medicamentosa, rhinitis sicca, and atrophic rhinitis.

Many serotonin binding receptors have been identified. These receptors are generally grouped into seven classes on the basis of their structure and the pharmacology of the receptor as determined by the binding efficiency and drug-related characteristics of numerous serotonin receptor-binding compounds. In some of the groups several subtypes have been identified. [For a relatively recent review of 5-hydroxytryptamine receptors, see, E. Zifa and G. Fillion, *Pharamcological Reviews*, 44:401–458 (1992); D. Hoyer, et al., *Pharamcological Reviews*, 46:157–203 (1994). The Hoyer, et al., reference describes for each class or subtype one or more compounds which have efficacy as antagonists or agonists for the receptor.]

The 5-$HT_1$ family includes subtypes which can be grouped together based on the absence of introns in the cloned genes, a common G-coupled protein transduction system (inhibition of adenylate cyclase), and similar operational characteristics. The 5-$HT_1$ family of inhibitory receptors includes subtypes A, B, D, E, and F. The 5-$HT_1$ G protein-linked receptors generally inhibit the production of cyclic adenosine monophosphate (cAMP), while the 5-$HT_2$ G protein linked receptors stimulate phosphoinosytol hydrolysis.

The 5-$HT_{1A}$ receptor was the first cloned human serotonin receptor. Activated 5-$HT_{1A}$ receptors expressed in HeLa cells inhibit forskolin-stimulated adenylate cyclase activity. The 5-$HT_{1D}$ receptor was originally identified in bovine brain membrane by Heuring and Peroutka. R. E. Heuring and S. J. Peroutka, *Journal of Neuroscience*, 7:894–903 (1987). The 5-$HT_{1D}$ receptors are the most common 5-HT receptor subtype in the human brain and may be identical to the 5-$HT_{1-like}$ receptor in the cranial vasculature. S. D. Silberstein, *Headache*, 34:408–417 (1994). Sumatriptan and the ergot alkaloids have high affinity for both the human 5-$HT_{1D}$ and the 5-$HT_{1B}$ receptors. Id.

The 5-$HT_{1F}$ subtype of receptor has low affinity for 5-carboxamidotryptamine (5-CT) unlike the other 5-HT receptors, except for the 5-$HT_{1E}$ subtype. Unlike the 5-$HT_{1E}$ receptors, however, the 5-$HT_{1F}$ receptors do show affinity for sumatriptan.

The biological efficacy of a compound believed to be effective as a serotonin 5-$HT_{1F}$ agonist may be confirmed by first employing an initial screening assay which rapidly and accurately measures the binding of the test compound to the serotonin 5-$HT_{1F}$ receptor. Once the binding of the test compound to the serotonin 5-$HT_{1F}$ receptor is established, the in vivo activity of the test compound on the receptor is established.

Serotonin Receptor Binding Activity
Binding to the 5-$HT_{1F}$ Receptor

The ability of a compound to bind to a serotonin receptor was measured using standard procedures. For example, the ability of a compound to bind to the 5-$HT_{1F}$ receptor subtype was performed essentially as described in N. Adham, et al., *Proceedings of the National Academy of Sciences (USA)*, 90:408–412 (1993).

The cloned 5-$HT_{1F}$ receptor was expressed in stably transfected LM(tk⁻) cells. Membrane preparations were made by growing these transfected cell lines to confluency. The cells were washed twice with phosphate-buffered saline, scraped into 5 ml of ice-cold phosphate-buffered saline, and centrifuged at 200×g for about five minutes at 4° C. The pellet was resuspended in 2.5 ml of cold Tris buffer (20 mM Tris.HCl, pH 7.4 at 23° C., 5 mM EDTA) and homogenized. The lysate was centrifuged at 200×g for about five minutes at 4° C. to pellet large fragments. The supernatant was then centrifuged at 40,000×g for about 20 minutes at 4° C. The membranes were washed once in the homogenization buffer and resuspended in 25 mM glycylclycine buffer, pH 7.6 at 23° C.

Radioligand binding studies were performed using [$^3$H] 5-HT (20–30 Ci/mmol). Competition experiments were done by using various concentrations of drug and 4.5–5.5 nM [$^3$H]5-HT. Nonspecific binding was defined by 10 $\mu$M 5-HT. Binding data were analyzed by nonlinear-regression analysis. $IC_{50}$ values were converted to $K_i$ values using the Cheng-Prusoff equation.

Serotonin Agonist Activity
Adenylate Cyclase Activity

Adenylate cyclase activity was determined in initial experiments in LM(tk−) cells, using standard techniques. See, e.g., N. Adham, et al., supra,; R. L. Weinshank, et al., *Proceedings of the National Academy of Sciences (USA)*, 89:3630–3634 (1992), and the references cited therein.

Intracellular levels of cAMP were measured using the clonally derived cell line described above. Cells were pre-incubated for about 20 minutes at 37° C. in 5% carbon dioxide, in Dulbecco's modified Eagle's medium containing 10 mM HEPES, 5 rnM theophylline, and 10 $\mu$M pargyline. Varying concentrations of the test compounds were added to the medium to determine inhibition of forskolin-stimulated adenylate cyclase.

Animal Models for Measuring Nasal Extravasation in Guinea Pigs and Rats
Electrical Stimulation of the Trigeminal Ganglion A guinea pig or rat is anesthetized and placed in a stereotaxic frame. Following midline sagittal scalp incisions, two pairs of stimulating electrodes are lowered into the trigeminal ganglion. The femoral artery is exposed and a 50 mg/kg dose of Evans blue dye is injected intravenously. The Evans blue dye complexes with proteins in the blood and functions as a marker for protein extravasation. Two minutes after the Evans blue injection, the left trigeminal ganglion is stimulated for 3 minutes at a current density of 1.0 mA (5 Hz, 4 msec duration). Fifteen minutes following the stimulation the animals are euthanised by exsanguination with 40 mL of saline perfused through the heart. The nose is cut immediately behind the incisors to collect the nasal mucosal tissue and turbinates of the rostal part of the nose. The nasal dorsum is then removed to expose the nasal cavity. The mucosa and parts of the naso- and maxilloturbinates are removed and weighed. These tissues are then incubated in 4 mL dimethylformamide for 18 to 24 hours to extract the extravasated Evans blue dye. The dimethylformamide extracts are quantified by measuring the optical density at 620 nm with a spectrophoto-meter. The concentration of Evans blue dye extravasated into the tissues is interpolated from a concentration standard curve of Evans blue in dimethylformamide. The ability of 5-$HT_{1F}$ agonists to block the Evans blue extravasation into the nasal tissues is assessed by dosing the test animals with a 5-$HT_{1F}$ agonist intravenously 8 minutes prior to the injection of the Evans blue dye.

Intravenous Injection and Nasal Instillation of Metachlorophenylpiperazine (mCPP) or Nitroglycerin Protein extravasation by the trigeminal ganglion may also be stimulated by either intravenous injection or nasal instillation of mCPP or nitroglycerin. A guinea pig or rat is anesthetized and the femoral artery is exposed. The animal is then either injected with an intravenous dose of mCPP or nitroglycerine, or a dose of mCPP or nitroglycer-ine is instilled into the nasal cavity directly. Two minutes after administration of mCPP or nitroglycerine, a 50 mg/kg dose of Evans blue dye is injected intravenously. Fifteen minutes following the Evans blue injection, the animals are euthanised by exsanguination with 40 mL of saline perfused through the heart. The nose is cut immediately behind the incisors to collect the nasal mucosal tissue and turbinates of the rostal part of the nose. The nasal dorsum is then removed to expose the nasal cavity. The mucosa and parts of the naso- and maxilloturbinates are removed and weighed. These tissues are then incubated in 4 mL dimethylformamide for 18 to 24 hours to extract the extravasated Evans blue dye. The dimethylformamide extracts are quantified by measuring the optical density at 620 nm with a spectrophoto-meter. The concentration of Evans blue dye extravasated into the tissues is interpolated from a concentration standard curve of Evans blue in dimethylformamide. The ability of 5-$HT_{1F}$ agonists to block the Evans blue extravasation into the nasal tissues is assessed by dosing the test animals with a 5-$HT_{1F}$ agonist intravenously 8 minutes prior to the injection of the Evans blue dye.

The term "5-$HT_{1F}$ agonist", as it is used in the description of this invention, is taken to mean a full or partial agonist. A compound which is a partial agonist at the 5-$HT_{1F}$ receptor must exhibit sufficient agonist activity to provide the desired biological effect at an acceptable dose. While a partial agonist of any intrinsic activity may be useful for the method of this invention, partial agonists of at least about 50% agonist effect ($E_{max}$) are preferred and partial agonists of at least about 80% agonist effect ($E_{max}$) are more preferred. Full agonists at the 5-$HT_{1F}$ receptor are most preferred.

A number of serotonin 5-$HT_{1F}$ agonists are known in the art and are useful for the method of the present invention. One such class of compounds are optionally substituted 3-<1,2,3,6-tetrahydro-<1-alkyleneheteroaryl>-4-pyridinyl>-1H-indoles and 3-<1-alkyleneheteroaryl>-4-piperidinyl>-1H-indoles of Formula I:

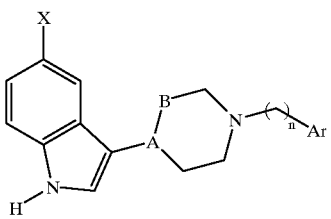

I in which

A—B is —CH—$CH_2$— or —C=CH—;

X is H, halo, $C_1$–$C_4$ alkoxy, $C_1$–$C_4$ alkylthio, $C_1$–$C_4$ alkyl, benzyloxy, hydroxy or carboxamido;

n is 1–4;

Ar is pyridinyl, pyrrolyl or a structure of Formula II:

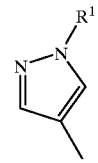

II where $R^1$ is H, $C_1$–$C_6$ alkyl, $C_3$–$C_7$ cycloalkyl, $C_3$–$C_7$ cycloalkylmethyl, benzyl, phenyl or substituted phenyl. These compounds, their synthesis, and use as serotonin 5-$HT_{1F}$ agonists are described in U.S. Pat. No. 5,521,196, issued May 28, 1996. This reference is hereby incorporated by reference in its entirety.

An additional class of 5-$HT_{1F}$ agonists are the optionally substituted 3-<1,2,3,6-tetrahydro-<1-alkylenearyl>-4-pyridinyl>-1H-indoles and 3-<1-alkylenearyl>-4-piperidinyl>-1H-indoles of Formula III:

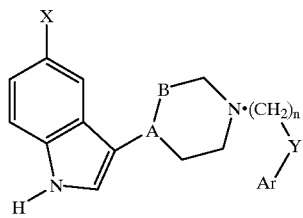

III in which

A—B is —CH—$CH_2$— or —C=CH—;

X is H, halo, $C_1$–$C_4$ alkoxy, $C_1$–$C_4$ alkylthio, $C_1$–$C_4$ alkyl, benzyloxy, hydroxy or carboxamido;

Y is O, S or a bond;

n is 1–4;

Ar is 1-naphthyl, 2-naphtyl, phenyl or phenyl monosubstituted with a substituent selected from the group consisting of halo, $C_1$–$C_4$ alkoxy, $C_1$–$C_4$ alkylthio, $C_1$–$C_4$ alkyl, benzyloxy, hydroxy or trifluoromethyl. These compounds, their synthesis, and use as serotonin 5-$HT_{1F}$ agonists are described in U.S. Pat. No. 5,521,197, issued May 28, 1996. This reference is hereby incorporated by reference in its entirety.

The compounds of Formulae I and III may be prepared by methods well known to the skilled artisan. Briefly, an appropriately substituted indole is reacted with an appropriate 1-substituted-4-piperidone in the presence of base to provide the corresponding 3-(1,2,3,6-tetrahydro-pyridin-4-yl)-1H-indole. These compounds may be used directly for the method of the invention or reduced to provide the corresponding 3-(piperidin-4-yl)-1H-indoles useful for the method of the invention. Compounds prepared in this matter may also serve as substrates for the preparation of other compounds useful for the method of the present invention.

A further class of compounds useful for the method of the present invention are 5-substituted-3-(1,2,3,6- tetrahydropyridin-4-yl)-1H-indoles and 5-substituted-3-(piperidin-4-yl)-1H-indoles of Formula IV:

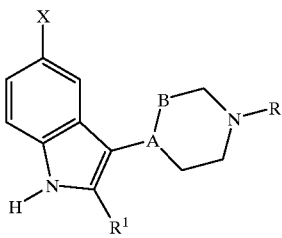

IV in which
A—B is —CH—CH$_2$— or —C=CH—;
R is H or C$_1$–C$_6$ alkyl;
R$^1$ is H or C$_1$–C$_4$ alkyl;
X is —S—R$^2$, —C(O)R$^3$, —C(O)NR$^4$R$^{15}$, —NR$^5$R$^6$, —R$^7$SO$_2$R$^8$, —NHC(Q)NR$^{10}$R$^{11}$, —NHC(O)OR$^{12}$ or —NR$^{13}$C(O)R$^{14}$;
where
Q is O, or S;
R$^2$ is phenyl, substituted phenyl, phenyl(C$_1$–C$_4$ alkylene), phenyl(C$_1$–C$_4$ alkylene) substituted in the phenyl ring, or pyridinyl;
R$^3$ is C$_1$–C$_6$ alkyl, phenyl(C$_1$–C$_4$ alkylene), phenyl (C$_1$–C$_4$ alkylene) substituted in the phenyl ring, naphthyl, N-methyl-N-methoxyamino, heteroaryl, substituted heteroaryl, heteroaryl(C$_1$–C$_4$ alkyl), or substituted heteroaryl(C$_1$–C$_4$ alkyl);
R$^4$ is heteroaryl, substituted heteroaryl, heteroaryl (C$_1$–C$_4$ alkyl), or substituted heteroaryl(C$_1$–C$_4$ alkyl);
R$^4$ and R$^{15}$ taken together with the nitrogen atom form a pyrrolidine, piperidine, substituted piperidine, piperazine, 4-substituted piperazine, morpholine or thiomorpholine ring;
R$^5$ and R$^6$ are both trifluoromethanesulfonyl;
R$^7$ is H or C$_1$–C$_4$ alkyl;
R$^8$ is C$_1$–C$_4$ alkyl, phenyl, substituted phenyl, or di(C$_1$–C$_4$ alkyl)amino;
R$^{10}$ and R$^{11}$ are independently selected from the group consisting of C$_1$–C$_6$ alkyl, C$_3$–C$_6$ alkenyl, C$_3$–C$_8$ cycloalkyl, phenyl, substituted phenyl, phenyl (C$_1$–C$_4$ alkylene), phenyl(C$_1$–C$_4$ alkylene) substituted in the phenyl ring, ((C$_1$–C$_4$ alkyl or C$_1$–C$_4$ alkoxycarbonyl substituted)C$_1$–C$_4$ alkyl)phenyl, C$_1$–C$_4$ alkyl α-substituted with C$_1$–C$_4$ alkoxycarbonyl; or
R$^{10}$ and R$^{11}$ taken together with the nitrogen atom form a pyrrolidine, piperidine, piperazine, 4-substituted piperazine, morpholine or thiomorpholine ring;
R$^{12}$ is C$_1$–C$_6$ alkyl, C$_3$–C$_6$ alkenyl, phenyl, substituted phenyl, C$_3$–C$_8$ cycloalkyl, C$_1$–C$_4$ alkyl ω-substituted with C$_1$–C$_4$ alkoxy;
R$^{13}$ is H or C$_1$–C$_4$ alkyl;
R$^{14}$ is C$_1$–C$_{10}$ alkyl substituted with up to three substituents selected from the group consisting of hydroxy, C$_1$–C$_4$ alkoxy, halo, aryloxy, C$_1$–C$_4$ alkoxycarbonyl and heteroaryloxy, C$_2$–C$_{10}$ alkenyl, C$_2$–C$_{10}$ alkynyl, C$_3$–C$_8$ cycloalkyl, phenyl, substituted phenyl, naphthyl, phenyl(C$_1$–C$_4$ alkylene), phenyl(C$_1$–C$_4$ alkylene) substituted on the phenyl ring, 2-phenylethylen-1-yl, diphenylmethyl, benzofused C$_4$–C$_8$ cycloalkyl, C$_1$–C$_4$ alkylene ω-substituted with C$_3$–C$_6$ cycloalkyl, or a heterocycle; and
R$^{15}$ is H or C$_1$–C$_6$ alkyl.

The general chemical terms used in the formulae above have their usual meanings. For example, the terms "alkyl, alkoxy and alkylthio" include such groups as methyl, ethyl, n-propyl, isopropyl, n-butyl, isobutyl, sec-butyl, tert-butyl, pentyl, 2-pentyl-, 3-pentyl-, neopentyl, hexyl, heptyl, octyl and the like. The term "alkenyl" includes vinyl, allyl, 1-buten-4-yl, 2-buten-4-yl, 1-penten-5-yl, 2-penten-5-yl, 3-penten-5-yl, 1-hexen-6-yl, 2-hexen-6-yl, 3-hexen-6-yl, 4-hexen-6-yl and the like. The term "alkynyl" includes acetylenyl, propynyl, 2-butyn-4-yl, 1-butyn-4-yl, 1-pentyn-5-yl, 2-pentyn-5-yl and the like. The term "acyl" includes, for example, formyl, acetyl, propanoyl, butanoyl, and 2-methylpropanoyl. The term "cycloalkyl" includes such groups as cyclopropyl, cyclobutyl, cyclopentyl, cyclohexyl, cycloheptyl and cyclooctyl. The term "phenyl(C$_1$–C$_4$ alkylene)" includes such groups as benzyl, phenethyl, phenpropyl and phenbutyl. The term "(C$_1$–C$_4$ alkyl)sulfonyl" includes methanesulfonyl, ethanesulfonyl propanesulfonyl, isopropanesulfonyl, butanesulfonyl and the like. The term "halo" includes fluoro, chloro, bromo and iodo.

The term "substituted phenyl" or "phenyl(C$_1$–C$_4$ alkylene) substituted in the phenyl ring" is taken to mean the phenyl moiety may be substituted with one substituent selected from the group consisting of halo, C$_1$–C$_4$ alkyl, C$_1$–C$_8$ alkoxy, C$_1$–C$_4$ alkylthio, nitro, cyano, di(C$_1$–C$_4$ alkyl)amino, trifluoromethyl, trifluoromethoxy, phenyl, C$_1$–C$_4$ acyl, benzoyl or (C$_1$–C$_4$ alkyl)sulfonyl, or two to three substituents independently selected from the group consisting of halo, nitro, C$_1$–C$_4$ alkyl, or C$_1$–C$_4$ alkoxy.

The term "heterocycle" is taken to mean stable aromatic and non-aromatic 5- and 6-membered rings containing from 1 to 3 heteroatoms selected from the group consisting of nitrogen, oxygen and sulfur, said rings being optionally benzofused. All of these rings may be substituted with up to three substituents independently selected from the group consisting of halo, C$_1$–C$_4$ alkoxy, C$_1$–C$_4$ alkyl, cyano, nitro, hydroxy, —S(O)$_n$—(C$_1$–C$_4$ alkyl) and —S(O)$_n$-phenyl where n is 0, 1 or 2. Non-aromatic rings include, for example, pyrrolidinyl, piperidinyl, piperazinyl, tetrahydrofuryl, oxazolidinyl, dioxanyl, pyranyl, and the like. Benzofused non-aromatic rings include indolinyl, 1,2,3,4-tetrahydroquinolinyl, 1,2,3,4-tetrahydroisoquinolinyl and the like. Aromatic rings include furyl, thienyl, pyridinyl, pyrrolyl, N-methylpyrrolyl, oxazolyl, isoxazolyl, pyrazolyl, imidazolyl, triazolyl, oxadiazolyl, thiadiazolyl, thiazolyl, pyrimidinyl, pyrazinyl, pyridazinyl, and the like. Benzofused aromatic rings include isoquinolinyl, benzoxazolyl, benzthiazolyl, quinolinyl, benzofuranyl, thionaphthyl, indolyl and the like.

The term "heteroaryl" is taken to mean an aromatic or benzofused aromatic heterocycle as defined in the previous paragraph. The term "substituted heteroaryl" is taken to mean an aromatic or benzofused aromatic heterocycle as defined in the previous paragraph substituted with up to three substituents independently selected from the group consisting of halo, C$_1$–C$_4$ alkoxy, C$_1$–C$_4$ alkyl, cyano, nitro, hydroxy, —S(O)$_n$—(C$_1$–C$_4$ alkyl) and —S(O)$_n$-phenyl where n is 0, 1 or 2. The term "heteroaryl(C$_1$–C$_4$ alkyl) is taken to mean a branched or linear alkyl chain of 1 to 4 carbon atoms substituted at some point with an aromatic or benzofused aromatic heterocycle moiety. The term "substituted heteroaryl(C$_1$–C$_4$ alkyl)" is taken to mean a branched or linear alkyl chain of 1 to 4 carbon atoms substituted at some point with an aromatic or benzofused aromatic heterocycle moiety which is substituted with up to three substituents independently selected from the group consisting of halo, C$_1$–C$_4$ alkoxy, C$_1$–C$_4$ alkyl, cyano, nitro, hydroxy, —S(O)$_n$—(C$_1$–C$_4$ alkyl) and —S(O)$_n$-phenyl where n is 0, 1 or 2.

9

The term "heteroaryloxy" is taken to mean a heteroaryl or substituted heteroaryl group, as defined in the previous paragraph, bonded to an oxygen atom.

The term "aryloxy" is taken to mean a phenyl or substituted phenyl group bonded to an oxygen atom.

The term "4-substituted piperazine" is taken to mean a piperazine ring substituted at the 4-position with a substituent selected from the group consisting of $C_1$–$C_6$ alkyl, $C_1$–$C_4$ alkoxy substituted $C_1$–$C_6$ alkyl, phenyl, substituted phenyl, phenyl($C_1$–$C_4$ alkylene), phenyl($C_1$–$C_4$ alkylene) substituted in the phenyl ring, heteroaryl, and heteroaryl ($C_1$–$C_4$ alkylene).

The term "substituted piperidine" is taken to mean a piperidine ring optionally substituted with a substituent selected from the group consisting of hydroxy, hydroxymethyl, and N,N-di($C_1$–$C_4$ alkyl)carboxamido.

The term "benzofused $C_4$–$C_8$ cycloalkyl" is taken to mean a $C_4$–$C_8$ cycloalkyl group fused to a phenyl ring. Examples of these groups include benzocyclobutyl, indanyl, 1,2,3,4-tetrahydronaphthyl, and the like.

The compounds of Formula IV are prepared by methods well known to one of ordinary skill in the art, such as that generally described in U.S. Pat. No. 4,443,451, hereby incorporated by reference. While the simple indoles required for the preparation of the compounds of this invention are generally commercially available, their preparations are described in Robinson, *The Fischer Indole Synthesis,* Wiley, New York (1983); Hamel, et al., *Journal of Organic Chemistry,* 59, 6372 (1994); and Russell, et al., *Organic Preparations and Procedures International,* 17, 391 (1985).

The compounds of the invention where X is —$NR^7SO_2R^8$ may be prepared by first modifying an appropriate 5-aminoindole. When $R^7$ is hydrogen, the 5-aminoindole is reacted with an appropriate sulfonyl halide or anhydride to give the corresponding sulfonamide. When $R^7$ is lower alkyl, however, the 5-aminoindole is first acylated, and then reduced with an appropriate hydride reducing agent. Alternatively, the 5-aminoindole may be reductively alkylated with an appropriate aldehyde or ketone in the presence of a suitable hydride reducing agent to give the appropriately substituted indole. These substituted indoles are then reacted with a sulfonyl halide or anhydride to give the corresponding sulfonamide. This chemistry is illustrated in Synthetic Scheme I, where M is methoxy, ethoxy, methyl, ethyl, propyl, or isopropyl, LG is chloro or bromo, and $R^1$, $R^7$, and $R^8$ are as defined supra.

Synthetic Scheme I

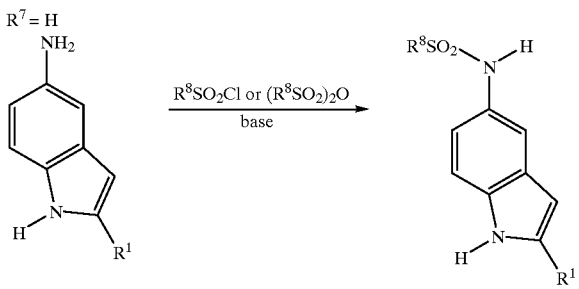

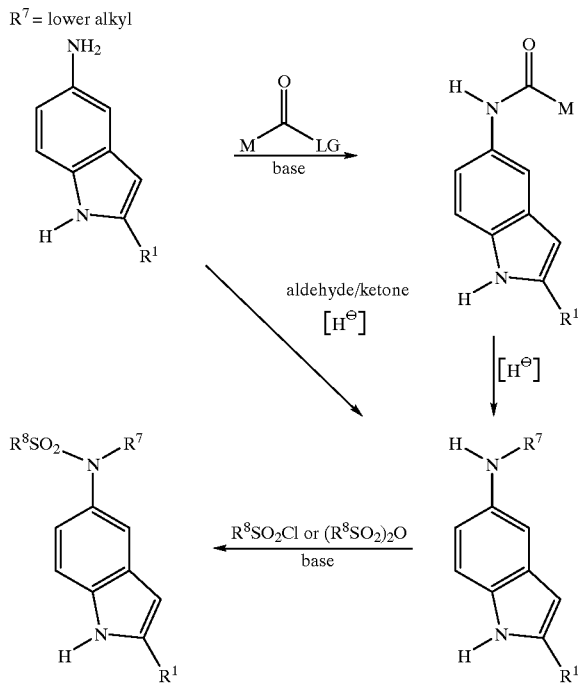

When $R^7$ is to be hydrogen, a solution of 5-aminoindole in a suitable solvent, such as tetrahydrofuran, dioxane, diethyl ether or dimethylformamide, at a temperature from about ambient to about 0° C., is reacted with a commercially available $R^8$-sulfonyl halide or $R^8$-sulfonic anhydride in the presence of a suitable base such as pyridine or triethylamine. The resultant sulfonamide may be isolated by dilution of the reaction mixture with water, adjustment of pH, and extraction with a water immiscible solvent such as dichloromethane. The product may be used for further reaction as recovered, or may be purified by chromatography, or by recrystallization from a suitable solvent.

When $R^7$ is to be lower alkyl, a solution of 5-aminoindole in a suitable solvent, such as tetrahydrofuran, dioxane, or diethyl ether, at a temperature from about ambient to about 0° C., is reacted with a compound of structure M—C(O)-halo in the presence of a suitable base such as pyridine or triethylamine. The resultant compound is isolated by dilution of the reaction mixture with water and extraction with a water immiscible solvent such as dichloromethane. This acylated product may either be purified chromatographically or used directly in the subsequent step. The acylated product is then dissolved in a suitable solvent, such as tetrahydrofuran or diethyl ether, at a temperature from about ambient to about 0° C., and is treated with a suitable hydride reducing agent such as diborane or lithium aluminum hydride. The reaction is stirred from 1 to 24 hours and is then treated with aqueous solution of sodium sulfate. The resultant suspension is filtered, and the filtrate concentrated under reduced pressure. The product may be used for further reaction as is, purified by chromatography, or recrystallized from a suitable solvent.

Alternatively, a solution of a 5-aminoindole in a solvent suitable for the azeotropic removal of water, such as toluene, benzene or cyclohexane, is reacted at reflux with an appropriate aldehyde or ketone, such as formaldehyde, acetaldehyde, propanal, butanal or acetone, in the presence of 0.1–10% of a proton source such as p-toluenesulfonic acid. When the reaction is complete the volatiles are removed under reduced pressure and the residue redissolved in an alkanol such as methanol or ethanol. This solution is then subjected to hydrogenation conditions, or is treated with an appropriate hydride reducing agent, such as sodium borohydride or, preferably, sodium cyanoborohydride in the presence of an anhydrous acid such as hydrogen chloride. The reaction is then diluted with water, treated with base and extracted into a water immiscible solvent such as dichloromethane. The product may be used as is for further reaction, purified by chromatography or crystallized from a suitable solvent. This product is now treated with a commercially available $R^8$-sulfonyl halide or $R^8$-sulfonic anhydride as described supra to give the required sulfonamides.

Compounds of the invention where X is —S—$R^2$, —C(O)$R^3$ or —C(O)NR$^4$R$^{15}$ are prepared by first converting a 5-bromoindole into a 5-bromo-3-(1,2,3,6-tetrahydropyridin-4-yl)-1H-indole or 5-bromo-3-(1-piperidin-4-yl)-1H-indole. Compounds of the invention where X is —NR$^5$R$^6$, —NHC(Q)NR$^{10}$R$^{11}$, —NHC(O)OR$^{12}$ or —NR$^{13}$C(O)R$^{14}$ are prepared by first converting a 5-nitro- or 5-aminoindole into a 5-nitro- or 5-amino-3-(1,2,3,6-tetrahydropyridin-4-yl)-1H-indole or into the corresponding 5-nitro- or 5-amino-(1-piperidin-4-yl)-1H-indole. Compounds of the invention where X is —NR$^7$SO$_2$R$^8$ or —NR$^{13}$C(O)R$^{14}$ may be prepared by converting the appropriately substituted indole into the corresponding 3-(1,2,3,6-tetrahydropyridin-4-yl)-1H-indole or 3-(1-piperidin-4-yl)-1H-indole. This chemistry is illustrated in Synthetic Scheme II, where Y is nitro, amino, bromo, —NR$^{13}$C(O)R$^{14}$, or —NR$^7$SO$_2$R$^8$, and R, R$^1$, R$^7$, R$^8$, R$^{13}$ and R$^{14}$ are as defined supra.

Synthetic Scheme II

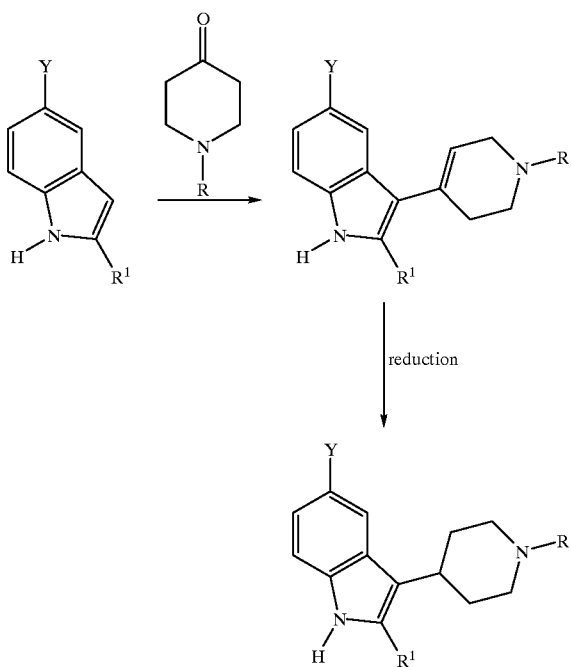

The 5-substituted indole is condensed with a 4-piperidone in the presence of a suitable base to give the corresponding 5-substituted-3-(1,2,3,6-tetrahydropyridin-4-yl)-1H-indole. The reaction is performed by first dissolving an excess of the base, typically sodium or potassium hydroxide, in a lower alkanol, typically methanol or ethanol. The indole and two equivalents of the 4-piperidone are then added and the reaction refluxed for 8–72 hours. The resulting 5-substituted-3-(1,2,3,6-tetrahydro-pyridin-4-yl)-1H-indoles may be isolated from the reaction mixture by the addition of water. Compounds which precipitate may be isolated directly by filtration while others may be extracted by adjusting the pH of the solution and extracting with a water immiscible solvent such as ethyl acetate or dichloromethane. The compounds recovered may be used directly in subsequent steps or first purified by silica gel chromatography or recrystallization from a suitable solvent.

The 5-substituted-3-(1-substituted-1,2,3,6-tetrahydro-pyridin-4-yl)-1H-indoles may be used to prepare other compounds of the invention or, if desired, may be hydrogenated over a precious metal catalyst, such as palladium on carbon, to give the corresponding 5-substituted-3-(piperidin-4-yl)-1H-indoles. When Y is bromo, a hydrogenation catalyst such as sulfided platinum on carbon, platinum oxide, or a mixed catalyst system of sulfided platinum on carbon with platinum oxide is used to prevent hydrogenolysis of the 5-bromo substituent during reduction of the tetrahydro-pyridinyl double bond. The hydrogenation solvent may consist of a lower alkanol, such as methanol or ethanol, tetrahydrofuran, or a mixed solvent system of tetrahydrofuran and ethyl acetate. The hydrogenation may be performed at an initial hydrogen pressure of 20–80 p.s.i., preferably from 50–60 p.s.i., at 0–60° C., preferably at ambient temperature to 40° C., for 1 hour to 3 days. Additional charges of hydrogen may be required to drive the reaction to completion depending on the specific substrate. The 5-substituted-3-(piperidin-4-yl)-1H-indoles prepared in this manner are isolated by removal of the catalyst by filtration followed by concentration of the reaction solvent under reduced pressure. The product recovered may be used directly in a subsequent step or further purified by chromatography, or by recrystallization from a suitable solvent.

As an alternative to hydrogenation, the 5-substituted-3-(1,2,3,6-tetrahydro-4-pyridinyl)-1H-indoles may be converted to the corresponding 5-substituted-3-(piperidin-4-yl)-1H-indoles by treatment with trifluoroacetic acid/triethylsilane if desired. The 5-substituted-3-(1-substituted-1,2,5,6-tetrahydro-4-pyridinyl)-1H-indole is dissolved in trifluoroacetic acid to which is added an excess, 1.1–10.0 equivalents, of triethylsilane. The reaction mixture is stirred at about ambient temperature for from about 1 to about 48 hours at which time the reaction mixture is concentrated under reduced pressure. The residue is then treated with 2N sodium or potassium hydroxide and the mixture extracted with a water immiscible solvent such as dichloromethane or diethyl ether. The resultant 5-substituted-3-(piperidin-4-yl)-1H-indole is purified by column chromatography if desired.

The skilled artisan will appreciate that the 5-nitro substituent may be reduced before or after condensation with an appropriate 4-piperidone. Additionally, the nitro group and the 1,2,3,6-tetrahydropyridinyl double bond may be hydrogenated simultaneously if desired.

Compounds where X is —S—$R^2$ are prepared from the corresponding 5-bromo-3-(1,2,3,6-tetrahydropyridin-4-yl)-1H-indoles or 5-bromo-3-(piperidin-4-yl)-1H-indoles as illustrated in Synthetic Scheme III, where A, B, $R^1$ and $R^2$ are as defined supra and R=$C_1$–$C_4$ alkyl.

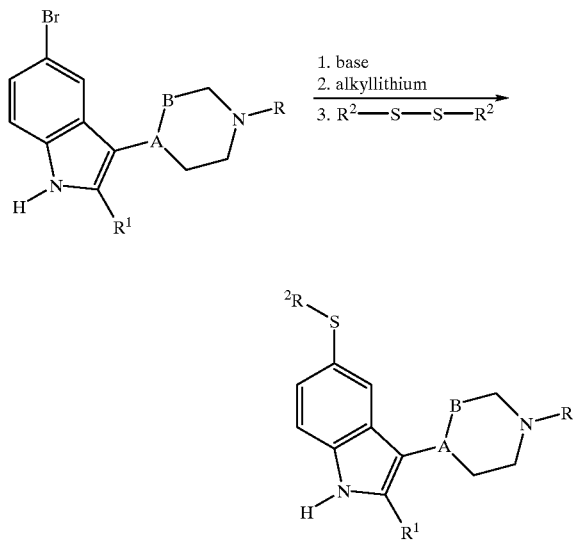

Synthetic Scheme III

The 5-bromo-3-(1,2,3,6-tetrahydropyridin-4-yl)-1H-indoles or 5-bromo-3-(piperidin-4-yl)-1H-indoles in a suitable aprotic solvent, such as diethyl ether or tetrahydrofuran, are cooled to about 0° C. and treated with potassium hydride to deprotonate the indole nucleus at the 1-position. While other hydrides are useful for this deprotonation, the resultant potassium salt is more soluble in typical reaction solvents. The reaction mixture is then cooled to about −78° C. and halogen-metal exchange effected by the addition of two equivalents of t-butyllithium. To this dianion solution are then added an appropriate disulfide and the reaction mixture allowed to warm to ambient temperature. The compound of the invention is isolated by treating the reaction mixture with aqueous base, such as sodium or potassium hydroxide, and then extracting with a water immisible solvent such as diethyl ether or dichloromethane. The reaction product may then be purified by column chromatography.

Compounds where X is —C(O)$R^3$ or —C(O)N$R^4R^{15}$ are prepared from the corresponding 5-bromo-3-(1,2,3,6-tetrahydropyridin-4-yl)-1H-indoles or 5-bromo-3-(piperidin-4-yl)-1H-indoles as illustrated in Synthetic Scheme IV, where A, B, $R^1$, $R^3$, $R^4$ and $R^{15}$ are as defined supra and R=$C_1$–$C_4$ alkyl.

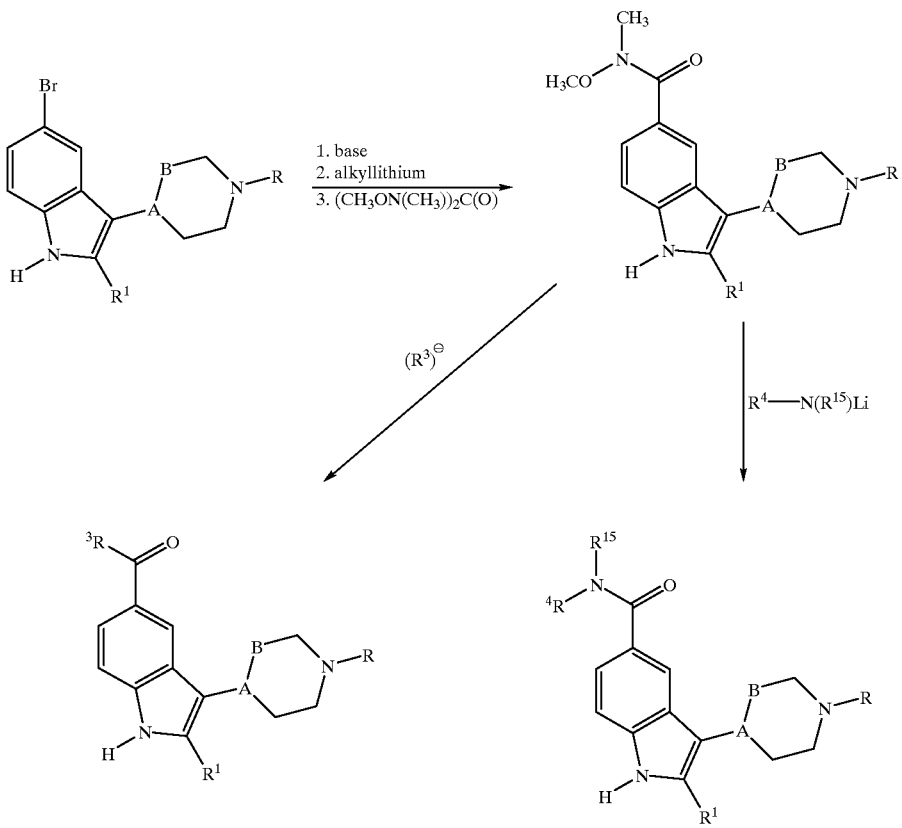

Synthetic Scheme IV

The dianion of the 5-bromo-3-(1,2,3,6-tetrahydropyridin-4-yl)-1H-indoles or 5-bromo-3-(1-substituted-piperidin-4-yl)-1H-indole, prepared as described supra, is then treated with N,N'-dimethyl-N,N'-dimethoxyurea. The resulting N-methyl-N-methoxy-5-carboxamido-1H-indole is isolated by treating the reaction mixture with aqueous base, such as sodium or potassium hydroxide, and then extracting with a water immisible solvent such as diethyl ether or dichloromethane. The reaction product may then be purified by column chromatography.

Compounds where X is —C(O)R$^3$ are prepared by reacting a solution of the N-methyl-N-methoxy-5-carboxamido-3-(1,2,3,6-tetrahydropyridin-4-yl)-1H-indole or N-methyl-N-methoxy-5-carboxamido-3-(piperidin-4-yl)-1H-indole in a suitable solvent, such as diethyl ether or tetrahydrofuran, at about 0° C., with an appropriate reagent such as an aryl- or alkyllithium or an alkyl or aryl Grignard reagent. These reagents are either commercially available or may be prepared by methods well known to one of ordinary skill in the art. The aryl- or alkyllithium reagents are conveniently prepared by treating an appropriate aryl or alkyl halide with n-butyllithium. The aryl or alkyl Grignard reagents may be prepared by treating an appropriate aryl or alkyl halide with magnesium. The compounds of interest may be isolated by aqueous work-up followed by extraction into a water immiscible solvent such as diethyl ether or dichloromethane, and then purified by chromatography, or by recrystallization from a suitable solvent.

The skilled artisan will also appreciate that the compounds where X is —C(O)R$^3$ are also available by the reaction of the dianion of either a 5-bromo-3-(1,2,3,6-tetrahydropyridin-4-yl)-1H-indole or a 5-bromo-3-(piperidin-4-yl)-1H-indole with an appropriate aryl or alkyl N-methyl-N-methoxycarboxamide. These carboxamides are prepared from the corresponding carboxylic acids and N-methyl-N-methoxyamine under standard peptide coupling conditions using N,N'-dicyclohexylcarbodiimide.

Compounds where X is —C(O)NR$^4$R$^{15}$ are prepared by reacting a solution of the N-methyl-N-methoxy-5-carboxamido-3-(1,2,3,6-tetrahydropyridin-4-yl)-1H-indole or N-methyl-N-methoxy-5-carboxamido-3-(piperidin-4-yl)-1H-indole in a suitable solvent, such as diethyl ether or tetrahydrofuran, at about 0° C., with the anion of an appropriate amine. These anions are prepared by treating the appropriate amine with n-butyllithium. The compounds of interest may be isolated by aqueous work-up followed by extraction into a water immiscible solvent such as diethyl ether or dichloromethane, and then purified by chromatography, or by recrystallization from a suitable solvent.

Alternatively, compounds where X is —C(O)NR$^4$R$^{15}$ are prepared by subjecting an appropriate indole 5-carboxylic acid and an appropriate amine to standard peptide coupling conditions. The indole 5-carboxylic acid in an appropriate solvent may be treated with oxalyl chloride, thionyl chloride or phosphorous tribromide in an appropriate solvent, for example toluene, to prepare the corresponding acid halide. The acid halide in a suitable solvent, for example tetrahydrofuran or dimethylformamide, may be treated with an amine of formula HNR$^4$R$^{14}$ in the presence of a suitable base such as triethylamine, pyridine or dimethylaminopyridine to provide the desired compound. The product may be isolated by aqueous work-up followed by extraction into a water immiscible solvent such as diethyl ether, ethyl acetate or dichloromethane, and then purified by chromatography, or by recrystallization from a suitable solvent.

Preferably, compounds where X is —C(O)NR$^4$R$^{15}$ are prepared by reacting the appropriate indole 5-carboxylic acid with an appropriate amine in the presence of typical peptide coupling reagents such as N,N'-carbonyldiimidazole (CDI), N,N'-dicyclohexylcarbodiimide (DCC) and 1-(3-dimethylaminopropyl)-3-ethylcarbodiimide hydrochloride (EDC).

Compounds where X is —NR$^5$R$^6$, —NHC(Q)NR$^{10}$R$^{11}$, —NHC(O)OR$^{12}$ or —NR$^{13}$C(O)R$^{14}$ are prepared by reacting the appropriate 5-amino-3-(1,2,3,6-tetrahydropyridin-4-yl)-1H-indole or 5-amino-3-(piperidin-4-yl)-1H-indole with a suitable electrophile. These reactions are illustrated in Synthetic Scheme V, where A, B, R$^1$, R$^5$, R$^6$, R$^{10}$, R$^{11}$, R$^{12}$, R$^{13}$ and R$^{14}$ are as described supra and R=C$_1$–C$_4$ alkyl.

Synthetic Scheme V

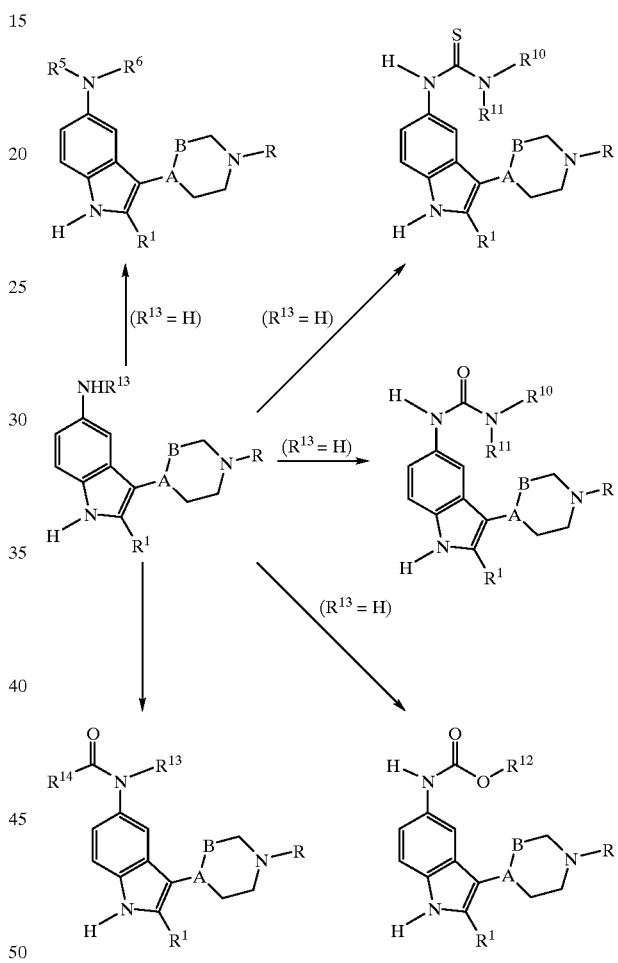

Compounds where X is —NR$^5$R$^6$ are prepared by treating a solution of the 5-amino-3-(1,2,3,6-tetrahydropyridin-4-yl)-1H-indole or 5-amino-3-(piperidin-4-yl)-1H-indole in a suitable solvent, such as dichloromethane, tetrahydrofuran, acetonitrile or dimethylformamide, with a suitable electrophile, such as trifluoromethanesulfonic anhydride or N-carbethoxyphthalimide, in the presence of a suitable base such as pyridine or triethylamine. The reaction product is isolated by evaporation of the reaction solvent under reduced pressure. The product may be purified by chromatography, or by crystallization from an appropriate solvent.

Compounds where X is —NHC(Q)NR$^{10}$R$^{11}$ are prepared by treating a solution of the 5-amino-3-(1,2,3,6-tetrahydropyridin-4-yl)-1H-indole or 5-amino-3-(piperidin-4-yl)-1H-indole in a suitable solvent, such as chloroform or dichloromethane, with an appropriate isocyanate, isothiocyanate, carbamoyl chloride or carbamoyl bromide. Appropriate carbamoyl chlorides are available by treating an amine of formula $HNR^{10}R^{11}$ with phosgene. When a carbamoyl chloride or carbamoyl bromide is used, the reactions are performed in the presence of a suitable base. Suitable bases include amines typically used as acid scavengers, such as pyridine or triethylamine, or commercially available polymer bound bases such as polyvinylpyridine. If necessary, an excess of the isocyanate, isothiocyanate, carbamoyl chloride or carbamoyl bromide is employed to ensure complete reaction of the starting amine. The reactions are performed at about ambient to about 80° C., for from about three hours to about three days. Typically, the product may be isolated by washing the reaction mixture with water and concentrating the remaining organics under reduced pressure. When an excess of isocyanate, isothiocyanate, carbamoyl chloride or carbamoyl bromide has been used, however, a polymer bound primary or secondary amine, such as an aminomethylated polystyrene, may be conveniently added to react with the excess reagent. Isolation of products from reactions where a polymer bound reagent has been used is greatly simplified, requiring only filtration of the reaction mixture and then concentration of the filtrate under reduced pressure. The product from these reactions may be purified chromatographically or recrystallized from a suitable solvent if desired. The skilled artisan will appreciate that compounds which are ureas may be converted into the corresponding thiourea by treatment with [2,4-bis(4-methoxyphenyl)-1,3-dithia-2,4-diphosphetane-2,4-disulfide] (Lawesson's Reagent) or phosphorus pentasulfide.

Compounds where X is —$NHC(O)OR^{12}$ are prepared by reacting the 5-amino-3-(1,2,3,6-tetrahydropyridin-4-yl)-1H-indole or 5-amino-3-(piperidin-4-yl)-1H-indole with an appropriately substituted chloroformate in the presence of a suitable amine under the conditions described in the previous paragraph. Likewise, compounds where X is —$NR^{13}C(O)R^{14}$ are prepared by reacting the 5-amino-3-(1,2,3,6-tetrahydropyridin-4-yl)-1H-indole or 5-amino-3-(piperidin-4-yl)-1H-indole with an appropriate carboxylic acid chloride, bromide or anhydride, optionally in the presence of an acylation catalyst such as dimethylaminopyridine, in the presence of a suitable base, such as those described supra.

Alternatively, compounds where X is —$NR^{13}C(O)R^{14}$ are prepared by reacting the 5-amino-3-(1,2,3,6-tetrahydropyridin-4-yl)-1H-indole or 5-amino-3-(piperidin-4-yl)-1H-indole with an appropriate carboxylic acid halide, carboxylic acid anhydride, or a carboxylic acid in the presence of typical peptide coupling reagents such as N,N'-carbonyldiimidazole (CDI), N,N'-dicyclohexylcarbodiimide (DCC) and 1-(3-dimethylaminopropyl)-3-ethylcarbodiimide hydrochloride (EDC). A polymer supported form of EDC has been described (*Tetrahedron Letters*, 34(48), 7685 (1993)) and is very useful for the preparation of the compounds of the present invention. The product from these reactions is isolated and purified as described above.

The skilled artisan will appreciate that the order in which the steps are performed to prepare these compounds is not important in many cases. For example, compounds where X is —$NR^7SO_2R^8$ are accessible by subjecting the 5-amino-3-(1,2,3,6-tetrahydropyridin-4-yl)-1H-indoles or 5-amino-3-(piperidin-4-yl)-1H-indoles to the conditions illustrated in Synthetic Scheme I. Likewise, 5-aminoindole may be subjected to the reaction sequences illustrated in Synthetic Scheme V prior to reaction with a 4-piperidone as illustrated in Synthetic Scheme II. The skilled artisan will also appreciate that compounds where R is H may be prepared by condensing 4-piperidone with a suitably substituted indole to give the corresponding 3-(1,2,3,6-tetrahydropyridin-4-yl)-1H-indoles which may then be hydrogenated if desired. Alternatively, 1-benzyl-4-piperidone may be substituted at any point in the synthesis for a suitably substituted 4-piperidone. The benzyl group may then be removed by standard hydrogenation conditions after reactions for which the secondary amine would be incompatible are complete. The 3-(1,2,3,6-tetrahydropyridin-4-yl)-1H-indoles may also be reduced to the corresponding 3-(piperidin-4-yl)-1H-indoles at any convenient point in the synthetic sequence. These variations are made apparent in the following Preparations and Examples.

Preparation I 5-bromo-3-(1-methylpiperidin-4-yl)-1H-indole

Preparation of 5-bromo-3-(1-methyl-1,2,3,6-tetrahydropyridin-4-yl)-1H-indole

To a solution of 56.11 gm (306 mMol) potassium hydroxide in 300 mL methanol were added 38 mL (306 mMol) 1-methyl-4-piperidone followed by 30.0 gm (153 mMol) 5-bromo-1H-indole. The reaction mixture was stirred at reflux for 18 hours. The reaction mixture was then cooled to ambient and diluted with 1.5 L water. The resultant white solid was filtered, washed sequentially with water and diethyl ether, and then dried under vacuum to give 44.6 gm (100%) 5-bromo-3-(1-methyl-1,2,3,6-tetrahydro-4-pyridinyl)-1H-indole.

Catalytic Hydrogenation

To a solution of 44.6 gm (153 mMol) 5-bromo-3-(1-methyl-1,2,3,6-tetrahydro-4-pyridinyl)-1H-indole in 1.95 L tetrahydrofuran were added 9.0 gm platinum oxide. The reaction mixture was hydrogenated with an initial hydrogen pressure of 60 p.s.i. at ambient temperature for 24 hours. The reaction mixture was filtered and the filtrate concentrated under reduced pressure. The residue was recrystallized from acetonitrile to give 32.6 gm (73.7%) of the title compound as a white solid.

MS(m/e): 293($M^+$).

Calculated for $C_{14}H_{17}N_2Br$: Theory: C, 57.32; H, 5.96; N, 9.69. Found: C, 57.35; H, 5.84; N, 9.55.

Preparation II

N-methyl-N-methoxy-5-carboxamido-3-(1-methylpiperidin-4-yl)-1H-indole

To a suspension of 0.72 gm (3.58 mMol) potassium hydride in 16.0 mL tetrahydrofuran at 0° C. was added a solution of 1.0 gm (3.41 mMol) 5-bromo-3-(1-methylpiperidin-4-yl)-1H-indole in 16.0 mL tetrahydrofuran and the solution stirred for about 30 minutes. The resulting mixture was cooled to about −78° C. and to it were added 4.4 mL (7.5 mMol) t-butyl lithium, which had been precooled to −78° C., via cannula. After about 15 minutes 0.66 gm (3.41 mMol) N,N'-dimethyl-N,N'-dimethoxyurea were added and the reaction mixture was allowed to warm gradually to ambient. The reaction mixture was then treated with 5N sodium hydroxide and extracted with diethyl ether. The ether extracts were combined, washed with saturated aqueous sodium chloride, dried over sodium sulfate and concentrated under reduced pressure. Purification by flash chromatography, eluting with 4.5:0.5:0.2 ethyl acetate:methanol:toluene, gave 0.61 gm (60%) of the title compound.

MS(m/e): 301(M⁺)

IR: 1632 cm⁻¹

Calculated for $C_{17}H_{23}N_3O_2 \cdot 0.25 H_2O$: Theory: C, 66.75; H, 7.74; N, 13.73. Found: C, 66.47; H, 7.72; N, 13.69.

Preparation III 2-methyl-5-amino-1H-indole

To a solution of 2.0 gm (11.4 mMol) 2-methyl-5-nitro-1H-indole in 100 mL 1:1 ethanol:tetrahydrofuran were added 0.25 gm 5% palladium on carbon. The suspension was hydrogenated at ambient temperature at an initial hydrogen pressure of 60 p.s.i. After 5 hours the reaction mixture was filtered and the filtrate concentrated under reduced pressure to give 1.5 gm of a dark brown solid. The solid was purified by flash chromatography, eluting with a gradient of dichloromethane containing 0–3% methanol, to give 1.19 gm (71.7%) of the title compound as light brown plates.

m.p.=154–156° C.

MS(m/e): 147(M+1)

Calculated for $C_9H_{10}N_2$: Theory: C, 73.94; H, 6.89; N, 19.16. Found: C, 74.15; H, 6.93; N, 19.27.

Many of the 5-($C_1$–$C_4$ alkyl)amino-1H-indoles required for the preparation of compounds of the invention are available through the procedure described in Preparation IV.

Preparation IV 5-methylamino-1H-indole

A. Preparation of N-ethoxycarbonyl-5-amino-1H-indole

To a solution of 4.27 gm (32.3 mMol) 5-amino-1H-indole in 50 mL tetrahydrofuran were added 5.4 mL (38.8 mMol) triethylamine and the reaction mixture was then cooled to 0° C. To this solution were then added dropwise 3.4 mL (35.5 mMol) ethyl chloroformate. After 4 hours the reaction mixture was diluted with 1N HCl and was then extracted with ethyl acetate. The organic phase was washed sequentially with 1N HCl, water and saturated aqueous sodium chloride. The remaining organics were dried over sodium sulfate and concentrated under reduced pressure to give 7.4 gm of a dark oil. This oil was purified by flash chromatography, eluting with a gradient of dichloromethane containing 0–2.5% methanol, to give 4.95 gm (75%) of the title compound as a tan solid.

m.p.=113–114° C.

MS(m/e): 204(M⁺)

Calculated for $C_{11}H_{12}N_2O_2$: Theory: C, 64.69; H, 5.92; N, 13.72. Found: C, 64.76; H, 5.92; N, 13.76.

B. Reduction of N-ethoxycarbonyl-5-amino-1H-indole

To a suspension of 6.3 gm (164.5 mMol) lithium aluminum hydride in 50 mL tetrahydrofuran was added dropwise a solution of 4.8 gm (23.5 mMol) N-ethoxycarbonyl-5-amino-1H-indole in 40 mL tetrahydrofuran. The reaction mixture was heated to reflux until the starting material was consumed as measured by thin-layer chromatography. The reaction mixture was then cooled to ambient and treated with saturated aqueous sodium sulfate to destroy excess lithium aluminum hydride. The resulting suspension was filtered and the filtrate concentrated under reduced pressure to give 3.6 gm of a dark solid. The solid was subjected to flash chromatography, eluting with a gradient of dichloromethane containing 0–2% methanol, to give 3.3 gm (97.1%) of the title compound as a tan solid.

MS(m/e): 146(M⁺)

Calculated for $C_9H_{10}N_2$: Theory: C, 73,94; H, 6.90; N, 19.16. Found: C, 73.78; H, 6.94; N, 19.04.

All of the 5-sulfonamido-1H-indoles required for the preparation of compounds of the invention are available by treating 5-amino-1H-indole with an appropriate sulfonyl chloride as described in Preparation V.

Preparation V 5-methanesulfonamido-1H-indole

To a solution of 2.0 gm (15.1 mMol) 5-amino-1H-indole in 25 mL tetrahydrofuran were added 2.4 mL (17.2 mMol) triethylamine. The reaction mixture was cooled in an ice bath as 1.23 mL (15.9 mMol) methanesulfonyl chloride were added dropwise. After 3.5 hours the reaction mixture was partitioned between 1N sodium hydroxide and ethyl acetate. The organic phase was extracted twice with 1N sodium hydroxide. All sodium hydroxide phases were combined, adjusted to pH=5 with acid and extracted well with ethyl acetate. These organic phases were combined, washed sequentially with water and saturated aqueous sodium chloride, dried over sodium sulfate and concentrated under reduced pressure to give 3.0 gm of a purple solid. This solid was crystallized from cyclohexane/ethyl acetate to give 2.5 gm (78.6%) of the title compound as light purple crystals.

m.p.=133–135° C.

MS(m/e): 210(M⁺)

Calculated for $C_9H_{13}N_2O_2S$: Theory: C, 51.41; H, 4.79; N, 13.32. Found: C, 51.16; H, 4.93; N, 13.27.

Preparation VI 5-amino-3-(1-methylpiperidin-4-yl)-1H-indole

A. From 5-nitro-1H-indole

To a solution of 10.38 gm (185 mMol) potassium hydroxide in 200 mL methanol were added 10.0 gm (61.7 mMol) 5-nitro-1H-indole followed by 13.96 gm (123 mMol) 1-methyl-4-piperidone. The mixture was heated to reflux for 4 days under a nitrogen atmosphere. The reaction mixture was then allowed to cool to ambient and the solid which formed filtered and washed with methanol. This solid was dried under vacuum at 50° C. The combined filtrates were then concentrated under reduced pressure and the residue subjected to flash chromatography, eluting with 92.5:7.5 dichloromethane:methanol. Fractions shown to contain product were combined and concentrated under reduced pressure. This solid was combined with that isolated directly from the reaction mixture to give 13.79 gm (87%) 5-nitro-3-(1-methyl-1,2,3,6-tetrahydropyridin-4-yl)-1H-indole.

To a solution of 38.2 gm (145 mMol) 5-nitro-3-(1-methyl-1,2,3,6-tetrahydropyridin-4-yl)-1H-indole in 1.9 L ethanol and 30 mL 5N HCl were added 10.0 gm 5% palladium on carbon. The reaction mixture was hydrogenated at ambient for 18 hours with an initial hydrogen pressure of 60 p.s.i. The reaction mixture was filtered and then concentrated under reduced pressure. The residue was dissolved in methanol and the solution filtered. This filtrate was concentrated under reduced pressure and the residue redissolved in ethanol. The solution was concentrated to about 500 mL and product allowed to crystallize. The crystals were filtered to give 48.9 gm (95%) of the title compound as its dihydrochloride salt, ethanol solvate.

m.p.=310–320° C. (dec.)

MS(m/e): 229(M$^+$)

Calculated for $C_{14}H_{19}N_3 \cdot 2HCl \cdot C_2H_6O$: Theory: C, 55.17; H, 7.81; N, 12.06. Found: C, 55.23; H, 7.61; N, 12.30.

B. Via 5-amino-1H-indole

To a solution of 1.29 gm (20 mMol) potassium hydroxide in 10 mL methanol were added 1.32 gm (10 mMol) 5-amino-1H-indole followed by 2.46 mL (20 mMol) 1-methyl-4-piperidone. The reaction mixture was then heated to reflux for 18 hours. The reaction mixture was cooled to ambient, diluted with 20 ml water and the precipitate collected by filtration. The solid was recrystallized from ethyl acetate-:methanol to give 1.11 gm (48.9%) 5-amino-3-(1-methyl-1,2,3,6-tetrahydropyr-idin-4-yl)-1H-indole as a tan solid (m.p.=200–203° C.). The tan solid was subjected to flash chromatography, eluting with 100:20:0.5 dichloromethane:methanol:ammonium hydroxide, to give 0.99 gm 5-amino-3-(1-methyl-1,2,3,6-tetrahydropyridin-4-yl)-1H-indole as a cream colored solid (m.p.=212–215° C. (ethyl acetate:methanol)).

MS(m/e): 227(M$^+$)

Calculated for $C_{14}H_{17}N_3$: Theory: C, 73.98; H, 7.54; N, 18.49. Found: C, 73.76; H, 7.48; N, 18.22.

To a solution of 11.3 gm (50 mMol) 5-amino-3-(1-methyl-1,2,3,6-tetrahydropyridin-4-yl)-1H-indole in 250 mL methanol were added 3.0 gm 5% palladium on carbon. The mixture was hydrogenated at room temperature under an initial hydrogen pressure of 60 p.s.i. for 18 hours. The reaction mixture was filtered and the filtrate concentrated under reduced pressure to give a dark gum which was slurried in hexane to give the title compound as a brown solid.

MS(m/e): 229(M$^+$)

Preparation VII 4-chloro-N-methyl-N-methoxybenzamide

To a solution of 11.38 gm (116.7 mMol) N-methoxy-N-methyl amine hydrochloride in 700 mL 1N sodium hydroxide was added a solution of 18.56 gm (106.04 mMol) 4-chlorobenzoyl chloride in 200 mL dichloromethane and the mixture was stirred at ambient. After 18 hours the phases were separated and the remaining aqueous was extracted well with dichloromethane. All organic phases were combined, dried over sodium sulfate and concentrated under reduced pressure to give 27.9 gm (95%) of the title compound as a clear oil.

MS(m/e): 165(M$^+$)

IR: 3011, 2974, 2938, 1634 cm$^{-1}$

Preparation VIII 5-carboxy-3-(1-methyl-1,2,5,6-tetrahydropyridin-4-yl)-1H-indole To a solution of 5.8 gm (90 mMol) potassium hydroxide in 50 mL methanol were added 4.83 gm (30 mMol) indole 5-carboxylic acid followed by 7.4 mL (60 mMol) 1-methyl-4-piperidone and the resulting solution was heated at reflux for 18 hours. The reaction mixture was then concentrated under reduced pressure and the resulting oil dissolved in 200 mL water. The solution was gradually neutralized by addition of 18 mL 5 N hydrochloric acid. The precipitate which formed was isolated by filtration and washed with water to provide 6.09 gm after drying. This solid was dissolved in 100 mL 0.5 N sodium hydroxide, filtered and the filtrate treated with 50 mL 1N hydrochloric acid. The solid which formed was filtered and dried under reduced pressure to provide 5.46 gm (71%) of the title compound.

m.p.=249° C.

MS(m/e): 256(M$^+$)

Calculated for $C_{15}H_{16}N_2O_2$: Theory: C, 70.29; H, 6.29; N, 10.93. Found: C, 70.02; H, 6.39; N, 11.02.

Preparation IX 5-carboxy-3-(1-methylpiperidin-4-yl)-1H-indole 5-ethoxycarbonyl-3-(1-methyl-1,2,5,6-tetrahydropyridin-4-yl)-1H-indole A solution of 0.513 gm (2 mMol) 5-carboxy-3-(1-methyl-1,2,5,6-tetrahydropyridin-4-yl)-1H-indole in 5.1 mL ethanol was cooled in an ice bath while 0.51 mL sulfuric acid was added dropwise. The resulting mixture was heated at reflux for 5 hours. The now homogeneous solution was poured into 50 mL cold water and was then made basic with saturated ammonium hydroxide. The light yellow precipitate was collected by filtration and then recrystallized from ethanol to provide 0.24 gm (42%) of the desired compound as light yellow crystals.

m.p.=249° C.

MS(m/e): 284(M$^+$)

Calculated for $C_{17}H_{20}N_2O_2$: Theory: C, 71.81; H, 7.09; N, 9.85. Found: C, 71.97; H, 7.25; N, 9.71.

5-ethoxycarbonyl-3-(1-methylpiperidin-4-yl)-1H-indole

To a solution of 3.24 gm (11.3 mMol) 5-ethoxycarbonyl-3-(1-methyl-1,2,5,6-tetrahydropyridin-4-yl)-1H-indole in 100 mL ethanol was added 0.8 gm 5% palladium an carbon and the reaction mixture hydrogenated at room temperature for 18 hours at an initial hydrogen pressure of 60 p.s.i. The reaction mixture was filtered and the filtrate concentrated under reduced pressure. The residual oil, which crystallized on standing at room temperature, was recrystallized from 30 mL acetonitrile to provide 1.79 gm (55%) of the desired compound as colorless crystals.

m.p.=155–157° C.

MS(m/e): 286(M$^+$)

Calculated for $C_{17}H_{22}N_2O_2$: Theory: C, 71.30; H, 7.74; N, 9.78. Found: C, 71.07; H, 7.88; N, 9.73.

Saponification/protonation

A mixture of 0.859 gm (3 mMol) 5-ethoxycarbonyl-3-(1-methylpiperidin-4-yl)-1H-indole, 6.0 mL ethanol and 6 mL 2N sodium hydroxide were heated at reflux for 2 hours. Ethanol was distilled from the resulting solution and the remaining aqueous solution was neutralized with 2.4 mL 5N hydrochloric acid. The resulting oil suspended in water is treated with a small amount of dichloromethane and cooled. The resulting solid is filtered, washed with water and acetone, and then recrystallized from 15 mL water to provide 0.308 gm (40%) of the title compound as colorless crystals.

m.p.>280° C.

MS(m/e): 258(M$^+$)

Calculated for $C_{15}H_{18}N_2O_2$: Theory: C, 69.74; H, 7.02; N, 10.84. Found: C, 69.66; H, 7.03; N, 10.92.

Preparation X

Preparation of a Polystyrene Bound Isocyanate Resin

To a stirred suspension of 50 gm (61 mMol) aminomethylated polystyrene resin (1.22 mMol/gm) in 800 mL toluene was added 193 mL (366 mMol) 1.9 M phosgene in toluene. After stirring the reaction mixture for 10 minutes, 67 mL (482 mMol) triethylamine was added and the reaction mixture was stirred for 18 hours at room temperature. The mixture was filtered and the recovered solid washed with 10 times with dichloromethane. A light pink resin mixed with a white solid was obtained. This solid mixture was resuspended in 700 mL dichloromethane, stirred for 10 minutes and then filtered and washed well with dichloromethane. The resulting solid was again suspended, stirred and washed with dichloromethane to provide the desired resin.

IR(KBr): 2252 cm$^{-1}$ (characteristic peak for —N═C═O)

EXAMPLE 1

5-phenylthio-3-(1-methylpiperidin-4-yl)-1H-indole

To a suspension of 0.21 gm (1.05 mMol) potassium hydride in 5.0 mL tetrahydrofuran at 0° C. was added a solution of 0.3 gm (1.0 mMol) 5-bromo-3-(1-methylpiperidin-4-yl)-1H-indole in 5.0 mL tetrahydrofuran and the solution stirred for about 30 minutes. The resulting mixture was cooled to about −78° C. and to it were added 1.47 mL (2.3 mMol) t-butyllithium, which had been pre-cooled to −78° C., via cannula. After about 15 minutes, 0.43 gm (2 mMol) diphenyl disulfide were added and the reaction mixture was allowed to warm gradually to ambient. The reaction mixture was then treated with 5N sodium hydroxide and extracted with diethyl ether. The ether extracts were combined, washed with saturated aqueous sodium chloride, dried over sodium sulfate and concentrated under reduced pressure. Purification by flash chromatography, eluting with 4.5:0.5:0.2 ethyl acetate:methanol:toluene, followed by recrystallization from hexane:diethyl ether gave 0.28 gm (85.1%) of the title compound as a white solid.

m.p.=147–150° C.

MS(m/e): 322(M$^+$)

Calculated for $C_{20}H_{22}N_2S$: Theory: C, 74.49; H, 6.89; N, 8.69. Found: C, 74.27; H, 6.96; N, 8.77.

The compounds of Examples 2–5 were prepared employing the method described in detail in Example 1.

EXAMPLE 2

5-(4-methoxyphenyl)thio-3-(1-methylpiperidin-4-yl)-1H-indole

Using 0.3 gm (1.0 mMol) 5-bromo-3-(1-methylpiperidin-4-yl)-1H-indole and 0.55 gm (1.99 mMol) di(4-methoxyphenyl) disulfide gave 0.28 gm (64.0%) of the title compound as a colorless solid.

m.p.=160–162° C.

MS(m/e): 352(M$^+$)

Calculated for $C_{21}H_{24}N_2OS$: Theory: C, 71.55; H, 6.86; N, 7.95. Found: C, 71.67; H, 6.89; N, 8.24.

EXAMPLE 3

5-benzylthio-3-(1-methylpiperidin-4-yl)-1H-indole

Using 0.325 gm (1.11 mMol) 5-bromo-3-(1-methylpiperidin-4-yl)-1H-indole and 0.55 gm (2.22 mMol) dibenzyl disulfide gave 0.065 gm (17.0%) of the title compound as a colorless solid.

m.p.=138–141° C.

MS(m/e): 336(M$^+$)

Calculated for $C_{21}H_{24}N_2S$: Theory: C, 74.96; H, 7.19; N, 8.33. Found: C, 75.55; H, 7.32; N, 7.95.

EXAMPLE 4

5-(pyridin-2-yl)thio-3-(1-methylpiperidin-4-yl)-1H-indole

Using 0.3 gm (1.0 mMol) 5-bromo-3-(1-methylpiperidin-4-yl)-1H-indole and 0.44 gm (1.99 mMol) di(pyridin-2-yl) disulfide gave 0.12 gm (37.0%) of the title compound as an off-white solid.

m.p.=83° C.

MS(m/e): 323(M$^+$)

Calculated for $C_{19}H_{21}N_3S$: Theory: C, 70.55; H, 6.54; N, 12.99. Found: C, 70.25;,H, 6.60; N, 12.80.

EXAMPLE 5

5-(4-chlorophenyl)thio-3-(1-methylpiperidin-4-yl)-1H-indole

Using 0.4 gm (1.36 mMol) 5-bromo-3-(1-methylpiperidin-4-yl)-1H-indole and 0.78 gm (2.73 mMol) di(4-chlorophenyl) disulfide gave 0.39 gm (79.6%) of the title compound as a colorless solid.

m.p.=148–150° C.

MS(m/e): 356(M$^+$)

Calculated for $C_{20}H_{21}N_2SCl$: Theory: C, 67.30; H, 5.93; N, 7.85. Found: C, 67.47; H, 6.10; N, 7.84.

EXAMPLE 6

5-benzoyl-3-(1-methylpiperidin-4-yl)-1H-indole

To a solution of 0.41 mL (0.73 mMol) phenyllithium in 4.0 mL tetrahydrofuran at 0° C. were added 0.10 gm (0.33 mMol) N-methyl-N-methoxy-5-carboxamido-3-(1-methylpiperidin-4-yl)-1H-indole (Preparation II) in 2.0 mL tetrahydrofuran. After 1 hour the reaction mixture was quenched with 2N sodium hydroxide and the mixture extracted well with diethyl ether. The ether extracts were then washed with saturated aqueous sodium chloride, dried over sodium sulfate and concentrated under reduced pressure. The residue was purified by radial chromatography (2 mm silica), eluting with 10:1 dichloromethane:methanol, to give 0.096 gm (91%) of the title compound as a light yellow solid.

m.p.=101° C.

MS(m/e): 319(M$^+$)

IR: 1644 cm$^{-1}$

Calculated for $C_{21}H_{22}N_2O \cdot H_2O$: Theory: C, 74.48; H, 7.19; N, 8.33. Found: C, 74.85; H, 7.00; N, 8.67.

The compounds of Examples 7–9 were prepared employing the method described in detail in Example 6.

EXAMPLE 7

5-acetyl-3-(1-methylpiperidin-4-yl)-1H-indole hydrochloride monohydrate

Using 0.30 gm (1.0 mMol) N-methyl-N-methoxy-5-carboxamido-3-(1-methylpiperidin-4-yl)-1H-indole (Preparation II) and 3.56 mL (4.98 mMol) methyllithium gave 5-acetyl-3-(1-methylpiperidin-4-yl)-1H-indole which was converted to its hydrochloride salt. 0.153 gm (60%) of the title compound were recovered.

m.p.=65° C.

MS(m/e): 256(M+)

Calculated for $C_{16}H_{20}N_2O \cdot HCl \cdot H_2O$: Theory: C, 61.82; H, 7.46; N, 9.01. Found: C, 62.13; H, 7.86; N, 9.24.

EXAMPLE 8

5-pentanoyl-3-(1-methylpiperidin-4-yl)-1H-indole hydrochloride

Using 0.20 gm (0.66 mMol) N-methyl-N-methoxy-5-carboxamido-3-(1-methylpiperidin-4-yl)-1H-indole (Preparation II) and 1.66 mL (2.67 mMol) n-butyllithium gave 5-pentanoyl-3-(1-methylpiperidin-4-yl)-1H-indole which was converted to its hydrochloride salt. 0.124 gm (63%) of the title compound were recovered as a tan solid which was crystallized from ethanol:diethyl ether.

m.p.=242–245° C.

MS(m/e): 299(M+)

Calculated for $C_{19}H_{26}N_2O \cdot HCl$: Theory: C, 68.15; H, 8.13; N, 8.37. Found: C, 67.89; H, 8.05; N, 8.64.

EXAMPLE 9

5-phenylacetyl-3-(1-methylpiperidin-4-yl)-1H-indole

Using 0.30 gm (1.0 mMol) N-methyl-N-methoxy-5-carboxamido-3-(1-methylpiperidin-4-yl)-1H-indole (Preparation II) and 2.5 mL (5.0 mMol) benzylmagnesium chloride gave 0.22 gm (66%) of the title compound as an off-white solid.

m.p.=69° C.

MS(m/e): 333(M+)

IR: 1662 cm$^{-1}$

Calculated for $C_{22}H_{24}N_2O$: Theory: C, 79.48; H, 7.28; N, 8.43. Found: C, 79.68; H, 7.47; N, 8.61.

EXAMPLE 10

5-(4-methoxybenzoyl)-3-(1-methylpiperidin-4-yl)-1H-indole

To a solution of 0.35 mL (2.82 mMol) 4-methoxy-1-bromobenzene in 3.0 mL tetrahydrofuran at −78° C. were added 1.83 mL (2.93 mMol) n-butyllithium and the reaction mixture stirred for 30 minutes at −78° C. To this solution were then added 0.17 gm (0.56 mMol) N-methyl-N-methoxy-5-carboxamido-3-(1-methylpiperidin-4-yl)-1H-indole (Preparation II) in 2.0 mL tetrahydrofuran. The reaction mixture was allowed to warm gradually to ambient and was then quenched with 2N sodium hydroxide. The resulting mixture was extracted well with diethyl ether. The ether extracts were then washed with saturated aqueous sodium chloride, dried over sodium sulfate and concentrated under reduced pressure. The residue was purified by radial chromatography (2 mm silica), eluting with 10:1 dichloromethane:methanol, to give 0.135 gm (72%) of the title compound as a light yellow solid.

MS(m/e): 349(M+)

Calculated for $C_{22}H_{24}N_2O_2$: Theory: C, 75.84; H, 6.94; N, 8.04. Found: C, 75.85; H, 7.11; N, 8.06.

The compounds of Examples 11–19 were prepared employing the method described in detail in Example 10.

EXAMPLE 11

5-(4-fluorobenzoyl)-3-(1-methylpiperidin-4-yl)-1H-indole

Using 0.20 gm (0.66 mMol) N-methyl-N-methoxy-5-carboxamido-3-(1-methylpiperidin-4-yl)-1H-indole (Preparation II) and 0.36 mL (4.98 mMol) 4-fluoro-1-bromobenzene gave 0.158 gm (71%) of the title compound as an off-white solid.

m.p.=89° C.

MS(m/e): 336(M+)

EXAMPLE 12

5-(4-methylbenzoyl)-3-(1-methylpiperidin-4-yl)-1H-indole

Using 0.20 gm (0.66 mMol) N-methyl-N-methoxy-5-carboxamido-3-(1-methylpiperidin-4-yl)-1H-indole (Preparation II) and 0.41 mL (3.32 mMol) 4-methyl-1-bromobenzene gave 0.180 gm (79%) of the title compound as a yellow solid.

m.p.=92° C.

MS(m/e): 332(M+)

Calculated for $C_{22}H_{24}N_2O$: Theory: C, 79.48; H, 7.28; N, 8.43. Found: C, 79.60; H, 7.40; N, 8.54.

EXAMPLE 13

5-(4-trifluoromethylbenzoyl)-3-(1-methylpiperidin-4-yl)-1H-indole

Using 0.15 gm (0.50 mMol) N-methyl-N-methoxy-5-carboxamido-3-(1-methylpiperidin-4-yl)-1H-indole (Preparation II) and 0.35 mL (2.49 mMol) 4-trifluoromethyl-1-bromobenzene gave 0.122 gm (64%) of the title compound as a yellow solid.

m.p.=160–162° C.

MS(m/e): 386(M+)

Calculated for $C_{22}H_{21}N_2OF_3$: Theory: C, 68.38; H, 5.48; N, 7.25. Found: C, 68.54; H, 5.72; N, 7.47.

EXAMPLE 14

5-(4-trifluoromethoxybenzoyl)-3-(1-methylpiperidin-4-yl)-1H-indole

Using 0.17 gm (0.56 mMol) N-methyl-N-methoxy-5-carboxamido-3-(1-methylpiperidin-4-yl)-1H-indole (Preparation II) and 0.49 mL (3.32 mMol) 4-trifluoromethoxy-1-bromobenzene gave 0.157 gm (69%) of the title compound as a light yellow solid.

m.p.=172–175° C.

MS(m/e): 402(M+)

Calculated for $C_{22}H_{21}N_2O_2F_3$: Theory: C, 65.66; H, 5.26; N, 6.96. Found: C, 65.86; H, 5.45; N, 7.20.

EXAMPLE 15

5-(4-dimethylaminobenzoyl)-3-(1-methylpiperidin-4-yl)-1H-indole

Using 0.20 gm (0.66 mMol) N-methyl-N-methoxy-5-carboxamido-3-(1-methylpiperidin-4-yl)-1H-indole (Preparation II) and 0.80 gm (3.98 mMol) 4-dimethylamino-1-bromobenzene gave 0.159 gm (66%) of the title compound as a light yellow solid.

m.p.=103–104° C.

MS(m/e): 361(M+)

Calculated for $C_{23}H_{27}N_3O \cdot 0.5\ H_2O$: Theory: C, 74.56; H, 7.62; N, 11.34. Found: C, 74.46; H, 7.53; N, 11.04.

EXAMPLE 16

5-(2-naphthoyl)-3-(1-methylpiperidin-4-yl)-1H-indole

Using 0.20 gm (0.66 mMol) N-methyl-N-methoxy-5-carboxamido-3-(1-methylpiperidin-4-yl)-1H-indole (Preparation II) and 0.60 gm (3.32 mMol) 2-bromonaphthalene gave 0.178 gm (73%) of the title compound as a light yellow solid.

m.p.=92° C.

MS(m/e): 368(M$^+$)

EXAMPLE 17

5-(2-pyridinecarbonyl)-3-(1-methylpiperidin-4-yl)-1H-indole

Using 0.20 gm (0.66 mMol) N-methyl-N-methoxy-5-carboxamido-3-(1-methylpiperidin-4-yl)-1H-indole (Preparation II) and 0.32 mL (3.32 mMol) 2-bromopyridine gave 0.089 gm (42%) of the title compound as a light yellow solid.

m.p.=90° C.

MS(m/e): 319(M$^+$)

EXAMPLE 18

5-(N-phenylcarboxamido)-3-(1-methylpiperidin-4-yl)-1H-indole

Using 0.20 gm (0.66 mMol) N-methyl-N-methoxy-5-carboxamido-3-(1-methylpiperidin-4-yl)-1H-indole (Preparation II) and 0.30 mL (3.32 mMol) aniline gave 0.118 gm (53%) of the title compound as a light tan solid.

m.p.=97° C.

MS(m/e): 333(M$^+$)

Calculated for $C_{21}H_{23}N_3O \cdot 0.25\ H_2O$: Theory: C, 74.64; H, 7.01; N, 12.43. Found: C, 74.29; H, 7.06; N, 12.51.

EXAMPLE 19

5-(N-benzylcarboxamido)-3-(1-methylpiperidin-4-yl)-1H-indole

Using 1.2 gm (4.0 mMol) N-methyl-N-methoxy-5-carboxamido-3-(1-methylpiperidin-4-yl)-1H-indole (Preparation II) and 2.2 mL (20.0 mMol) benzylamine gave 0.788 gm (57%) of the title compound as a white solid.

m.p.=87° C.

MS(m/e): 347(M$^+$)

Calculated for $C_{22}H_{25}N_3O$: Theory: C, 76.05; H, 7.25; N, 12.09. Found: C, 76.06; H, 7.51; N, 12.35.

EXAMPLE 20

5-(4-chlorobenzoyl)-3-(1-methylpiperidin-4-yl)-1H-indole

To a suspension of 0.21 gm (1.05 mMol) potassium hydride in 5.0 mL tetrahydrofuran at 0° C. were added a solution of 0.3 gm (1.0 mMol) 5-bromo-3-(1-methylpiperidin-4-yl)-1H-indole in 5.0 mL tetrahydrofuran and the solution stirred for about 30 minutes. The resulting mixture was cooled to about −78° C. and to it were added 1.47 mL (2.3 mMol) t-butyllithium, which had been precooled to −78° C., via cannula. After about 15 minutes, a solution of 1.0 gm (5.0 mMol) N-methyl-N-methoxy-4-chlorobenzamide (Preparation VII) in 3.0 mL tetrahydrofuran were added. The reaction mixture was allowed to gradually warm to ambient and was then quenched with 2N sodium hydroxide. The mixture extracted well with diethyl ether and the ether extracts were then washed with saturated aqueous sodium chloride, dried over sodium sulfate and concentrated under reduced pressure. The residue was purified by radial chromatography (2 mm silica), eluting with 95:5 ethyl acetate:methanol, to give the title compound as a light yellow solid.

m.p.=133° C.

MS(m/e): 352(M$^+$)

Calculated for $C_{21}H_{21}N_2OCl \cdot 0.5H_2O$: Theory: C, 69.70; H, 6.13; N, 7.74. Found: C, 70.02; H, 6.20; N, 7.93.

EXAMPLE 21

5-methanesulfonylamino-3-(1-methyl-1,2,3,6-tetrahydropyridin-4-yl)-1H-indole

To a solution of 1.2 gm (21.4 mMol) potassium hydroxide in 12 mL methanol was added 1.0 gm (4.76 mmol) 5-methanesulfonylamino-1H-indole followed by 0.76 mL (6.2 mMol) 1-methyl-4-piperidone. The homogeneous solution was heated to reflux for 18 hours under nitrogen. The reaction mixture was then cooled and concentrated under reduced pressure. The residue was dissolved in water and the pH of the solution adjusted from 14 to 8–9 by the addition of acid. The precipitate that formed was filtered, washed with water and dried under vacuum to give 1.3 gm (89.6%) of the title compound as a tan solid.

m.p.=210–214° C.

MS(m/e): 305(M$^+$)

Calculated for $C_{15}H_{19}N_3O_2S$: Theory: C, 58.99; H, 6.27; N, 13.76. Found: C, 59.00; H, 6.20; N, 13.74.

The compounds of Examples 22–29 were prepared employing the procedure described in detail in Example 21.

EXAMPLE 22

N-methyl-5-methanesulfonylamino-3-(1-methyl-1,2,3,6-tetrahydropyridin-4-yl)-1H-indole Beginning with 1.23 gm (5.5 mMol) N-methyl-5-methanesulfonylamino-1H-indole and 0.88 mL (7.1 mMol) 1-methyl-4-piperidone, 1.4 gm (80%) of the title compound were recovered as a tan, crystalline powder.

m.p.=198–202° C.

MS(m/e): 319(M$^+$)

Calculated for $C_{16}H_{21}N_3O_2S$: Theory: C, 60.16; H, 6.63; N, 13.16. Found: C, 60.30; H, 6.76; N, 12.97.

EXAMPLE 23

2-methyl-5-methanesulfonylamino-3-(1-methyl-1,2,3,6-tetrahydropyridin-4-yl)-1H-indole Beginning with 1.37 gm (6.1 mMol) 2-methyl-5-methanesulfonylamino-1H-indole and 0.98 mL (7.9 mMol) 1-methyl-4-piperidone, 0.65 gm (33.3%) of the title compound were recovered as a yellow solid.

m.p.=176–184° C.

MS(m/e): 320(M+1)

Calculated for $C_{16}H_{21}N_3O_2S$: Theory: C, 60.16; H, 6.63; N, 13.16. Found: C, 60.39; H, 6.48; N, 13.10.

EXAMPLE 24

5-ethanesulfonylamino-3-(1-methyl-1,2,3,6-tetrahydropyridin-4-yl)-1H-indole

Beginning with 1.45 gm (6.5 mMol) 5-ethanesulfonylamino-1H-indole and 1.03 mL (8.4 mMol) 1-methyl-4-piperidone, 1.23 gm (59.7%) of the title compound were recovered as pale orange crystals.

m.p.=224–226° C.

MS(m/e): 319(M$^+$)

Calculated for $C_{16}H_{21}N_3O_2S$: Theory: C, 60.16; H, 6.63; N, 13.16. Found: C, 60.45; H, 6.69; N, 13.22.

EXAMPLE 25

5-(N,N-dimethylamino)sulfonylamino-3-(1-methyl-1,2,3,6-tetrahydropyridin-4-yl)-1H-indole Beginning with 1.17 gm (4.89 mMol) 5-(N,N-dimethylamino)sulfonylamino-1H-indole and 0.78 mL (6.4 mMol) 1-methyl-4-piperidone, 1.19 gm (72.6%) of the title compound were recovered as a pale yellow powder.

m.p.=207–208° C.

MS(m/e): 334(M$^+$)

Calculated for $C_{16}H_{22}N_4O_2S$: Theory: C, 57.46; H, 6.63; N, 16.75. Found: C, 57.69; H, 6.71; N, 16.60.

EXAMPLE 26

5-methanesulfonylamino-3-(1-ethyl-1,2,3,6-tetrahydropyridin-4-yl)-1H-indole

Beginning with 1.50 gm (7.1 mMol) 5-methanesulfonylamino-1H-indole and 1.25 mL (9.3 mMol) 1-ethyl-4-piperidone, 1.34 gm (58.8%) of the title compound were recovered as a light yellow, crystalline powder.

m.p=218–219° C. (dec.)

MS(m/e) : 320(M+1)

Calculated for $C_{16}H_{21}N_3O_2S$: Theory: C, 60.16; H, 6.63; N, 13.16. Found: C, 59.89; H, 6.39; N, 13.24.

EXAMPLE 27

5-methanesulfonylamino-3-(1-propyl-1,2,3,6-tetrahydropyridin-4-yl)-1H-indole

Beginning with 1.50 gm (7.1 mMol) 5-methanesulfonylamino-1H-indole and 1.4 mL (9.3 mMol) 1-propyl-4-piperidone, 2.1 gm (88.2%) of the title compound were recovered as a yellow powder.

m.p.=217–218.5° C. (dec.)

MS(m/e): 334(M+1)

Calculated for $C_{17}H_{23}N_3O_2S$: Theory: C, 61.23; H, 6.95; N, 12.60. Found: C, 61.51; H, 7.23; N, 12.30.

EXAMPLE 28

5-methanesulfonylamino-3-(1-isopropyl-1,2,3,6-tetrahydropyridin-4-yl)-1H-indole

Beginning with 1.0 gm (4.76 mMol) 5-methanesulfonylamino-1H-indole and 0.873 gm (6.2 mMol) 1-isopropyl-4-piperidone, 1.02 gm (64.2%) of the title compound were recovered as a tan powder.

m.p.=211–213° C. (dec.)

MS(m/e): 333(M$^+$)

Calculated for $C_{17}H_{23}N_3O_2S$: Theory: C, 61.23; H, 6.95; N, 12.60. Found: C, 60.95; H. 6.87; N, 12.60.

EXAMPLE 29

5-methanesulfonylamino-3-(1-butyl-1,2,3,6-tetrahydropyridin-4-yl)-1H-indole

Beginning with 1.0 gm (4.76 mMol) 5-methanesulfonylamino-1H-indole and 0.96 gm (6.2 mMol) 1-butyl-4-piperidone, 1.4 gm (84.8%) of the title compound were recovered as a yellow powder.

m.p.=202–204° C.

MS(m/e): 347(M$^+$)

Calculated for $C_{18}H_{25}N_3O_2S$: Theory: C, 62.22; H, 7.25; N, 12.09. Found: C, 62.10; H, 7.11; N, 12.28.

EXAMPLE 30

5-methanesulfonylamino-3-(1-methylpiperidin-4-yl)-1H-indole oxalate

To a solution 0.815 gm (2.67 mMol) 5-methanesulfonylamino-3-(1-methyl-1,2,3,6-tetrahydropyridin-4-yl)-1H-indole in 125 mL methanol were added 0.815 gm 5% palladium on carbon. The mixture was hydrogenated at ambient for 18 hours with an initial hydrogen pressure of 60 p.s.i. The reaction mixture was filtered and the filtrate concentrated under reduced pressure. The residual oil was purified by flash chromatography, eluting with 90:10 dichlorometh-ane:methanol. Fractions shown to contain product were combined and concentrated under reduced pressure. The residue was dissolved in methanol and to it were added oxalic acid. The suspension was filtered to give 0.261 gm (25%) of the title compound.

m.p.=119.1° C.

MS(m/e): 307(M$^+$)

EXAMPLE 31

5-(N-methyl)methanesulfonylamino-3-(1-methylpiperidin-4-yl)-1H-indole

Following the procedure described in detail in Example 30, 0.807 gm (2.53 mMol) 5-(N-methyl)methanesulfonylamino-3-(1-methyl-1,2,3,6-tetrahydropyridin-4-yl)-1H-indole (Example 22) was hydrogenated to give 0.075 gm (9.3%) of the title compound as a tan foam.

MS(m/e): 322(M+1)

Calculated for $C_{16}H_{23}N_3O_2S$: Theory: C, 59.79; H, 7.21; N, 13.07. Found: C, 59.62; H, 7.33; N, 12.82.

EXAMPLE 32

2-methyl-5-methanesulfonylamino-3-(1-methylpiperidin-4-yl)-1H-indole

To a solution of 0.45 gm (1.41 mMol) 2-methyl-5-methanesulfonylamino-3-(1,2,3,6-tetrahydropyridin-4-yl)-1H-indole (Example 23) in 125 mL methanol were added 0.11 gm 5% palladium on carbon and the reaction mixture hydrogenated at ambient temperature with an initial hydrogen pressure of 60 p.s.i. After 18 hours the reaction mixture was filtered and the filtrate concentrated under reduced pressure to give a yellow oil. The oil was purified by radial chromatography (2 mm silica gel), eluting with 100:5:0.5 dichloromethane: methanol:ammonium hydroxide, to give 0.21 gm of a yellow foam which was then precipitated from ethyl acetate/hexanes to give 0.18 gm (39.7%) of the title compound as a white powder.

m.p.=124–128° C.

MS(m/e): 321(M$^+$)

Calculated for $C_{16}H_{23}N_3O_2S$: Theory: C, 59.79; H, 7.21; N, 13.07. Found: C, 59.88; H, 7.24; N, 13.33.

The compounds of Examples 33–38 were prepared by the procedure described in detail in Example 32.

EXAMPLE 33

5-ethanesulfonylamino-3-(1-methylpiperidin-4-yl)-1H-indole 0.70 gm (2.2 mMol) 5-ethanesulfonylamino-3-(1-methyl-1,2,3,6-tetrahydropyridin-4-yl)-1H-indole (Example 24) were hydrogenated to give 0.545 gm (77.4%) of the title compound as a white powder.

m.p.=176–178° C.

MS(m/e): 322(M+1)

Calculated for $C_{16}H_{23}N_3O_2S$: Theory: C, 59.79; H, 7.21; N, 13.07. Found: C, 60.07; H, 7.22; N, 12.79.

EXAMPLE 34

5-(N,N-dimethylamino)sulfonylamino-3-(1-methylpiperidin-4-yl)-1H-indole 0.66 gm (2.0 mMol) 5-(N,N-dimethylamino)sulfonylamino-3-(1-methyl-1,2,3,6-tetrahydropyridin-4-yl)-1H-indole (Example 25) were hydrogenated to give 0.333 gm (50.2%) of the title compound as an off-white powder.

m.p.=179–181° C. (dec.)

MS(m/e): 336(M+)

Calculated for $C_{16}H_{24}N_4O_2S$: Theory: C, 57.12; H, 7.19; N, 16.65. Found: C, 57.38; H, 7.27; N, 16.87.

EXAMPLE 35

5-methanesulfonylamino-3-(1-ethylpiperidin-4-yl)-1H-indole 0.96 gm (3.0 mMol) 5-methanesulfonylamino-3-(1-ethyl-1,2,3,6-tetrahydropyridin-4-yl)-1H-indole (Example 26) were hydrogenated to give 0.531 gm (55.0%) of the title compound as an off-white powder.

m.p.=179–181° C.

MS(m/e): 321(M+)

Calculated for $C_{16}H_{23}N_3O_2S$: Theory: C, 59.79; H, 7.21; N, 13.07. Found: C, 59.50; H, 7.11; N, 12.81.

EXAMPLE 36

5-methanesulfonylamino-3-(1-propylpiperidin-4-yl)-1H-indole 1.0 gm (3.0 mMol) 5-methanesulfonylamino-3-(1-propyl-1,2,3,6-tetrahydropyridin-4-yl)-1H-indole (Example 27) were hydrogenated to give 0.376 gm (37.2%) of the title compound as an off-white powder.

m.p.=87–90° C.

MS(m/e): 335(M+)

Calculated for $C_{17}H_{25}N_3O_2S$: Theory: C, 60.87; H, 7.51; N, 12.53. Found: C, 61.12; H, 7.32; N, 12.70.

EXAMPLE 37

5-methanesulfonylamino-3-(1-isopropylpiperidin-4-yl)-1H-indole 0.75 gm (2.25 mMol) 5-methanesulfonylamino-3-(1-isopropyl-1,2,3,6-tetrahydropyridin-4-yl)-1H-indole (Example 28) were hydrogenated to give 0.310 gm (41.1%) of the title compound as a white powder.

m.p.=104–108° C.

MS(m/e): 335(M+)

Calculated for $C_{17}H_{25}N_3O_2S \cdot C_2H_2O_4$: Theory: C, 53.63; H, 6.40; N, 9.87. Found: C, 53.38; H, 6.34; N, 9.66.

EXAMPLE 38

5-methanesulfonylamino-3-(1-butylpiperidin-4-yl)-1H-indole 1.05 gm (3.02 mMol) 5-methanesulfonylamino-3-(1-butyl-1,2,3,6-tetrahydropyridin-4-yl)-1H-indole (Example 29) were hydrogenated to give 0.255 gm (24.0%) of the title compound as a tan foam.

m.p.=78° C.

MS(m/e): 349(M+)

Calculated for $C_{18}H_{27}N_3O_2S$: Theory: C, 61.86; H, 7.79; N, 12.02. Found: C, 61.66; H, 7.74; N, 11.87.

EXAMPLE 39

5-benzenesulfonylamino-3-(1-methylpiperidin-4-yl)-1H-indole

To a solution of 2.00 gm (5.74 mMol) 5-amino-3-(1-methylpiperidin-4-yl)-1H-indole in 50.0 mL dichloromethane were added 1.63 gm (20.7 mMol) pyridine and the solution was cooled to 0° C. To this cooled solution were then added dropwise a solution of 2.23 gm (12.6 mMol) benzenesulfonyl chloride in 50 mL dichloromethane. The reaction mixture was allowed to warm gradually to ambient. After 24 hours the reaction mixture was washed with 100 mL water and the remaining organics concentrated under reduced pressure. The residue was suspended in water and the pH adjusted to 14 with sodium hydroxide. The aqueous phase was then extracted well with dichloromethane. The organic phase was washed sequentially with water and saturated aqueous sodium chloride, dried over sodium sulfate and concentrated under reduced pressure. The aqueous phases were combined and the pH adjusted to 10 by the addition of acid and extracted again with 3:1 chloroform:isopropanol. These organic extracts were combined and concentrated under reduced pressure. The combined residues were subjected to flash chromtography, eluting with a gradient system of 100:10:0.5 to 100:11:0.5 dichloromethane:methanol:ammonium hydroxide, giving 0.83 gm (39.1%) of the title compound as a white powder.

m.p.=246–249° C. (dec.)

MS(m/e): 370(M+1)

Calculated for $C_{20}H_{23}N_3O_2S$: Theory: C, 65.02; H, 6.27; N, 11.37. Found: C, 64.78; H, 6.09; N, 11.44.

EXAMPLE 40

5-(4-iodobenzenesulfonyl)amino-3-(1-methylpiperidin-4-yl)-1H-indole

Following the procedure described in detail in Example 39, 0.791 gm (3.45 mMol) 5-amino-3-(1-methylpiperidin-4-yl)-1H-indole and 1.1 gm (3.62 mMol) 4-iodobenzenesulfonyl chloride were used to prepare 0.809 (47.3%) of the title compound as a white powder.

m.p.>250° C.

MS(m/e): 495(M+)

Calculated for $C_{20}H_{22}IN_3O_2S$: Theory: C, 48.49; H, 4.48; N, 8.48. Found: C, 48.68; H, 4.47; N, 8.26.

EXAMPLE 41

5-(di(trifluoromethanesulfonyl))amino-3-(1-methylpiperidin-4-yl)-1H-indole hydrochloride To a suspension of 1.00 gm (2.87 mMol) 5-amino-3-(1-methylpiperidin-4-yl)-1H-indole dihydrochloride in 100 mL dichloromethane were added 2.5 mL (14.3 mMol) diisopropyl-ethylamine followed by 1.06 mL (6.3 mMol) trifluoromethane-sulfonic anhydride. After 20 minutes the reaction mixture was washed with water, dried over sodium sulfate and concentrated under reduced pressure. The residue was purified by flash chromatography, eluting with dichloromethane containing 15% methanol, to give 5-(di(trifluoromethanesulfonyl))amino-3-(1-methylpiperidin-4-yl)-1H-indole. This material was converted to its hydrochloride salt and was crystallized from acetonitrile to give 0.34 gm (22.3%) of the title compound.

m.p.=175–185° C. (dec.)

MS(m/e) : 493(M$^+$)

Calculated for $C_{16}H_{17}N_3O_4S_2F_6$.HCl: Theory: C, 36.27; H, 3.23; N, 7.93. Found: C, 36.48; H, 3.58; N, 7.85.

EXAMPLE 42

5-(methoxycarbonyl)amino-3-(1-methylpiperidin-4-yl)-1H-indole

To a mixture of 10 mg (0.0437 mMol) 5-amino-3-(1-methylpiperidin-4-yl)-1H-indole and 15.0 mg (0.131 mMol) polyvinylpyridine in 3.0 mL dichloromethane were added 4.3 mg (0.0458 mMol) methyl chloroformate. The reaction mixture was mixed for 18 hours at ambient temperature. To this mixture were then added 170 mg (0.137 mMol) aminomethylated polystyrene and the reaction mixed for an additional 18 hours. The reaction mixture was then filtered and the volatiles evaporated to give 10.2 mg (81%) of the title compound.

MS(m/e): 287(M$^+$)

The compounds of Examples 43–50 were prepared by the procedure described in detail in Example 42.

EXAMPLE 43

5-(ethoxycarbonyl)amino-3-(1-methylpiperidin-4-yl)-1H-indole

Beginning with 10 mg (0.0437 mMol) 5-amino-3-(1-methylpiperidin-4-yl)-1H-indole and 4.97 mg (0.0458 mMol) ethyl chloroformate, 11.1 mg (84%) of the title compound were recovered.

MS(m/e): 301(M$^+$)

EXAMPLE 44

5-(propoxycarbonyl)amino-3-(1-methylpiperidin-4-yl)-1H-indole

Beginning with 10 mg (0.0437 mMol) 5-amino-3-(1-methylpiperidin-4-yl)-1H-indole and 5.62 mg (0.0458 mMol) propyl chloroformate, 11.2 mg (81%) of the title compound were recovered.

MS(m/e): 316(M$^+$)

EXAMPLE 45

5-(allyloxycarbonyl)amino-3-(1-methylpiperidin-4-yl)-1H-indole

Beginning with 10 mg (0.0437 mMol) 5-amino-3-(1-methylpiperidin-4-yl)-1H-indole and 5.5 mg (0.0458 mMol) allyl chloroformate, 9.7 mg (71%) of the title compound were recovered.

MS(m/e): 314(M$^+$)

EXAMPLE 46

5-((2-methoxyethyl)carbonyl)amino-3-(1-methylpiperidin-4-yl)-1H-indole

Beginning with 13 mg (0.0567 mMol) 5-amino-3-(1-methylpiperidin-4-yl)-1H-indole and 8.65 mg (0.062 mMol) 2-methoxyethyl chloroformate, 10.25 mg (54%) of the title compound were recovered.

MS(m/e): 332(M$^+$)

EXAMPLE 47

5-(cyclopentyloxycarbonyl)amino-3-(1-methylpiperidin-4-yl)-1H-indole

Beginning with 13 mg (0.0567 mMol) 5-amino-3-(1-methylpiperidin-4-yl)-1H-indole and 9.27 mg (0.062 mMol) cyclopentyl chloroformate, 18.1 mg (93%) of the title compound were recovered.

MS(m/e): 342(M$^+$)

EXAMPLE 48

5-(phenoxycarbonyl)amino-3-(1-methylpiperidin-4-yl)-1H-indole

Beginning with 10 mg (0.0437 mMol) 5-amino-3-(1-methylpiperidin-4-yl)-1H-indole and 7.2 mg (0.0458 mMol) phenyl chloroformate, 13.9 mg (91%) of the title compound were recovered.

MS(m/e): 350(M$^+$)

EXAMPLE 49

5-(4-methoxyphenyl)oxycarbonyl)amino-3-(1-methylpiperidin-4-yl)-1H-indole

Beginning with 13 mg (0.0567 mMol) 5-amino-3-(1-methylpiperidin-4-yl)-1H-indole and 11.1 mg (0.062 mMol) 4-methoxyphenyl chloroformate, 13.4 mg (63%) of the title compound were recovered.

MS(m/e): 380(M$^+$)

EXAMPLE 50

5-(4-chlorophenyl)oxycarbonyl)amino-3-(1-methylpiperidin-4-yl)-1H-indole

Beginning with 13 mg (0.0567 mMol) 5-amino-3-(1-methylpiperidin-4-yl)-1H-indole and 11.1 mg (0.062 mMol) 4-chlorophenyl chloroformate, 18.1 mg (93%) of the title compound were recovered. MS(m/e):

EXAMPLE 51

N-methyl-N'-(3-(1-methylpiperidin-4-yl)-1H-indol-5-yl)urea

To a solution of 2.0 gm (5.74 mMol) 5-amino-3-(1-methylpiperidin-4-yl)-1H-indole dihydrochloride monoethanolate and 5.0 mL (36 mMol) triethylamine in 100 mL dichloromethane were added 0.74 mL (12.6 mMol) methyl isocyanate. The reaction mixture was stirred for 15 minutes and was then washed with 100 mL of water. The remaining organics were dried over sodium sulfate and concentrated under reduced pressure. The resultant residue was crystallized from acetonitrile to give 1.05 gm (64%) of the title compound.

MS(m/e) : 287(M+1)

Calculated for $C_{16}H_{22}N_4O$: Theory: C, 69.11; H, 7.74; N, 19.56. Found: C, 69.37; H, 7.82; N, 19.67.

EXAMPLE 52

N-phenyl-N'-(3-(1-methylpiperidin-4-yl)-1H-indol-5-yl)urea hydrochloride

To a solution of 2.0 gm (5.74 mMol) 5-amino-3-(1-methylpiperidin-4-yl)-1H-indole dihydrochloride monoethanolate and 5.0 mL (36 mMol) triethylamine in 100 mL dichloromethane were added 1.37 mL (12.6 mMol) phenyl isocyanate. The reaction mixture was stirred for 15 minutes and was then washed with 100 mL of water. The remaining organics were dried over sodium sulfate and concentrated under reduced pressure. The resultant residue was crystallized from acetonitrile to give 1.40 gm (70%) N-phenyl-N'-(3-(1-methylpiperidin-4-yl)-1H-indol-5-yl)urea. This material was dissolved in methanol and to it was added an equivalent of methanolic hydrogen chloride. The solution was then concentrated under reduced pressure and the residual oil crystallized from ethanol to give the title compound.

m.p.=215–220° C.

MS(m/e): 348(M$^+$)

Calculated for $C_{21}H_{24}N_4O$·HCl: Theory: C, 65.53; H, 6.55; N, 14.56. Found: C, 65.27; H, 6.43; N, 14.35.

EXAMPLE 53

N-ethyl-N'-(3-(1-methylpiperidin-4-yl)-1H-indol-5-yl)urea

To a solution of 15.0 mg (0.0655 mMol) 5-amino-3-(1-methylpiperidin-4-yl)-1H-indole in 3.0 mL chloroform were added 9.3 mg (0.131 mMol) ethyl isocyanate. The reaction was mixed for 48 hours and to it were then added 0.23 gm (0.131 mMol) aminomethylated polystyrene and the reaction mixed for an additional 18 hours. The reaction mixture was then filtered and the volatiles evaporated to give 16.1 mg (82%) of the title compound.

MS(m/e):

The compounds of Examples 54–75 were prepared by the procedure described in detail in Example 53.

EXAMPLE 54

N-propyl-N'-(3-(1-methylpiperidin-4-yl)-1H-indol-5-yl)urea

Beginning with 15.0 mg (0.0655 mMol) 5-amino-3-(1-methylpiperidin-4-yl)-1H-indole and 11.1 mg (0.131 mMol) propyl isocyanate, 5.8 mg of the title compound were recovered.

MS(m/e): 315(M$^+$)

EXAMPLE 55

N-allyl-N'-(3-(1-methylpiperidin-4-yl)-1H-indol-5-yl)urea

Beginning with 15.0 mg (0.0655 mMol) 5-amino-3-(1-methylpiperidin-4-yl)-1H-indole and 11.1 mg (0.131 mMol) allyl isocyanate, 19.6 mg (96%) of the title compound were recovered.

MS(m/e): 313(M$^+$)

EXAMPLE 56

N-isopropyl-N'-(3-(1-methylpiperidin-4-yl)-1H-indol-5-yl)urea

Beginning with 15.0 mg (0.0655 mMol) 5-amino-3-(1-methylpiperidin-4-yl)-1H-indole and 11.13 mg (0.131 mMol) isopropyl isocyanate, 21.9 mg of the title compound were recovered.

MS(m/e): 315(M$^+$)

EXAMPLE 57

N-n-butyl-N'-(3-(1-methylpiperidin-4-yl)-1H-indol-5-yl)urea

Beginning with 15.0 mg (0.0655 mMol) 5-amino-3-(1-methylpiperidin-4-yl)-1H-indole and 11.1 mg (0.131 mMol) n-butyl isocyanate, 20.6 mg (96%) of the title compound were recovered.

MS(m/e): 329(M$^+$)

EXAMPLE 58

N-cyclohexyl-N'-(3-(1-methylpiperidin-4-yl)-1H-indol-5-yl)urea

Beginning with 15.0 mg (0.0655 mMol) 5-amino-3-(1-methylpiperidin-4-yl)-1H-indole and 16.37 mg (0.131 mMol) cyclohexyl isocyanate, 20.1 mg (87%) of the title compound were recovered.

MS(m/e): 355(M$^+$)

EXAMPLE 59

N-(1-ethoxycarbonyl-2-methylpropyl)-N'-(3-(1-methylpiperidin-4-yl)-1H-indol-5-yl)urea Beginning with 15.0 mg (0.0655 mMol) 5-amino-3-(1-methylpiperidin-4-yl)-1H-indole and 14.56 mg (0.0852 mMol) ethyl 2-isocyanato-3-methylbutyrate, 25.0 mg (95%) of the title compound were recovered.

MS(m/e) 401(M$^+$)

EXAMPLE 60

N-(4-fluoro)phenyl-N'-(3-(1-methylpiperidin-4-yl)-1H-indol-5-yl)urea

Beginning with 15.0 mg (0.0655 mMol) 5-amino-3-(1-methylpiperidin-4-yl)-1H-indole and 9.9 mg (0.072 mMol) 4-fluorophenyl isocyanate, 20.7 mg (86%) of the title compound were recovered.

MS(m/e): 367(M$^+$)

EXAMPLE 61

N-(4-chloro)phenyl-N'-(3-(1-methylpiperidin-4-yl)-1H-indol-5-yl)urea

Beginning with 15.0 mg (0.0655 mMol) 5-amino-3-(1-methylpiperidin-4-yl)-1H-indole and 11.0 mg (0.072 mMol) 4-chlorophenyl isocyanate, 21.4 mg (86%) of the title compound were recovered.

MS(m/e): 383(M$^+$)

EXAMPLE 62

N-(4-methyl)phenyl-N'-(3-(1-methylpiperidin-4-yl)-1H-indol-5-yl)urea

Beginning with 15.0 mg (0.0655 mMol) 5-amino-3-(1-methylpiperidin-4-yl)-1H-indole and 9.6 mg (0.072 mMol) 4-methylphenyl isocyanate, 23.7 mg (99%) of the title compound were recovered.

MS(m/e): 363(M$^+$)

EXAMPLE 63

N-(3-trifluoromethyl)phenyl-N'-(3-(1-methylpiperidin-4-yl)-1H-indol-5-yl)urea

Beginning with 15.0 mg (0.0655 mMol) 5-amino-3-(1-methylpiperidin-4-yl)-1H-indole and 16.0 mg (0.0852 mMol) 3-trifluoromethylphenyl isocyanate, 26.0 mg (95%) of the title compound were recovered.

MS(m/e): 417(M$^+$)

EXAMPLE 64

N-(4-methoxy)phenyl-N'-(3-(1-methylpiperidin-4-yl)-1H-indol-5-yl)urea

Beginning with 15.0 mg (0.0655 mMol) 5-amino-3-(1-methylpiperidin-4-yl)-1H-indole and 10.7 mg (0.072 mMol)

4-methoxyphenyl isocyanate, 22.4 mg (91%) of the title compound were recovered.

MS(m/e): 379(M$^+$)

EXAMPLE 65

N-(2-methoxy)phenyl-N'-(3-(1-methylpiperidin-4-yl)-1H-indol-5-yl)urea

Beginning with 15.0 mg (0.0655 mMol) 5-amino-3-(1-methylpiperidin-4-yl)-1H-indole and 10.7 mg (0.072 mMol) 2-methoxyphenyl isocyanate, 21.7 mg (88%) of the title compound were recovered.

MS(m/e): 379(M$^+$)

EXAMPLE 66

N-(4-methylthio)phenyl-N'-(3-(1-methylpiperidin-4-yl)-1H-indol-5-yl)urea

Beginning with 15.0 mg (0.0655 mMol) 5-amino-3-(1-methylpiperidin-4-yl)-1H-indole and 14.05 mg (0.0852 mMol) 4-methylthiophenyl isocyanate, 24.1 mg (93%) of the title compound were recovered.

MS(m/e): 395(M$^+$)

EXAMPLE 67

N-(3-acetyl)phenyl-N'-(3-(1-methylpiperidin-4-yl)-1H-indol-5-yl)urea

Beginning with 15.0 mg (0.0655 mMol) 5-amino-3-(1-methylpiperidin-4-yl)-1H-indole and 13.7 mg (0.0852 mMol) 3-acetylphenyl isocyanate, 25.0 mg (98%) of the title compound were recovered.

MS(m/e): 391(M$^+$)

EXAMPLE 68

N-(4-butoxycarbonyl)phenyl-N'-(3-(1-methylpiperidin-4-yl)-1H-indol-5-yl)urea

Beginning with 15.0 mg (0.0655 mMol) 5-amino-3-(1-methylpiperidin-4-yl)-1H-indole and 15.8 mg (0.072 mMol) 4-carbobutoxyphenyl isocyanate, 27.1 mg (92%) of the title compound were recovered.

MS(m/e): 449(M$^+$)

EXAMPLE 69

N-(2-phenyl)phenyl-N'-(3-(1-methylpiperidin-4-yl)-1H-indol-5-yl)urea

Beginning with 15.0 mg (0.0655 mMol) 5-amino-3-(1-methylpiperidin-4-yl)-1H-indole and 16.6 mg (0.0852 mMol) 2-phenylphenyl isocyanate, 26.7 mg (96%) of the title compound were recovered.

MS(m/e): 425(M$^+$)

EXAMPLE 70

N-(4-phenyl)phenyl-N'-(3-(1-methylpiperidin-4-yl)-1H-indol-5-yl)urea

Beginning with 15.0 mg (0.0655 mMol) 5-amino-3-(1-methylpiperidin-4-yl)-1H-indole and 16.6 mg (0.0852 mMol) 4-phenylphenyl isocyanate, 26.2 mg (95%) of the title compound were recovered.

MS(m/e): 425(M$^+$)

EXAMPLE 71

N-(2,3-dichloro)phenyl-N'-(3-(1-methylpiperidin-4-yl)-1H-indol-5-yl)urea

Beginning with 15.0 mg (0.0655 mMol) 5-amino-3-(1-methylpiperidin-4-yl)-1H-indole and 16.0 mg (0.0852 mMol) 2,3-dichlorophenyl isocyanate, 26.7 mg (98%) of the title compound were recovered.

MS(m/e): 417(M$^+$)

EXAMPLE 72

N-benzyl-N'-(3-(1-methylpiperidin-4-yl)-1H-indol-5-yl)urea

Beginning with 15.0 mg (0.0655 mMol) 5-amino-3-(1-methylpiperidin-4-yl)-1H-indole and 11.32 mg (0.0852 mMol) benzyl isocyanate, 9.4 mg of the title compound were recovered.

MS(m/e): 363(M$^+$)

EXAMPLE 73

N-phenethyl-N'-(3-(1-methylpiperidin-4-yl)-1H-indol-5-yl)urea

Beginning with 15.0 mg (0.0655 mMol) 5-amino-3-(1-methylpiperidin-4-yl)-1H-indole and 12.51 mg (0.0852 mMol) 2-phenethyl isocyanate, 15.8 mg (65%) of the title compound were recovered.

MS(m/e): 377(M$^+$)

EXAMPLE 74

N-(α-methylbenzyl)-N'-(3-(1-methylpiperidin-4-yl)-1H-indol-5-yl)urea

Beginning with 15.0 mg (0.0655 mMol) 5-amino-3-(1-methylpiperidin-4-yl)-1H-indole and 12.51 mg (0.0852 mMol) α-methylbenzyl isocyanate, 24.0 mg (97%) of the title compound were recovered.

MS(m/e) 377(M$^+$)

EXAMPLE 75

N-(β-(ethoxycarbonyl)phenethyl)-N'-(3-(1-methylpiperidin-4-yl)-1H-indol-5-yl)urea Beginning with 15.0 mg (0.0655 mMol) 5-amino-3-(1-methylpiperidin-4-yl)-1H-indole and 16.6 mg (0.0852 mMol) ethyl 2-isocyanato-3-phenylpropionate, 28.0 mg (95%) of the title compound were recovered.

MS(m/e): 449(M$^+$)

The compounds of Examples 76–79 were prepared at about 50° C. by the procedure described in detail in Example 42.

EXAMPLE 76

N,N-dimethyl-N'-(3-(1-methylpiperidin-4-yl)-1H-indol-5-yl)urea

Beginning with 13.0 mg (0.056 mMol) 5-amino-3-(1-methylpiperidin-4-yl)-1H-indole and 6.4 mg (0.059 mMol) dimethyl carbamoyl chloride, 13.2 mg (79%) of the title compound were recovered.

MS(m/e): 301(M$^+$)

EXAMPLE 77

N,N-diethyl-N'-(3-(1-methylpiperidin-4-yl)-1H-indol-5-yl)urea

Beginning with 13.0 mg (0.056 mMol) 5-amino-3-(1-methylpiperidin-4-yl)-1H-indole and 8.0 mg (0.062 mMol) diethyl carbamoyl chloride, 16.05 mg (86%) of the title compound were recovered.

MS(m/e): 329(M$^+$)

EXAMPLE 78

N-methyl-N-phenyl-N'-(3-(1-methylpiperidin-4-yl)-1H-indol-5-yl)urea

Beginning with 13.0 mg (0.056 mMol) 5-amino-3-(1-methylpiperidin-4-yl)-1H-indole and 10.1 mg (0.059 mMol) N-methyl-N-phenyl carbamoyl chloride, 17.4 (86%) of the title compound were recovered.

MS(m/e): 363(M$^+$)

EXAMPLE 79

5-(morpholin-1-yl)carbonylamino-3-(1-methylpiperidin-4-yl)-1H-indole

Beginning with 13.0 mg (0.056 mMol) 5-amino-3-(1-methylpiperidin-4-yl)-1H-indole and 8.9 mg (0.059 mMol) morpholine-1-carbonyl chloride, 16.2 (85%) of the title compound were recovered.

MS(m/e) 343(M$^+$)

The compounds of Examples 80–86 were prepared by the procedure described in detail in Example 53.

EXAMPLE 80

N-methyl-N'-(3-(1-methylpiperidin-4-yl)-1H-indol-5-yl)thiourea

Beginning with 15.0 mg (0.0655 mMol) 5-amino-3-(1-methylpiperidin-4-yl)-1H-indole and 9.56 mg (0.098 mMol) methyl isothiocyanate, 17.0 mg (86%) of the title compound were recovered.

MS(m/e): 303(M$^+$)

EXAMPLE 81

N-phenyl-N'-(3-(1-methylpiperidin-4-yl)-1H-indol-5-yl)thiourea

Beginning with 15.0 mg (0.0655 mMol) 5-amino-3-(1-methylpiperidin-4-yl)-1H-indole and 13.26 mg (0.098 mMol) phenyl isothiocyanate, 16.8 mg (71%) of the title compound were recovered.

MS(m/e): 365(M$^+$)

EXAMPLE 82

N-(4-methoxy)phenyl-N'-(3-(1-methylpiperidin-4-yl)-1H-indol-5-yl)thiourea

Beginning with 15.0 mg (0.0655 mMol) 5-amino-3-(1-methylpiperidin-4-yl)-1H-indole and 16.21 mg (0.098 mMol) 4-methoxyphenyl isothiocyanate, 18.4 mg (71%) of the title compound were recovered.

MS(m/e): 395(M$^+$)

EXAMPLE 83

N-(3-trifluoromethyl)phenyl-N'-(3-(1-methylpiperidin-4-yl)1H-indol-5-yl)thiourea Beginning with 15.0 mg (0.0655 mMol) 5-amino-3-(1-methylpiperidin-4-yl)-1H-indole and 19.94 mg (0.098 mMol) 3-trifluoromethylphenyl isothiocyanate, 15.6 mg (55%) of the title compound were recovered.

MS (m/e): 433 (M$^+$)

EXAMPLE 84

N-(2-phenyl)phenyl-N'-(3-(1-methylpiperidin-4-yl)-1H-indol-5-yl)thiourea

Beginning with 15.0 mg (0.0655 mMol) 5-amino-3-(1-methylpiperidin-4-yl)-1H-indole and 20.73 mg (0.098 mMol) 2-biphenyl isothiocyanate, 21.2 mg (74%) of the title compound were recovered.

MS(m/e): 441(M$^+$)

EXAMPLE 85

N-(2,3-dichloro)phenyl-N'-(3-(1-methylpiperidin-4-yl)-1H-indol-5-yl)thiourea Beginning with 15.0 mg (0.0655 mMol) 5-amino-3-(1-methylpiperidin-4-yl)-1H-indole and 20.04 mg (0.098 mMol) 2,3-dichlorophenyl isothiocyanate, 17.7 mg (62%) of the title compound were recovered.

MS(m/e): 433(M$^+$)

EXAMPLE 86

N-benzyl-N'-(3-(1-methylpiperidin-4-yl)-1H-indol-5-yl)thiourea

Beginning with 15.0 mg (0.0655 mMol) 5-amino-3-(1-methylpiperidin-4-yl)-1H-indole and 14.63 mg (0.098 mMol) benzyl isothiocyanate, 17.0 mg (86%) of the title compound were recovered.

MS(m/e): 379(M$^+$)

EXAMPLE 87

5-phthalimido-3-(1-methylpiperidin-4-yl)-1H-indole oxalate

To a solution of 0.458 gm (2.0 mMol) 5-amino-3-(1-methylpiperidin-4-yl)-1H-indole in 8.0 mL dichloromethane were added 0.438 gm (2.0 mMol) N-carbethoxyphthalimide. The reaction mixture was stirred 18 hours at ambient temperature, at which time the solvent was removed under reduced pressure. The residue was subjected to flash chromatography, eluting with 100:20:0.5 dichloromethane:methanol:ammonium hydroxide, giving 0.467 gm (65%) of 5-phthalimido-3-(1-methylpiperidin-4-yl)-1H-indole as a yellow foam. The yellow foam was dissolved in a mixture of methanol:ethyl acetate and to it was added an equivalent of oxalic acid. The colorless precipitate which formed was recrystallized from methanol to give 0.267 gm of the title compound as colorless crystals.

m.p.=224° C.

MS(m/e): 359(M$^+$)

Calculated for $C_{22}H_{21}N_3O_2 \cdot C_2H_2O_4$: Theory: C, 64.13; H, 5.16; N, 9.35. Found: C, 63.88; H, 5.27; N, 9.51.

EXAMPLE 88

5-(acetyl)amino-3-(1-methyl-1,2,3,6-tetrahydropyridin-4-yl)-1H-indole

To a solution of 1.0 gm (4.4 mMol) 5-amino-3-(1-methyl-1,2,3,6-tetrahydropyridin-4-yl)-1H-indole in 60 mL tetrahydrofuran were added 0.67 mL (4.8 mMol) triethylamine and the solution was cooled to 0° C. To this solution were then added 0.32 mL (4.6 mMol) acetyl chloride and the reaction mixture was stirred at ambient temperature for 18 hours. The reaction mixture was filtered and concentrated under reduced pressure to give a dark oil. The oil was treated with water to give a black gum. This residue was purified by radial chromatography (2 mm, silica), eluting with 100:10:1 dichloromethane:methanol:ammonium hydroxide, to give 0.20 gm (16.9%) of the title compound as a yellow solid.

m.p.=186–189° C.

MS(m/e): 269(M⁺)

Calculated for $C_{16}H_{19}N_3O$: Theory: C, 71.35; H, 7.11; N, 15.60. Found: C, 71.18; H, 6.97; N, 15.46.

The compounds of Examples 89–110 are prepared by the procedure described in detail in Example 88.

EXAMPLE 89

5-(propanoyl)amino-3-(1-methyl-1,2,3,6-tetrahydropyridin-4-yl)-1H-indole fumarate Beginning with 1.0 gm (4.4 mMol) 5-amino-3-(1-methyl-1,2,3,6-tetrahydropyridin-4-yl)-1H-indole and 0.74 mL (5.3 mMol) propanoyl chloride, 0.287 gm (23%) of the title compound were recovered as a red powder.

m.p.=170–173° C.

MS(m/e): 283(M⁺)

Calculated for $C_{17}H_{21}N_3O \cdot C_4H_4O_4$: Theory: C, 63.15; H, 6.31; N, 10.52. Found: C, 62.97; H, 6.04; N, 10.66.

EXAMPLE 90

5-(benzoyl)amino-3-(1-methyl-1,2,3,6-tetrahydropyridin-4-yl)-1H-indole

Beginning with 1.13 gm (5.0 mMol) 5-amino-3-(1-methyl-1,2,3,6-tetrahydropyridin-4-yl)-1H-indole and 0.58 mL (5.0 mMol) benzoyl chloride, 0.477 gm (28.9%) of the title compound were recovered as a light green solid.

m.p.>250° C.

MS(m/e): 331(M⁺)

Calculated for $C_{21}H_{21}N_3O$: Theory: C, 76.11; H, 6.39; N, 12.68. Found: C, 75.84; H, 6.22; N, 12.41.

EXAMPLE 91

5-(4-chlorobenzoyl)amino-3-(1-methyl-1,2,3,6-tetrahydropyridin-4-yl)-1H-indole

Beginning with 1.13 gm (5.0 mMol) 5-amino-3-(1-methyl-1,2,3,6-tetrahydropyridin-4-yl)-1H-indole and 0.64 mL (5.0 mMol) 4-chlorobenzoyl chloride, 0.544 gm (29.9%) of the title compound were recovered as a tan solid.

m.p.=224–226° C.

MS(m/e): 365(M⁺)

Calculated for $C_{21}H_{20}N_3OCl$: Theory: C, 68.94; H, 5.51; N, 11.48. Found: C, 68.75; H, 5.65; N, 11.63.

EXAMPLE 92

5-(4-methoxybenzoyl)amino-3-(1-methyl-1,2,3,6-tetrahydropyridin-4-yl)-1H-indole

Beginning with 1.13 gm (5.0 mMol) 5-amino-3-(1-methyl-1,2,3,6-tetrahydropyridin-4-yl)-1H-indole and 0.853 gm (5.0 mMol) 4-methoxybenzoyl chloride, 0.367 gm (20.4%) of the title compound were recovered as a light yellow solid.

m.p.=232° C. (dec.)

MS(m/e): 361(M⁺)

Calculated for $C_{22}H_{23}N_3O_2$: Theory: C, 73.11; H, 6.41; N, 11.63. Found: C, 72.86; H, 6.39; N, 11.33.

EXAMPLE 93

5-(2-chloro-4-fluorobenzoyl)amino-3-(1-methyl-1,2,3,6-tetrahydropyridin-4-yl)-1H-indole Beginning with 2.0 gm (8.8 mMol) 5-amino-3-(1-methyl-1,2,3,6-tetrahydropyridin-4-yl)-1H-indole and 1.9 gm (9.7 mMol) 2-chloro-4-fluorobenzoyl chloride, 0.67 gm (19.8%) of the title compound were recovered as a light yellow solid.

m.p.=212–222° C.

MS(m/e): 383(M⁺)

Calculated for $C_{21}H_{19}N_3OClF$: Theory: C, 65.71; H, 4.99; N, 10.95. Found: C, 66.00; H, 5.10; N, 10.84.

EXAMPLE 94

5-(4-fluorobenzoyl)amino-3-(1-ethyl-1,2,3,6-tetrahydropyridin-4-yl)-1H-indole

Beginning with 2.69 gm (11.1 mMol) 5-amino-3-(1-ethyl-1,2,3,6-tetrahydropyridin-4-yl)-1H-indole and 1.45 mL (12.3 mMol) 4-fluorobenzoyl chloride, 2.39 gm (59.0%) of the title compound were recovered as a burnt orange powder.

m.p.=127–135° C. (dec.)

MS(m/e): 363(M⁺)

Calculated for $C_{22}H_{22}N_3OF$: Theory: C, 72.71; H, 6.10; N, 11.56. Found: C, 72.42; H, 6.14; N, 11.33.

EXAMPLE 95

5-(2-furoyl)amino-3-(1-methyl-1,2,3,6-tetrahydropyridin-4-yl)-1H-indole

Beginning with 1.13 gm (5.0 mMol) 5-amino-3-(1-methyl-1,2,3,6-tetrahydropyridin-4-yl)-1H-indole and 0.52 mL (5.0 mMol) 2-furoyl chloride, 0.129 gm (8.1%) of the title compound were recovered as a tan solid.

m.p.=190° C. (dec.)

MS(m/e): 321(M⁺)

Calculated for $C_{19}H_{19}N_3O_2$: Theory: C, 71.01; H, 5.96; N, 13.08. Found: C, 71.26; H, 6.17; N, 12.85.

EXAMPLE 96

5-(2-thienoyl)amino-3-(1-methyl-1,2,3,6-tetrahydropyridin-4-yl)-1H-indole

Beginning with 1.0 gm (4.4 mMol) 5-amino-3-(1-methyl-1,2,3,6-tetrahydropyridin-4-yl)-1H-indole and 0.494 mL (4.6 mMol) 2-thiophenecarbonyl chloride, 0.489 gm (33.0%) of the title compound were recovered as a bright yellow solid.

m.p.=229–233° C. (dec.)

MS(m/e): 337(M⁺)

Calculated for $C_{19}H_{19}N_3OS$: Theory: C, 67.63; H, 5.67; N, 12.45. Found: C, 67.44; H, 5.70; N, 12.22.

EXAMPLE 97

5-(acetyl)amino-3-(1-methylpiperidin-4-yl)-1H-indole

Beginning with 2.00 gm (5.74 mMol) 5-amino-3-(1-methylpiperidin-4-yl)-1H-indole dihydrochloride ethanolate and 1.13 gm (25.8 mMol) acetyl chloride, 1.22 gm (78.3%) of the title compound were recovered as a white powder.

m.p.=161–165° C. (dec.)

MS(m/e): 271(M⁺)

Calculated for $C_{16}H_{21}N_3O$: Theory: C, 70.82; H, 7.80; N, 15.48. Found: C, 70.52; H, 7.83; N, 15.37.

EXAMPLE 98

5-(propanoyl)amino-3-(1-methylpiperidin-4-yl)-1H-indole fumarate

Beginning with 0.945 gm (4.12 mMol) 5-amino-3-(1-methylpiperidin-4-yl)-1H-indole and 0.689 mL (4.94 mMol)

propanoyl chloride, 1.3 gm (81.2%) of the title compound were recovered as a tan solid.

m.p.=88–92° C. (dec.)

MS(m/e): 285(M⁺)

Calculated for $C_{17}H_{23}N_3O.C_4H_4O_4$: Theory: C, 62.83; H, 6.78; N, 10.47. Found: C, 62.61; H, 6.84; N, 10.25.

EXAMPLE 99

5-(trimethylacetyl)amino-3-(1-methylpiperidin-4-yl)-1H-indole

Beginning with 2.00 gm (5.74 mMol) 5-amino-3-(1-methylpiperidin-4-yl)-1H-indole dihydrochloride ethanolate and 1.78 gm (14.4 mMol) trimethylacetyl chloride, 0.623 gm (34.6%) of the title compound were recovered as an off-white powder.

m.p.=214–216° C. (dec.)

MS(m/e): 313(M⁺)

Calculated for $C_{19}H_{27}N_3O$: Theory: C, 72.81; H, 8.68; N, 13.41. Found: C, 72.56; H, 8.73; N, 13.28.

EXAMPLE 100

5-(benzoyl)amino-3-(1-methylpiperidin-4-yl)-1H-indole oxalate

Beginning with 0.545 gm (2.4 mMol) 5-amino-3-(1-methylpiperidin-4-yl)-1H-indole and 0.398 mL (2.85 mMol) benzoyl chloride, 0.92 gm (90.5%) of the title compound were recovered as an off-white solid.

m.p.=130° C.

MS(m/e): 333(M⁺)

Calculated for $C_{21}H_{23}N_3O.C_2H_2O_4$: Theory: C, 65.24; H, 5.95; N, 9.92. Found: C, 64.98; H, 6.12; N, 9.84.

EXAMPLE 101

5-(4-fluorobenzoyl)amino-3-(1-methylpiperidin-4-yl)-1H-indole fumarate

Beginning with 15.2 gm (66 mMol) 5-amino-3-(1-methylpiperidin-4-yl)-1H-indole and 7.8 mL (66 mMol) 4-fluorobenzoyl chloride, 13.01 gm (42.2%) of the title compound were recovered as an off-white solid.

m.p.=139–140° C. (dec.)

MS(m/e): 351(M⁺)

Calculated for $C_{21}H_{22}N_3OF.C_4H_4O_4$: Theory: C, 64.23; H, 5.61; N, 8.99. Found: C, 63.96; H, 5.65; N, 9.05.

EXAMPLE 102

5-(2-chlorobenzoyl)amino-3-(1-methylpiperidin-4-yl)-1H-indole fumarate

Beginning with 1.14 gm (5.0 mMol) 5-amino-3-(1-methylpiperidin-4-yl)-1H-indole and 0.63 mL (5.0 mMol) 2-chlorobenzoyl chloride, 0.406 gm (16.8%) of the title compound were recovered as colorless crystals.

m.p.=209° C. (dec.)

MS(m/e): 367(M⁺)

Exact Mass: Theory: 368.1530. Found: 368.1531.

EXAMPLE 103

5-(3-chlorobenzoyl)amino-3-(1-methylpiperidin-4-yl)-1H-indole fumarate

Beginning with 1.14 gm (5.0 mMol) 5-amino-3-(1-methylpiperidin-4-yl)-1H-indole and 0.62 mL (5.0 mMol) 3-chlorobenzoyl chloride, 0.942 gm (38.9%) of the title compound were recovered as a colorless solid.

m.p.=185° C. (dec.)

MS(m/e): 367(M⁺)

Calculated for $C_{21}H_{22}N_3OCl.C_4H_4O_4$: Theory: C, 62.05; H, 5.41; N, 8.68. Found: C, 61.77; H, 5.60; N, 8.61.

EXAMPLE 104

5-(4-chlorobenzoyl)amino-3-(1-methylpiperidin-4-yl)-1H-indole fumarate

Beginning with 1.14 gm (5.0 mMol) 5-amino-3-(1-methylpiperidin-4-yl)-1H-indole and 0.64 mL (5.0 mMol) 4-chlorobenzoyl chloride, 0.339 gm (14.0%) of the title compound were recovered as a colorless solid.

m.p.=163° C. (dec.)

MS(m/e): 367(M⁺)

Calculated for $C_{21}H_{22}N_3OCl.C_4H_4O_4$: Theory: C, 62.05; H, 5.42; N, 8.68. Found: C, 61.92; H, 5.47; N, 8.52.

EXAMPLE 105

5-(2-methoxybenzoyl)amino-3-(1-methylpiperidin-4-yl)-1H-indole fumarate

Beginning with 1.14 gm (5.0 mMol) 5-amino-3-(1-methylpiperidin-4-yl)-1H-indole and 0.74 mL (5.0 mMol) 2-methoxybenzoyl chloride, 0.569 gm (23.7%) of the title compound were recovered as an off-white solid.

m.p.=90° C. (dec.)

MS(m/e): 364(M⁺)

Exact Mass: Theory: 364.2025. Found: 364.2029.

EXAMPLE 106

5-(3-methoxybenzoyl)amino-3-(1-methylpiperidin-4-yl)-1H-indole fumarate

Beginning with 1.14 gm (5.0 mMol) 5-amino-3-(1-methylpiperidin-4-yl)-1H-indole and 0.70 mL (5.0 mMol) 3-methoxybenzoyl chloride, 0.653 gm (27.2%) of the title compound were recovered as an off-white solid.

m.p.=152° C. (dec.)

MS(m/e): 364(M⁺)

Calculated for $C_{22}H_{25}N_3O_2.C_4H_4O_4$: Theory: C, 65.12; H, 6.10; N, 8.76. Found: C, 64.85; H, 6.38; N, 8.48.

EXAMPLE 107

5-(4-methoxybenzoyl)amino-3-(1-methylpiperidin-4-yl)-1H-indole fumarate

Beginning with 1.14 gm (5.0 mMol) 5-amino-3-(1-methylpiperidin-4-yl)-1H-indole and 0.853 gm (5.0 mMol) 4-methoxybenzoyl chloride, 0.398 gm (16.6%) of the title compound were recovered as an off-white solid.

m.p.=151° C. (dec.)

MS(m/e): 364(M⁺)

Exact Mass: Theory: 364.2025. Found: 364.2032.

EXAMPLE 108

5-(2-furoyl)amino-3-(1-methylpiperidin-4-yl)-1H-indole fumarate

Beginning with 1.14 gm (5.0 mMol) 5-amino-3-(1-methylpiperidin-4-yl)-1H-indole and 0.52 mL (5.0 mMol)

2-furoyl chloride, 0.420 gm (19.1%) of the title compound were recovered as an off-white solid.

m.p.=114° C. (dec.)
MS(m/e): 324(M+)
Calculated for $C_{19}H_{21}N_3O_2 \cdot C_4H_4O_4$: Theory: C, 62.86; H, 5.73; N, 9.56. Found: C, 63.15; H, 5.89; N, 9.84.

EXAMPLE 109

5-(2-thienoyl)amino-3-(1-methylpiperidin-4-yl)-1H-indole oxalate

Beginning with 0.72 gm (3.14 mMol) 5-amino-3-(1-methylpiperidin-4-yl)-1H-indole and 0.525 mL (3.8 mMol) 2-thienoyl chloride, 1.2 gm of the title compound were recovered as an off-white solid.

m.p.=135° C. (dec.)
MS(m/e): 339(M+)
Calculated for $C_{19}H_{21}N_3OS \cdot C_2H_2O_4$: Theory: C, 58.61; H, 5.54; N, 9.64. Found: C, 58.90; H, 5.41; N, 9.89.

EXAMPLE 110

5-(phenylacetyl)amino-3-(1-methylpiperidin-4-yl)-1H-indole oxalate

Beginning with 2.00 gm (5.74 mMol) 5-amino-3-(1-methylpiperidin-4-yl)-1H-indole dihydrochloride ethanolate and 2.23 gm (14.4 mMol) phenylacetyl chloride, 0.80 gm of the title compound were recovered as a tan solid.

m.p.<90° C.
MS(m/e): 347(M+)
Calculated for $C_{22}H_{25}N_3O \cdot C_2H_2O_4$: Theory: C, 65.89; H, 6.22; N, 9.60. Found: C, 65.68; H, 6.29; N, 9.83.

EXAMPLE 111

5-(fur-2-oyl)amino-3-(1-methyl-1,2,3,6-tetrahydropyridin-4-yl)-1H-indole

A. Preparation of 5-(2-furoyl)amino-1H-indole

To a solution of 2.09 gm (15.8 mMol) 5-amino-1H-indole in 20 mL tetrahydrofuran were added 2.6 mL (18.97 mMol) triethylamine and the solution was cooled in an ice bath. To the reaction mixture were then added dropwise 1.71 ml (17.4 mMol) 2-furoyl chloride. When this addition was complete the cooling bath was removed and the reaction mixture was stirred 1.5 hours at ambient temperature. At this point the reaction was diluted with water and extracted well with ethyl acetate. The organic solutions were combined and washed sequentially with water, 2N sodium hydroxide, water and saturated aqueous sodium chloride. The remaining organics were then dried over sodium sulfate and concentrated under reduced pressure to give a dark purple solid. The solid was subjected to flash chromatography, eluting with a gradient of dichloromethane containing 0–2% methanol. The recovered solid was crystallized from ethyl acetate to give 1.8 gm (50.3%) of 5-(2-furoyl)amino-1H-indole as pale purple crystals.

m.p.=181–182° C.
MS(m/e) 227(M+1)
Calculated for $C_{13}H_{10}N_2O_2$: Theory: C, 69.02; H, 4.46; N, 12.38. Found: C, 68.79; H, 4.52; N, 12.25.

B. Condensation of Substituted Indole with 1-ethyl-4-piperidone

To a solution of 0.868 gm (15.5 mMol) potassium hydroxide in 8 mL methanol were added 1.0 gm (4.42 mMol) 5-(2-furoyl)amino-1H-indole and 0.774 mL 1-ethyl-4-piperidone and the solution was stirred at reflux for 18 hours. The reaction mixture was cooled to ambient and then diluted with ice/water. The resultant precipitate was collected and dried under vacuum. This solid was purified by radial chromatography (2 mm silica), eluting with a gradient of dichloromethane containing 5–7.5% methanol and 0.5–1.0% ammonium hydroxide. The product was then crystallized from ethyl acetate to give 0.715 gm (48.3%) of the title compound as a bright yellow powder.

m.p.=120–122° C.
MS(m/e): 336(M+1)
Calculated for $C_{20}H_{21}N_3O_2$: Theory: C, 71.62; H, 6.31; N, 12.53. Found: C, 71.51; H, 6.33; N, 12.73.

EXAMPLE 112

5-(2-furoyl)amino-3-(1-ethylpiperidin-4-yl)-1H-indole

To a solution of 0.780 gm (3.2 mMol) 5-amino-3-(1-ethylpiperidin-4-yl)-1H-indole in 10 mL tetrahydrofuran and 10 mL dimethylformamide were added 0.536 mL (3.85 mMol) triethylamine followed by the dropwise addition of 0.348 mL (3.5 mMol) 2-furoyl chloride. After 18 hours the reaction mixture was cooled in an ice bath. The reaction mixture was the partitioned between 100 mL ethyl acetate and 100 mL 2N sodium hydroxide. The phases were separated and the aqueous extracted again with ethyl acetate. Organic extracts were combined and washed sequentially with 2N sodium hydroxide, water and saturated aqueous sodium chloride. The remaining organics were dried over sodium sulfate and concentrated under reduced pressure. The residue was subjected to radial chromatography (2 mm silica), eluting with 100:10:1 dichloromethane:methanol:ammonium hydroxide. Fractions containing product were combined and concentrated under reduced pressure. The residue was crystallized from ethyl acetate/hexane to give 0.789 gm (73.1%) of the title compound as an off-white solid.

m.p.=178–179° C.
MS(m/e): 338(M+1)
Calculated for $C_{20}H_{23}N_3O_2$: Theory: C, 71.19; H, 6.87; N, 12.45. Found: C, 71.44; H, 7.09; N, 12.40.

EXAMPLE 113

5-(4-fluorobenzoyl)amino-3-(1-ethylpiperidin-4-yl)-1H-indole fumarate

Following the procedure described in detail in Example 32, 1.14 gm (3.14 mMol) 5-(4-fluorobenzoyl)amino-3-(1-ethyl-1,2,3,6-tetrahydropyridin-4-yl)-1H-indole were hydrogenated to give 0.527 gm (34.8%) of the title compound as a tan powder.

m.p.=152–155° C.
MS(m/e): 366(M+1)
Calculated for $C_{22}H_{24}N_3OF \cdot C_4H_4O_4$: Theory: C, 64.85; H, 5.86; N, 8.73. Found: C, 65.15; H, 5.95; N, 8.95.

EXAMPLE 114

5-(2-chloro-4-fluorobenzoyl)amino-3-(1-methylpiperidin-4-yl)-1H-indole

To a solution of 0.40 gm (1.04 mMol) 5-(2-chloro-4-fluorobenzoyl)amino-3-(1-methyl-1,2,3,6- tetrahydropyridin-4-yl)-1H-indole in 5.2 mL trifluoroacetic acid were added 0.208 mL (1.3 mMol) triethylsilane and the reaction mixture was stirred at ambient. After 2 hours, the reaction mixture was concentrated under reduced pressure. To the residue was added 2N sodium hydroxide and the aqueous was extracted with dichloromethane. The combined organic extracts were washed with 2N sodium hydroxide, dried over sodium sulfate and then concentrated under reduced pressure to give an orange foam. The foam was subjected to radial chromatography (2 mm silica), eluting with 100:10:1 dichloromethane:methanol: ammonium hydroxide. The residue was crystallized from ethyl acetate/hexanes to give 0.27 gm (67.3%) of the title compound as a burnt orange powder.

MS(m/e) : 385(M+)

The compounds of Examples 115–124 were prepared by the procedure described in detail in Example 42.

EXAMPLE 115

5-(methoxyacetyl)amino-3-(1-methylpiperidin-4-yl)-1H-indole

Beginning with 13 mg (0.056 mMol) 5-amino-3-(1-methylpiperidin-4-yl)-1H-indole and 6.5 mg (0.059 mMol) methoxyacetyl chloride, 14.2 mg (84%) of the title compound were recovered.

MS(m/e): 302(M$^+$)

EXAMPLE 116

5-((2-thienyl)acetyl)amino-3-(1-methylpiperidin-4-yl)-1H-indole

Beginning with 13 mg (0.056 mMol) 5-amino-3-(1-methylpiperidin-4-yl)-1H-indole and 9.6 mg (0.059 mMol) (2-thiophene)acetyl chloride, 14.1 mg (72%) of the title compound were recovered.

MS(m/e): 354(M$^+$)

EXAMPLE 117

5-(3-(methoxycarbonyl)propanoyl)amino-3-(1-methylpiperidin-4-yl)-1H-indole

Beginning with 13 mg (0.056 mMol) 5-amino-3-(1-methylpiperidin-4-yl)-1H-indole and 9.0 mg (0.059 mMol) (3-methoxycarbonyl)propanoyl chloride, 14.1 mg (75%) of the title compound were recovered.

MS(m/e): 344(M$^+$)

EXAMPLE 118

5-(2-fluorobenzoyl)amino-3-(1-methylpiperidin-4-yl)-1H-indole

Beginning with 10 mg (0.0437 mMol) 5-amino-3-(1-methylpiperidin-4-yl)-1H-indole and 5.4 µL (0.0458 mMol) 2-fluorobenzoyl chloride, 12.2 mg (80%) of the title compound were recovered.

MS(m/e): 351(M$^+$)

EXAMPLE 119

5-(2-methylbenzoyl)amino-3-(1-methylpiperidin-4-yl)-1H-indole

Beginning with 10 mg (0.0437 mMol) 5-amino-3-(1-methylpiperidin-4-yl)-1H-indole and 6.0 µL (0.0458 mMol) 2-methylbenzoyl chloride, 14.3 mg (95%) of the title compound were recovered.

MS(m/e): 348(M+1)

EXAMPLE 120

5-(3-methylbenzoyl)amino-3-(1-methylpiperidin-4-yl)-1H-indole

Beginning with 13 mg (0.056 mMol) 5-amino-3-(1-methylpiperidin-4-yl)-1H-indole and 9.2 mg (0.059 mMol) 3-methylbenzoyl chloride, 17.1 mg (88%) of the title compound were recovered.

MS(m/e): 348(M$^+$)

EXAMPLE 121

5-(2-trifluoromethylbenzoyl)amino-3-(1-methylpiperidin-4-yl)-1H-indole

Beginning with 13 mg (0.056 mMol) 5-amino-3-(1-methylpiperidin-4-yl)-1H-indole and 13.0 mg (0.062 mMol) 2-trifluoromethylbenzoyl chloride, 20.3 mg (89%) of the title compound were recovered.

MS(m/e): 401(M$^+$)

EXAMPLE 122

5-(3,4-dichlorobenzoyl)amino-3-(1-methylpiperidin-4-yl)-1H-indole

Beginning with 10 mg (0.0437 mMol) 5-amino-3-(1-methylpiperidin-4-yl)-1H-indole and 9.6 mg (0.0458 mMol) 3,4-dichlorobenzoyl chloride, 14.4 mg (82%) of the title compound were recovered.

MS(m/e): 401(M$^+$)

EXAMPLE 123

5-(2,4-dichlorobenzoyl)amino-3-(1-methylpiperidin-4-yl)-1H-indole

Beginning with 10 mg (0.0437 mMol) 5-amino-3-(1-methylpiperidin-4-yl)-1H-indole and 6.4 µL (0.0458 mMol) 2,4-dichlorobenzoyl chloride, 12.2 mg (80%) of the title compound were recovered.

MS(m/e): 401(M$^+$)

EXAMPLE 124

5-(isoxazol-5-oyl)amino-3-(1-methylpiperidin-4-yl)-1H-indole

Beginning with 13 mg (0.056 mMol) 5-amino-3-(1-methylpiperidin-4-yl)-1H-indole and 8.21 mg (0.062 mMol) isoxazole-5-carbonyl chloride, 10.4 mg (57%) of the title compound were recovered.

MS(m/e) 325(M$^+$)

EXAMPLE 125

Alternate Synthesis of 5-(2-thienoyl)amino-3-(1-methylpiperidin-4-yl)-1H-indole oxalate To a solution of 0.615 gm (4.8 mMol) 2-thienoic acid in 10 mL dichloromethane were added 0.778 gm (4.8 mMol) N,N-carbonyldiimidazole in 2 mL dichloromethane. After 1.5 hour, a solution of 1.0 gm (4.4 mMol) 5-amino-3-(1-methylpiperidin-4-yl)-1H-indole in 15 mL dichloromethane was added and the reaction mixture stirred for 18 hours at ambient. The reaction mixture was washed sequentially with 1N sodium hydroxide, water and saturated aqueous sodium chloride. The remaining organics were dried over sodium sulfate and the volatiles removed under reduced pressure. The residual brown foam was subjected to radial chromatography (2 mm silica), eluting with a gradient of dichloromethane containing 5–7.5% methanol and 0.5% ammonium hydroxide. Fractions shown to contain product were combined and concentrated under reduced pressure. This material was dissolved in ethyl acetate/ethanol and was treated with oxalic acid to give 0.20 gm (10.7%) of the title compound as a tan solid.

m.p.=160° C.

MS(m/e): 339(M$^+$)

Calculated for $C_{19}H_{21}N_3OS \cdot C_2H_2O_4$: Theory: C, 58.73; H, 5.40; N, 9.78. Found: C, 58.61; H, 5.54; N, 9.64.

General Procedure for the Coupling of Carboxylic Acids with 5-amino-3-(1-methylpiperidin-4-yl)-1H-indole To a suspension of 4-5 equivalents of polymer bound 1-ethyl-3-(3-dimethylaminopropyl)carbodiimide (Desai, et al., *Tetrahedron Letters*, 34(48), 7685 (1993)) in chloroform are added 1 equivalent of 5-amino-3-(1-methylpiperidin-4-yl)-1H-indole and 2-3 equivalents of the carboxylic acid. The reaction is agitated until the reaction is complete, heat may be applied if necessary. The resin is removed by filtration and the product isolated by evaporation of solvent. This procedure is illustrated by Examples 126–178.

EXAMPLE 126

5-(1-propanoyl)amino-3-(1-methylpiperidin-4-yl)-1H-indole

Beginning with 12.0 mg (0.05 mMol) 5-amino-3-(1-methylpiperidin-4-yl)-1H-indole and 8 μL (0.1 mMol) 1-propanoic acid, 13.0 mg (91%) of the title compound were recovered.

MS(m/e): 286(M+1)

EXAMPLE 127

5-(2-methylpropanoyl)amino-3-(1-methylpiperidin-4-yl)-1H-indole

Beginning with 12.0 mg (0.05 mMol) 5-amino-3-(1-methylpiperidin-4-yl)-1H-indole and 8.8 mg (0.10 mMol) isobutyric acid, 11.8 mg (79%) of the title compound were recovered.

MS(m/e): 300(M+1)

EXAMPLE 128

5-(3-methylbutanoyl)amino-3-(1-methylpiperidin-4-yl)-1H-indole

Beginning with 12.0 mg (0.05 mMol) 5-amino-3-(1-methylpiperidin-4-yl)-1H-indole and 10.0 mg (0.10 mMol) isovaleric acid, 17.0 mg (100+%) of the title compound were recovered.

MS(m/e): 314(M$^+$)

EXAMPLE 129

5-(-pentanoyl)amino-3-(1-methylpiperidin-4-yl)-1H-indole

Beginning with 12.0 mg (0.05 mMol) 5-amino-3-(1-methylpiperidin-4-yl)-1H-indole and 10.0 mg (0.10 mMol) pentanoic acid, 12.8 mg (82%) of the title compound were recovered.

MS(m/e): 314(M+1)

EXAMPLE 130

5-(ethoxyacetyl)amino-3-(1-methylpiperidin-4-yl)-1H-indole

Beginning with 12.0 mg (0.05 mMol) 5-amino-3-(1-methylpiperidin-4-yl)-1H-indole and 11.0 μL (0.10 mMol) ethoxyacetic acid, 15.2 mg (97%) of the title compound were recovered.

MS (m/e): 316(M+1)

EXAMPLE 131

5-(phenoxyacetyl)amino-3-(1-methylpiperidin-4-yl)-1H-indole

Beginning with 12.0 mg (0.05 mMol) 5-amino-3-(1-methylpiperidin-4-yl)-1H-indole and 15.0 mg (0.10 mMol) phenxoyacetic acid, 9.44 mg (52%) of the title compound were recovered.

MS(m/e): 364(M+1)

EXAMPLE 132

5-(diphenylacetyl)amino-3-(1-methylpiperidin-4-yl)-1H-indole

Beginning with 12.0 mg (0.05 mMol) 5-amino-3-(1-methylpiperidin-4-yl)-1H-indole and 21.0 mg (0.10 mMol) diphenylacetic acid, 14.0 mg (66%) of the title compound were recovered.

MS(m/e): 424(M+1)

EXAMPLE 133

5-(cinnamoyl)amino-3-(1-methylpiperidin-4-yl)-1H-indole

Beginning with 12.0 mg (0.05 mMol) 5-amino-3-(1-methylpiperidin-4-yl)-1H-indole and 15.0 mg (0.10 mMol) cinnamic acid, 7.2 mg (40%) of the title compound were recovered.

MS(m/e): 360(M+1)

EXAMPLE 134

5-(cyclopropanecarbonyl)amino-3-(1-methylpiperidin-4-yl)-1H-indole

Beginning with 12.0 mg (0.05 mMol) 5-amino-3-(1-methylpiperidin-4-yl)-1H-indole and 9.0 μL (0.10 mMol) cyclopropanecarboxylic acid, 11.4 mg (77%) of the title compound were recovered.

MS(m/e): 298(M+1)

EXAMPLE 135

5-(cyclobutanecarbonyl)amino-3-(1-methylpiperidin-4-yl)-1H-indole

Beginning with 12.0 mg (0.05 mMol) 5-amino-3-(1-methylpiperidin-4-yl)-1H-indole and 15.0 mg (0.10 mMol) cyclobutanecarboxylic acid, 15.0 mg (96%) of the title compound were recovered.

MS (m/e) : 312(M+1)

EXAMPLE 136

5-(cyclopentanecarbonyl)amino-3-(1-methylpiperidin-4-yl)-1H-indole

Beginning with 12.0 mg (0.05 mMol) 5-amino-3-(1-methylpiperidin-4-yl)-1H-indole and 11.0 mg (0.10 mMol)

cyclopentanecarboxylic acid, 16.4 mg (100+%) of the title compound were recovered.

MS(m/e): 326(M+1)

EXAMPLE 137

5-(cyclohexanecarbonyl)amino-3-(1-methylpiperidin-4-yl)-1H-indole

Beginning with 12.0 mg (0.05 mMol) 5-amino-3-(1-methylpiperidin-4-yl)-1H-indole and 13.0 mg (0.10 mMol) cyclohexanecarboxylic acid, 20.6 mg (100+%) of the title compound were recovered.

MS(m/e): 340(M+1)

EXAMPLE 138

5-(1,2,3,4-tetrahydronaphth-1-oyl)amino-3-(1-methylpiperidin-4-yl)-1H-indole

Beginning with 12.0 mg (0.05 mMol) 5-amino-3-(1-methylpiperidin-4-yl)-1H-indole with 16.2 mg (0.10 mMol) 1,2,3,4-tetrahydro-1-naphthoic acid at 70° C., 16.2 mg (84%) of the title compound were recovered.

MS(m/e): 388(M+1)

EXAMPLE 139

5-(3-fluorobenzoyl)amino-3-(1-methylpiperidin-4-yl)-1H-indole

Beginning with 12.0 mg (0.05 mMol) 5-amino-3-(1-methylpiperidin-4-yl)-1H-indole and 21.0 mg (0.15 mMol) 3-fluorobenzoic acid, 11.8 mg (67%) of the title compound were recovered.

MS(m/e): 352(M+1)

EXAMPLE 140

5-(4-bromobenzoyl)amino-3-(1-methylpiperidin-4-yl)-1H-indole

Beginning with 20.0 mg (0.087 mMol) 5-amino-3-(1-methylpiperidin-4-yl)-1H-indole and 52.0 mg (0.131 mMol) 4-bromobenzoic acid, 27.3 mg (75.8%) of the title compound were recovered.

MS(m/e): 413(M+)

EXAMPLE 141

5-(4-iodobenzoyl)amino-3-(1-methylpiperidin-4-yl)-1H-indole

Beginning with 10.0 mg (0.044 mMol) 5-amino-3-(1-methylpiperidin-4-yl)-1H-indole and 32.0 mg (0.131 mMol) 4-iodobenzoic acid, 12.0 mg (60%) of the title compound were recovered.

MS(m/e): 459(M+)

EXAMPLE 142

5-(3-iodobenzoyl)amino-3-(1-methylpiperidin-4-yl)-1H-indole

Beginning with 10.0 mg (0.044 mMol) 5-amino-3-(1-methylpiperidin-4-yl)-1H-indole and 32.0 mg (0.131 mMol) 3-iodobenzoic acid, 15.9 mg (80%) of the title compound were recovered.

MS(m/e): 459(M+)

EXAMPLE 143

5-(4-methylbenzoyl)amino-3-(1-methylpiperidin-4-yl)-1H-indole

Reacting 12.0 mg (0.05 mMol) 5-amino-3-(1-methylpiperidin-4-yl)-1H-indole with 14.0 mg (0.10 mMol) 4-methylbenzoic acid at 70° C., 12.0 mg (69%) of the title compound were recovered.

MS(m/e) : 348(M+1)

EXAMPLE 144

5-(4-hexyloxybenzoyl)amino-3-(1-methylpiperidin-4-yl)-1H-indole

Beginning with 10.0 mg (0.044 mMol) 5-amino-3-(1-methylpiperidin-4-yl)-1H-indole and 30.0 mg (0.131 mMol) 4-hexyloxybenzoic acid, 16.8 mg (89%) of the title compound were recovered.

MS(m/e): 434(M+1)

EXAMPLE 145

5-(4-trifluoromethylbenzoyl)amino-3-(1-methylpiperidin-4-yl)-1H-indole

Beginning with 12.0 mg (0.05 mMol) 5-amino-3-(1-methylpiperidin-4-yl)-1H-indole and 29.0 mg (0.15 mMol) 4-trifluoromethylbenzoic acid, 11.6 mg (58%) of the title compound were recovered.

MS(m/e): 402(M+1)

EXAMPLE 146

5-(3-trifluoromethylbenzoyl)amino-3-(1-methylpiperidin-4-yl)-1H-indole

Beginning with 7.0 mg (0.03 mMol) 5-amino-3-(1-methylpiperidin-4-yl)-1H-indole and 17.1 mg (0.09 mMol) 3-trifluoromethylbenzoic acid, 8.7 mg (72%) of the title compound were recovered.

MS(m/e): 403(M+2)

EXAMPLE 147

5-(4-cyanobenzoyl)amino-3-(1-methylpiperidin-4-yl)-1H-indole

Beginning with 20.0 mg (0.087 mMol) 5-amino-3-(1-methylpiperidin-4-yl)-1H-indole and 38.0 mg (0.131 mMol) 4-cyanobenzoic acid, 13.5 mg (43.1%) of the title compound were recovered.

MS(m/e): 359(M+1)

EXAMPLE 148

5-(4-nitrobenzoyl)amino-3-(1-methylpiperidin-4-yl)-1H-indole

Beginning with 20.0 mg (0.087 mMol) 5-amino-3-(1-methylpiperidin-4-yl)-1H-indole and 44.0 mg (0.131 mMol) 4-nitrobenzoic acid, 13.8 mg (41.8%) of the title compound were recovered.

MS(m/e): 379(M+1)

EXAMPLE 149

5-(4-(methylthio)benzoyl)amino-3-(1-methylpiperidin-4-yl)-1H-indole

Beginning with 20.0 mg (0.087 mMol) 5-amino-3-(1-methylpiperidin-4-yl)-1H-indole and 44.0 mg (0.131 mMol) 4-(methylthio)benzoic acid, 18.9 mg (57.1%) of the title compound were recovered.

MS(m/e): 380(M+1)

EXAMPLE 150

5-(3-(dimethylamino)benzoyl)amino-3-(1-methylpiperidin-4-yl)-1H-indole

Reacting 12.0 mg (0.05 mMol) 5-amino-3-(1-methylpiperidin-4-yl)-1H-indole with 17.0 mg (0.10 mMol)

3-(dimethylamino)benzoic acid at 70° C., 12.4 mg (66%) of the title compound were recovered.

MS(m/e): 377(M+1)

EXAMPLE 151

5-(4-phenylbenzoyl)amino-3-(1-methylpiperidin-4-yl)-1H-indole

Reacting 12.0 mg (0.05 mMol) 5-amino-3-(1-methylpiperidin-4-yl)-1H-indole with 20.0 mg (0.10 mMol) 4-phenylbenzoic acid at 70° C., 10.0 mg (49%) of the title compound were recovered.

MS(m/e): 410(M+1)

EXAMPLE 152

5-(4-(acetyl)benzoyl)amino-3-(1-methylpiperidin-4-yl)-1H-indole

Beginning with 20.0 mg (0.087 mMol) 5-amino-3-(1-methylpiperidin-4-yl)-1H-indole and 44.0 mg (0.131 mMol) 4-(acetyl)benzoic acid, 16.5 mg (50.5%) of the title compound were recovered.

MS(m/e): 376(M+1)

EXAMPLE 153

5-(4-(benzoyl)benzoyl)amino-3-(1-methylpiperidin-4-yl)-1H-indole

Beginning with 10.0 mg (0.044 mMol) 5-amino-3-(1-methylpiperidin-4-yl)-1H-indole and 30.0 mg (0.131 mMol) 4-(benzoyl)benzoic acid, 14.4 mg (75%) of the title compound were recovered.

MS(m/e): 438(M+1)

EXAMPLE 154

5-(4-(methanesulfonyl)benzoyl)amino-3-(1-methylpiperidin-4-yl)-1H-indole

Beginning with 7.0 mg (0.03 mMol) 5-amino-3-(1-methylpiperidin-4-yl)-1H-indole and 18.0 mg (0.09 mMol) 4-(methanesulfonyl)benzoic acid, 7.2 mg of the title compound were recovered.

MS(m/e): 411(M+)

EXAMPLE 155

5-(3,5-dichlorobenzoyl)amino-3-(1-methylpiperidin-4-yl)-1H-indole

Beginning with 7.0 mg (0.03 mMol) 5-amino-3-(1-methylpiperidin-4-yl)-1H-indole and 17.2 mg (0.09 mMol) 3,5-dichlorobenzoic acid, 10.3 mg of the title compound were recovered.

MS(m/e): 402(M+)

EXAMPLE 156

5-(3,4-dimethylbenzoyl)amino-3-(1-methylpiperidin-4-yl)-1H-indole

Beginning with 10.0 mg (0.044 mMol) 5-amino-3-(1-methylpiperidin-4-yl)-1H-indole and 19.6 mg (0.131 mMol) 3,4-dimethylbenzoic acid, 12.0 mg (76%) of the title compound were recovered.

MS(m/e): 362(M+1)

EXAMPLE 157

5-(3,5-dimethylbenzoyl)amino-3-(1-methylpiperidin-4-yl)-1H-indole

Beginning with 10.0 mg (0.044 mMol) 5-amino-3-(1-methylpiperidin-4-yl)-1H-indole and 19.6 mg (0.131 mMol) 3,5-dimethylbenzoic acid, 15.0 mg (95%) of the title compound were recovered.

MS(m/e): 362(M+1)

EXAMPLE 158

5-(2,3-dimethoxybenzoyl)amino-3-(1-methylpiperidin-4-yl)-1H-indole

Beginning with 7.0 mg (0.03 mMol) 5-amino-3-(1-methylpiperidin-4-yl)-1H-indole and 16.4 mg (0.09 mMol) 2,3-dimethoxybenzoic acid, 11.4 mg (97%) of the title compound were recovered.

MS(m/e): 394(M+1)

EXAMPLE 159

5-(3-nitro-4-chlorobenzoyl)amino-3-(1-methylpiperidin-4-yl)-1H-indole

Beginning with 10.0 mg (0.044 mMol) 5-amino-3-(1-methylpiperidin-4-yl)-1H-indole and 26.4 mg (0.131 mMol) 3-nitro-4-chlorobenzoic acid, 11.4 mg (63.3%) of the title compound were recovered.

MS(m/e): 412(M+)

EXAMPLE 160

5-(3,4,5-trimethoxybenzoyl)amino-3-(1-methylpiperidin-4-yl)-1H-indole

Beginning with 10.0 mg (0.044 mMol) 5-amino-3-(1-methylpiperidin-4-yl)-1H-indole and 27.8 mg (0.131 mMol) 3,4,5-trimethoxybenzoic acid, 13.8 mg (75%) of the title compound were recovered.

MS(m/e): 424(M+1)

EXAMPLE 161

5-(3,5-(di-t-butyl)-4-hydroxybenzoyl)amino-3-(1-methylpiperidin-4-yl)-1H-indole

Beginning with 10.0 mg (0.044 mMol) 5-amino-3-(1-methylpiperidin-4-yl)-1H-indole and 32.8 mg (0.131 mMol) 3,5-di(t-butyl)-4-hydroxybenzoic acid, 15.0 mg (75%) of the title compound were recovered.

MS(m/e): 462(M+1)

EXAMPLE 162

5-(pyridine-2-carbonyl)amino-3-(1-methylpiperidin-4-yl)-1H-indole

Beginning with 12.0 mg (0.05 mMol) 5-amino-3-(1-methylpiperidin-4-yl)-1H-indole and 19.0 mg (0.15 mMol) pyridine-2-carboxylic acid, 14.2 mg (85%) of the title compound were recovered.

MS(m/e): 335(M+1)

EXAMPLE 163

5-(pyridine-3-carbonyl)amino-3-(1-methylpiperidin-4-yl)-1H-indole

Beginning with 7.0 mg (0.03 mMol) 5-amino-3-(1-methylpiperidin-4-yl)-1H-indole and 11.1 mg (0.09 mMol) pyridine-3-carboxylic acid, 7.4 mg of the title compound were recovered.

MS(m/e) 335(M+1)

EXAMPLE 164

5-(pyridine-4-carbonyl)amino-3-(1-methylpiperidin-4-yl)-1H-indole

Beginning with 7.0 mg (0.03 mMol) 5-amino-3-(1-methylpiperidin-4-yl)-1H-indole and 11.1 mg (0.09 mMol)

EXAMPLE 165

5-(6-chloropyridine-3-carbonyl)amino-3-(1-methylpiperidin-4-yl)-1H-indole

Beginning with 7.0 mg (0.03 mmol) 5-amino-3-(1-methylpiperidin-4-yl)-1H-indole and 14.2 mg (0.09 mMol) 6-chloropyridine-3-carboxylic acid, 4.4 mg (40%) of the title compound were recovered.

MS(m/e): 369(M+1)

EXAMPLE 166

5-(2-quinolinoyl)amino-3-(1-methylpiperidin-4-yl)-1H-indole

Beginning with 12.0 mg (0.05 mMol) 5-amino-3-(1-methylpiperidin-4-yl)-1H-indole and 17.0 mg (0.10 mMol) 2-quinaldic acid, 17.6 mg (92%) of the title compound were recovered.

MS(m/e): 385(M+1)

EXAMPLE 167

5-(pyrazine-2-carbonyl)amino-3-(1-methylpiperidin-4-yl)-1H-indole

Beginning with 20.0 mg (0.087 mMol) 5-amino-3-(1-methylpiperidin-4-yl)-1H-indole and 32 mg (0.131 mMol) pyrazine-2-carboxylic acid, 6.9 mg (24%) of the title compound were recovered.

MS(m/e): 336(M+1)

EXAMPLE 168

5-(2-pyrroyl)amino-3-(1-methylpiperidin-4-yl)-1H-indole

Beginning with 10.0 mg (0.044 mMol) 5-amino-3-(1-methylpiperidin-4-yl)-1H-indole and 21.1 mg (0.131 mmol) pyrrole-2-carboxylic acid, 12.6 mg (78%) of the title compound were recovered.

MS (m/e): 323(M+1)

EXAMPLE 169

5-(N-methyl-2-pyrroyl)amino-3-(1-methylpiperidin-4-yl)-1H-indole

Beginning with 12.0 mg (0.05 mMol) 5-amino-3-(1-methylpiperidin-4-yl)-1H-indole and 19.0 mg (0.15 mMol) N-methylpyrrole-2-carboxylic acid, 18.0 mg (100+%) of the title compound were recovered.

MS (m/e): 337(M+1)

EXAMPLE 170

5-(2-methyl-3-furoyl)amino-3-(1-methylpiperidin-4-yl)-1H-indole

Beginning with 7.0 mg (0.03 mMol) 5-amino-3-(1-methylpiperidin-4-yl)-1H-indole and 11.3 mg (0.09 mMol) 2-methyl-3-furoic acid, 0.4 mg (4%) of the title compound were recovered.

MS(m/e): 338(M+1)

EXAMPLE 171

5-(3-furoyl)amino-3-(1-methylpiperidin-4-yl)-1H-indole

Beginning with 12.0 mg (0.05 mMol) 5-amino-3-(1-methylpiperidin-4-yl)-1H-indole and 17.0 mg (0.15 mMol) 3-furoic acid, 13.8 mg (85%) of the title compound were recovered.

MS(m/e): 324(M+1)

EXAMPLE 172

5-(5-methyl-2-furoyl)amino-3-(1-methylpiperidin-4-yl)-1H-indole

Beginning with 7.0 mg (0.03 mMol) 5-amino-3-(1-methylpiperidin-4-yl)-1H-indole and 11.3 mg (0.09 mMol) 5-methyl-2-furoic acid, 8.8 mg (87%) of the title compound were recovered.

MS(m/e): 338(M+1)

EXAMPLE 173

5-(5-bromo-2-furoyl)amino-3-(1-methylpiperidin-4-yl)-1H-indole

Beginning with 10.0 mg (0.044 mMol) 5-amino-3-(1-methylpiperidin-4-yl)-1H-indole and 25.0 mg (0.131 mMol) 5-bromo-2-furoic acid, 8.4 mg (48%) of the title compound were recovered.

MS(m/e): 403(M$^+$)

EXAMPLE 174

5-(benzofuran-2-carbonyl)amino-3-(1-methylpiperidin-4-yl)-1H-indole

Beginning with 12.0 mg (0.05 mMol) 5-amino-3-(1-methylpiperidin-4-yl)-1H-indole and 24.0 mg (0.15 mMol) benzofuran-2-carboxylic acid, 15.6 mg (84%) of the title compound were recovered.

MS(m/e): 374(M+1)

EXAMPLE 175

5-(3-thienoyl)amino-3-(1-methylpiperidin-4-yl)-1H-indole

Beginning with 7.0 mg (0.03 mMol) 5-amino-3-(1-methylpiperidin-4-yl)-1H-indole and 11.5 mg (0.09 mMol) 3-thienoic acid, 9.4 mg (92%) of the title compound were recovered.

MS(m/e): 340(M+1)

EXAMPLE 176

5-(3-methyl-2-thienoyl)amino-3-(1-methylpiperidin-4-yl)-1H-indole

Beginning with 7.0 mg (0.03 mMol) 5-amino-3-(1-methylpiperidin-4-yl)-1H-indole and 12.8 mg (0.09 mMol) 3-methyl-2-thienoic acid, 9.6 mg (90%) of the title compound were recovered.

MS(m/e): 354(M+1)

EXAMPLE 177

5-(5-methyl-2-thienoyl)amino-3-(1-methylpiperidin-4-yl)-1H-indole

Beginning with 12.0 mg (0.05 mMol) 5-amino-3-(1-methylpiperidin-4-yl)-1H-indole and 21.0 mg (0.10 mMol) 5-methyl-2-thienoic acid, 13.0 mg (74%) of the title compound were recovered.

MS(m/e): 354(M+1)

EXAMPLE 178

5-(4-methoxy-3-thienoyl)amino-3-(1-methylpiperidin-4-yl)-1H-indole

Beginning with 7.0 mg (0.03 mMol) 5-amino-3-(1-methylpiperidin-4-yl)-1H-indole and 14.2 mg (0.09 mMol)

--- pyridine-4-carboxylic acid, 7.0 mg of the title compound were recovered.

MS(m/e): 335(M+1)

4-methoxy-3-thienoic acid, 12.1 mg of the title compound were recovered.

MS(m/e): 369(M$^+$)

EXAMPLE 179

5-(1-naphthoyl)amino-3-(1-methylpiperidin-4-yl)-1H-indole hydrochloride

To a suspension of 1.2 gm (5.2 mMol) 5-amino-3-(1-methylpiperidin-4-yl)-1H-indole in 50 mL tetrahydrofuran were added 0.946 mL (6.3 mMol) 1-naphthoyl chloride dropwise. After 18 hours the reaction mixture was filtered. The recovered filtrate was dissolved in 10 mL dimethylformamide to which were added 1.5 mL (10.5 mMol) triethylamine followed by 0.8 mL (5.3 mMol) 1-naphthoyl chloride. After 18 hours the reaction mixture was partitioned between ethyl acetate and 1N sodium hydroxide. The phases were separated and the aqueous extracted again with ethyl acetate. The combined ethyl acetate extracts were then washed sequentially with 1N sodium hydroxide, water and saturated aqueous sodium chloride. The remaining organics were dried over sodium sulfate and concentrated under reduced pressure. The residue was subjected to flash chromatography, eluting with 100:10:1 dichloromethane:methanol:ammonium hydroxide. Fractions shown to contain product were combined and concentrated under reduced pressure. The residue was taken up in ethanol and treated with ethanolic hydrogen chloride. The solution was concentrated under reduced pressure and the residue crystallized from ethylacetate/ethanol to give 1.28 gm (58.2%) of the title compound as a tan powder.

m.p.=193–203° C.

MS(m/e): 384(M+1)

Calculated for $C_{25}H_{25}N_3O \cdot HCl \cdot 0.3\ CH_3CO_2CH_2CH_3$: Theory: C, 70.50; H, 6.41; N, 9.41; Cl, 7.94. Found: C, 70.10; H, 6.41; N, 9.41; Cl, 8.34.

EXAMPLE 180

5-(2-naphthoyl)amino-3-(1-methylpiperidin-4-yl)-1H-indole

To a solution of 0.989 gm (4.31 mMol) 5-amino-3-(1-methylpiperidin-4-yl)-1H-indole in 20 mL tetrahydrofuran and 10 mL dimethylformamide were added 0.721 mL (5.2 mMol) triethylamine followed by 0.904 gm (4.74 mMol) 2-naphthoyl chloride. After 18 hours the reaction mixture was cooled in an ice bath and then diluted with 100 mL ethyl acetate followed by 50 mL 2N sodium hydroxide. The phases were separated and the aqueous extracted with ethyl acetate. The organic extracts were combined then washed sequentially with 2N sodium hydroxide, water and saturated aqueous sodium chloride. The remaining organics were dried over sodium sulfate and concentrated under reduced pressure. The residue was subjected to flash chromatography, eluting with 100:10:1 dichloromethane:methanol:ammonium hydroxide. Fractions shown to contain product were combined and concentrated under reduced pressure. The residue was precipitated from ethyl acetate/hexane to give 1.355 gm (82.1%) of the title compound as a tan powder.

m.p.=153–155.5° C.

MS(m/e): 383(M$^+$)

Calculated for $C_{25}H_{25}N_3O$: Theory: C, 78.30; H, 6.57; N, 10.96. Found: C, 78.24; H, 6.63; N, 11.10.

EXAMPLE 181

Alternate Synthesis of 5-(2-chloro-4-fluorobenzoyl)amino-3-(1-methylpiperidin-4-yl)-1H-indole To a suspension of 0.804 gm (3.5 mMol) 5-amino-3-(1-methylpiperidin-4-yl)-1H-indole in 10 mL tetrahydrofuran and 5.0 mL dimethylformamide were added 0.586 mL (4.2 mMol) triethylamine followed by a solution of 0.744 gm (3.86 mMol) 2-chloro-4-fluorobenzoyl chloride in 5 mL tetrahydrofuran. After 18 hours the reaction mixture was diluted with ethyl acetate followed by 2N sodium hydroxide. The phases were separated and the aqueous extracted with ethyl acetate. The organic extracts were combined then washed sequentially with 2N sodium hydroxide, water and saturated aqueous sodium chloride. The remaining organics were dried over sodium sulfate and concentrated under reduced pressure. The residue was subjected to flash chromatography, eluting with 100:10:1 dichloromethane:methanol:ammonium hydroxide. Fractions shown to contain product were combined and concentrated under reduced pressure. The residue was precipitated from ethyl acetate to give 0.921 gm (68.2%) of the title compound as a light pink powder.

m.p.=159–162° C.

MS(m/e): 385(M$^+$)

Calculated for $C_{21}H_{21}N_3OClF$: Theory: C, 65.37; H, 5.49; N, 10.89. Found: C, 65.15; H, 5.55; N, 10.74.

EXAMPLE 182

Alternate Synthesis of 5-(4-fluorobenzoyl)amino-3-(1-methylpiperidin-4-yl)-1H-indole fumarate A. Preparation of 5-(4-fluorobenzoyl)amino-1H-indole To a solution of 3.96 gm (30.0 mMol) 5-amino-1H-indole in 150 mL tetrahydrofuran were added 5.6 mL triethylamine followed by a solution of 5.2 gm (33.0 mMol) 4-fluorobenzoyl chloride in 30 mL tetrahydrofuran. After 18 hours the reaction mixture was poured into water, made basic with sodium hydroxide solution, and extracted with dichloromethane. The organic extracts were combined, dried over sodium sulfate and concentrated under reduced pressure to give a purple solid. This residue was recrystallized from ethyl acetate/hexane to give 6.37 gm (84%) 5-(4-fluoro-benzoyl)amino-1H-indole as brown crystals in two crops.

m.p.=205–207° C.

MS(m/e): 254(M$^+$)

Calculated for $C_{15}H_{11}N_2OF$: Theory: C, 70.86; H, 4.36; N, 11.02. Found: C, 70.64; H, 4.43; N, 10.73.

B. Preparation of 5-(4-fluorobenzoyl)amino-3-(1-methyl-1,2,3,6-tetrahydropyridin-4-yl)-1H-indole A solution of 2.54 gm (10 mMol) 5-(4-fluorobenzoyl)-amino-1H-indole and 1.7 gm (15.0 mMol) 1-methyl-4-piperidone in 20 mL 10% methanolic potassium hydroxide was heated to reflux for 3.5 hours and then allowed to stir without heating. After 18 hours the resultant suspension was filtered, the solid washed with methanol and then dried under reduced pressure to give 2.30 gm (65.8%) 5-(4-fluorobenzoyl)-amino-3-(1-methyl-1,2,3,6-tetrahydropyridin-4-yl)-1H-indole as a tan powder.

m.p.=187.5–189.5° C.

MS(m/e): 349(M$^+$)

Calculated for $C_{21}H_{20}N_3OF$: Theory: C, 72.19; H, 5.77; N, 12.03. Found: C, 72.36; H, 5.87; N, 12.01.

C. Hydrogenation of 5-(4-fluorobenzoyl)amino-3-(1-methyl-1,2,3,6-tetrahydropyridin-4-yl)-1H-indole To a solution of 0.84 gm (2.4 mMol) 5-(4-fluorobenzoyl)-amino-3-(1-methyl-1,2,3,6-tetrahydropyridin-4-yl)-1H- indole in 100 mL methanol were added 0.25 gm 5% palladium on carbon and the mixture stirred under a hydrogen atmosphere maintained with a hydrogen filled balloon. After 15 hours the mixture was filtered and the filtrate concentrated under reduced pressure. The residual light yellow glass was then subjected to Florisil™ chromatography, eluting with 4:1 dichloromethane:methanol containing a trace of ammonium hydroxide. Fractions shown to contain product were combined and concentrated under reduced pressure. The residue was dissolved in ethyl acetate and this solution treated with a saturated solution of fumaric acid in methanol. The solvent was decanted from the precipitate which was recrystallized from ethyl acetate/methanol to give 0.377 gm (33.6%) of the title compound as colorless needles in two crops.

m.p.=155–158° C. (dec.)

MS(m/e): 351(M$^+$)

Calculated for $C_{21}H_{22}N_3OF \cdot C_4H_4O_4$: Theory: C, 64.23; H, 5.61; N, 8.99. Found: C, 64.50; H, 5.58; N, 8.78.

EXAMPLE 183

5-((4-fluorobenzoyl)-N-methyl)amino-3-(1,2,3,6-tetrahydro-pyridin-4-yl)-1H-indole fumarate To a solution of 0.59 gm (2.45 mMol) 5-methylamino-3-(1,2,3,6-tetrahydropyridin-4-yl)-1H-indole in 20 mL dimethylformamide were added 0.409 mL (2.9 mMol) triethylamine followed by 0.318 mL (2.7 mMol) 4-fluorobenzoyl chloride. After 3 hours the reaction mixture was diluted with 100 mL 2N sodium hydroxide followed by 100 mL ethyl acetate. The phases were separated and the aqueous extracted with ethyl acetate. The organic extracts were combined and washed sequentially with water and saturated aqueous sodium chloride. The remaining organics were dried over sodium sulfate and concentrated under reduced pressure. The residue was subjected to flash chromatography, eluting with a gradient of dichloromethane containing 0–5% methanol and 0–0.5% ammonium hydroxide. Fractions shown to contain product were combined and concentrated under reduced pressure. Fumarate salt was formed in and crystallized from ethyl acetate/ethanol to give 0.868 gm (73.9%) of the title compound as a tan powder.

m.p.=203–206° C. (dec.)

MS(m/e): 363(M$^+$)

Calculated for $C_{22}H_{22}N_3OF \cdot C_4H_4O_4$: Theory: C, 65.13; H, 5.47; N, 8.76. Found: C, 65.43; H, 5.73; N, 8.92.

EXAMPLE 184

5-(2-tetrahydrofuranoyl)-3-(1-ethylpiperidin-4-yl)-1H-indole oxalate

To a solution of 0.52 gm (1.55 mMol) 5-(2-furoyl)amino-3-(1-ethyl-1,2,3,6-tetrahydropyridin-4-yl)-1H-indole in 50 mL ethanol and 25 mL tetrahydrofuran were added 0.13 gm 5% palladium on carbon and the mixture hydrogenated at ambient temperature at an initial hydrogen pressure of 60 p.s.i. After 24 hours the reaction mixture was filtered and concentrated under reduced pressure. The residue was purified by radial chromatography (2 mm Silica), eluting with 100:5:1 dichloromethane:methanol:ammonium hydroxide. Fractions shown to contain product were combined and concentrated under reduced pressure. The residue was dissolved in ethyl acetate and treated with an equivalent of oxalic acid. The solid which formed was filtered, washed with ethyl acetate and dried under reduced pressure to give 0.32 gm (47.9%) of the title compound as a white powder.

m.p.=103–105° C.

MS(m/e): 341(M$^+$1)

Calculated for $C_{20}H_{27}N_3O_2 \cdot C_2H_2O_4$: Theory: C, 61.24; H, 6.77; N, 9.74. Found: C, 61.42; H, 6.80; N, 9.65.

EXAMPLE 185

5-methanesulfonylamino-3-(1,2,3,6-pyridin-4-yl)-1H-indole hydrochloride

To a solution of 1.47 gm (26.2 mMol) potassium hydroxide in 10 mL methanol were added 1.0 gm (4.76 mMol) 5-methanesulfonylamino-1H-indole in 5 mL methanol followed by 1.1 gm (7.1 mMol) 4-piperidone hydrochloride monohydrate. The resulting suspension was stirred at reflux for 18 hours. The reaction mixture was then concentrated under reduced pressure. The residual oil was then dissolved in water and the pH of the solution adjusted to 8.0 with 5.0 N hydrochloric acid. The solution was saturated with sodium chloride and then extracted with dichloromethane. The organic phases were combined and concentrated under reduced pressure. The residual solid was crystallized from methanol/water to give 0.815 gm (52.2%) of the title compound as yellow needles.

m.p.>250° C.

MS(m/e): 291(M$^+$)

Calculated for: $C_{14}H_{17}N_3SO_2 \cdot HCl$: Theory: C, 51.29; H, 5.53; N, 12.82. Found: C, 51.53; H, 5.55; N, 12.73.

EXAMPLE 186

5-(4-fluorobenzoyl)amino-3-(1,2,3,6-tetrahydro-pyridin-4-yl)-1H-indole

To a solution of 5.8 gm (90 mMol) potassium hydroxide in 75 mL methanol were added 9.22 gm (60 mMol) 4-piperidone hydrochloride monohydrate followed by 7.8 gm (30 mMol) 5-(4-fluorobenzoyl)amino-3-(piperidin-4-yl)-1H-indole (Example 182A). This solution was stirred at reflux for 18 hours. The reaction mixture was cooled to ambient and then poured slowly into 150 mL water, maintaining the temperature of the solution at about 20° C. The resulting precipitate was filtered and recrystallized from ethanol to give 4.72 gm (47.2%) of the title compound as tan crystals. 0.725 gm of the material were crystallized again from ethanol to provide 0.241 gm light yellow crystals for analysis.

m.p.=241° C. (dec.)

MS(m/e): 335(M$^+$)

Calculated for: $C_{20}H_{18}N_3OF$: Theory: C, 71.63; H, 5.41; N, 12.53. Found: C, 71.85; H, 5.50; N, 12.61.

EXAMPLE 187

5-(4-fluorobenzoyl)amino-3-(piperidin-4-yl)-1H-indole

Following the procedure described in detail in Example 30, 3.93 gm (11.7 mMol) 5-(4-fluorobenzoyl)amino-3-(1,2,3,6-tetrahydropyridin-4-yl)-1H-indole were hydrogenated to give 1.83 gm (49%) of the title compound as colorless crystals.

m.p.=229–230° C. (methanol)

MS(m/e): 337(M$^+$)

Calculated for: $C_{20}H_{20}N_3OF$: Theory: C, 71.20; H, 5.98; N, 12.45. Found: C, 71.46; H, 6.17; N, 12.40.

General Procedure for the Coupling of Amines with Indole 5-carboxylic Acids

A mixture of 15 mg (0.058 mMol) 5-carboxy-3-(1-methyl-1,2,5,6-tetrahydropyridin-4-yl)-1H-indole, 18 mg (0.088 mMol) dicyclohexylcabodiimide, 12 mg (0.088 mMol) hydroxybenztriazole, and 1.5 equivalents of an appropriate amine in 2 mL dimethylformamide are heated at 75° C. for 18 hours. The reaction is allowed to cool and is then loaded onto a VARIAN BOND ELUT SCX™ (Varian, Harbor City, Calif., U.S.A.) ion exchange column (3 mL/0.5 gm). The column is washed with 6 mL methanol and then the desired compound is stripped from the column by eluting with 2M ammonium hydroxide in methanol. This eluant is concentrated under reduced pressure and the residue dissolved in 2 mL dichloromethane. To this solution is added 0.118 gm (0.118 mMol) of a polystyrene bound isocyanate resin and the mixture agitated for 18 hours. The reaction mixture is filtered and concentrated under reduced pressure to provide the amides of the invention. If desired, the compound may be further purified by loading onto a VARIAN BOND ELUT SAX™ (Varian, Harbor City, Calif., U.S.A.) ion exchange column (10 mL/0.5 gm). The desired compound is stripped from the column by eluting with methanol and concentrating the eluant under reduced pressure. The compounds of Examples 188–202 were prepared by this procedure.

EXAMPLE 188

N-[(pyridin-2-yl)methyl]-5-carboxamido-3-(1-methyl-1,2,5,6-tetrahydropyridin-4-yl)-1H-indole Using 2-aminomethylpyridine, 5.2 mg (26%) of the title compound was recovered.

MS(m/e): 337(M+1)

EXAMPLE 189

N-[(pyridin-3-yl)methyl]-5-carboxamido-3-(1-methyl-1,2,5,6-tetrahydropyridin-4-yl)-1H-indole Using 3-aminomethylpyridine, 8.3 mg (42%) of the title compound was recovered.

MS(m/e): 337(M+1)

EXAMPLE 190

N-[(pyridin-4-yl)methyl]-5-carboxamido-3-(1-methyl-1,2,5,6-tetrahydropyridin-4-yl)-1H-indole Using 4-aminomethylpyridine, 7.9 mg (40%) of the title compound was recovered.

MS(m/e) 337(M+1)

EXAMPLE 191

N-[(fur-2-yl)methyl]-5-carboxamido-3-(1-methyl-1,2,5,6-tetrahydropyridin-4-yl)-1H-indole Using 2-aminomethylfuran, 8.0 mg (51%) of the title compound was recovered.

MS (m/e) 335(M$^+$)

EXAMPLE 192

N-[(tetrahydrofur-2-yl)methyl]-5-carboxamido-3-(1-methyl-1,2,5,6-tetrahydropyridin-4-yl)-1H-indole Using 2-aminomethyltetrahydrofuran, 3.8 mg (20%) of the title compound was recovered.

MS(m/e): 340(M+1)

EXAMPLE 193

5-(pyrrolidin-1-yl)carbonyl-3-(1-methyl-1,2,5,6-tetrahydropyridin-4-yl)-1H-indole Using pyrrolidine, 7.1 mg (39%) of the title compound was recovered.

MS (m/e) 309(M$^+$)

EXAMPLE 194

5-(piperidin-1-yl) carbonyl-3-(1-methyl-1,2,5,6-tetrahydropyridin-4-yl)-1H-indole Using piperidine, 9.7 mg (51%) of the title compound was recovered.

MS(m/e): 323(M$^+$)

EXAMPLE 195

5-(morpholin-1-yl)carbonyl-3-(1-methyl-1,2,5,6-tetrahydropyridin-4-yl)-1H-indole Using morpholine, 7.2 mg (38%) of the title compound was recovered.

MS(m/e): 325(M$^+$)

EXAMPLE 196

5-(thiomorpholin-1-yl)carbonyl-3-(1-methyl-1,2,5,6-tetrahydropyridin-4-yl)-1H-indole Using thiomorpholine, 11.2 mg (56%) of the title compound was recovered.

MS(m/e): 341(M$^+$)

EXAMPLE 197

5-(4-hydroxypiperidin-1-yl)carbonyl-3-(1-methyl-1,2,5,6-tetrahydropyridin-4-yl)-1H-indole Using 4-hydroxypiperidine, 3.6 mg (18%) of the title compound was recovered.

MS(m/e) 340(M+1)

EXAMPLE 198

5-(3-hydroxymethylpiperidin-1-yl)carbonyl-3-(1-methyl-1,2,5,6-tetrahydropyridin-4-yl)-1H-indole Using 3-hydroxymethylpiperidine, 10.1 mg (49%) of the title compound was recovered.

MS(m/e): 353(M$^+$)

EXAMPLE 199

5-(3-(N,N-diethylcarboxamido)piperidin-1-yl)carbonyl-3-(1-methyl-1,2,5,6-tetrahydropyridin-4-yl)-1H-indole Using 3-(N,N-diethylcarboxamido)piperidine, 11.0 mg (44%) of the title compound was recovered.

MS(m/e): 422(M$^+$)

EXAMPLE 200

5-(4-cyclopentylpiperazin-1-yl)carbonyl-3-(1-methyl-1,2,5,6-tetrahydropyridin-4-yl)-1H-indole Using 4-cyclopentylpiperazine, 8.7 mg (38%) of the title compound was recovered.

MS(m/e): 393(M+1)

EXAMPLE 201

5-(4-(2-methoxyethyl)piperazin-1-yl)carbonyl-3-(1-methyl-1,2,5,6-tetrahydropyridin-4-yl)-1H-indole Using 4-(2-methoxyethyl)piperazine, 9.6 mg (43%) of the title compound was recovered.

MS(m/e): 383(M+1)

EXAMPLE 202

5-(4-(pyridin-2-yl)piperazin-1-yl)carbonyl-3-(1-methyl-1,2,5,6-tetrahydropyridin-4-yl)-1H-indole Using 4-(pyridin-2-yl)piperazine, 8.6 mg (36%) of the title compound was recovered.

MS(m/e) 402(M+1)

Yet another class of serotonin 5-HT$_{1F}$ receptor agonists are 6-substituted-1,2,3,4-tetrahydro-9H-carbazoles and 7-substituted-10H-cyclohepta[7,6-b]indoles of Formula V:

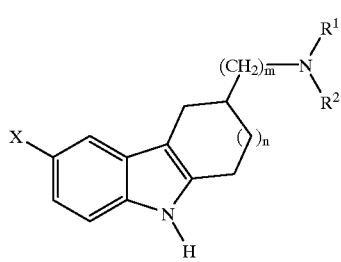

V wherein:

$R^1$ and $R^2$ are independently hydrogen, $C_1$–$C_4$ alkyl, or —CH$_2$CH$_2$-Aryl where Aryl is phenyl, phenyl monosubstituted with halo, or 1-($C_1$–$C_6$ alkyl)pyrazol-4-yl;

X is —OH, —NHC(O)R$^3$, —NHC(Y)NHR$^4$, —NHC(O)OR$^5$, —C(O)R$^6$ or —NHSO$_2$R$^7$;

$R^3$ is $C_1$–$C_6$ alkyl, $C_2$–$C_6$ alkenyl, $C_3$–$C_8$ cycloalkyl, phenyl, substituted phenyl, naphthyl, ($C_1$–$C_4$ alkylene) phenyl, thienylmethyl, or a heterocycle;

$R^4$ is $C_1$–$C_6$ alkyl, phenyl, or phenyl disubstituted with halo;

$R^5$ is $C_1$–$C_6$ alkyl, $C_2$–$C_6$ alkenyl, benzyl or phenyl monosubstituted with halo;

$R^6$ is $C_1$–$C_6$ alkyl, phenyl, or phenyl monosubstituted with halo or $C_1$–$C_4$ alkoxy;

$R^7$ is dimethylamino, phenyl or phenyl monosubstituted with halo or $C_1$–$C_4$ alkyl;

m is 0 or 1;

n is 1 or 2; and

Y is S or O; and pharmaceutically acceptable salts and hydrates thereof.

The general chemical terms used in the formulae above have their usual meanings. For example, the terms "alkyl, alkoxy and alkylthio" include such groups as methyl, ethyl, n-propyl, isopropyl, n-butyl, isobutyl, sec-butyl, tert-butyl, pentyl, 2-pentyl-, 3-pentyl-, neopentyl, hexyl, heptyl, and the like. The term "alkenyl" includes allyl, 1-buten-4-yl, 2-methyl-1-buten-4-yl, 2-buten-4-yl, 1-penten-5-yl, 4-methyl-2-penten-5-yl, 2-penten-5-yl, 3-penten-5-yl, 1-hexen-6-yl, 2-hexen-6-yl, 3-hexen-6-yl, 4-hexen-6-yl and the like. The term "acyl" includes formyl, acetyl, propanoyl, butanoyl, and 2-methylpropanoyl. The term "cycloalkyl" includes such groups as cyclopropyl, cyclobutyl, cyclopentyl, cyclohexyl, cycloheptyl and cyclooctyl. The term "($C_1$–$C_4$ alkylene)phenyl" includes such groups as benzyl, phenethyl, 1-phenyl-2-methylpropyl, phenpropyl and phenbutyl. The term "($C_1$–$C_4$ alkyl)sulfonyl" includes methanesulfonyl, ethanesulfonyl, propanesulfonyl, isopropanesulfonyl, butanesulfonyl and the like. The term "halo" includes fluoro, chloro, bromo and iodo.

The term "substituted phenyl" is taken to mean a phenyl group substituted with one substituent selected from the group consisting of halo, $C_1$–$C_4$ alkyl, $C_1$–$C_8$ alkoxy, $C_1$–$C_4$ alkylthio, nitro, cyano, di($C_1$–$C_4$ alkyl)amino, trifluoromethyl, trifluoromethoxy, phenyl, $C_1$–$C_4$ acyl, benzoyl or ($C_1$–$C_4$ alkyl)sulfonyl, or two to three substituents independently selected from the group consisting of halo, nitro, $C_1$–$C_4$ alkyl, or $C_1$–$C_4$ alkoxy.

The term "heterocycle" is taken to mean furyl, thienyl, pyridinyl, pyrrolyl, N-methylpyrrolyl, oxazolyl, isoxazolyl, pyrazolyl, imidazolyl, triazolyl, oxadiazolyl, thiadiazolyl, pyrimidinyl, pyrazinyl, pyridazinyl, quinolinyl, benzofuranyl, thionaphthyl, or indolyl all optionally substituted with halo, $C_1$–$C_4$ alkyl or $C_1$–$C_4$ alkoxy.

The compounds of Formula V are prepared by methods well known to one of ordinary skill in the art. Compounds where m is 0 and n is 1 are members of the class commonly known as 6-substituted-3-amino-1,2,3,4-tetrahydro-9H-carbazoles. Members of this class are conveniently prepared by the Fischer indole synthesis as illustrated in Synthetic Scheme B-I. X' is bromo, benzyloxy, R$^3$C(O)NH—, R$^4$NHC(Y)NH—, R$^5$OC(O)NH—, or R$^7$SO$_2$NH—; R$^1$ and R$^2$ are independently $C_1$–$C_6$ alkyl, benzyl or, together with the nitrogen, form a phthalimido group; and Y, R$^3$, R$^4$, R$^5$ and R$^7$ are as previously defined.

Synthetic Scheme B-I

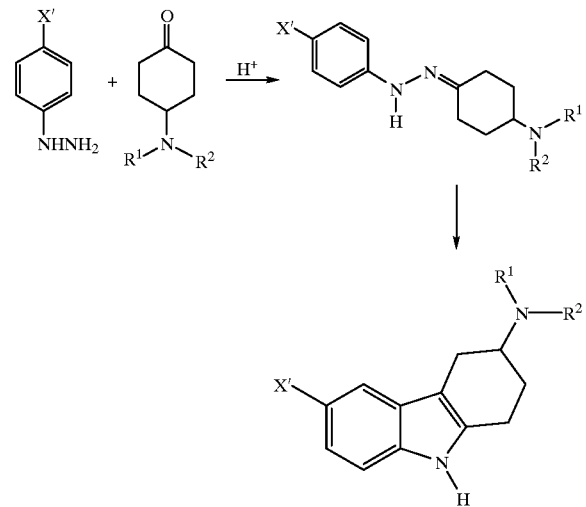

The phenylhydrazine and 4-aminocyclohexanone are condensed together in a suitable solvent, typically a lower alkanol such as ethanol, in the presence of a catalytic amount of acid, such as hydrogen chloride, to give the resultant phenylhydrazone. The reaction is typically performed at from about room temperature to reflux for from about 1 to 24 hours. Once the condensation is complete, the resulting phenylhydrazone may be isolated from the reaction mixture by the addition of water or an aqueous solution of a base such as potassium carbonate if desired. The product separates from the mixture as an oil or a solid. The product may be extracted with a water immiscible solvent, typically dichloromethane, or filtered if appropriate. The product may be used in the next step with or without further purification. The phenylhydrazone undergoes a Fischer indole cyclization in the presence of excess acid. This may be accomplished by dissolving the phenylhydrazone in a neat acid, for example, acetic acid. Alternatively, the phenyl hydrazone may be dissolved in a lower alkanol which has been treated with an acid, for example, ethanolic hydrogen chloride. If the phenylhydrazone prepared as described above requires no further purification, the original reaction mixture may conveniently be treated with an appropriate acid without isolation of the phenylhydrazone. Many times, the Fischer indole cyclization occurs upon formation of the phenylhydrazone, giving the desired product in one step.

The reaction is performed at from about room temperature to reflux for from about 1 to 24 hours. The reaction product may be recovered by direct filtration, or by extraction after removal of solvent and neutralization of acid by the addition of aqueous base. The product may be purified by recrystallization or chromatography as required.

The phenylhydrazines required for the preparation of compounds of Formula V are either commercially available or may be prepared by methods well known to those skilled in the art. Phenylhydrazines where X' is $R^3C(O)NH-$, $R^4NHC(Y)NH-$, $R^5OC(O)NH-$ and $R^7SO_2NH-$ are prepared from 4-nitroaniline as described in Synthetic Scheme B-II. Y, $R^3$, $R^4$ $R^5$ and $R^7$ are as previously defined.

Synthetic Scheme B-II

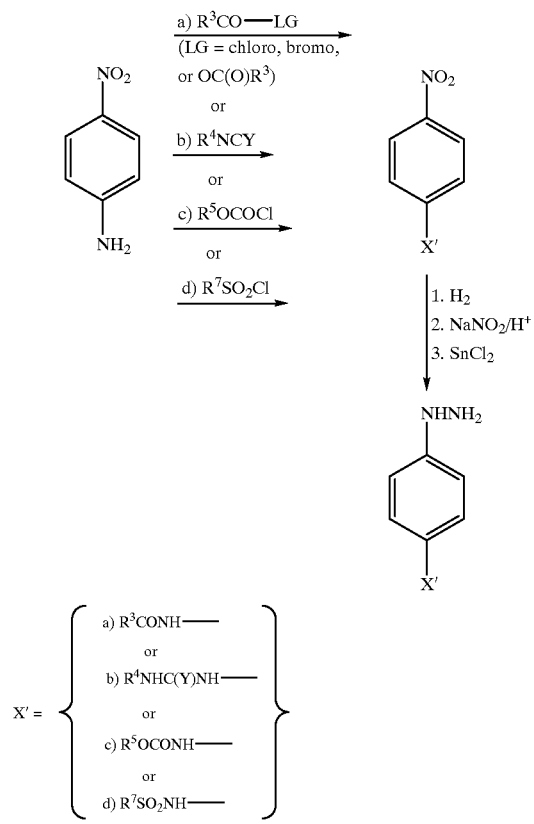

Compounds where X' is $R^4NHC(Y)NH-$ are prepared by treating a solution of 4-nitroaniline in a suitable solvent, such as chloroform or dichloromethane, with an appropriate isocyanate or isothiocyanate. If necessary, an excess of the isocyanate or isothiocyanate is employed to ensure complete reaction of the starting amine. The reactions are performed at about ambient to about 45° C., for from about three hours to about three days. Typically, the product may be isolated by washing the reaction with water and concentrating the remaining organics under reduced pressure. When an excess of isocyanate or isothiocyanate has been used, however, a polymer bound primary or secondary amine, such as an aminomethylated polystyrene, may be conveniently added to react with the excess reagent. Isolation of products from reactions where a polymer bound reagent has been used is greatly simplified, requiring only filtration of the reaction mixture and then concentration of the filtrate under reduced pressure. The product from these reactions may be purified chromatographically or recrystallized from a suitable solvent if desired.

Substituted nitroanilines where X' is $R^5OC(O)NH-$ are prepared by treating a solution of 4-nitroaniline in a suitable solvent, such as chloroform or dichloromethane, with an appropriate chloroformate in the presence of a base, or by treatment with an appropriate carbonate of structure $(R^5O)_2C(O)$. Suitable bases include amines typically used as acid scavengers, such as pyridine or triethylamine, or commercially available polymer bound bases such as polyvinylpyridine. Likewise, substituted nitroanilines where X' is $R^3C(O)NH-$ or $R^7SO_2NH-$ are prepared by reacting 4-nitroaniline with an appropriate carboxylic acid or sulfonyl chloride, bromide or anhydride, optionally in the presence of an acylation catalyst such as dimethylaminopyridine, in the presence of a suitable base, such as those described supra.

Alternatively, substituted nitroanilines where X' is $R^3C(O)NH-$ are prepared by reacting 4-nitroaniline with an appropriate carboxylic acid in the presence of typical peptide coupling reagents such as N,N'-carbonyldiimidazole (CDI), N,N'-dicyclohexylcarbodiimide (DCC) and 1-(3-dimethylaminopropyl)-3-ethylcarbodiimide hydrochloride (EDC). A polymer supported form of EDC has been described (Tetrahedron Letters, 34(48), 7685 (1993)) and is very useful for the preparation of the compounds of the present invention. The product from these reactions is isolated and purified as described above.

The substituted nitroanilines are hydrogenated over a precious metal catalyst, preferably platinum on carbon, and hydrogenated at about ambient temperature at an initial pressure of about 60 p.s.i. for from about 1 to 24 hours in a suitable solvent, such as a lower alkanol or tetrahydrofuran, to give the corresponding amino derivative. This amino derivative is then dissolved in a concentrated acid, such as phosphoric, hydrochloric or hydrobromic acid, and treated with sodium nitrite at a temperature about or below 0° C. After stirring for about an hour, the reaction mixture is added to a solution of tin(II) chloride in concentrated hydrochloric acid and the mixture stirred at about 0° C. for about an hour. The product is isolated by treating the reaction mixture with an aqueous base until it is strongly basic and then extracting with a water immiscible solvent such as ethyl acetate. The hydrazine product may be further purified by chromatography or crystallization prior to further reaction if desired.

The 4-substituted cyclohexanones required for the preparation of compounds of Formula V are available by methods well known in the art as illustrated in Synthetic Scheme B-III. $R^1$ and $R^2$ independently hydrogen, $C_1$–$C_6$ alkyl or benzyl.

Synthetic Scheme B-III

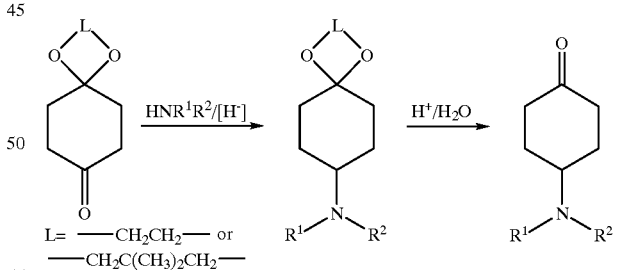

The 1,4-cyclohexanedione monoketal is reductively aminated with an appropriate amine under standard conditions to give the corresponding 4-aminocyclohexanone ketal. The ketal is then deprotected under aqueous acid conditions to prepare the corresponding 4-aminocyclohexanone.

Compounds of Formula V where $R^1=R^2=H$ are prepared from 4-(1-phthlimidyl)cyclohexanone which is available by methods well known in the art, for example, King et al. (Journal of Medicinal Chemistry, 36, 1918 (1993)). Briefly, 4-aminocyclohexanol is reacted first with N-carbethoxyphthalimide and the resulting 4-(1-phthalimidyl)cyclohexanol treated with pyridinium chlorochromate to give the desired ketone. The resultant 4-(1-phthlimidyl)cyclohexanone is then reacted with an appropriate phenylhydrazine followed by Fischer indole cyclization to prepare the corresponding 3-(1-phthalimidyl) carbazole. The phthalimide is then removed by reaction with hydrazine at a convenient point after the Fischer indole synthesis to provide compounds where $R^1=R^2=H$.

Compounds of Formula V where m=0 and n=1 are 7-substituted-4-amino-10H-cyclohepta[6,7-b]indoles. These compounds are prepared substantially as described for the 6-substituted-3-amino-1,2,3,4-tetrahydro-9H-carbazoles as illustrated in Synthetic Scheme B-I, except that a 4-aminocycloheptanone replaces the 4-aminocyclohexanone in the synthesis. The 4-aminocycloheptanones required for the synthesis of compounds of Formula V may be prepared as described in Synthetic Scheme B-IV. $R^1$ and $R^2$ are independently $C_1$–$C_6$ alkyl or benzyl, or together with the nitrogen form the phthalimide moiety.

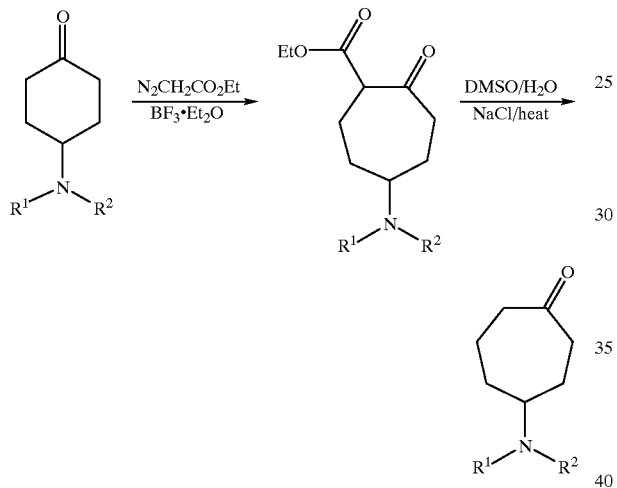

Synthetic Scheme B-IV

The appropriate 4-aminocyclohexanone in an appropriate solvent, for example diethyl ether, is treated with an appropriate Lewis acid such as boron trifluoride for about 20 minutes to about an hour at room temperature. To this solution is then added ethyl diazoacetate and the resulting mixture is stirred for about 1 hour to about 24 hours at room temperature. The resulting 2-ethoxycarbonyl-5-aminocycloheptanone is isolated by diluting the reaction mixture with aqueous sodium carbonate and extracting with a water immiscible solvent such as diethyl ether. The reaction product is then directly dissolved in dimethylsulfoxide which contains sodium chloride and water. The reaction mixture is heated to about 170° for from about 1 to about 24 hours to effect the decarboxylation. The desired 4-aminocycloheptanone is recovered by diluting the reaction mixture with water and extracting with an appropriate solvent such as diethyl ether. The reaction product may be purified by column chromatography, if desired, prior to further reaction.

After reaction with an appropriate phenylhydrazine, the corresponding 4-aminocycloheptanonephenylhydrazone is subjected to the same Fischer indole cyclization conditions as described above. The asymmetry in the cycloheptanone, however, leads to the production of the following two isomers:

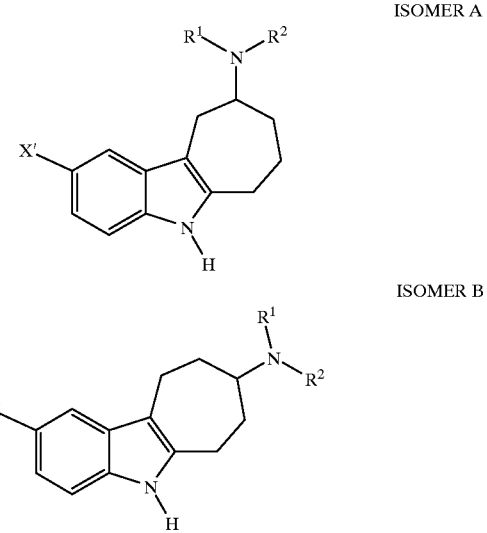

ISOMER A

ISOMER B

Isomers A and B may be separated by crystallization or chromatography at any convenient point in the synthesis of the compounds of the invention.

Compounds of Formula V where m=1 and n=1 are conveniently prepared by the procedure described in Synthetic Scheme B-V. $R^1$ and $R^2$ are independently $C_1$–$C_6$ alkyl or benzyl; and X' is benzyloxy or bromo.

Synthetic Scheme B-V

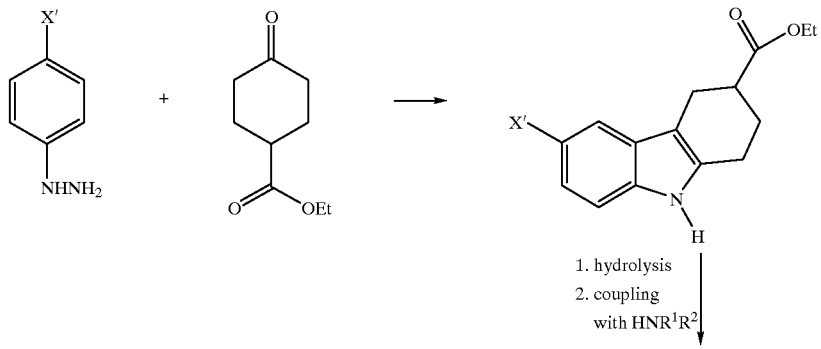

1. hydrolysis
2. coupling with $HNR^1R^2$

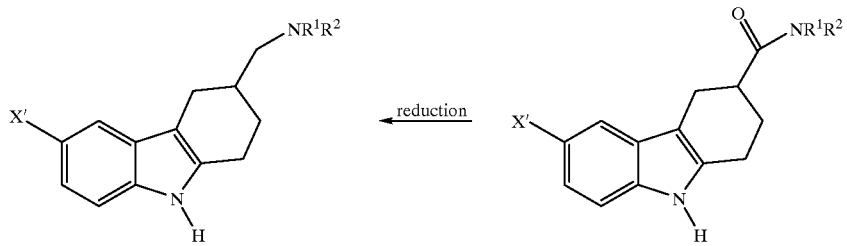

The appropriate phenylhydrazine and ethyl cyclohexanone-4-carboxylate are condensed together to prepare the corresponding phenylhydrazone which is then subjected to Fischer indolization conditions as described previously. The resultant ethyl 3-carboxy-6-substituted-9H-1,2,3,4-tetrahydrocarbazole is subjected to basic ester hydrolysis conditions and the carboxylate subsequently protonated to give the corresponding carboxylic acid. The carboxylic acid is coupled to an amine of structure $HNR^1R^2$ under any of the amide forming conditions described earlier. The resulting amide is reduced with an appropriate hydride reducing agent, such as lithium aluminum hydride or diborane, under standard conditions to give the corresponding N-substituted-3-methylamino-6-substituted-9H-1,2,3,4-tetrahydrocarbazole. This product may be used as is, or may be purified by chromatography or crystallization as desired prior to further reaction.

The skilled artisan will appreciate that ethyl 4-carboxycyclohexanone may undergo the ring expansion described above to give the corresponding ethyl 4-carboxycycloheptanone. This substrate may then be subjected to the same sequence of steps described in Synthetic Scheme B-V to give the corresponding 3- and 4-aminomethylcyclohepta[7,6-b]indoles. The isomers may be separated at any convenient point in the synthesis after the Fischer indolization step.

Compounds of Formula V where X is bromo are useful intermediates for the introduction of a variety of substituents into the 6- or 7-position of the corresponding tetrahydrocarbazole or cyclohepta[7,6-b]indole nuclei respectively. Prior to manipulation of the bromo substituent, however, the indole nitrogen must first be protected as illustrated in Synthetic Scheme B-VI. $R^1$ and $R^2$ are $C_1$–$C_6$ alkyl or benzyl; and Ar is phenyl or 2,4,6-triisopropylphenyl.

Synthetic Scheme B-VI

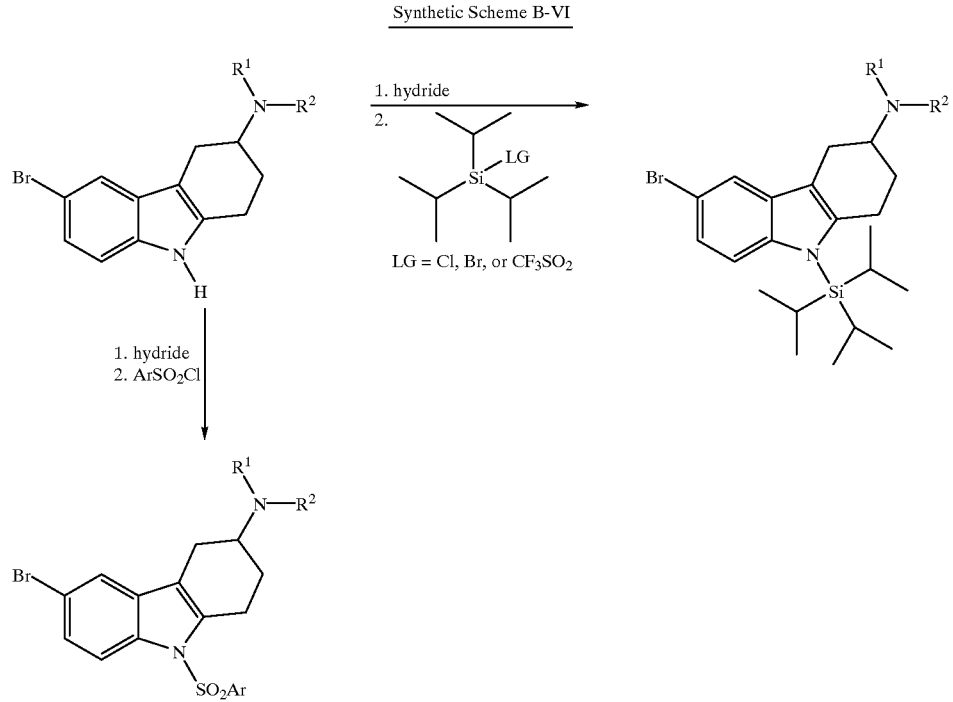

A solution of the starting material in an a suitable solvent, such as tetrahydrofuran or diethyl ether, are added to a suspension of an alkali metal hydride, preferably potassium hydride, in the same solvent. The deprotonation is performed at from about −10° C. to about ambient temperature for about an hour. To this solution is then added an appropriate arylsulfonyl chloride, triisopropylsilyl halide, or triisopropylsilyl triflate and the reaction is allowed to proceed for from about 1 to 24 hours. The indole nitrogen protected derivative is isolated by treating the reaction mixture with ice to decompose any unreacted hydride, diluting the reaction mixture with water, and then extracting the product with a water immiscible solvent such as dichloromethane, diethyl ether or ethyl acetate. The isolated product may be used as recovered for further reactions, or purified by crystallization or chromatography as desired. The bromo substituted substrate so protected may be used to provide compounds of Formula V where X is $R^6C(O)$— as described in Synthetic Scheme B-VII. $R^1$ and $R^2$ are $C_1$–$C_6$ alkyl or benzyl; and Z is phenylsulfonyl, 2,4,6-triisopropylphenylsulfonyl, or triisopropylsilyl; and $R^6$ is as previously defined.

A solution of the bromo compound in an appropriate solvent, such as tetrahydrofuran or diethyl ether, is treated with an alkyllithium, such as n-butyl- or t-butyllithium, at a temperature of about −70° C. for about an hour to effect a hologen-metal exchange. The resultant anion solution is added to a solution of the appropriate N-methyl-N-methoxyamide in an appropriate solvent, such as tetrahydrofuran or diethyl ether, at a temperature of about −70° C. The reaction mixture is then allowed to warm gradually to room temperature over from about 1 hour to about 24 hours. The resulting product is isolated by diluting the reaction mixture with water or aqueous ammonium chloride and extracting with a water immiscible solvent such as dichloromethane. The product may be further purified by chromatography or recrystallization as necessary.

The N-methyl-N-methoxyamides are conveniently prepared by reacting a carboxylic acid of formula $R^6$—$CO_2H$ with oxalyl chloride or thionyl chloride under standard conditions to prepare the corresponding acid chloride. This acid chloride is then treated with N-methoxymethylamine to prepare the required amide.

Alternatively, the compounds where X is $R^6C(O)$— may be prepared by the procedure illustrated in Synthetic Scheme B-VIII. $R^1$ and $R^2$ are $C_1$–$C_6$ alkyl or benzyl; and Z is phenylsulfonyl, 2,4,6-triisopropylphenylsulfonyl, or triisopropylsilyl; and $R^6$ is as previously defined.

Synthetic Scheme B-VII

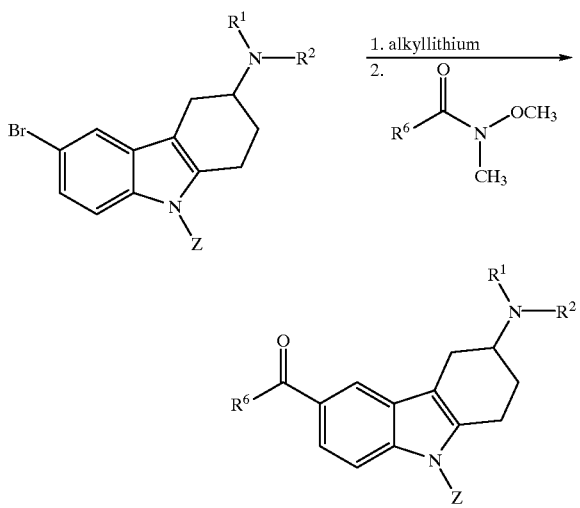

Synthetic Scheme B-VIII

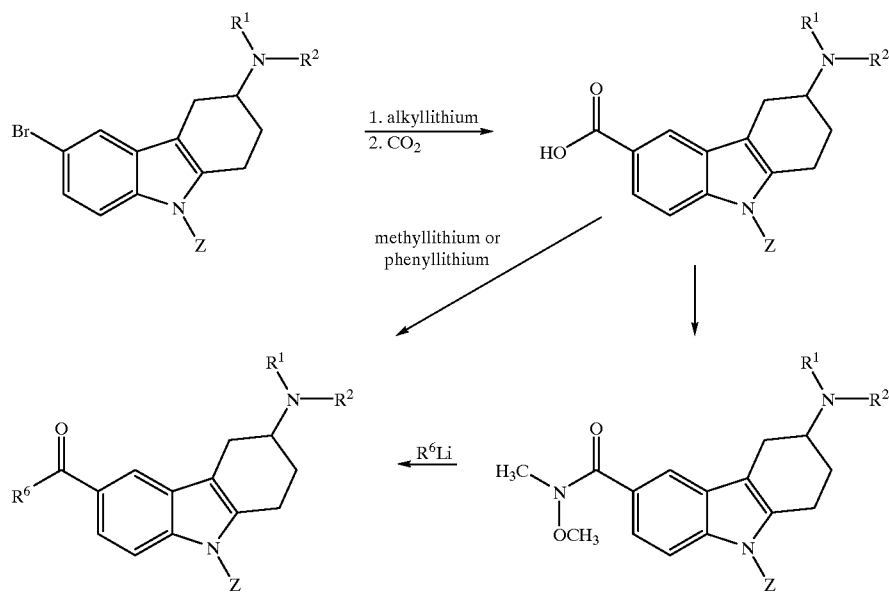

The anion solution is prepared as previously described and is then saturated with carbon dioxide to prepare the corresponding carboxylic acid. This is acid may then be treated directed with an alkyllithium, such as methyllithium, to prepare compounds where $R^6$ is $C_1$–$C_4$ alkyl. Alternatively, the carboxylic acid may be converted to its corresponding N-methyl-N-methoxyamide using the procedures previously described. This amide is then treated with a compound of formula $R^6Li$ to give the desired compound. Compounds of formula $R^6Li$ are commercially available or may be prepared by halogen-metal exchange from an $R^6$-halide under the conditions previously described.

The final step in the sequence requires deprotection of the indolic nitrogen to give the compounds of the invention as illustrated in Synthetic Scheme B-IX. $R^1$ and $R^2$ are independently hydrogen, $C_1$–$C_6$ alkyl or benzyl; Z is phenylsulfonyl, 2,4,6-triisopropylphenylsulfonyl, or triisopropylsilyl; and $R^6$ is as previously defined.

Synthetic Scheme B-IX

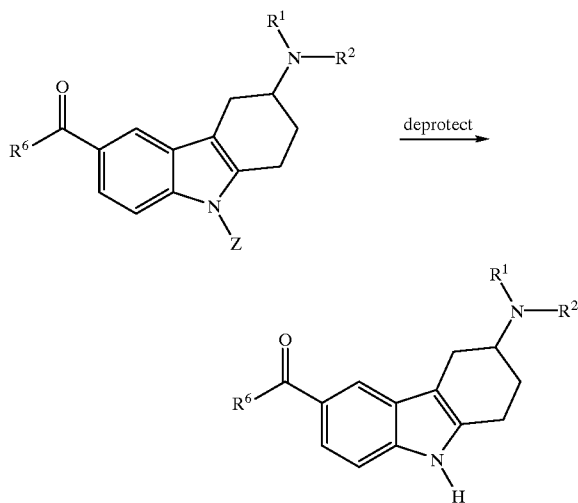

When Z is arylsulfonyl, the protecting group may be removed by basic hydrolysis in a lower alkanol such as methanol or ethanol. When Z is triisopropylsilyl, deprotection is conveniently effected by treatment with a fluoride anion reagent, preferably tetrabutylammonium fluoride, under standard conditions.

Compounds of Formula V where X is $R^6C(O)$— and $R^1$ and $R^2$ are independently hydrogen are available by subjecting the corresponding 3-benzylamino compounds to catalytic hydrogenation conditions over a precious metal catalyst, such as palladium or platinum on carbon, or over Raney nickel. These reactions are typically performed in a lower alkanol or tetrahydrofuran at room temperature to about 60° C., for from about 1 hour to 24 hours, at a hydrogen pressure of about 60 p.s.i. This hydrogenolysis may be performed before or after the deprotection of the indole nitrogen as desired. Additionally, compounds of Formula V where X is —OH are prepared by hydrogenolysis of the corresponding benzyl ether under the same conditions as described above.

The protected bromo compounds described in Synthetic Scheme B-VI are also useful for the preparation of the corresponding amine derivatives as described in Synthetic Scheme B-X. $R^1$ and $R^2$ are independently $C_1$–$C_6$ alkyl or benzyl; and Z is phenylsulfonyl, 2,4,6-triisopropylphenylsulfonyl, or triisopropylsilyl.

Synthetic Scheme B-X

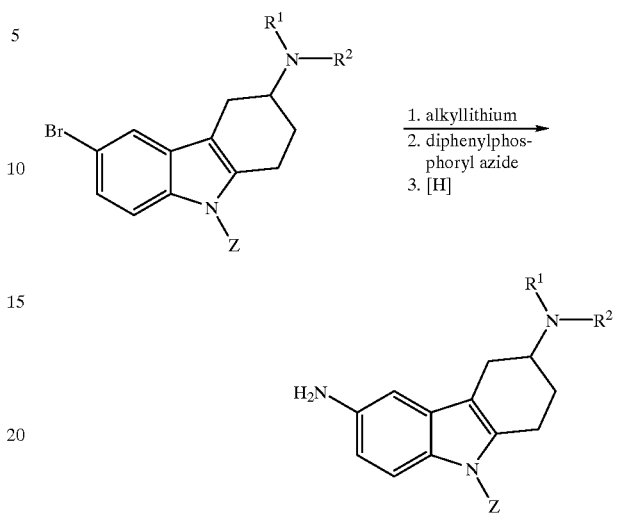

The anion is prepared according to the procedure previously described. The anion solution is then added to a solution of diphenylphosporyl azide in an appropriate solvent, such as such as tetrahydrofuran or diethyl ether, at a temperature of about −70° C. The reaction mixture is maintained at this temperature for about two hours and is then treated with an appropriate hydride reducing agent, such as sodium bis(2-methoxyethoxy)aluminum hydride in toluene. The resulting reaction mixture is allowed to warm to room temperature over about an hour. The amine product is isolated by first treating the reaction mixture with ice to destroy any excess hydride reagent, filtering any solid which has formed, diluting the filtrate with water and extracting the product into a water immiscible solvent such as dichloromethane. The amine product prepared by this procedure is useful for preparation of compounds where X is $R^3C(O)NH$—, $R^4NHC(Y)NH$—, $R^5OC(O)NH$—, or $R^7SO_2NH$— by the reaction conditions described previously for the functionalization of nitroanilines in Synthetic Scheme II. Alternatively, compounds where X is $R^3C(O)NH$— or $R^5OC(O)NH$— may be subjected to acidic or basic hydrolysis conditions to prepare the corresponding amine, which may then be converted to other compounds of Formula V.

Compounds where either or both of $R^1$ or $R^2$ are hydrogen may be further functionalized to prepare other compounds of Formula V by reductive alkylation. Under these conditions the primary or secondary amine is reacted with an appropriate aldehyde or ketone to prepare the corresponding imine or enamine. The imine or enamine is then reduced to the desired compound by catalytic hydrogenation or by reduction with an appropriate hydride reducing reagent in the presence of an acid. Preferably, the transformation is performed by direct alkylation as illustrated in Synthetic Scheme B-XI. $R^1$ is hydrogen or $C_1$–$C_6$ alkyl; $R^{2*}$ is $C_1$–$C_6$ alkyl or arylethyl; and X and arylethyl are as previously defined.

Synthetic Scheme B-XI

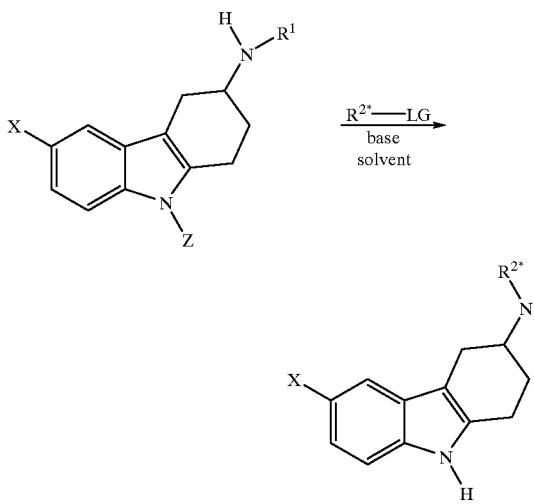

The starting amine and a base are combined in the reaction solvent followed by the addition of the alkylating agent. The reaction solvent may be any non-reactive solvent typically used for alkylations of this type such as acetonitrile, dimethylformamide or N-methyl-2-pyrrolidinone, limited by the solubility of the substrates. The base must be sufficiently basic to neutralize the acid generated during the progress of the reaction but not so basic as to deprotonate other sites in the substrate giving rise to other products. Additionally, the base must not compete to any great extent with the substrate for the alkylating agent. Bases typically used for these reactions are sodium carbonate or potassium carbonate. The reaction mixture is typically stirred at room temperature to 80° C., for about 8 hours to 3 days. The alkylated products are isolated by concentration of the reaction mixture under reduced pressure followed by partitioning of the resultant residue between water and a suitable organic solvent such as ethyl acetate, diethyl ether, dichloromethane, ethylene chloride, chloroform or carbon tetrachloride. The isolated product may be purified by chromatography, crystallization from a suitable solvent, salt formation or a combination of these techniques.

The leaving group (LG) of the alkylating agents may be chloro, bromo, iodo, methanesulfonyloxy, trifluoromethanesulfonyloxy, 2,2,2-trifluoroethanesulfonyloxy, benzenesulfonyloxy, p-bromobenzenesulfonyloxy, p-nitrobenzenesulfonyloxy or p-toluenesulfonyloxy, all of which are useful for the preparation of compounds of Formula V. The specific alkylating agent employed is determined by its commercial availability or a convenient synthesis from commercially available starting materials. The preferred alkylating agents for synthesis of compounds of Formula V are selected from those where the leaving group is chloro, bromo, iodo or methanesulfonyloxy. Alkylating agents where the leaving group is chloro are prepared from the corresponding alcohol by standard methods, preferably by treating the alcohol with neat thionyl chloride at ambient temperature. Alkylating agents where the leaving group is methanesulfonyloxy are prepared from the corresponding alcohols as described below.

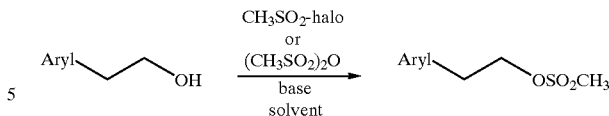

The alcohol is dissolved in a suitable anhydrous solvent such as tetrahydrofuran, diethyl ether, p-dioxane or acetonitrile which contains the base. The base must be sufficiently basic to neutralize the acid generated during the progress of the reaction but not so basic as to deprotonate other sites in the substrate giving rise to other products. Additionally, the base must not compete to any great extent with the substrate for the sulfonating reagent and must have sufficient solubility in the reaction solvent. Bases typically used in these reactions are tertiary amines such as pyridine, triethylamine or N-methylmorpholine. To the reaction mixture is then added the sulfonating reagent with cooling. The sulfonating reagent may be a methanesulfonyl halide such as the chloride, or methanesulfonic anhydride. The reaction mixture is allowed to react from 1 hour to 24 hours at ambient temperature. The product is isolated by concentrating the reaction mixture under reduced pressure followed by partitioning the residue between water and an appropriate organic solvent such as dichloromethane, ethylene chloride, chloroform or carbon tetrachloride. The isolated product is used directly in the alkylation step.

The starting alcohols required for the synthesis of compounds of Formula V are either commercially available or may be prepared by employing well established synthetic methodology. A general scheme for the synthesis of a number of the required alcohols is described below.

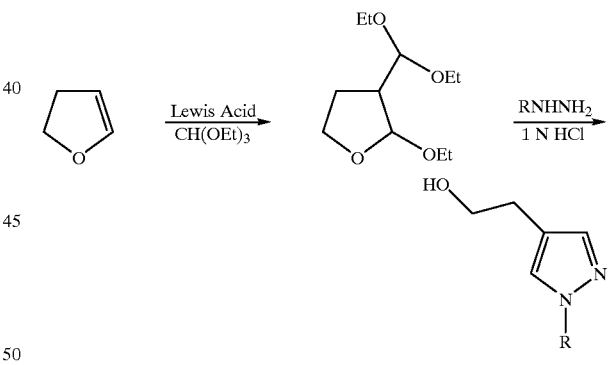

4,5-Dihydrofuran or 3,4-dihydro-2H-pyran is treated with triethylorthoformate in the presence of a Lewis acid, preferably boron trifluoride diethyl etherate, for from 1 to 4 days at ambient temperature. After treating the reaction mixture with an anhydrous base such as potassium carbonate the intermediate diacetal is distilled from the reaction mixture. This diacetal is now treated with an appropriate hydrazine, typically commercially available or synthesized by standard techniques, in aqueous acid at reflux for 4–24 hours. The product is recovered by treatment of the reaction mixture with base and extraction of the base into methylene chloride. The alcohol so recovered is suitable for use without further purification. When R is hydrogen, the alcohol can be further modified by direct alkylation of one of the pyrazole nitrogens as described below.

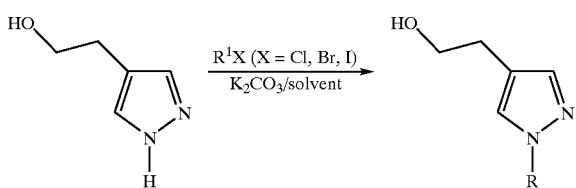

The alkylation is performed in a suitable solvent, typically dimethylformamide, acetonitrile or acetone, with potassium carbonate and the desired alkylating agent. The alkylating agent is a lower alkyl halide, preferably the bromide or iodide. The reaction is performed at ambient to reflux temperature for 1 hour to 3 days.

The compounds of Formula V possess a chiral center, and as such exist as racemic mixtures or individual enantiomers. Racemates and the individual enantiomers are all useful for the method of the present invention. The individual enantiomers may be resolved by fractional crystallization of salts of the racemic bases and enantiomerically pure acids, for example, ditolyltartaric acid. Alternatively, the individual enantiomers may be prepared by the use of a chiral auxiliary during the preparation of the compound as described in the following Synthetic Scheme B-XII. X is bromo, benzyloxy, nitro, $R^3C(O)NH—$, $R^4NHC(Y)NH—$, $R^5OC(O)NH—$, or $R^7SO_2NH—$; and Y, $R^3$, $R^4$, $R^5$ and $R^7$ are as previously defined.

Synthetic Scheme B-XII

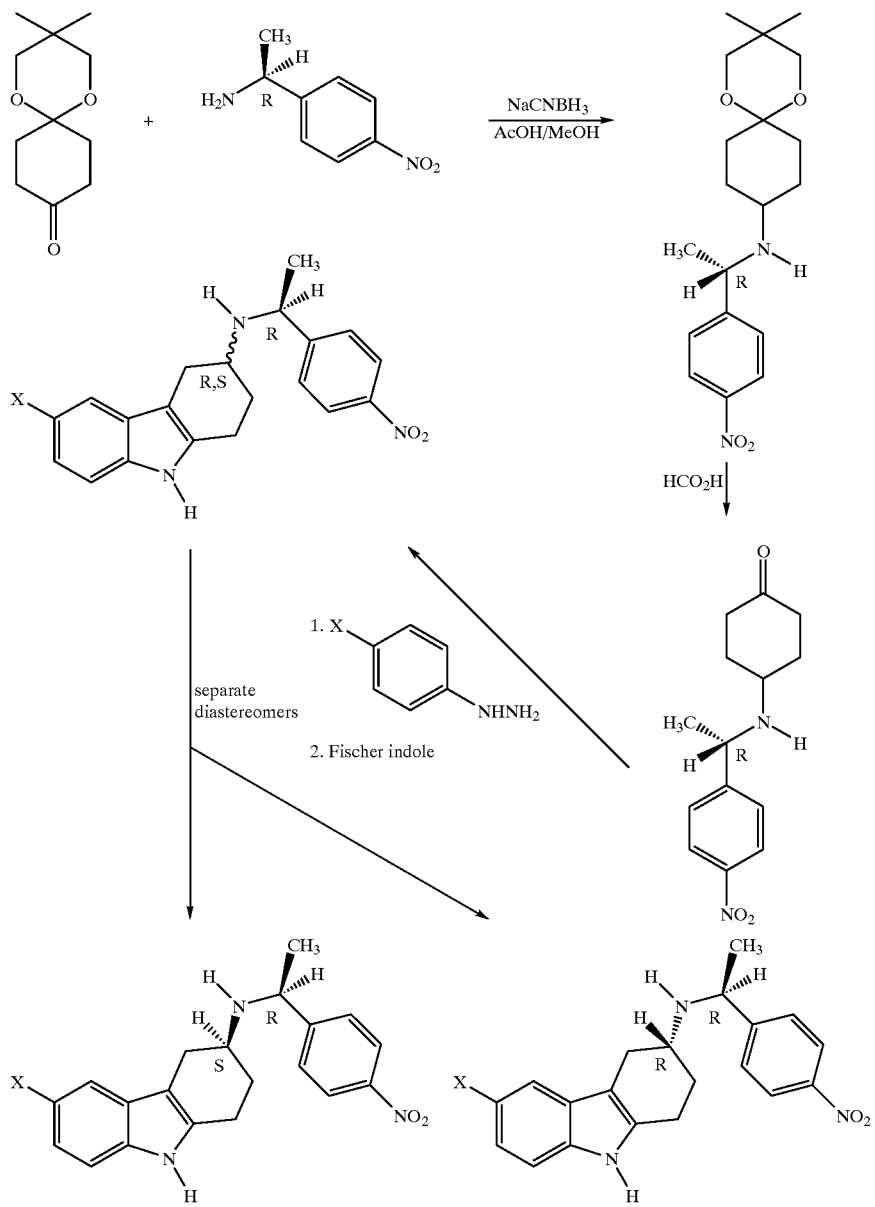

1,4-cyclohexanedione mono-(2,2-dimethylpropane-1,3-diol)ketal is reductively aminated under standard conditions with an enantiomer of α-methyl-(4-nitrophenyl)ethylamine (Synthetic Scheme B-XII illustrates the use of the R-(+)-enantiomer). The ketal is removed as described previously and the resulting aminocyclohexanone is subjected to the reaction conditions described for Synthetic Scheme I to give a diastereomeric mixture. The diastereomers are then separated by chromatography or fractional crystallization. The amine may then be treated, if desired, with an appropriate alkylating agent, for example an appropriate alkyl halide, to prepare the corresponding quaternary salt prior to cleavage of the α-methyl-(4-nitrophenyl)ethyl moiety.

Cleavage of the α-methyl-(4-nitrophenyl)ethyl moiety is achieved by reduction of the 4-nitro group followed by acid catalyzed solvolysis of the resulting α-methyl-(4-aminophenyl)ethyl moiety. Reduction of the nitro group can be accomplished by a wide range of reducing agents including, for example, titanium tetrachloride, lithium aluminum hydride, or zinc/acetic acid, or by catalytic hydrogenation. Solvolytic cleavage takes place when the monohydrochloride (or other monobasic salt) of the reduction product is treated with water or an alcohol at room temperature or, in some instances, at elevated temperatures. A particularly convenient condition for removing the α-methyl-(4-nitrophenyl)ethyl moiety is hydrogenation of the amine monohydrochloride in methanol over a platinum catalyst.

The reactions as illustrated in Synthetic Schemes B-VI through B-XII are for the compounds of Formula V which are carbazoles. The skilled artisan, however, will appreciate that the chemistry illustrated is applicable to the other classes of compounds of Formula V as well. The skilled artisan will also appreciate that the order in which the steps are performed to prepare the compounds of Formula V are not important in many cases.

Preparation B-I 6-bromo-3-dimethylamino-9-triisopropylsilyl-1,2,3,4-tetrahydro-9H-carbazole 4-dimethylaminocyclohexanone (2,2-dimethylpropane-1,3-diol)ketal To a solution of 25.0 gm (554.6 mMol) dimethylamine in 500 mL methanol were added 50.0 gm (252.2 mMol) 1,4-cyclohexanedione mono-2,2-dimethylpropane-1,3-diol ketal and the reaction mixture was allowed to stir for 2 hours at room temperature. To this solution were then gradually added 31.69 gm (504.3 mMol) sodium cyanoborohydride. Once this addition was complete, acetic acid was added to adjust the mixture to a pH of about 6. The pH was monitored periodically and acetic acid additions continued to maintain the pH at about 6. When the addition of acetic acid no longer resulted in gas evolution, the reaction mixture was allowed to stir at room temperature for 18 hours. The reaction mixture was then concentrated under reduced pressure to a volume of about 100 mL and was then partitioned between 1N sodium hydroxide and dichloromethane. The remaining aqueous phase was treated with saturated aqueous sodium chloride and was again extracted with dichloromethane. These organic phases were combined, dried over sodium sulfate and concentrated under reduced pressure to give 40.15 gm (70%) of the desired compound as a yellow oil.

MS(m/e): 228(M+1)

4-dimethylaminocyclohexanone

A solution of 18.4 gm (81 mMol) 4-dimethylaminocyclohexanone (2,2-dimethylpropane-1,3-diol)ketal in 250 mL 90% formic acid were heated at reflux for 3 hours. The reaction mixture was then stirred at room temperature for 3 days. The reaction mixture was then diluted with 250 mL water and was concentrated to a volume of about 250 mL on a rotary evaporator. The dilution/concentration sequence was then repeated two more times. The residue was then further concentrated to a volume of about 50 mL, made basic with 5 N sodium hydroxide and extracted with dichloromethane. The organic phases were combined, dried over sodium sulfate and concentrated under reduced pressure to give 11.8 gm (100%) of the desired compound as a yellow oil.

MS(m/e): 141 (M$^+$)

NMR(CDCl$_3$): δ2.50 (m, 2H), 2.28 (m, 2H), 2.28 (m, 6H), 2.01 (m, 2H), 1.80 (m, 2H).

4-dimethylaminocyclohexanone 4-bromophenylhydrazone

To a mixture of 6.0 gm (42.0 mMol) 4-dimethylaminocyclohexanone and 9.5 gm (42.0 mMol) 4-bromophenylhydrazine hydrochloride in 100 mL ethanol were added 3.4 mL (42 mMol) pyridine. The resultant mixture was then heated at reflux for 2 hours and then stirred at ambient temperature for 18 hours. The reaction mixture was then treated with aqueous potassium carbonate and extracted well with dichloromethane. The organic phases were combined, dried over sodium sulfate and concentrated under reduced pressure. The resultant residue was treated with toluene and concentrated again under reduced pressure to give 11.3 gm (87%) of the desired compound.

6-bromo-3-(dimethyl)amino-1,2,3,4-tetrahydro-9H-carbazole hydrochloride

A solution of 11.3 gm (36.4 mMol) 4-dimethylaminocyclohexanone 4-bromophenylhydrazone in 250 mL 4M ethanolic hydrogen chloride were heated to reflux under nitrogen for 3 hours. The reaction mixture was allowed to cool to room temperature and was then concentrated under reduced pressure. The residual paste was dissolved in 200 mL water and to this solution were then added 50 mL 6 M hydrochloric acid. The mixture was cooled to 0° C. for 18 hours. The desired product which had crystallized was filtered and dried to give 8.66 gm (72%).

Silylation 8.66 gm (26.2 mMol) 6-bromo-3-(dimethyl)amino-1,2,3,4-tetrahydro-9H-carbazole hydrochloride were partitioned between 1N sodium hydroxide and dichloromethane. The organic phase was dried over sodium sulfate and concentrated under reduced pressure. The residue was dissolved in 50 mL tetrahydrofuran and the resultant solution was added to a suspension of 8.0 gm (40 mMol) potassium hydride (20% in mineral oil) in 100 mL tetrahydrofuran cooled to about 0° C. The resultant mixture was stirred for an hour at this temperature and then to it were added 8.0 mL (30 mMol) triisopropylsilyltriflate and the mixture was allowed to warm gradually to room temperature. After 18 hours the reaction mixture was treated with ice to decompose excess potassium hydride. Once all of the hydride had been destroyed, the reaction mixture was diluted with 200 mL of water and was then extracted well with dichloromethane. The organic phases were combined, dried over sodium sulfate and concentrated under reduced pressure. The residual oil was subjected to silica gel chromatography, eluting sequentially with toluene, 9:1 toluene:ethyl acetate, 4:1 toluene:ethyl acetate, 1:1 toluene:ethyl acetate, and ethyl acetate. The ethyl acetate fractions were combined and concentrated under reduced pressure to give 7.08 gm (60%) of the title compound as a solid.

m.p.=92–93° C.

NMR(CDCl$_3$): δ7.52 (d, 1H), 7.39 (dd, 1H), 7.13 (d, 1H), 3.04 (br dd, 1H), 2.88 (m, 2H), 2.70 (m, 1H), 2.58 (dd, 1H), 2.41 (s, 6H), 2.20 (d, 1H), 1.78 (m, 3H), 1.70 (m, 1H), 1.14 (m, 18H).

All N-methyl-N-methoxyamides useful for the preparation of the compounds of Formula V are available by substituting an appropriate carboxylic acid for 4-chlorobenzoic acid in the following procedure.

Preparation B-II 4-chloro-N-methyl-N-methoxybenzamide

To a solution 11.38 gm (116.7 mMol) N-methoxy-N-methyl amine hydrochloride in 700 mL 1N sodium hydroxide was added a solution of 18.56 gm (106.04 mMol) 4-chlorobenzoyl chloride in 200 mL dichloromethane and the mixture was stirred at ambient temperature. After 18 hours the phases were separated and the remaining aqueous was extracted well with dichloromethane. All organic phases are combined, dried over sodium sulfate and concentrated under reduced pressure to give 27.9 gm (95%) of the title compound as a clear oil.

MS(m/e): 199(M$^+$)

IR: 3011, 2974, 2938, 1634 cm$^{-1}$

Preparation B-III 6-amino-3-(dimethyl)amino-1,2,3,4-tetrahydro-9H-carbazole hydrochloride 6-(t-butoxycarbonyl)amino-3-(dimethyl)amino-9-trimethylsilyl-1,2,3,4-tetrahydro-9H-carbazole To a solution of 0.898 gm (2.0 mMol) 6-bromo-3-(dimethyl)amino-9-triisopropylsilyl-1,2,3,4-tetrahydro-9H-carbazole in 20 mL tetrahydrofuran at −70° C. were added 1.56 mL (2.2 mMol) n-butyllithium (1.41 M in hexane). The solution was allowed to stir at this temperature for 45 minutes and then it was siphoned over 15 minutes into a solution of 0.50 mL (2.3 mMol) diphenylphosphoryl azide in 20 mL tetrahydrofuran at −70° C. The wine red solution was maintained at −70° C. for 2 hours at which point the reaction mixture was treated with 2.5 mL (8.9 mMol) sodium bis(2-methoxyethoxy)aluminum hydride (65% in toluene). The reaction mixture was allowed to warm to 0° C. during which time gas evolution was observed and the reaction mixture became pale yellow. After 30 minutes at 0° C. the reaction mixture was allowed to warm to room temperature. After 30 minutes at room temperature the reaction mixture was again cooled to 0° C. and was cautiously treated with ice to decompose excess hydride. The reaction mixture was then filtered to remove the precipitate that had formed and the precipitate was washed thoroughly with diethyl ether. The combined filtrates were washed sequentially with dilute aqueous sodium hydroxide and saturated aqueous sodium chloride, dried over sodium sulfate and concentrated under reduced pressure to a viscous oil. This oil was then dissolved in 10 mL dichloromethane and to it were added 0.50 gm (2.3 mMol) di-(t-butyl)carbonate. The resulting solution was then stirred for 18 hours at room temperature. The reaction mixture was then concentrated under reduced pressure. The residue was then dissolved in toluene and concentrated under reduced pressure to remove and residual t-butanol. The residue was then subjected to column chromatography, eluting with a gradient of chloroform (2–8% 95:5 methanol:ammonium hydroxide) to give 0.45 gm (46%) of the desired compound as a colorless glass.

MS(m/e): 486(M$^+$)

Calculated for C$_{28}$H$_{47}$N$_3$OSi: Theory: C, 69.23; H, 9.75; N, 8.65. Found: C, 68.93; H, 9.50; N, 8.44.

6-(t-butoxycarbonyl)amino-3-(dimethyl)amino-1,2,3,4-tetrahydro-9H-carbazole

To a solution of 0.44 gm (0.91 mMol) 6-(t-butoxycarbonyl)amino-3-(dimethyl)amino-9-triisopropylsilyl-1,2,3,4-tetrahydro-9H-carbazole in 10 mL tetrahydrofuran at 0° C. were added 0.30 gm boric acid followed by 1.5 mL 1M aqueous tetrabutylammonium fluoride. After 3 hours the reaction mixture was added to dilute aqueous tartaric acid and the resulting mixture extracted several times with dichloromethane. The remaining aqueous phase was made basic with dilute aqueous sodium hydroxide and extracted well with dichloromethane. This organic phase was dried over sodium sulfate and concentrated under reduced pressure. This residue was subjected to radial chromatography (2 mm silica gel), eluting with 96:4 chloroform:methanol containing 5% ammonium hydroxide. Fractions shown to contain product were combined and concentrated under reduced pressure to give 0.246 gm (83%) of the desired product.

MS(m/e): 330(M$^+$)

Deprotection of 6-amino group 0.385 gm (1.17 mMol) 6-(t-butoxycarbonyl)amino-3-(dimethyl)amino-1,2,3,4-tetrahydro-9H-carbazole were dissolved in 10 mL trifluoroacetic acid and the mixture allowed to stir for 1 hour at room temperature. The reaction mixture was then concentrated under reduced pressure and the residue dissolved in dichloromethane. The organic phase was washed with aqueous potassium carbonate, dried over sodium sulfate and concentrated under reduced pressure to give 0.261 gm (97%) of the title compound as a grayish-tan foam.

The phenylhydrazines required for the synthesis of the compounds of Formula V may be prepared by the procedure described in detail in Preparation B-IV.

Preparation B-IV 4-(4-fluorobenzoyl)aminophenylhydrazine 4-(4-fluorobenzoyl)aminonitrobenzene To a suspension of 30.0 gm (0.217 mole) 4-nitroaniline in 225 mL dichloromethane were added 17.57 mL (0.217 mole) pyridine. The suspension was cooled to 0° C. and then 25.66 mL (0.217 mole) 4-fluorobenzoyl chloride were added slowly. Within 15 minutes the reaction mixture became homogeneous and was allowed to warm to room temperature. After an hour an additional 2.56 mL (21.7 mMol) 4-fluorobenzoyl chloride and 1.75 mL (21.7 mMol) pyridine were added and the reaction continued at room temperature for an additional hour. The reaction mixture was then washed with 200 mL water at which point a precipitate formed. The solid was filtered, washed with 100 mL hexane, washed with 200 mL water and dried under reduced pressure at 60° C. to give 56.6 gm (100%) of the desired compound.

4-(4-fluorobenzoyl)aminoaniline

To a solution of 56.6 gm (0.217 mole) 4-(4-fluorobenzoyl)aminonitrobenzene in 875 mL tetrahydrofuran were added 5.7 gm 5% platinum on carbon. The reaction mixture was hydrogenated at room temperature for 18 hours at initial hydrogen pressure of 60 p.s.i. The reaction mixture was then filtered and the filtrate concentrated under reduced pressure to give 49.3 gm (98.5%) of the desired compound.

Diazotization/Reduction

To a suspension of 1.00 gm (4.34 mMol) 4-(4-fluorobenzoyl)aminoaniline in 4.25 mL concentrated hydrochloric acid at 0° C. were added very slowly a solution of 0.329 gm (4.77 mMol) sodium nitrite in 3.2 mL water. The mixture was stirred at this temperature for 10 minutes and was then cannulated into a solution of 3.917 gm (17.36 mMol) stannous chloride dihydrate in 4.25 mL concentrated hydrochloric acid at 0° C. The resultant suspension was stirred at this temperature for 1 hour. The reaction was then treated with 50 mL 5N sodium hydroxide and was extracted well with ethyl acetate. The organic extracts were combined, dried over magnesium sulfate and concentrated under reduced pressure to give 0.90 gm (82%) of the title compound.

MS(m/e): 245(M$^+$)

The reaction described in Preparation B-V is representative of the Fischer Indole conditions for the preparation of the compounds of Formula V.

Preparation B-V 6-(4-flucrobenzoyl)amino-3-(1-phthalimidiyl)-1,2,3,4-tetrahydro-9H-carbazole A suspension of 0.28 gm (1.11 mMol) 4-(1-phthalimidyl) cyclohexanone and 0.256 gm (1.05 mMol) 4-(4-fluoro benzoyl)aminophenylhydrazine in 8.0 mL ethanol were heated to reflux for 1 hour. To this mixture were then added 10 drops concentrated hydrochloric acid. The resulting mixture was heated to reflux for 18 hours. The reaction mixture was then cooled to room temperature and was diluted with 10 mL diethyl ether followed by 30 mL hexanes. The resulting solid was filtered and dried under vacuum to give 0.288 gm of the title compound. The filtrate was concentrated under reduced pressure and the residue subjected to silica gel chromatography, eluting with 40:60:5 ethyl acetate:hexane: methanol, to give an additional 0.128 gm of product. Total yield: 0.416 gm (87%).

Preparation B-VI 4-(1-phthalimidyl)cycloheptanone

To a stirred solution of 5.00 gm (20.55 mMol) 4-(1-phthalimidyl)cyclohexanone in 30 mL diethyl ether were added 3.79 mL (30.8 mMol) boron trifluoride ethereate. After stirring for 20 minutes at room temperature, 3.24 mL (30.8 mMol) ethyl diazoacetate were added dropwise. The resultant solution was stirred for 16 hours at room temperature. The reaction mixture was diluted with saturated aqueous sodium carbonate and was then extracted with diethyl ether. The combined organic extracts were dried over sodium sulfate and concentrated under reduced pressure. The residue was dissolved in 15 mL dimethylsulfoxide. To this wolution was added 1.3 mL water and 1.5 gm sodium chloride. The resulting mixture was heated at 170° C. for 7 hours. The reaction mixture was then cooled, poured into 150 mL water and extracted well with diethyl ether. The combined organic phases were washed sequentially with water and saturated aqueous sodium chloride, dried over sodium sulfate and concentrated under reduced pressure. The residue was subjected to silica gel chromatography, eluting with 6:4 hexane:ethyl acetate. Fractions shown to contain product were combined and concentrated under reduced pressure to give 4.17 gm (79%) of the title compound.

MS(m/e): 257(M$^+$)

Preparation B-VII 7-(benzyloxycarbonyl)amino-3- and 4-(1-phthalimidyl)cyclohepta[7,6-b]indole A suspension of 1.09 gm (4,25 mMol) 4-(1-phthalimidyl) cycloheptanone and 1.60 gm (6.2 mMol) 4-(benzyloxycarbonyl)aminophenylhydrazine in 40.0 mL ethanol were heated to reflux for 1 hour. To this mixture were then added 0.2 mL concentrated hydrochloric acid. The resulting mixture was heated to reflux for 18 hours. The reaction mixture was then concentrated under reduced pressure and the residue subjected to silica gel chromatography, eluting with 40% ethyl acetate in hexane. Fractions containing product were combined and concentrated under reduced pressure to give 1.61 gm (79%) of the title compound.

MS(m/e): 479(M$^+$)

Preparation B-VIII 6-benzyloxy-3-carboxy-1,2,3,4-tetrahydro-9H-carbazole

Ethyl 6-benzyloxy-3-carboxy-1,2,3,4-tetrahydro-9H-carbazole

To a suspension of 3.242 gm (12.93 mMol) 4-benzyloxyphenylhydrazine hydrochloride in 80 mL ethanol were added 1.05 mL (12.93 mMol) pyridine. The resulting mixture was heated to 50° C. for about 20 minutes and then 1.87 mL (11.75 mMol) ethyl 4-oxocyclohexanecarboxylate were added. The resulting mixture was stirred at reflux for 18 hours. The reaction mixture was then concentrated under reduced pressure and the residue partitioned between water and ethyl acetate. The organic phase was separated, washed with water, dried over magnesium sulfate and concentrated under reduced pressure. The residue was subjected to silica gel chromatography, eluting with 35% ethyl acetate in hexane. Fractions containing product were combined and concentrated under reduced pressure to give 3.38 gm (83%) of the desired compound.

Hydrolysis

To a suspension of 3.107 gm (8.9 mMol) ethyl 6-benzyloxy-3-carboxy-6-benzyloxy-1,2,3,4-tetrahydro-9H-carbazole in 100 mL 2N sodium hydroxide were added 100 mL methanol and the reaction mixture stirred at reflux for 3.5 hours. The reaction mixture was concentrated to about half volume and the pH adjusted to between 5 and 7 by the addition of concentrated hydrochloric acid. The mixture was extracted well with 4:1 dichloromethane:isopropanol. The organic phases were combined, dried over sodium sulfate and concentrated under reduced pressure to give 2.71 gm (95%) of the title compound.

Preparation B-IX 2-(1-methyl-1H-pyrazol-3-yl)-1-ethanol

To a mixture of 200 gm (2.85 mole) 2,3-dihydrofuran and 800 mL (4.81 mole) triethylorthoformate were added 0.8 mL (6.5 mMol) boron trifluoride diethyl etherate dropwise. After an initial exotherm the reaction mixture was allowed to stir at ambient temperature for four days. To the reaction mixture was then added 4.0 gm potassium carbonate and the reaction mixture was distilled under 6.0 mm Hg. Fractions distilling between 60° C. and 130° C. were collected to give 261.64 gm (42.1%) of a light yellow oil.

MS(m/e): 219(M⁺)

To a solution of 87.2 gm (0.40 mole) of the previously prepared yellow oil in 787 mL 1N HCl were added 21.3 mL (0.40 mole) methyl hydrazine and the reaction mixture was stirred at reflux for four hours. The reaction mixture was cooled to ambient temperature and the volatiles were removed under reduced pressure. The residual oil was treated with 2N NaOH until basic and the aqueous extracted well with dichloromethane. The combined organic extracts were dried over sodium sulfate and concentrated under reduced pressure to give 32.15 gm (64.5%) of the title compound as a brown oil.

MS(m/e): 126(M⁺)

$^1$H-NMR(DMSO-$d_6$): δ7.45 (s, 1H); 7.25 (s, 1H); 4.65 (t, 1H) 3.75 (s,3H); 3.55 (m, 2H); 2.55 (t, 2H).

Preparation B-X 2-(1-isopropyl-1H-pyrazol-3-yl)-1-ethanol

To a solution of 1.0 gm (9.0 mMol) 2-(3-pyrazolyl)-1-ethanol in 36 mL dimethylformamide were added 2.38 gm (22.5 mMol) sodium carbonate followed by the dropwise addition of a solution of 0.89 mL (9.0 mMol) 2-iodopropane in 8 mL dimethylformamide. The reaction mixture was heated to 100° C. for 18 hours. The reaction mixture was then cooled to ambient and then concentrated under reduced pressure. The residue was partitioned between water and dichloromethane. The organic phase was then washed with water followed by saturated aqueous sodium chloride and was then dried over sodium sulfate. The remaining organics were concentrated under reduced pressure to give 0.36 gm (26.0%) of the title compound as a brown oil.

$^1$H-NMR(DMSO-$d_6$): δ7.50 (s, 1H); 7.25 (s, 1H); 4.60 (t, 1H); 4.40 (m, 1H); 3.50 (m, 2H); 2.55 (t, 2H); 1.35(d, 6H).

Preparation B-XI 2-(4-chloro)phenyl-1-mesyloxyethane

To a stirring solution of 3.00 mL (22.16 mMol) 2-(4-chloro)phenyl-1-ethanol in 75 mL tetrahydrofuran at 0° C. were added 4.63 mL (33.24 mMol) triethylamine followed by 1.89 mL (24.38 mMol) methanesulfonyl chloride. The reaction mixture was allowed to stir at room temperature for 18 hours. The reaction mixture was then poured into water and extracted well with ethyl acetate. The organic phases were combined, washed with water, dried over sodium sulfate and concentrated under reduced pressure to give 5.18 gm (99.6%) of the title compound.

Example B-1

6-acetyl-3-(dimethyl)amino-1,2,3,4-tetrahydro-9H-carbazole 6-carboxy-3-(dimethyl)amino-9-triisopropylsilyl-1,2,3,4-tetrahydro-9H-carbazole To a solution of 2.95 gm (6.56 mMol) 6-bromo-3-(dimethyl)amino-9-triisopropylsilyl-1,2,3,4-tetrahydro-9H-carbazole in 150 mL tetrahydrofuran at −78° C. were added 16.4 mL (26.24 mMol) t-butyllithium (1.6 M in pentane). The dark solution was allowed to stir at this temperature for 1 hour and then carbon dioxide gas was bubbled through the solution until the dark color discharged to light yellow. After allowing the reaction mixture to warm to room temperature it was poured into water, the pH adjusted to about 7, and the mixture extracted well with dichloromethane. The organic phases were combined, dried over magnesium sulfate and concentrated under reduced pressure. The residue was triturated with hexane to give 2.31 gm (85%) of the desired compound as a tan foam.

IR: 3022, 2958, 2871, 1465, 1249 cm⁻¹

MS(m/e): 414(M⁺)

6-acetyl-3-(dimethyl)amino-6-acetyl-9-triisopropylsilyl-1,2,3,4-tetrahydro-9H-carbazole To a solution of 2.0 gm (4.8 mMol) 6-carboxy-3-(dimethyl)amino-6-carboxy-9-triisopropylsilyl-1,2,3,4-tetrahydro-9H-carbazole in 100 mL diethyl ether at 0° C. were added 8 mL (9.6 mMol) methyllithium (1.2 M in diethyl ether) over a 15 minute period. After an hour an additional 0.4 mL of the methyllithium solution were added. 0.4 mL additions were continued until all of the starting material had reacted. The reaction mixture was then allowed to warm to room temperature and to it was first added ice and then the reaction mixture was diluted with 100 mL of water. The mixture was shaken and the phases separated. The aqueous phase was twice extracted with 100 mL aliquots of fresh diethyl ether. All of the organic extracts were combined, washed with saturated aqueous sodium chloride and concentrated under reduced pressure. The residue was subjected to florisil chromatography, eluting sequentially with toluene, 9:1 toluene:ethyl acetate, 4:1 toluene:ethyl acetate, 1:1 toluene:ethyl acetate, and ethyl acetate. Fractions containing product were combined and concentrated under reduced pressure to give 1.37 gm (69%) of the desired product as a solid.

MS(m/e): 412(M⁺)

Calculated for $C_{25}H_{40}N_2OSi$: Theory: C, 72.76; H, 9.77; N, 6.79. Found: C, 72.65; H, 9.84; N, 6.74.

Deprotection

To a solution of 1.37 m (3.29 mMol) 6-acetyl-3-(dimethyl)amino-6-acetyl-9-triisopropylsilyl-1,2,3,4-tetrahydro-9H-carbazole in 25 mL tetrahydrofuran at 0° C. containing 1.5 gm boric acid were added 5 mL 1M aqueous tetrabutylammonium fluoride. After 1 hour the reaction mixture was added to dilute aqueous tartaric acid and the resulting mixture extracted several times with dichloromethane. The remaining aqueous phase was made basic and was then extracted well with dichloromethane. This organic phase was dried over sodium sulfate and concentrated under reduced pressure to give a clear oil. This oil was crystallized from toluene 0.72 gm (86%) of the title compound as a crystalline solid.

m.p.=181–182° C.

MS(m/e): 256(M⁺)

Calculated for $C_{16}H_{20}N_2O$: Theory: C, 74.97; H, 7.86; N, 10.93. Found: C, 74.71; H, 7.91; N, 10.76.

Example B-2

6-benzoyl-3-(dimethyl)amino-1,2,3,4-tetrahydro-9H-carbazole 6-benzoyl-3-(dimethyl)amino-9-triisopropylsilyl-1,2,3,4-tetrahydro-9H-carbazole To a solution of 0.50 gm (1.11 mMol) 6-bromo-3-(dimethyl)amino-9-triisopropylsilyl-1,2,3,4-tetrahydro-9H-carbazole in 50 mL tetrahydrofuran at −78° C. were added 1.96 mL (3.33 mMol) t-butyllithium (1.7 M in pentane) and the resulting dark solution was allowed to stir for 30 minutes. To this mixture were then added 0.20 gm (1.22 mMol) N-methyl-N-methoxybenzamide and the reaction mixture was allowed to warm to room temperature over 1 hour. The reaction mixture was then treated with 0.1 N sodium hydroxide and then extracted well with chloroform. The organic phases were combined, dried over potassium carbonate and concentrated under reduced pressure to give 0.48 gm (91%) of the desired compound as a red-orange oil.

MS(m/e) : 474(M$^+$)

Deprotection

To a solution of 1.00 gm (2.11 mMol) 6-benzoyl-3-(dimethyl)amino-9-triisopropylsilyl-1,2,3,4-tetrahydro-9H-carbazole in 50 mL tetrahydrofuran at 0° C. were added 5 mL tetrabutylammonium fluoride (1M in tetrahydrofuran) and 3 mL 1N boric acid. The reaction mixture was allowed to stir for 1 hour. The reaction mixture was then poured into dilute aqueous tartaric acid and the aqueous phase washed with dichloromethane. The remaining aqueous phase was made basic and was then extracted well with dichloromethane. This organic phase was dried over sodium sulfate and concentrated under reduced pressure. The residue was subjected to silica gel chromatography, eluting with dichloromethane containing from 0 to 20% methanol. Fractions containing product were combined and concentrated under reduced pressure to give 0.64 gm (96%) of the title compound as a tan foam.

MS(m/e): 319(M$^+$)

The compounds of the following Examples 3–4 were prepared by the procedure described in EXAMPLE B-2.

Example B-3

6-(4-methoxy)benzoyl-3-(dimethyl)amino-1,2,3,4-tetrahydro-9H-carbazole

Beginning with 1.0 gm (2.22 mMol) 6-bromo-3-(dimethyl)amino-9-triisopropylsilyl-1,2,3,4-tetrahydro-9H-carbazole, 0.08 gm (10%) of the title compound were recovered as a yellow foam.

MS(m/e): 348(M$^+$)

Example B-4

6-(4-chloro)benzoyl-3-(dimethyl)amino-1,2,3,4-tetrahydro-9H-carbazole

Beginning with 0.5 gm (1.11 mMol) 6-bromo-3-(dimethyl)amino-9-triisopropylsilyl-1,2,3,4-tetrahydro-9H-carbazole, 0.17 gm (43.7%) of the title compound were recovered as a yellow foam.

MS(m/e): 352(M$^+$)

Example B-5

6-(methoxycarbonyl)amino-3-(dimethyl)amino-1,2,3,4-tetrahydro-9H-carbazole

To a mixture of 6.0 mg (0.026 mMol) 6-amino-3-(dimethyl)amino-1,2,3,4-tetrahydro-9H-carbazole and 8.0 mg (0.07 mMol) polyvinylpyridine in 3.0 mL dichloromethane were added 2.4 mg (0.0273 mMol) methyl chloroformate. The reaction mixture was mixed for 2 days at ambient temperature. To this mixture were then added 90 mg (0.073 mMol) aminomethylated polystyrene and the reaction mixed for an additional 18 hours. The reaction mixture was then filtered and the volatiles evaporated to give 4.0 mg (53%) of the title compound.

MS(m/e): 288(M$^+$)

The compounds of the following Examples 6–8 were prepared by the procedure described in detail in EXAMPLE B-5.

Example B-6

6-(ethoxycarbonyl)amino-3-(dimethyl)amino-1,2,3,4-tetrahydro-9H-carbazole

Beginning with 6.0 mg (0.026 mMol) 6-amino-3-(dimethyl)amino-1,2,3,4-tetrahydro-9H-carbazole and 2.96 mg (0.0273 mMol) ethyl chloroformate, 4.1 mg (52%) of the title compound were recovered.

MS(m/e): 302(M$^+$)

Example B-7

6-(allyloxycarbonyl)amino-3-(dimethyl)amino-1,2,3,4-tetrahydro-9H-carbazole

Beginning with 10.0 mg (0.0437 mMol) 6-amino-3-(dimethyl)amino-1,2,3,4-tetrahydro-9H-carbazole and 5.5 mg (0.0458 mMol) allyl chloroformate, 4.4 mg (33%) of the title compound were recovered.

MS(m/e): 313(M$^+$)

Example B-8

6-(4-fluorophenoxycarbonyl)amino-3-(dimethyl)amino-1,2,3,4-tetrahydro-9H-carbazole Beginning with 6.0 mg (0.026 mMol) 6-amino-3-(dimethyl)amino-1,2,3,4-tetrahydro-9H-carbazole and 4.8 mg (0.0273 mMol) 4-fluorophenyl chloroformate, 3.8 mg (40%) of the title compound were recovered.

MS(m/e): 368(M$^+$)

Example B-9

N-methyl-N'-(3-(dimethyl)amino-1,2,3,4-tetrahydro-9H-carbazol-6-yl)thiourea

To a solution of 10.0 mg (0.0437 mMol) 6-amino-3-(dimethyl)amino-1,2,3,4-tetrahydro-9H-carbazole in 3.0 mL dichloromethane were added 6.2 mg (0.0874 mMol) methyl isothiocyanate. The reaction was mixed for 48 hours and to it were then added 0.15 gm (0.0874 mMol) aminomethylated polystyrene and the reaction mixed for an additional 18 hours. The reaction mixture was then filtered and the volatiles evaporated to give 6.3 mg (48%) of the title compound.

MS(m/e): 302(M$^+$)

The compounds of the following Examples 10–11 were prepared according to the procedure described in detail in EXAMPLE B-9.

Example B-10

N-phenyl-N'-(3-(dimethyl)amino-1,2,3,4-tetrahydro-9H-carbazol-6-yl)thiourea

Beginning with 10.0 mg (0.0437 mMol) 6-amino-3-(dimethyl)amino-1,2,3,4-tetrahydro-9H-carbazole and 11.8 mg (0.0874 mMol) phenyl isothiocyanate, 7.2 mg (39%) of the title compound were recovered.

MS(m/e): 364(M$^+$)

Example B-11

N-(2,3-dichloro)phenyl-N'-(3-(dimethyl)amino-1,2,3,4-tetrahydro-9H-carbazol-6-yl)thiourea Beginning with 10.0 mg (0.0437 mMol) 6-amino-3-(dimethyl)amino-1,2,3,4-tetrahydro-9H-carbazole and 17.8 mg (0.0874 mMol) 2,3-dichlorophenyl isothiocyanate, 6.1 mg (33%) of the title compound were recovered.

MS(m/e): 432(M$^+$)

Example B-12

N-ethyl-N'-(3-(dimethyl)amino-1,2,3,4-tetrahydro-9H-carbazol-6-yl)urea

To a solution of 10.0 mg (0.0437 mMol) 6-amino-3-(dimethyl)amino-1,2,3,4-tetrahydro-9H-carbazole in 3.0 mL dichloromethane were added 6.2 mg (0.0874 mMol) ethyl isocyanate. The reaction was mixed for 48 hours and to it were then added 0.15 gm (0.0874 mMol) aminomethylated polystyrene and the reaction mixed for an additional 18 hours. The reaction mixture was then filtered and the filtrate washed with 1N hydrochloric acid. The aqueous phase was washed several times with dichloromethane and was then made basic with dilute aqueous sodium hydroxide. The aqueous phase was then extracted several times with an equal volume of dichloromethane. These organic extracts were dried over sodium sulfate and then concentrated under reduced pressure to give 3.0 mg (23%) of the title compound.

MS(m/e): 300(M$^+$)

Example B-13

N-phenyl-N'-(3-(dimethyl)amino-1,2,3,4-tetrahydro-9H-carbazol-6-yl)urea

Beginning with 10.0 mg (0.0437 mMol) 6-amino-3-(dimethyl)amino-1,2,3,4-tetrahydro-9H-carbazole and 10.4 mg (0.0874 mMol) phenyl isocyanate, 1.0 mg (7%) of the title compound was recovered using the procedure described in detail in EXAMPLE B-12.

MS(m/e): 348(M$^+$)

Example B-14

6-(3-methylbutanoyl)amino-3-(dimethyl)amino-6-(3-methylbutanoyl)amino-1,2,3,4-tetrahydro-9H-carbazole hydrochloride To a solution of 0.25 gm (1.091 mMol) 6-amino-3-(dimethyl)amino-1,2,3,4-tetrahydro-9H-carbazole and 0.115 µL (1.418 mMol) pyridine in 15 mL dichloromethane at 0° C. were added 0.160 mL (1.309 mMol) isovaleryl chloride. The reaction mixture was allowed to warm to room temperature. After about 40 minutes the reaction was partitioned between dichloromethane and 2N sodium hydroxide. The phases were separated and the organic phase was washed with saturated aqueous sodium chloride, dried over sodium sulfate and concentrated under reduced pressure. The residue was subjected to silica gel chromatography, eluting with dichloromethane containing 15% methanol and 1.5% ammonium hydroxide. Fractions shown to contain product were combined and concentrated under reduced pressure. The residue was converted to the hydrochloride salt which was crystallized from ethanol/diethyl ether to give 0.208 gm (54%) of the title compound.

m.p.=171° C. (decomp.)

Calculated for $C_{19}H_{27}N_3O \cdot HCl$: Theory: C, 65.22; H, 8.07; N, 12.01. Found: C, 64.94; H, 8.12; N, 11.90.

The compounds of the following Examples 15–19 are prepared by the procedure described in detail in EXAMPLE B-14.

Example B-15

6-(propanoyl)amino-3-(dimethyl)amino-6-(propanoyl)amino-1,2,3,4-tetrahydro-9H-carbazole hydrochloride Beginning with 0.25 gm (1.091 mMol) 6-amino-3-(dimethyl)amino-1,2,3,4-tetrahydro-9H-carbazole and 0.114 mL (1.309 mMol) propanoyl chloride, 0.268 gm of the title compound were recovered.

m.p.=279° C. (decomp.)

Calculated for $C_{17}H_{23}N_3O \cdot HCl$: Theory: C, 63.44; H, 7.52; N, 13.06. Found: C, 63.24; H, 7.65; N, 13.09.

Example B-16

6-(2-methylprop-1-en-3-oyl)amino-3-(dimethyl)amino-1,2,3,4-tetrahydro-9H-carbazole hydrobromide Beginning with 0.046 gm (0.20 mMol) 6-amino-3-(dimethyl)amino-1,2,3,4-tetrahydro-9H-carbazole and 0.023 mL (0.24 mMol) 2-methylprop-1-en-3-oyl chloride, 0.035 gm (59%) of 6-(2-methylprop-1-en-3-oyl)amino-3-(dimethyl)amino-1,2,3,4-tetrahydro-9H-carbazole were recovered and then treated with hydrogen bromide to give the title compound.

m.p.=236–238° C.

MS(m/e): 297(M$^+$)

Example B-17

6-(cyclopropanoyl)amino-3-(dimethyl)amino-1,2,3,4-tetrahydro-9H-carbazole hydrobromide Beginning with 0.169 gm (0.74 mMol) 6-amino-3-(dimethyl)amino-1,2,3,4-tetrahydro-9H-carbazole and 0.077 mL (0.85 mMol) cyclopropanoyl chloride, 0.195 gm (89%) of 6-(cyclopropanoyl)amino-3-(dimethyl)amino-1,2,3,4-tetrahydro-9H-carbazole were recovered and then treated with hydrogen chloride to give the title compound.

m.p.=216–218° C.

MS(m/e): 297(M$^+$)

Calculated for $C_{18}H_{23}N_3O \cdot HCl$: Theory: C, 64.76; H, 7.25; N, 12.59. Found: C, 64.52; H, 7.13; N, 12.35.

Example B-18

6-(cyclobutanoyl)amino-3-(dimethyl)amino-1,2,3,4-tetrahydro-9H-carbazole hydrobromide Beginning with 0.169 gm (0.74 mMol) 6-amino-3-(dimethyl)amino-1,2,3,4-tetrahydro-9H-carbazole and 0.097 mL (0.85 mMol) cyclobutanoyl chloride, 0.230 gm (99%) of 6-(cyclobutanoyl)amino-3-(dimethyl)amino-1,2,3,4-tetrahydro-9H-carbazole were recovered and then treated with hydrogen chloride to give the title compound.

m.p.=214–216° C.

MS(m/e): 311(M$^+$)

Example B-19

6-(cyclohexanoyl)amino-3-(dimethyl)amino-1,2,3,4-tetrahydro-9H-carbazole hydrobromide Beginning with 0.132 gm (0.58 mMol) 6-amino-3-(dimethyl)amino-1,2,3,4-tetrahydro-9H-carbazole and 0.085 mL (0.635 mMol) cyclohexanoyl chloride, 0.173 gm (88%) of 6-(cyclohexanoyl)amino-3-(dimethyl)amino-1,2,3,4-tetrahydro-9H-carbazole were recovered and then treated with hydrogen chloride to give the title compound.

m.p.=224–226° C.

MS(m/e): 340(M$^+$)

Calculated for $C_{21}H_{29}N_3O \cdot HCl$: Theory: C, 67.09; H, 8.04; N, 11.17. Found: C, 66.89; H, 7.74; N, 11.40.

Example B-20

6-(4-chlorobenzoyl)amino-3-(dimethyl)amino-1,2,3,4-tetrahydro-9H-carbazole

To a mixture of 10.6 mg (0.046 mMol) 6-amino-3-(dimethyl)amino-1,2,3,4-tetrahydro-9H-carbazole and 14.0 mg (0.12 mMol) polyvinylpyridine in 3.0 mL dichloromethane were added 8.8 µL (0.069 mMol) 4-chlorobenzoyl chloride. The reaction mixture was mixed for 1 day at ambient temperature. To this mixture were then added 160 mg (0.128 mMol) aminomethylated polystyrene and the reaction mixed for an additional 18 hours. The reaction mixture was diluted with 1.0 mL methanol, treated with potassium carbonate, and filtered through a short column of sodium sulfate. The filtrate was then evaporated to give 2.9 mg (17%) of the title compound as a beige solid.

MS(m/e): 367(M$^+$)

The compounds of the following Examples 21–51 were prepared by the procedure described in detail in EXAMPLE B-20.

Example B-21

6-(4-methoxybenzoyl)amino-3-(dimethyl)amino-1,2, 3,4-tetrahydro-9H-carbazole

Beginning with 10.6 mg (0.046 mMol) 6-amino-3-(dimethyl)amino-1,2,3,4-tetrahydro-9H-carbazole and 8.8 µL (0.063 mMol) 4-methoxybenzoyl chloride, 6.9 mg (41%) of the title compound were recovered as a light brown foam.

MS (m/e): 3 63 (M$^+$)

Example B-22

6-(3-chlorobenzoyl)amino-3-(dimethyl)amino-1,2,3, 4-tetrahydro-9H-carbazole

Beginning with 10.6 mg (0.046 mMol) 6-amino-3-(dimethyl)amino-1,2,3,4-tetrahydro-9H-carbazole and 8.8 µL (0.063 mMol) 3-chlorobenzoyl chloride, 4.2 mg (25%) of the title compound were recovered as a brown solid.

MS(m/e): 367(M$^+$)

Example B-23

6-(3-methoxybenzoyl)amino-3-(dimethyl)amino-1,2, 3,4-tetrahydro-9H-carbazole

Beginning with 10.6 mg (0.046 mMol) 6-amino-3-(dimethyl)amino-1,2,3,4-tetrahydro-9H-carbazole and 8.8 µL (0.063 mMol) 3-methoxybenzoyl chloride, 9.8 mg (59%) of the title compound were recovered as a brown foam.

MS(m/e): 363(M$^+$)

Example B-24

6-(2-thienoyl)amino-3-(dimethyl)amino-1,2,3,4-tetrahydro-9H-carbazole

Beginning with 10.6 mg (0.046 mMol) 6-amino-3-(dimethyl)amino-1,2,3,4-tetrahydro-9H-carbazole and 8.8 µL (0.082 mMol) 2-thienoyl chloride, 9.7 mg (62%) of the title compound were recovered as a brown solid.

MS(m/e): 339(M$^+$)

Example B-25

6-(2-fluorobenzoyl)amino-3-(dimethyl)amino-1,2,3, 4-tetrahydro-9H-carbazole

Beginning with 10.4 mg (0.046 mMol) 6-amino-3-(dimethyl)amino-1,2,3,4-tetrahydro-9H-carbazole and 5.4 mg (0.051 mMol) 2-fluorobenzoyl chloride, 11.6 mg (74%) of the title compound were recovered as a beige solid.

MS(m/e): 351(M$^+$)

Example B-26

6-(2-chlorobenzoyl)amino-3-(dimethyl)amino-1,2,3, 4-tetrahydro-9H-carbazole

Beginning with 10.4 mg (0.046 mMol) 6-amino-3-(dimethyl)amino-1,2,3,4-tetrahydro-9H-carbazole and 5.7 mg (0.051 mMol) 2-chlorobenzoyl chloride, 12.3 mg (73%) of the title compound were recovered as a beige solid.

MS(m/e): 367(M$^+$)

Example B-27

6-(2-methoxybenzoyl)amino-3-(dimethyl)amino-1,2, 3,4-tetrahydro-9H-carbazole

Beginning with 10.4 mg (0.046 mMol) 6-amino-3-(dimethyl)amino-1,2,3,4-tetrahydro-9H-carbazole and 8.6 µL (0.051 mMol) 2-methoxybenzoyl chloride, 13.4 mg (80%) of the title compound were recovered as a beige solid.

MS(m/e) 367(M$^+$)

Example B-28

6-(2-methylbenzoyl)amino-3-(dimethyl)amino-1,2,3, 4-tetrahydro-9H-carbazole

Beginning with 10.4 mg (0.046 mMol) 6-amino-3-(dimethyl)amino-1,2,3,4-tetrahydro-9H-carbazole and 8.9 µL (0.051 mMol) 2-methylbenzoyl chloride, 11.3 mg (71%) of the title compound were recovered as a beige solid.

MS(m/e): 347(M$^+$)

Example B-29

6-(3-methylbenzoyl)amino-3-(dimethyl)amino-1,2,3, 4-tetrahydro-9H-carbazole

Beginning with 10.4 mg (0.046 mMol) 6-amino-3-(dimethyl)amino-1,2,3,4-tetrahydro-9H-carbazole and 8.9 µL (0.051 mMol) 3-methylbenzoyl chloride, 12.3 mg (77%) of the title compound were recovered as a beige solid.

MS(m/e) 347(M$^+$)

Example B-30

6-(4-methylbenzoyl)amino-3-(dimethyl)amino-1,2,3, 4-tetrahydro-9H-carbazole

Beginning with 10.4 mg (0.046 mMol) 6-amino-3-(dimethyl)amino-1,2,3,4-tetrahydro-9H-carbazole and 8.9 µL (0.051 mMol) 4-methylbenzoyl chloride, 14.6 mg (91%) of the title compound were recovered as a beige solid.

MS(m/e): 447(M$^+$)

Example B-31

6-(2,3-difluorobenzoyl)amino-3-(dimethyl)amino-1, 2,3,4-tetrahydro-9H-carbazole

Beginning with 10.4 mg (0.046 mMol) 6-amino-3-(dimethyl)amino-1,2,3,4-tetrahydro-9H-carbazole and 8.6 µL (0.051 mMol) 2,3-difluorobenzoyl chloride, 13.4 mg (79%) of the title compound were recovered as a beige solid.

MS(m/e): 369(M$^+$)

Example B-32

6-(2,4-difluorobenzoyl)amino-3-(dimethyl)amino-1, 2,3,4-tetrahydro-9H-carbazole

Beginning with 10.4 mg (0.046 mMol) 6-amino-3-(dimethyl)amino-1,2,3,4-tetrahydro-9H-carbazole and 8.6

µL (0.051 mMol) 2,4-difluorobenzoyl chloride, 13.8 mg (81%) of the title compound were recovered as a beige solid.
MS(m/e): 369(M+)

Example B-33

6-(2,5-difluorobenzoyl)amino-3-(dimethyl)amino-1, 2,3,4-tetrahydro-9H-carbazole

Beginning with 10.4 mg (0.046 rmMol) 6-amino-3-(dimethyl)amino-1,2,3,4-tetrahydro-9H-carbazole and 8.6 µL (0.051 mMol) 2,5-difluorobenzoyl chloride, 13.3 mg (78%) of the title compound were recovered as a beige solid.
MS(m/e): 369(M+)

Example B-34

6-(3,4-difluorobenzoyl)amino-3-(dimethyl)amino-1, 2,3,4-tetrahydro-9H-carbazole

Beginning with 10.4 mg (0.046 mMol) 6-amino-3-(dimethyl)amino-1,2,3,4-tetrahydro-9H-carbazole and 8.6 µL (0.051 mMol) 3,4-difluorobenzoyl chloride, 7.2 mg (42%) of the title compound were recovered as a beige solid.
MS(m/e): 369(M+)

Example B-35

6-(3,5-difluorobenzoyl)amino-3-(dimethyl)amino-1, 2,3,4-tetrahydro-9H-carbazole

Beginning with 10.4 mg (0.046 mMol) 6-amino-3-(dimethyl)amino-1,2,3,4-tetrahydro-9H-carbazole and 8.6 µL (0.051 mMol) 3,5-difluorobenzoyl chloride, 6.2 mg (36%) of the title compound were recovered as a beige solid.
MS(m/e): 369(M+)

Example B-36

6-(2,3-dichlorobenzoyl)amino-3-(dimethyl)amino-1, 2,3,4-tetrahydro-9H-carbazole

Beginning with 10.4 mg (0.046 mMol) 6-amino-3-(dimethyl)amino-1,2,3,4-tetrahydro-9H-carbazole and 9.5 mg (0.051 mMol) 2,3-dichlorobenzoyl chloride, 14.1 mg (76%) of the title compound were recovered as a brown solid.
MS(m/e): 401(M+)

Example B-37

6-(1-naphthoyl)amino-3-(dimethyl)amino-1,2,3,4-tetrahydro-9H-carbazole

Beginning with 10.4 mg (0.046 mMol) 6-amino-3-(dimethyl)amino-1,2,3,4-tetrahydro-9H-carbazole and 10.2 µL (0.051 mMol) 1-naphthoyl chloride, 13.8 mg (78%) of the title compound were recovered as a dark brown solid.
MS(m/e): 383(M+)

Example B-38

6-(2-naphthoyl)amino-3-(dimethyl)amino-1,2,3,4-tetrahydro-9H-carbazole

Beginning with 10.4 mg (0.046 mMol) 6-amino-3-(dimethyl)amino-1,2,3,4-tetrahydro-9H-carbazole and 10.2 µL (0.051 mMol) 2-naphthoyl chloride, 12.6 mg (72%) of the title compound were recovered as a dark brown solid.
MS(m/e): 383(M+)

Example B-39

6-(4-phenylbenzoyl)amino-3-(dimethyl)amino-1,2,3, 4-tetrahydro-9H-carbazole

Beginning with 10.4 mg (0.046 mMol) 6-amino-3-(dimethyl)amino-1,2,3,4-tetrahydro-9H-carbazole and 15 mg (0.051 mMol) 4-phenylbenzoyl chloride, 13.4 mg (71%) of the title compound were recovered as a brown solid.
MS(m/e): 409(M+)

Example B-40

6-(2-thionaphthoyl)amino-3-(dimethyl)amino-1,2,3, 4-tetrahydro-9H-carbazole

Beginning with 10.4 mg (0.046 mMol) 6-amino-3-(dimethyl)amino-1,2,3,4-tetrahydro-9H-carbazole and 14 mg (0.051 mMol) 2-thionaphthoyl chloride, 14.8 mg (83%) of the title compound were recovered as a dark brown solid.
MS(m/e): 389(M+)

Example B-41

6-(phenylacetyl)amino-3-(dimethyl)amino-1,2,3,4-tetrahydro-9H-carbazole

Beginning with 10.4 mg (0.046 mMol) 6-amino-3-(dimethyl)amino-1,2,3,4-tetrahydro-9H-carbazole and 8.1 µL (0.051 mMol) phenylacetyl chloride, 13.6 mg (85%) of the title compound were recovered as a grey-brown solid.
MS(m/e): 348(M+1)

Example B-42

6-(2-thienylacetyl)amino-3-(dimethyl)amino-1,2,3,4-tetrahydro-9H-carbazole

Beginning with 10.4 mg (0.046 mMol) 6-amino-3-(dimethyl)amino-1,2,3,4-tetrahydro-9H-carbazole and 8.1 µL (0.051 mMol) 2-thienylacetyl chloride, 13.7 mg (84%) of the title compound were recovered as a dark brown solid.
MS(m/e) 354(M+1)

Example B-43

6-(3-fluorobenzoyl)amino-3-(dimethyl)amino-1,2,3, 4-tetrahydro-9H-carbazole

Beginning with 10.4 mg (0.046 mMol) 6-amino-3-(dimethyl)amino-1,2,3,4-tetrahydro-9H-carbazole and 8.1 µL (0.051 mMol) 3-fluorobenzoyl chloride, 10.8 mg (69%) of the title compound were recovered as a beige solid.
MS(m/e): 352(M+1)

Example B-44

6-(4-bromobenzoyl)amino-3-(dimethyl)amino-1,2,3, 4-tetrahydro-9H-carbazole

Beginning with 10.4 mg (0.046 mMol) 6-amino-3-(dimethyl)amino-1,2,3,4-tetrahydro-9H-carbazole and 14.7 mg (0.051 mMol) 4-bromobenzoyl chloride, 3.6 mg (20%) of the title compound were recovered as a light beige solid.
MS(m/e) 413(M+)

Example B-45

6-(4-iodobenzoyl)amino-3-(dimethyl)amino-1,2,3,4-tetrahydro-9H-carbazole

Beginning with 10.4 mg (0.046 mMol) 6-amino-3-(dimethyl)amino-1,2,3,4-tetrahydro-9H-carbazole and 17.9 mg (0.051 mMol) 4-iodobenzoyl chloride, the title compound was recovered as a light beige solid.

MS(m/e): 459(M⁺)

Example B-46

6-(2,4-dichlorobenzoyl)amino-3-(dimethyl)amino-1,2,3,4-tetrahydro-9H-carbazole

Beginning with 10.4 mg (0.046 mMol) 6-amino-3-(dimethyl)amino-1,2,3,4-tetrahydro-9H-carbazole and 9.5 µL (0.051 mMol) 2,4-dichlorobenzoyl chloride, 12.8 mg (72%) of the title compound were recovered as a light beige solid.

MS(m/e): 401(M⁺)

Example B-47

6-(benzenesulfonyl)amino-3-(dimethyl)amino-1,2,3,4-tetrahydro-9H-carbazole

Beginning with 10.4 mg (0.046 mMol) 6-amino-3-(dimethyl)amino-1,2,3,4-tetrahydro-9H-carbazole and 8.6 µL (0.051 mMol) benzenesulfonyl chloride, 5.6 mg (34%) of the title compound were recovered as a light beige solid.

MS(m/e): 370(M⁺)

Example B-48

6-(4-fluorobenzenesulfonyl)amino-3-(dimethyl)amino-1,2,3,4-tetrahydro-9H-carbazole Beginning with 10.4 mg (0.046 mMol) 6-amino-3-(dimethyl)amino-1,2,3,4-tetrahydro-9H-carbazole and 13.1 mg (0.067 mMol) 4-fluorobenzenesulfonyl chloride, the title compound was recovered as a light beige solid.

MS(m/e): 388(M⁺)

Example B-49

6-(4-methylbenzenesulfonyl)amino-3-(dimethyl)amino-1,2,3,4-tetrahydro-9H-carbazole Beginning with 10.4 mg (0.046 mMol) 6-amino-3-(dimethyl)amino-1,2,3,4-tetrahydro-9H-carbazole and 12.8 mg (0.067 mMol) 4-methylbenzenesulfonyl chloride, 5.3 mg (31%) of the title compound were recovered as a light beige solid.

MS(m/e): 383(M⁺)

Example B-50

6-(4-chlorobenzenesulfonyl)amino-3-(dimethyl)amino-1,2,3,4-tetrahydro-9H-carbazole Beginning with 10.4 mg (0.046 mMol) 6-amino-3-(dimethyl)amino-1,2,3,4-tetrahydro-9H-carbazole and 14.1 mg (0.067 mMol) 4-chlorobenzenesulfonyl chloride, 11.5 mg (64%) of the title compound were recovered as a light beige solid.

MS(m/e) 403(M⁺)

Example B-51

6-(4-iodobenzenesulfonyl)amino-3-(dimethyl)amino-1,2,3,4-tetrahydro-9H-carbazole Beginning with 10.4 mg (0.046 mMol) 6-amino-3-(dimethyl)amino-1,2,3,4-tetrahydro-9H-carbazole and 20.3 mg (0.067 mMol) 4-iodobenzenesulfonyl chloride, 10.3 mg (47%) of the title compound were recovered as a light beige solid.

MS(m/e): 495(M⁺)

Example B-52

6-(4-fluorobenzoyl)amino-3-(dimethyl)amino-1,2,3,4-tetrahydro-9H-carbazole oxalate hemihydrate A solution of 0.10 gm (0.30 mMol) 6-(t-butoxycarbonyl)amino-3-(dimethyl)amino-1,2,3,4-tetrahydro-9H-carbazole in 1.0 mL trifluoroacetic acid was stirred for 20 minutes at room temperature. The reaction mixture was then concentrated under reduced pressure. The residual oil was then dissolved in 5 mL tetrahydrofuran. To this solution was added 1.5 mL triethylamine followed by 5.0 µL (0.42 mMol) 4-fluorobenzoyl chloride and the solution was stirred for 1 hour at room temperature. The reaction mixture was concentrated under reduced pressure and the residue was dissolved in dichloromethane. This solution was washed with aqueous potassium carbonate and was then concentrated under reduced pressure. The residue was dissolved in dilute aqueous tartaric acid and the solution was extracted well with dichloromethane. The remaining aqueous phase was made basic with dilute aqueous sodium hydroxide and was extracted well with dichloromethane. These organic phases were combined, dried over sodium sulfate and concentrated under reduced pressure. The residue was subjected to silica gel chromatography, eluting with 95:5 chloroform:5% ammonium hydroxide in methanol. Fractions containing the product were combined and concentrated under reduced pressure to give 0.102 gm (95%) of 6-(4-fluorobenzoyl)amino-3-(dimethyl)amino-1,2,3,4-tetrahydro-9H-carbazole.

MS(m/e): 351(M⁺)

Calculated for $C_{21}H_{22}N_3OF$: Theory: C, 71.27; H, 6.31; N, 11.96. Found: C, 71.47; H, 6.32; N, 11.86.

A solution of 0.82 mg (0.23 mMol) 6-(4-fluorobenzoyl)amino-3-(dimethyl)amino-1,2,3,4-tetrahydro-9H-carbazole in 1 mL ethyl acetate were added to a solution of 0.21 mg (0.23 mMol) oxalic acid in 1 mL ethyl acetate. The solid which formed was filtered, washed with ethyl acetate and dried to give 0.77 mg (75%) of the title compound.

m.p.>150° C. (decomp.)

The compounds of Examples 53–55 were prepared by the procedure described in detail in EXAMPLE B-52.

Example B-53

6-(benzoyl)amino-3-(dimethyl)amino-1,2,3,4-tetrahydro-9H-carbazole

Beginning with 0.198 gm (0.60 mMol) 6-(t-butoxycarbonyl)amino-3-(dimethyl)amino-1,2,3,4-tetrahydro-9H-carbazole and 9.7 µL (0.84 mMol) benzoyl chloride, 0.075 gm (38%) of the title compound were prepared as a light grey foam.

MS(m/e): 333(M⁺)

Calculated for $C_{21}H_{23}N_3O$: Theory: C, 75.65; H, 6.95; N, 12.60. Found: C, 75.35; H, 6.97; N, 12.50.

Example B-54

6-(2-furoyl)amino-3-(dimethyl)amino-1,2,3,4-tetrahydro-9H-carbazole oxalate hemihydrate Beginning with 0.10 gm (0.30 mMol) 6-(t-butoxycarbonyl)amino-3-(dimethyl)amino-1,2,3,4-tetrahydro-9H-carbazole and 5.0 µL (0.51 mMol) 2-furoyl chloride, 0.080 gm (82%) of 6-(2-furoyl)amino-3-(dimethyl)amino-1,2,3,4-tetrahydro-9H-carbazole were prepared.

MS(m/e): 323(M$^+$)

Calculated for C$_{19}$H$_{21}$N$_3$O$_2$: Theory: C, 70.57; H, 6.54; N, 12.99. Found: C, 70.29; H, 6.54; N, 12.99.

0.063 gm (0.20 mMol) of 6-(2-furoyl)amino-3-(dimethyl) amino-1,2,3,4-tetrahydro-9H-carbazole were treated with oxalic acid to give 0.052 gm (64%) ofthe title compound.

m.p.>110° C. (decomp.)

Example B-55

6-(2-chloro-4-fluorobenzoyl)amino-3-(dimethyl) amino-1,2,3,4-tetrahydro-9H-carbazole Beginning with 0.081 gm (0.245 mMol) 6-(t-butoxycarbonyl)amino-3-(dimethyl)amino-1,2,3,4-tetrahydro-9H-carbazole and 0.046 gm (0.27 mMol) 2-chloro-4-fluorobenzoyl chloride, 0.089 gm (94%) of the title compound were recovered as a light beige solid.

MS(m/e): 385(M$^+$)

IR(KBr): 3626, 3472, 3427, 2975, 2962, 2786, 1666, 1603, 1478 cm$^{-1}$

Calculated for C$_{21}$H$_{21}$N$_3$OClF: Theory: C, 65.37; H, 5.49; N, 10.89. Found: C, 65.17; H, 5.50; N, 10.73.

Example B-56

6-(indol-5-oyl)amino-3-(dimethyl)amino-1,2,3,4-tetrahydro-9H-carbazole hydrochloride To a solution of 43.5 mg (0.27 mMol) indole-5-carboxylic acid in 1.5 mL dimethylformamide were added 44.3 mg (0.27 mMol) carbonyldiimidazole resulting in immediate gas evolution. The reaction mixture was stirred for 4 hours at room temperature and then 60.0 mg (0.26 mMol) 6-amino-3-(dimethyl)amino-1,2,3,4-tetrahydro-9H-carbazole were added. After 3 days the reaction mixture was concentrated under reduced pressure. The residue was subjected to silica gel chromatography, eluting with 4:1 dichloromethane:2% ammonium hydroxide in methanol. Fractions shown to contain product were combined and concentrated under reduced pressure to give 66.7 mg (69%) of 6-(indol-5-oyl)amino-3-(dimethyl)amino-1,2,3,4-tetrahydro-9H-carbazole. The compound was converted to its corresponding hydrochloride salt, crystallizing from ethanol:diethyl ether.

m.p.=235–237° C.

Exact Mass: Calculated for C$_{23}$H$_{25}$N$_4$O: Theory: 373.2028; Found: 373.2042.

Example B-57

6-(4-fluorobenzoyl)amino-3-amino-1,2,3,4-tetrahydro-9H-carbazole hydrochloride

To a solution of 0.187 gm (0.41 mMol) 6-(4-fluorobenzoyl)amino-3-(1-phthalimido)-1,2,3,4-tetrahydro-9H-carbazole in 6 mL ethanol and 1.5 mL water were added 0.45 mL hydrazine monohydrate and the reaction mixture was stirred at room temperature. After 12 hours the reaction mixture was concentrated under reduced pressure and the residue partitioned between ethyl acetate and saturated aqueous sodium carbonate. The organic phase was washed with water, dried over sodium sulfate and concentrated under reduced pressure. The residue was subjected to silica gel chromatography. Fractions shown to contain product were combined and concentrated under reduced pressure to give 0.101 gm (76%) of 6-(4-fluorobenzoyl)amino-3-amino-1,2,3,4-tetrahydro-9H-carbazole. The compound was converted to its corresponding hydrochloride salt, crystallizing from ethanol:diethyl ether.

m.p.=252–255° C.

MS(m/e): 323(M$^+$)

Calculated for C$_{19}$H$_{18}$N$_3$OF.HCl: Theory: C, 63.42; H, 5.32; N, 11.68. Found: C, 63.20; H, 5.57; N, 11.91.

Example B-58

6-(4-fluorobenzoyl)amino-3-(ethyl)amino-1,2,3,4-tetrahydro-9H-carbazole hydrobromide and 6-(4-fluorobenzoyl)amino-3-(diethyl)amino-1,2,3,4-tetrahydro-9H-carbazole hydrochloride To a solution of 0.194 gm (0.60 mMol) 6-(4-fluorobenzoyl)amino-3-amino-1,2,3,4-tetrahydro-9H-carbazole in 15 mL ethanol were added 300 mg Raney Nickel and the reaction mixture heated to reflux. After 2 hours the reaction mixture was filtered through a pad of celite. The pad was washed with 400 mL of methanol and the filtrates were concentrated under reduced pressure. The residue was subjected to silica gel chromatography, eluting with 100:10:3 dichloromethane: methanol:ammonium hydroxide. Fractions containing the first eluting product were combined and concentrated under reduced pressure to give 137.3 mg (60.3 %) of 6-(4-fluorobenzoyl)amino-3-(diethyl)amino-1,2,3,4-tetrahydro-9H-carbazole. The corresponding hydrochloride salt was prepared.

m.p.=222–224° C.

Exact Mass: Calculated for C$_{23}$H$_{27}$N$_3$OF: Theory: 380.2138;

Found: 380.2144.

Fractions containing the second eluting spot were combined and concentrated under reduced pressure to give 0.033 gm (16%) of 6-(4-fluorobenzoyl)amino-3-(ethyl)amino-1,2,3,4-tetrahydro-9H-carbazole. The corresponding hydrobromide salt was prepared.

m.p.=226–230° C.

Exact Mass: Calculated for C$_{21}$H$_{23}$N$_3$OF: Theory: 352.1825; Found: 352.1825.

Example B-59

6-(4-fluorobenzoyl)amino-3-(2-phenylethyl)amino-1,2,3,4-tetrahydro-9H-carbazole hydrochloride To a mixture of 0.568 gm (1.758 mMol) 6-(4-fluorobenzoyl)amino-3-amino-1,2,3,4-tetrahydro-9H-carbazole, 0.485 gm (3.512 mMol) potassium carbonate and 0.316 gm (2.109 mMol) sodium iodide in 10 mL acetonitrile were added 0.288 mL (2.109 mMol) 2-phenyl-1-ethyl bromide and the reaction mixture was heated at reflux for 5 hours. The reaction mixture was then cooled to room temperature and partitioned between dichloromethane and water. The aqueous phase was extracted well with dichloromethane. The dichloromethane phases were combined, dried over magnesium sulfate and concentrated under reduced pressure. The residue was subjected to silica gel chromatography, eluting with 97:2.5:0.5 dichloromethane:methanol:ammonium hydroxide. Fractions shown to contain product were combined and concentrated under reduced pressure to give 0.543 gm (72.3%) 6-(4-fluorobenzoyl)amino-3-(2-phenethyl)amino-1,2,3,4-tetrahydro-9H-carbazole. The corresponding hydrochloride salt was prepared to provide the title compound.

m.p.207–208° C.

Calculated for C$_{27}$H$_{26}$N$_3$OF.HCl: Theory: C, 68.89; H, 5.87; N, 9.06. Found: C, 68.69; H, 6.07; N, 8.94.

Example B-60

6-(4-fluorobenzoyl)amino-3-(2-(4-fluorophenyl)ethyl)amino-1,2,3,4-tetrahydro-9H-carbazole hydrochloride Beginning with 0.601 gm (1.860 mMol) 6-(4-fluorobenzoyl)amino-3-amino-1,2,3,4-tetrahydro-9H-carbazole and 0.525 gm (2.405 mMol) 2-(4-fluorophenyl)-1-mesyloxyethane, 0.270 gm (32.8%) of the title compound were prepared by the procedure described in EXAMPLE B-31.

m.p.210–211° C.

Calculated for $C_{27}H_{25}N_3OF_2 \cdot HCl$: Theory: C, 67.29; H, 5.44; N, 8.72. Found: C, 67.05; H, 5.61; N, 8.45.

Example B-61

6-(4-fluorobenzoyl)amino-3-(2-(1-methyl-1H-pyrazol-4-yl)ethyl)amino-1,2,3,4-tetrahydro-9H-carbazole hydrochloride To a mixture of 0.40 gm (1.24 mMol) 6-(4-fluorobenzoyl)amino-3-amino-1,2,3,4-tetrahydro-9H-carbazole and 0.257 gm (1.86 mMol) potassium carbonate in 8.0 mL dimethylform-amide were added 0.303 gm (1.49 mMol) 2-(1-methyl-1H-pyrazol-4-yl)-1-mesyloxyethane in 2.0 mL dimethylformamide and the mixture was stirred at 60–75° C. for 18 hours. An additional 0.101 gm (0.50 mMol) 2-(1-methyl-1H-pyrazol-4-yl)-1-mesyloxyethane were added and the reaction heated to 150° C. After 1.5 hours the reaction mixture was cooled to room temperature and was then partitioned between water and dichloromethane. The aqueous phase was extracted again with dichloromethane. The combined organic phases were dried over sodium sulfate and concentrated under reduced pressure. The residue was subjected to silica gel chromatography, eluting with 95:5:0.5 dichloromethane:methanol:ammonium hydroxide. Fractions shown to contain product were combined and concentrated under reduced pressure to give 0.180 gm (33.6%) of 6-(4-fluorobenzoyl)amino-3-(2-(1-methyl-1H-pyrazol-4-yl)ethyl)amino-1,2,3,4-tetrahydro-9H-carbazole. The corresponding hydrochloride salt was prepared to provide the title compound.

m.p.=185–190° C.

Exact Mass: Calculated for $C_{25}H_{26}N_5OF$: Theory: 432.2202; Found: 432.2200.

Example B-62

3-(2-(1-isopropyl-1H-pyrazol-4-yl)ethyl)amino-6-(4-fluorobenzoyl)amino-1,2,3,4-tetrahydro-9H-carbazole hydrochloride Beginning with 0.400 gm (1.24 mMol) 6-(4-fluorobenzoyl)amino-3-amino-1,2,3,4-tetrahydro-9H-carbazole and 0.346 gm (1.49 mMol) 2-(1-methyl-1H-pyrazol-3-yl)-1-mesyloxyethane, 0.0632 gm (10.3%) of the title compound were prepared by the procedure described in EXAMPLE B-33.

Exact Mass: Calculated for $C_{27}H_{30}N_5OF$: Theory: 460.2513; Found: 460.2491.

Example B-63

6-hydroxy-3-amino-1,2,3,4-tetrahydro-9H-carbazole

To a solution of 0.871 gm (2.98 mMol) 6-benzyloxy-3-amino-1,2,3,4-tetrahydro-9H-carbazole in 200 mL ethanol were added about 2.0 gm Raney Nickel and hydrogen introduced to the reaction mixture under balloon pressure. After stirring for 18 hours at room temperature the balloon was refilled with hydrogen and the reaction stirred an additional 3 days at room temperature. The reaction mixture was filtered and the filtrate concentrated under reduced pressure to give a colorless solid. The residual solid was subjected to silica gel chromatography, eluting with 80:15:5 dichloromethane: methanol:ammonium hydroxide. Fractions shown to contain product were combined and concentrated under reduced pressure to give 0.335 gm (56%) of the title compound.

m.p.=230° C. (decomp.)

Calculated for $C_{12}H_{14}N_2O$: Theory: C, 71.26; H, 6.98; N, 13.85. Found: C, 71.00; H, 7.01; N, 13.70.

Example B-64

6-hydroxy-3-(methyl)amino-1,2,3,4-tetrahydro-9H-carbazole 6-benzyloxy-3-(t-butyloxycarbonyl)amino-1,2,3,4-tetrahydro-9H-carbozole To a solution of 1.00 gm (3.42 mMol) 6-benzyloxy-3-amino-1,2,3,4-tetrahydro-9H-carbazole in 30 mL tetrahydrofuran were added 1.79 mL 2N sodium hydroxide followed by 0.784 gm (3.59 mMol) di(t-butyl)dicarbonate. The reaction mixture was stirred at room temperature for about 45 minutes and was then concentrated under reduced pressure. The residue was dissolved in dichloromethane and washed well with water. The remaining organics were dried over magnesium sulfate and concentrated under reduced pressure to give 1.339 gm (99%) of the desired compound.

6-benzyloxy-3-(methyl)amino-1,2,3,4-tetrahydro-9H-carbazole

A solution of 1.35 gm (3.44 mMol) 6-benzyloxy-3-(t-butyloxycarbonyl)amino-1,2,3,4-tetrahydro-9H-carbazole in 15 mL tetrahydrofuran were added dropwise over 30–40 minutes to a suspension of 0.46 gm (12.04 mMol) lithium aluminum hydride in 30 mL tetrahydrofuran at 0° C. The reaction mixture was allowed to stir at this temperature for 20 minutes after the addition was complete and was then warmed to 75° C. for 4.5 hours. The reaction mixture was then cooled to room temperature and treated with sodium sulfate decahydrate. The mixture was cooled to 0° C. and was then filtered. The solid collected was washed sequentially with tetrahydrofuran and dichloromethane, and the combined filtrates were concentrated under reduced pressure. The residue was subjected to silica gel chromatography, eluting with ethyl acetae. Fractions shown to contain product were combined and concentrated under reduced pressure to 0.797 gm (76%) of the desired product.

m.p.=146–147° C.

Calculated for $C_{20}H_{22}N_2O$: Theory: C, 78.40; H, 7.24; N, 9.16. Found: C, 78.53; H, 7.36; N, 9.14.

Hydrogenolysis

Beginning with 0.522 gm (1.70 mMol) 6-benzyloxy-3-(methyl)amino-1,2,3,4-tetrahydro-9H-carbazole, 0.226 mg (61%) of the title compound were recovered as described in EXAMPLE B-35.

m.p.=120–121° C.

Exact Mass: Calculated for: $C_{13}H_{16}N_2O$: Theory: 217.1341; Found: 217.1336.

Example B-65

6-hydroxy-3-(ethyl)amino-1,2,3,4-tetrahydro-9H-carbazole 6-benzyloxy-3-(ethyl)amino-1,2,3,4-tetrahydro-9H-carbazole To a solution of 0.225 gm (0.77 mMol) 6-benzyloxy-3-amino-1,2,3,4-tetrahydro-9H-carbazole in 20 mL acetonitrile were added 0.223 gm (1.617 mMol) potassium carbonate followed by 130 μL (1.617 mMol) iodoethane and the reaction mixture was stirred at room temperature for 18 hours. The reaction mixture was then heated at 60° C. for 4 hours and then at 50–45° C. for 3 hours. The reaction mixture was then concentrated under reduced pressure and the residue partitioned between dichloromethane and water. The organic phase was then dried over magnesium sulfate and concentrated under reduced pressure. The residue was subjected to radial chromatography (silica gel, 2 mm), eluting with 97:3:1 dichloromethane: methanol:ammonium hydroxide. Fractions shown to contain the desired compound were concentrated under reduced pressure to give 0.045 gm (6%) of the desired compound.

Exact Mass: Calculated for: $C_{21}H_{25}N_2O$: Theory: 321.1967; Found: 321.1970.

Hydrogenolysis

Beginning with 0.492 gm (1.536 mMol) 6-benzyloxy-3-(ethyl)amino-1,2,3,4-tetrahydro-9H-carbazole, 0.271 mg (76.6%) of the title compound were recovered as described in EXAMPLE B-35.

m.p.=117–118° C.

Exact Mass: Calculated for: $C_{14}H_{18}N_2O$: Theory: 231.1497; Found: 231.1490.

Example B-66

6-hydroxy-3-(propyl)amino-1,2,3,4-tetrahydro-9H-carbazole hydrochloride 6-benzyloxy-3-(propyl)amino-1,2,3,4-tetrahydro-9H-carbazole To a solution of 0.600 gm (2.05 mMol) 6-benzyloxy-3-amino-1,2,3,4-tetrahydro-9H-carbazole in 35 mL acetonitrile were added 0.283 gm (2.05 mMol) potassium carbonate followed by 240 μL (2.46 mMol) iodopropane and the reaction mixture was stirred at room temperature for 2.5 days. Additional iodopropane was added and the reaction stirred at room temperature until all of the starting material had been consumed. The reaction mixture was then partitioned between dichloromethane and water. The aqueous phase was extracted with dichloromethane and the combined organic phases were then dried over magnesium sulfate and concentrated under reduced pressure. The residue was subjected to silica gel chromatography, eluting with 96.5:3:0.5 dichloromethane: isopropanol:ammonium hydroxide. Fractions shown to contain the desired compound were concentrated under reduced pressure to give 0.270 gm (39%) of the desired compound.

Hydrogenolysis

To a solution of 0.27 gm 6-benzyloxy-3-(propyl)amino-1,2,3,4-tetrahydro-9H-carbazole in 50 mL ethanol were added 100 mg 5% palladium on carbon and the reaction mixture was hydrogenated at room temperature for 16 hours with an initial hydrogen pressure of 60 p.s.i. The reaction mixture was then filtered through celite, washing the filter pad well with methanol. The combined filtrates were concentrated under reduced pressure. The residue was subjected to silica gel chromatography, eluting with 90:9:1 dichloromethane:methanol:ammonium hydroxide. Fractions shown to contain product were combined and concentrated under reduced pressure to give 0.083 gm (42%) of the title compound. The corresponding hydrochloride salt was formed and crystallized from methanol/diethyl ether.

m.p.=105° C. (decomp.)

Exact Mass: Calculated for: $C_{15}H_{20}N_2O$: Theory: 245.1654; Found: 245.1659.

The compounds of the following Examples 67–68 were prepared by the procedure described in detail in EXAMPLE B-66.

Example B-67

6-hydroxy-3-(diethyl)amino-1,2,3,4-tetrahydro-9H-carbazole hydrochloride

Beginning with 1.00 gm (2.05 mMol) 6-benzyloxy-3-amino-1,2,3,4-tetrahydro-9H-carbazole and 820 μL (10.27 mMol) iodoethane, 0.0882 gm (10%) of 6-hydroxy-3-(diethyl)amino-1,2,3,4-tetrahydro-9H-carbazole were recovered. The hydrochloride salt was prepared to give the title compound.

m.p.=271–271° C.

Exact Mass: Calculated for: $C_{16}H_{22}N_2O$: Theory: 259.1810; Found: 259.1816.

Example B-68

6-hydroxy-3-(dipropyl)amino-1,2,3,4-tetrahydro-9H-carbazole hydrochloride

Beginning with 1.00 gm (2.05 mMol) 6-benzyloxy-3-amino-1,2,3,4-tetrahydro-9H-carbazole and 1.67 mL (17.11 mMol) 1-iodopropane, 0.200 gm (70%) of 6-hydroxy-3-(dipropyl)amino-1,2,3,4-tetrahydro-9H-carbazole were recovered. The hydrochloride salt was prepared to give the title compound.

Calculated for $C_{18}H_{26}N_2O\cdot HCl$: Theory: C, 66.96; H, 8.43; N, 8.68. Found: C, 66.69; H, 8.25; N, 8.90.

Example B-69

6-hydroxy-3-(2-phenyleth-1-yl)amino-1,2,3,4-tetrahydro-9H-carbazole hydrochloride 6-benzyloxy-3-(2-phenyleth-1-yl)amino-1,2,3,4-tetrahydro-9H-carbazole To a solution of 0.32 gm (1.1 mMol) 6-benzyloxy-3-amino-1,2,3,4-tetrahydro-9H-carbazole in 8 mL acetonitrile were added 0.30 gm (1.68 mMol) potassium carbonate, 0.25 gm (1.68 mMol) sodium iodide and 0.23 mL (1.68 mMol) 2-phenyl-1-ethyl bromide. The resulting mixture was stirred 4 hours at room temperature followed by 5 hours at reflux. The reaction mixture was cooled to room temperature and then partitioned between dichloromethane and water. The aqueous phase was extracted well with dichloromethane. All of the organic phases were combined, dried over magnesium sulfate and concentrated under reduced pressure. The residue was subjected to silica gel chromatography, eluting with 7% methanol in dichloromethane. Fractions shown to contain product were concentrated under reduced pressure to give 0.345 gm (79%) of the desired compound. A portion was converted to the corresponding hydrochloride salt, m.p.=242–244° C. (ethanol/diethyl ether).

Hydrogenolysis

Beginning with 0.336 gm (0.85 mMol) 6-benzyloxy-3-(2-phenyleth-1-yl)-amino-1,2,3,4-tetrahydro-9H-carbazole, 0.175 gm (67%) of 6-hydroxy-3-(2-phenylethyl)amino-1,2,3,4-tetrahydro-9H-carbazole were prepared by the procedure described in detail in EXAMPLE B-35. The hydrochloride salt was prepared and crystallized from ethanol/diethyl ether to give the title compound.

m.p.=178–180° C.

MS (m/e): 307(M+)

Calculated for $C_{20}H_{22}N_2O\cdot HCl$: Theory: C, 70.06; H, 6.76; N, 8.17. Found: C, 70.32; H, 6.78; N, 8.22.

Example B-70

6-hydroxy-3-(2-(4-fluorophenyl)eth-1-yl)amino-1,2,3,4-tetrahydro-9H-carbazole hydrochloride 6-benzyloxy-3-(2-(4-fluorophenyl)eth-1-yl)amino-1,2,3,4-tetrahydro-9H-carbazole Beginning with 1.00 gm (3.422 mMol) 6-benzyloxy-3-amino-1,2,3,4-tetrahydro-9H-carbazole and 1.274 gm (5.82 mMol) 2-(4-fluorophenyl)-1-mesyloxyethane, 0.896 gm (63%) of 6-benzyloxy-3-(2-(4-fluorophenyl)eth-1-yl)amino-1,2,3,4-tetrahydro-9H-carbazole were recovered by the procedure described in detail in EXAMPLE B-33. A portion was converted to the corresponding hydrochloride salt and crystallized from ethanol/diethyl ether.

m.p.=244–245° C.

Calculated for $C_{27}H_{27}N_2OF \cdot HCl$: Theory: C, 71.91; H, 6.26; N, 6.21. Found: C, 71.70; H, 6.26; N, 6.09.

Hydrogenolysis

To a solution of 0.700 gm (1.69 mMol) 6-benzyloxy-3-(2-(4-fluorophenyl)eth-1-yl)amino-1,2,3,4-tetrahydro-9H-carbazole in 50 mL methanol were added 1.07 gm (16.90 mMol) ammonium formate followed by 0.190 gm 5% palladium on carbon. The resulting mixture was stirred at reflux for 15 minutes. The reaction mixture was then filtered through a bed of celite and the filter cake washed well with methanol. The combined filtrates were concentrated under reduced pressure and the residue partitioned between water and dichloromethane. The phases were separated and the aqueous was extracted again with 4:1 isopropanol:dichloromethane. The combined extracts were dried over magnesium sulfate, concentrated under reduced pressure, and the residue subjected to silica gel chromatography, eluting with 91:8:1 dichloromethane:methanol:ammonium hydroxide. Fractions shown to contain product were combined and concentrated under reduced pressure to give 0.245 gm (52%) of 6-hydroxy-3-(2-(4-fluorophenyl)eth-1-yl)amino-1,2,3,4-tetrahydro-9H-carbazole. The hydrochloride salt was prepared and crystallized from ethanol/diethyl ether to give the title compound.

m.p.=160° C. (decomp.)

Calculated for $C_{20}H_{21}N_2OF \cdot HCl$: Theory: C, 66.57; H, 6.14; N, 7.76. Found: C, 66.34; H, 6.14; N, 7.59.

Example B-71

6-benzyloxy-3-(2-(4-chlorophenyl)eth-1-yl)amino-1,2,3,4-tetrahydro-9H-carbazole hydrochloride Beginning with 1.00 gm (3.422 mMol) 6-benzyloxy-3-amino-1,2,3,4-tetrahydro-9H-carbazole and 1.371 gm (5.82 mMol) 2-(4-chlorophenyl)-1-mesyloxyethane, 0.833 gm (56%) of 6-benzyloxy-3-(2-(4-chlorophenyl)eth-1-yl)amino-1,2,3,4-tetrahydro-9H-carbazole were recovered by the procedure described in detail in EXAMPLE B-33. A portion was converted to the corresponding hydrochloride salt and crystallized from ethanol/diethyl ether.

m.p.=238–240° C.

Calculated for $C_{27}H_{27}N_2OCl \cdot HCl$: Theory: C, 68.38; H, 6.04; N, 5.99. Found: C, 68.63; H, 6.17; N, 6.05.

Example B-72

6-hydroxy-3-(2-(1-methyl-1H-pyrazol-4-yl)ethyl)amino-1,2,3,4-tetrahydro-9H-carbazole hydrochloride 6-benzyloxy-3-(2-(1-methyl-1H-pyrazol-4-yl)ethyl)amino-1,2,3,4-tetrahydro-9H-carbazole To a solution of 1.00 gm (3.422 mMol) 6-benzyloxy-3-amino-1,2,3,4-tetrahydro-9H-carbazole in 50 mL acetonitrile were added 1.04 gm (7.53 mMol) potassium carbonate followed by 1.26 gm (6.16 mMol) 2-(1-methyl-1H-pyrazol-4-yl)-1-mesyloxyethane and the reaction mixture was heated to reflux for 18 hours. To the reaction mixture were then added 0.021 gm (0.171 mMol) 4-dimethylaminopyridine and reflux was continued for 36 additional hours. The reaction mixture was cooled to room temperature and then partitioned between dichloromethane and water. The aqueous phase was extracted well with dichloromethane. All of the organic phases were combined, dried over magnesium sulfate and concentrated under reduced pressure. The residue was subjected to silica gel chromatography, eluting with 2.5% methanol in dichloromethane containing 0.5 % ammonium hydroxide. Fractions shown to contain product were concentrated under reduced pressure to give 0.610 gm (44%) of the desired compound.

Hydrogenolysis

Beginning with 0.610 gm (1.524 mMol) 6-benzyloxy-3-(2-(1-methyl-1H-pyrazol-4-yl)ethyl)amino-1,2,3,4-tetrahydro-9H-carbazole, 0.245 gm (52%) of 6-hydroxy-3-(2-(1-methyl-1H-pyrazol-4-yl)ethyl)amino-1,2,3,4-tetrahydro-9H-carbazole were prepared by the hydrogenolysis procedure described in detail in EXAMPLE B-42. The hydrochloride salt was prepared and crystallized from ethanol/diethyl ether to give the title compound.

m.p.=286° C. (decomp.)

Calculated for $C_{18}H_{21}N_4O \cdot HCl$: Theory: C, 62.33; H, 6.68; N, 16.15. Found: C, 62.54; H, 6.71; N, 16.20.

Example B-73

6-hydroxy-3-(2-(1-isopropyl-1H-pyrazol-4-yl)ethyl)amino-1,2,3,4-tetrahydro-9H-carbazole hydrochloride 6-benzyloxy-3-(2-(1-isopropyl-1H-pyrazol-4-yl)ethyl)amino-1,2,3,4-tetrahydro-9H-carbazole Beginning with 0.698 gm (2.39 mMol) 6-benzyloxy-3-amino-1,2,3,4-tetrahydro-9H-carbazole and 0.787 gm (3.39 mMol) 2-(1-isopropyl-1H-pyrazol-4-yl)-1-mesyloxyethane, 0.649 gm (63.4%) of the desired compound were prepared by the procedure described in detail in EXAMPLE B-72.

MS(m/e): 428(M⁺)

A portion of the material was converted to its corresponding hydrochloride salt, m.p.=258–260° C. (ethanol/diethyl ether).

Hydrogenolysis

Beginning with 0.532 gm (1.24 mMol) 6-benzyloxy-3-(2-(1-isopropyl-1H-pyrazol-4-yl)ethyl)amino-1,2,3,4-tetrahydro-9H-carbazole, 0.322 gm (77%) of 6-hydroxy-3-(2-(1-isopropyl-1H-pyrazol-4-yl)ethyl)amino-1,2,3,4-tetrahydro-9H-carbazole were prepared by the hydrogenolysis procedure described in detail in EXAMPLE B-42. The hydrochloride salt was prepared and crystallized from ethanol/diethyl ether to give the title compound.

m.p.=251–253° C.

MS(m/e): 338(M⁺)

Calculated for $C_{20}H_{26}N_4O \cdot HCl$: Theory: C, 64.07; H, 7.26; N, 14.94. Found: C, 64.29; H, 7.28; N, 15.17.

Example B-74

N-methyl-N-(2-phenyleth-1-yl)-6-hydroxy-3-amino-1,2,3,4-tetrahydro-9H-carbazole hydrochloride N-methyl-N-(2-phenyleth-1-yl)-6-benzyloxy-3-amino-1,2,3,4-tetrahydro-9H-carbazole To a solution of 0.30 gm (0.98 mMol) 6-benzyloxy-3-(methyl)amino-1,2,3,4-tetrahydro-9H-carbazole in 15 mL acetonitrile were added 0.271 (1.96 mMol) potassium carbonate, 0.177 gm (1.18 mMol) sodium iodide and 0.161 mL (1.18 mMol) 2-phenyl-1-ethyl bromide. The reaction mixture was heated to reflux for 18 hours. At this time an additional 0.07 mL (0.49 mMol) 2-phenyl-1-ethyl bromide were added and reflux was continued for 4 hours. The reaction mixture was cooled to room temperature and then partitioned between dichloromethane and water. The aqueous phase was extracted well with dichloromethane. All organic phases were combined, dried over magnesium sulfate and concentrated under reduced pressure. The residue was subjected to radial chromatography (4 mm, silica gel), eluting with 4.5% methanol in dichloromethane containing 0.55% ammonium hydroxide. Fractions containing product were combined and concentrated under reduced pressure to give 0.324 gm (80.6%) of the desired compound.
Hydrogenolysis Beginning with 0.324 gm (0.79 mMol) N-methyl-N-(2-phenyleth-1-yl)-6-benzyloxy-3-amino-1,2,3,4-tetrahydro-9H-carbazole, 0.205 gm (78%) of N-methyl-N-(2-phenylethyl)-6-hydroxy-3-amino-1,2,3,4-tetrahydro-9H-carbazole were prepared by the hydrogenolysis procedure described in detail in EXAMPLE B-70. The hydrochloride salt was prepared and crystallized from ethanol/diethyl ether to give the title compound.

m.p.=159–160° C.

Calculated for $C_{21}H_{24}N_2O \cdot HCl$: Theory: C, 70.67; H, 7.06; N, 7.85. Found: C, 70.41; H, 7.05; N, 7.83.

Example B-75

N-methyl-N-(2-(4-fluorophenyl)eth-1-yl)-6-hydroxy-3-amino-1,2,3,4-tetrahydro-9H-carbazole hydrochloride N-methyl-N-(2-(4-fluorophenyl)eth-1-yl)-6-benzyloxy-3-amino-1,2,3,4-tetrahydro-9H-carbazole Beginning with 0.30 gm (0.98 mMol) 6-benzyloxy-3-(methyl)amino-1,2,3,4-tetrahydro-9H-carbazole in 15 mL acetonitrile and 0.406 mg (1.86 mMol) 2-(4-fluorophenyl)-1-mesyloxyethane, 0.262 gm (62%) of the desired compound were recovered by the procedure described in detail in EXAMPLE B-46.
Hydrogenolysis Beginning with 0.262 gm (0.61 mMol) N-methyl-N-(2-(4-fluorophenyl)eth-1-yl)-6-benzyloxy-3-amino-1,2,3,4-tetrahydro-9H-carbazole, 0.183 gm (88%) of N-methyl-N-(2-(4-fluorophenyl)eth-1-yl)-3-amino-6-hydroxy-1,2,3,4-tetrahydro-9H-carbazole were prepared by the hydrogenolysis procedure described in detail in EXAMPLE B-70. The hydrochloride salt was prepared and crystallized from ethanol/diethyl ether to give the title compound.

m.p.=165–166° C.

Calculated for $C_{21}H_{23}N_2OF \cdot HCl$: Theory: C, 67.28; H, 6.45; N, 7.47. Found: C, 67.48; H, 6.64; N, 7.52.

Example B-76

N-methyl-N-(2-(1-isopropyl-1H-pyrazol-4-yl)ethyl)-6-hydroxy-3-amino-1,2,3,4-tetrahydro-9H-carbazole hydrochloride N-methyl-N-(2-(1-isopropyl-1H-pyrazol-4-yl)ethyl)-6-benzyloxy-3-amino-1,2,3,4-tetrahydro-9H-carbazole Beginning with 0.202 gm (0.66 mMol) 6-benzyloxy-3-(methyl)amino-1,2,3,4-tetrahydro-9H-carbazole in 15 mL acetonitrile and 0.284 mg (1.22 mMol) 2-(1-isopropyl-1H-pyrazol-4-yl)-1-mesyloxyethane, 0.253 gm (87%) of the desired compound were recovered by the procedure described in detail in EXAMPLE B-74.

MS(m/e): 442($M^+$)

A portion was converted to the corresponding hydrochloride salt, m.p.=134–136° C. (ethanol/diethyl ether).
Hydrogenolysis Beginning with 0.196 gm (0.44 mMol) N-methyl-N-(2-(1-isopropyl-1H-pyrazol-4-yl)ethyl)-6-benzyloxy-3-amino-1,2,3,4-tetrahydro-9H-carbazole, 0.120 gm (77%) of N-methyl-N-(2-(1-isopropyl-1H-pyrazol-4-yl)ethyl)-6-hydroxy-3-amino-1,2,3,4-tetrahydro-9H-carbazole were prepared by the hydrogenolysis procedure described in detail in EXAMPLE B-70. The hydrochloride salt was prepared and crystallized from ethanol/diethyl ether to give the title compound.

m.p.=184–186° C.

MS(m/e): 352($M^+$)

Calculated for $C_{21}H_{28}N_4O \cdot HCl$: Theory: C, 64.85; H, 7.52; N, 14.40. Found: C, 65.08; H, 7.52; N,14.46.

Example B-77

7-(4-fluorobenzoyl)amino-4-amino-10H-cyclohepta[7,6-b]indole

To a solution of 0.854 gm (1.827 mMol) of a mixture of 7-(4-fluorobenzoyl)amino-3- and 4-(1-phthalimidoyl)-10H-cyclohepta[7,6-b]indole in 50 mL ethanol were added 3.5 mL hydrazine hydrate and 12 mL water. The mixture was stirred at room temperature for 18 hours. The reaction mixture was then concentrated under reduced pressure and the residue subjected to silica gel chromatography, eluting with 84:15:1 dichloromethane:methanol:ammonium hydroxide. Fractions containing the desired compound were combined and concentrated under reduced pressure to give 0.196 gm (32%) of the title compound.

m.p.=121–122° C.

Exact Mass: Calculated for: $C_{20}H_{21}N_3OF$: Theory: 338.1669; Found: 338.1679.

Example B-78

7-(4-fluorobenzoyl)amino-4-(dimethyl)amino-10H-cyclohepta[7,6-b]indole hydrochloride To a solution of 0.165 gm (0.489 mMol) 7-(4-fluorobenzoyl)amino-4-amino-10H-cyclohepta[7,6-b]indole in 15 mL tetrahydrofuran were added 1.96 mL (3.9 mMol) 2N sodium hydroxide followed by 104 μL (1.223 mMol) methyl mesylate and the resulting mixture was stirred at room temperature for 18 hours. The reaction mixture was diluted with 100 mL dichloromethane and was then washed with 1N sodium hydroxide. The remaining organics were dried over magnesium sulfate and then concentrated under reduced pressure. The residue was subjected to radial chromatography (silica gel, 1 mm), eluting with 88.5:10:1.5 dichloromethane:methanol:ammonium hydroxide. Fractions containing the desired compound were concentrated under reduced pressure to give 0.035 gm (19%) 7-(4-fluorobenzoyl)amino-4-(dimethyl)amino-10H-cyclohepta-[7,6-b]indole. The corresponding hydrochloride salt was prepared to give the title compound.

m.p.=198° C.

Exact Mass: Calculated for: $C_{22}H_{25}N_3OF$: Theory: 366.1982; Found: 366.1991.

Example B-79

7-(benzyloxycarbonyl)amino-4-amino-10H-cyclohepta[7,6-b]indole hydrochloride

Beginning with 1.61 gm (3.36 mMol) of a mixture of 7-(benzyloxycarbonyl)amino-3- and 4-(1-phthalimidoyl)-10H-cyclohepta[7,6-b]indole, 0.527 gm (44.9%) 7-(benzyloxycarbonyl)amino-4-amino-10H-cyclohepta[7,6-b]indole were prepared by the procedure described in detail in EXAMPLE B-49 The corresponding hydrochloride salt was prepared to give the title compound.

m.p. =201–203° C.
MS(m/e) 350(M$^+$)

Example B-80

7-(benzyloxycarbonyl)amino-4-(dimethyl)amino-10H-cyclohepta[7,6-b]indole hydrobromide To a solution of 0.276 gm (0.79 mMol) 7-(benzyloxycarbonyl)amino-4-amino-10H-cyclohepta[7,6-b]indole in 10 mL acetonitrile were added 0.22 mL (1.5 mMol) triethylamine followed by 0.10 mL (1.6 mMol) iodomethane and the resulting solution stirred for 2 hours at room temperature. To the mixture were then added 3.2 mL (6.4 mMol) 2N sodium hydroxide and the reaction stirred for 48 hours at room temperature. The reaction mixture was then partitioned between dichloromethane and water. The organic phase was dried over sodium sulfate and concentrated under reduced pressure. The residue was subjected to silica gel chromatography, eluting with 88:10:2 dichloromethane:methanol:ammonium hydroxide. Fractions containing product were combined and concentrated under reduced pressure to give 0.056 gm (19%) 7-(benzyloxycarbonyl)amino-4-(dimethyl)-amino-10H-cyclohepta[7,6-b]indole. The corresponding hydrobromide salt was prepared to give the title compound.

m.p.=91–93° C.
Exact Mass: Calculated for: $C_{23}H_{28}N_3O_2$: Theory: 378.2182; Found: 378.2199.

Example B-81

7-hydroxy-4-amino-10H-cyclohepta[7,6-b]indole 7-benzyloxy-4-amino-10H-cyclohepta[7,6-b]indole Beginning with 1.19 gm (2.73 mMol) of a mixture of 7-benzyloxy-3- and 4-(1-phthalimidoyl)-10H-cyclohepta[7,6-b]indole, 0.334 gm (40%) 7-benzyloxy-4-amino-10H-cyclohepta-[7,6-b]indole were prepared by the procedure described in detail in EXAMPLE B-78
Hydrogenolysis Beginning with 0.166 gm (0.54 mMol) 7-benzyloxy-4-amino-10H-cyclohepta[7,6-b]indole, 0.054 gm (46%) of the title compound were prepared by the procedure described in detail in EXAMPLE B-63.

m.p.=215° C. (decomp.)
Exact Mass: Calculated for: $C_{13}H_{17}N_2O$: Theory: 217.1341; Found: 217.1306.

Example B-82

7-hydroxy-4-(methyl)amino-10H-cyclohepta[7,6-b]indole hydrochloride 7-benzyloxy-4-(t-butyloxycarbonyl)amino-10H-cyclohepta[7,6-b]indole To a solution of 1.08 gm (3.52 mMol) 7-benzyloxy-4-amino-10H-cyclohepta[7,6-b]indole in 30 mL tetrahydrofuran were added 1.85 mL 2N sodium hydroxide followed by 0.808 gm (3.7 mMol) di(t-butyl)dicarbonate and the mixture was stirred for 1 hour at room temperature. The reaction mixture was concentrated under reduced pressure and the residue partitioned between dichloromethane and water. The organic phase was separated, dried over sodium sulfate and concentrated unde reduced pressure. The residue was subjected to silica gel chromatography, eluting with 30% hexane in ethyl acetate. Fractions containing product were combined and concentrated under reduce pressure to give 1.37 gm (96%) of the desired compound.

7-benzyloxy-4-(methyl)amino-10H -cyclohepta[7,6-b]indole

A solution of 1.37 gm (3.37 mMol) 7-benzyloxy-4-(t-butyloxycarbonyl)amino-10H-cyclohepta[7,6-b]indole in 15 mL tetrahydrofuran was added dropwise over 30 minutes to a suspension of 0.47 gm (12.4 mMol) lithium aluminum hydride in 30 mL tetrahydrofuran at 0OC. After the addition was complete, the reaction mixture was stirred for 30 minutes at room temperature and then for 4 hours at reflux. The reaction mixture was cooled to room temperature and then to it was added sodium sulfate decahydrate until no more gas evolution was observed. The resulting suspension was filtered and the filter cake washed with dichloromethane. The combined filtrates were concentrated under reduced pressure and the residue subjected to silica gel chromatography, eluting with 10% methanol in dichloromethane containing 0.5% ammonium hydroxide. Fractions containing product were combined and concentrated under reduced pressure to give 0.97 gm (90%) of the desired compound.
Hydrogenolysis Beginning with 0.233 gm (0.73 mMol) 7-benzyloxy-4-(methyl)amino-10H -cyclohepta[7,6-b]indole, 0.104 gm (62%) of 7-hydroxy-4-(methyl)amino-10H-cyclohepta[7,6-b]indole were prepared by the procedure described in detail in EXAMPLE B-73. The corresponding hydrochloride was prepared and crystallized from ethanol/diethyl ether to give the title compound.

m.p.=262° C. (decomp.)
Exact Mass: Calculated for: $C_{14}H_{19}N_2O$: Theory: 231.1497; Found: 231.1487.

Example B-83

7-hydroxy-4-(dimethyl)amino-10H-cyclohepta[7,6-b]indole hydrochloride 7-benzyloxy-4-(dimethyl)amino-10H-cyclohepta[7,6-b]indole Beginning with 0.483 gm (1.5 mMol) 7-benzyloxy-4-(methyl)amino-10H-cyclohepta[7,6-b]indole, 0.410 gm (82%) of the desired product were prepared by the acylation/hydride reduction sequence described in detail in EXAMPLE B-82.
Hydrogenolysis Beginning with 0.405 gm (1.21 mMol) 7-benzyloxy-4-(dimethyl)amino-10H-cyclohepta[7,6-b]indole, 0.305 gm (90%) of, 7-hydroxy-4-(dimethyl)amino-10H-cyclohepta[7,6-b]indole were prepared by the procedure described in detail in EXAMPLE B-63. The corresponding hydrochloride was prepared and crystallized from ethanol/diethyl ether to give the title compound.

m.p.=186–194° C.
Exact Mass: Calculated for: $C_{15}H_{21}N_2O$: Theory: 245.1654; Found: 245.1655.

Example B-84

7-hydroxy-4-(ethyl)amino-10H-cyclohepta[7,6-b]indole hydrochloride

Beginning with 0.288 gm (0.94 mMol) 7-benzyloxy-4-amino-10H-cyclohepta[7,6-b]indole, 0.140 gm (69%) of 7-hydroxy-4-(ethyl)-amino-10H-cyclohepta[7,6-b]indole were prepared by the procedure described in detail in EXAMPLE B-35, except that the reaction mixture was heated to 60° C. during the course of the reaction. The corresponding hydrochloride was prepared and crystallized from ethanol/diethyl ether to give the title compound.

m.p.=270° C. (decomp.)

MS(m/e): 245(M$^+$)

Calculated for $C_{15}H_{20}N_2O.HCl$: Theory: C, 64.16; H, 7.54; N, 9.98. Found: C, 64.46; H, 7.54; N, 9.94.

Example B-85

N,N-diethyl-6-hydroxy-3-aminomethyl-1,2,3,4-tetrahydro-9H-carbazole hydrochloride

N,N-diethyl-6-benzyloxy-3-carboxamido-1,2,3,4-tetrahydro-9H-carbazole

To a solution of 0.322 gm (1.00 mMol) 6-benzyloxy-3-carboxy-1,2,3,4-tetrahydro-9H-carbazole in 2.5 mL tetrahydrofuran at 0° C. were added a solution of 96.0 µL (1.10 mMol) oxalyl chloride in 1.5 mL tetrahydrofuran dropwise followed by 73 µL (0.90 mMol) pyridine. The reaction mixture was allowed to stir at room temperature for 3 hours. The reaction mixture was then concentrated under reduced pressure and the residue redissolved in 15 mL tetrahydrofuran. This solution was then cooled to 0° C. and to it was added a solution of 145 µL diethylamine in 1.5 mL tetrahydrofuran dropwise. The resulting solution was stirred at room temperature for 18 hours. The reaction mixture was then partitioned between saturated aqueous potassium carbonate and dichloromethane. The organic phase was washed well with 2N sodium hydroxide, dried over magnesium sulfate and concentrated under reduced pressure. The residue was subjected to silica gel chromatography, eluting with 98:2 dichloromethane:methanol. Fractions containing product were combined and concentrated under reduced pressure to give 0.155 gm (41%) of the desired compound.

N,N-diethyl-6-benzyloxy-3-aminomethyl-6-benzyloxy-1,2,3,4-tetrahydro-9H-carbazole A solution of 0.368 gm (0.978 mMol) N,N-diethyl-6-benzyloxy-3-carboxamido-1,2,3,4-tetrahydro-9H-carbazole in 15 mL tetrahydrofuran were added dropwise to a suspension of 56.0 mg (1.47 mMol) lithium aluminum hydride in 10 mL tetrahydrofuran at 0° C. The reaction was stirred for 2.5 hours at room temperature after the addition was complete. The reaction mixture was then again cooled to 0° C. and 100 mg sodium sulfate decahydrate were added. After 2 hours the reaction mixture was diluted with dichloromethane, dried over magnesium sulfate and concentrated under reduced pressure to give the desired compound. Hydrogenolysis Beginning with 0.354 gm (0.978 mMol) N,N-diethyl-6-benzyloxy-3-aminomethyl-1,2,3,4-tetrahydro-9H-carbazole, 0.145 gm (55%) of N,N-diethyl-6-hydroxy-3-aminomethyl-1,2,3,4-tetrahydro-9H-carbazole were prepared by the procedure described in detail in EXAMPLE B-63. The corresponding hydrochloride salt was prepared to give the title compound.

m.p.=240° C. (decomp.)

Calculated for $C_{17}H_{24}N_2O.HCl$: Theory: C, 66.11; H, 8.16; N, 9.07. Found: C, 66.38; H, 8.27; N, 8.81.

Example B-86

N-methyl-6-hydroxy-3-aminomethyl-1,2,3,4-tetrahydro-9H-carbazole hydrochloride Beginning with 1.00 gm 6-benzyloxy-3-carboxy-1,2,3,4-tetrahydro-9H-carbazole, 0.195 gm (27%) of N-methyl-6-hydroxy-3-aminomethyl-1,2,3,4-tetrahydro-9H-carbazole were prepared by the procedure described in detail in EXAMPLE B-85. The corresponding hydrochloride salt was prepared to give the title compound.

m.p.=145–146° C.

Exact Mass: Calculated for: $C_{14}H_{18}N_2O$: Theory: 231.1497; Found: 231.1485.

Example B-87

N,N-dimethyl-6-hydroxy-3-aminomethyl-1,2,3,4-tetrahydro-9H-carbazole

Beginning with 1.00 gm 6-benzyloxy-3-carboxy-1,2,3,4-tetrahydro-9H-carbazole, 0.141 gm (18%) of the title compound were prepared by the procedure described in detail in EXAMPLE B-85.

m.p.=107–108° C.

Calculated for $C_{15}H_{20}N_2O$: Theory: C, 73.73; H, 8.25; N, 11.47. Found: C, 73.95; H, 8.49; N, 11.32.

Example B-88

N,N-dipropyl-6-hydroxy-3-aminomethyl-1,2,3,4-tetrahydro-9H-carbazole hydrochloride Beginning with 1.00 gm 6-benzyloxy-3-carboxy-1,2,3,4-tetrahydro-9H-carbazole, 0.096 gm (10%) of N,N-dipropyl-6-hydroxy-3-aminomethyl-1,2,3,4-tetrahydro-9H-carbazole were prepared by the procedure described in detail in EXAMPLE B-85. The corresponding hydrochloride salt was prepared to give the title compound.

m.p.=261–263° C. (decomp.)

Calculated for $C_{19}H_{28}N_2O.HCl$: Theory: C, 67.74; H, 8.68; N, 8.31. Found: C, 67.51; H, 8.77; N, 8.22.

Example B-89

N-ethyl-N-propyl-6-hydroxy-3-aminomethyl-1,2,3,4-tetrahydro-9H-carbazole hydrochloride Beginning with 0.811 gm 6-benzyloxy-3-carboxy-1,2,3,4-tetrahydro-9H-carbazole, 0.189 gm (16%) of N-ethyl-N-propyl-6-hydroxy-3-aminomethyl-1,2,3,4-tetrahydro-9H-carbazole were prepared by the procedure described in detail in EXAMPLE B-85, except that the hydrogenolysis was performed at 50° C. The corresponding hydrochloride salt was prepared to give the title compound.

m.p.>220° C (decomp.)

MS(m/e): 286(M$^+$)

Calculated for $C_{18}H_{26}N_2O.HCl$: Theory: C, 66.96; H, 8.43; N, 8.68. Found: C, 66.68; H, 8.24; N, 8.60.

General Procedure for the Coupling of Carboxylic Acids with 6-amino-3-(dimethyl)amino-1 2,3,4-tetrahydro-9H-carbazole To a suspension of 4–5 equivalents of polymer bound 1-ethyl-3-(3-dimethylaminopropyl)carbodiimide (Desai, et al., *Tetrahedron Letters*, 34(48), 7685 (1993)) in chloroform are added 1 equivalent of 6-amino-3-(dimethyl)amino-1,2,3,4-tetrahydro-9H-carbazole and 2–3 equivalents of the carboxylic acid. The reaction is agitated until the reaction is complete, heat may be applied if necessary. The resin is removed by filtration and the product isolated by evaporation of solvent. This procedure is illustrated by Examples 90–108.

Example B-90

6-(2-thienoyl)amino-3-(dimethyl)amino-1,2,3,4-tetrahydro-9H-carbazole

Beginning with 8.7 mg (0.038 mMol) 6-amino-3-(dimethyl)amino-1,2,3,4-tetrahydro-9H-carbazole and 11.0 mg (0.086 mMol) thiophene-2-carboxylic acid, 6.0 mg (47%) of the title compound were recovered as a beige solid.

MS(m/e): 339($M^+$)

Example B-91

6-(5-methylfur-3-oyl)amino-3-(dimethyl)amino-1,2,3,4-tetrahydro-9H-carbazole

Beginning with 8.7 mg (0.038 mMol) 6-amino-3-(dimethyl)amino-1,2,3,4-tetrahydro-9H-carbazole and 10.0 mg (0.090 mMol) 5-methylfuran-3-carboxylic acid, 7.9 mg (62%) of the title compound were recovered as a beige solid.

MS(m/e): 337($M^+$)

Example B-92

6-(2-methylfur-3-oyl)amino-3-(dimethyl)amino-1,2,3,4-tetrahydro-9H-carbazole

Beginning with 8.7 mg (0.038 mMol) 6-amino-3-(dimethyl)amino-1,2,3,4-tetrahydro-9H-carbazole and 11 mg (0.087 mMol) 2-methylfuran-3-carboxylic acid, 12.7 mg (99%) of the title compound were recovered as a beige solid.

MS(m/e): 337($M^+$)

Example B-93

6-(5-methylfur-2-oyl)amino-3-(dimethyl)amino-1,2,3,4-tetrahydro-9H-carbazole

Beginning with 8.7 mg (0.038 mMol) 6-amino-3-(dimethyl)amino-1,2,3,4-tetrahydro-9H-carbazole and 11.0 mg (0.084 mMol) 5-methylfuran-2-carboxylic acid, 6.8 mg (53%) of the title compound were recovered as a beige solid.

MS(m/e): 337($M^+$)

Example B-94

6-(3-methylthien-2-oyl)amino-3-(dimethyl)amino-1,2,3,4-tetrahydro-9H-carbazole

Beginning with 8.7 mg (0.038 mMol) 6-amino-3-(dimethyl)amino-1,2,3,4-tetrahydro-9H-carbazole and 12 mg (0.084 mMol) 3-methylthiophene-2-carboxylic acid, the title compound was recovered as a beige solid.

Example B-95

6-(4-methoxythien-3-oyl)amino-3-(dimethyl)amino-1,2,3,4-tetrahydro-9H-carbazole

Beginning with 8.7 mg (0.038 mMol) 6-amino-3-(dimethyl)amino-1,2,3,4-tetrahydro-9H-carbazole and 13.0 mg (0.082 mMol) 5-methoxythiophene-2-carboxylic acid, 9.6 mg (69%) of the title compound were recovered as a beige solid.

MS(m/e): 369($M^+$)

Example B-96

6-(2,6-dichlorobenzoyl)amino-3-(dimethyl)amino-1,2,3,4-tetrahydro-9H-carbazole

Beginning with 8.7 mg (0.038 mMol) 6-amino-3-(dimethyl)amino-1,2,3,4-tetrahydro-9H-carbazole and 18.0 mg (0.086 mMol) 2,6-dichlorobenzoic acid, 2.4 mg (16%) of the title compound were recovered as a beige solid.

MS(m/e): 401($M^+$)

Example B-97

6-(3-furoyl)amino-3-(dimethyl)amino-1,2,3,4-tetrahydro-9H-carbazole

Beginning with 8.7 mg (0.038 mMol) 6-amino-3-(dimethyl)amino-1,2,3,4-tetrahydro-9H-carbazole and 10.0 mg (0.089 mMol) furan-3-carboxylic acid, 5.8 mg (47%) of the title compound were recovered as a beige solid.

MS(m/e): 324($M^+$)

Example B-98

6-(3-thienoyl)amino-3-(dimethyl)amino-1,2,3,4-tetrahydro-9H-carbazole

Beginning with 8.7 mg (0.038 mMol) 6-amino-3-(dimethyl)amino-1,2,3,4-tetrahydro-9H-carbazole and 11.0 mg (0.086 mMol) thiophene-3-carboxylic acid, 6.8 mg (53%) of the title compound were recovered as a beige solid.

MS(m/e): 339($M^+$)

Example B-99

6-(4-methansulfonylbenzoyl)amino-3-(dimethyl)amino-1,2,3,4-tetrahydro-9H-carbazole Beginning with 8.7 mg (0.038 mMol) 6-amino-3-(dimethyl)amino-1,2,3,4-tetrahydro-9H-carbazole and 17.0 mg (0.085 mMol) 4-methanesulfonylbenzoic acid, 2.0 mg (13%) of the title compound were recovered as a beige solid.

MS(m/e): 411($M^+$)

Example B-100

6-(4-pyridinecarbonyl)amino-3-(dimethyl)amino-1,2,3,4-tetrahydro-9H-carbazole

Beginning with 9.2 mg (0.040 mMol) 6-amino-3-(dimethyl)amino-1,2,3,4-tetrahydro-9H-carbazole and 12.5 mg (0.101 mMol) 4-pyridinecarboxylic acid, 5.0 mg (37%) of the title compound were recovered as a beige solid.

MS(m/e): 334($M^+$)

Example B-101

6-(3-pyridinecarbonyl)amino-3-(dimethyl)amino-1,2,3,4-tetrahydro-9H-carbazole

Beginning with 9.2 mg (0.040 mMol) 6-amino-3-(dimethyl)amino-1,2,3,4-tetrahydro-9H-carbazole and 12.5 mg (0.101 mMol) 3-pyridinecarboxylic acid, 7.2 mg (54%) of the title compound were recovered as a beige solid.

MS(m/e): 334($M^+$)

Example B-102

6-(2-chloro-3-pyridinecarbonyl)amino-3-(dimethyl)amino-1,2,3,4-tetrahydro-9H-carbazole Beginning with 9.2 mg (0.040 mMol) 6-amino-3-(dimethyl)amino-1,2,3,4-tetrahydro-9H-carbazole and 15.9 mg (0.101 mMol) 2-chloro-3-pyridinecarboxylic acid, the title compound was recovered as a white solid.

Example B-103

6-(6-chloro-3-pyridinecarbonyl)amino-3-(dimethyl)amino-1,2,3,4-tetrahydro-9H-carbazole Beginning with 9.2 mg (0.040 mMol) 6-amino-3-(dimethyl)amino-1,2,3,4-tetrahydro-9H-carbazole and 4.9 mg (0.101 mMol) 6-chloro-3-pyridinecarboxylic acid, 4.9 mg (31%) of the title compound were recovered as a brown solid.

MS(m/e): 369(M$^+$)

Example B-104

6-(cyclopentanoyl)amino-3-(dimethyl)amino-1,2,3,4-tetrahydro-9H-carbazole

Beginning with 9.2 mg (0.040 mMol) 6-amino-3-(dimethyl)amino-1,2,3,4-tetrahydro-9H-carbazole and 11.6 mg (0.101 mMol) cyclopentanecarboxylic acid, 7.5 mg (53%) of the title compound were recovered as a light beige solid.

MS(m/e): 326(M$^+$)

Example B-105

6-(4-nitrobenzoyl)amino-3-(dimethyl)amino-1,2,3,4-tetrahydro-9H-carbazole

Beginning with 9.2 mg (0.040 mMol) 6-amino-3-(dimethyl)amino-1,2,3,4-tetrahydro-9H-carbazole and 16.9 mg (0.101 mMol) 4-nitrobenzoic acid, 1.2 mg (8%) of the title compound were recovered as a dark brown solid.

MS(m/e): 379(M$^+$)

Example B-106

6-(4-trifluoromethylbenzoyl)amino-3-(dimethyl)amino-1,2,3,4-tetrahydro-9H-carbazole Beginning with 9.2 mg (0.040 mMol) 6-amino-3-(dimethyl)amino-1,2,3,4-tetrahydro-9H-carbazole and 19.2 mg (0.101 mMol) 4-trifluoromethylbenzoic acid, 5.7 mg (35%) of the title compound were recovered as a beige solid.

MS(m/e): 401(M$^+$)

Example B-107

6-(4-cyanobenzoyl)amino-3-(dimethyl)amino-1,2,3,4-tetrahydro-9H-carbazole

Beginning with 9.2 mg (0.040 mMol) 6-amino-3-(dimethyl)amino-1,2,3,4-tetrahydro-9H-carbazole and 14.9 mg (0.101 mMol) 4-cyanobenzoic acid, 6.7 mg (47%) of the title compound were recovered as a beige solid.

MS(m/e): 358(M$^+$)

Example B-108

6-(4-acetylbenzoyl)amino-3-(dimethyl)amino-1,2,3,4-tetrahydro-9H-carbazole

Beginning with 9.2 mg (0.040 mMol) 6-amino-3-(dimethyl)amino-1,2,3,4-tetrahydro-9H-carbazole and 16.6 mg (0.101 mMol) 4-acetylbenzoic acid, 7.8 mg (52%) of the title compound were recovered as a beige solid.

MS(m/e): 375(M$^+$)

Example B-109

6-(dimethylsulfonyl)amino-3-(dimethyl)amino-1,2,3,4-tetrahydro-9H-carbazole hydrochloride To a solution of 0.197 gm (0.86 mMol) 6-amino-3-(dimethyl)amino-1,2,3,4-tetrahydro-9H-carbazole in 8 mL dichloromethane at 0° C. were added 0.14 mL (6.18 mMol) pyridine followed by 0.14 mL (6.51 mMol) dimethylsulfamoyl chloride. The reaction mixture was stirred at 0° C. for 2 hours and was then allowed to warm to room temperature over 2 hours. After storage at 0° C. for 18 hours, the reaction mixture was partitioned between 2N sodium hydroxide and 8% methanol in dichloromethane. The phases were separated and the aqueous phase was extracted several times with 8% methanol in dichloromethane. The organic phases were combined, dried over sodium sulfate and concentrated under reduced pressure. The residue was subjected to silica gel chromatography, eluting with dichloromethane containing 15% methanol and 2% ammonium hydroxide. Fractions containing product were combined and concentrated under reduced pressure to give 0.20 gm (69%) of 6-(dimethylsulfonyl)amino-3-(dimethyl)amino-1,2,3,4-tetrahydro-9H-carbazole. The corresponding hydrochloride salt was prepared to give the title compound which crystallized from ethanol/diethyl ether.

m.p.=217–219° C.

Exact Mass: Calculated for: $C_{16}H_{25}N_4O_2S$. Theory: 337.1698; Found: 337.1688.

Example B-110

(R)- and (S)-N-((R)-(+)-α-methyl-(4-nitrophenyl)ethyl)-6-bromo-2-amino-1,2,3,4-tetrahydro-9H-carbazole Reductive Animation To a solution of 20.0 gm (100.9 mMol) 1,4-cyclohexanedione mono-(2,2-dimethyl)propane-1,3-diol monoketal in 250 mL methanol were added 35.0 gm (172.7 mMol) R-(+)-α-methyl-(4-nitrophenyl)ethylamine hydrochloride, 25.0 gm (398 mMol) sodium cyanoborohydride and 10 mL acetic acid. The reaction mixture was allowed to stir for 18 hours at room temperature. To the reaction mixture were then added an additional charge of 25.0 gm (398 mMol) sodium cyanoborohydride hydride and the reaction mixture stirred for an additional 18 hours at room temperature. The reaction mixture was then diluted with dilute aqueous tartaric acid and the solution exhaustively extracted with dichloromethane. The remaining aqueous phase was made basic with aqueous sodium hydroxide and extracted well with dichloromethane. These dichloromethane extracts were combined, dried over sodium sulfate and concentrated under reduced pressure to give 33.7 gm (96%) of N-((R)-(+)-α-methyl-(4-nitrophenyl)ethyl)-4-aminocyclohexanone 2,2-dimethylpropane-1,2-diol ketal as a brownish yellow oil.

MS(m/e): 348(M$^+$)

Ketal Deprotection

A solution of 33.42 gm (95.91 mMol) N-((R)-(+)-α-methyl-(4-nitrophenyl)ethyl)-4-aminocyclohexanone 2,2-dimethylpropane-1,2-diol ketal in 250 mL 98% formic acid was heated to 40° C. for 66 hours. The reaction mixture was concentrated under reduced pressure to a volume of about 50 mL and was then treated with aqueous potassium carbonate.

The basic aqueous mixture was extracted well with dichloromethane. These organic phases were combined, dried over sodium sulfate and concentrated under reduced pressure to give 22.36 gm (89%) N-((R)-(+)-α-methyl-(4-nitrophenyl)ethyl)-4-aminocyclohexanone as a brown oil.

Preparation B—of Phenylhydrazone

To a solution of 22.3 gm (85.01 mMol) N-((R)-(+)-α-methyl-(4-nitrophenyl)ethyl)-4-aminocyclohexanone in 375 mL ethanol were added 19.0 gm (85.0 mMol) 4-bromophenylhydrazine hydrochloride and 6.73 gm (85.1 mMol) pyridine. The reaction mixture was heated to 80° C. for 48 hours. The reaction mixture was cooled to room temperature and concentrated under reduced pressure. The residue was dissolved in dichloromethane and the organic solution was washed sequentially with aqueous potassium carbonate and saturated aqueous sodium chloride. The remaining organics were dried over sodium sulfate and concentrated under reduced pressure to give 31.66 gm (86%) N-((R)-(+)-α-methyl-(4-nitrophenyl)-ethyl)-4-aminocyclohexanone 4-bromophenylhydrazone as a brown solid.

Fischer Indole Reaction

A solution of 31.66 gm (73.4 mMol) N-((R)-(+)-α-methyl-(4-nitrophenyl)ethyl)-4-aminocyclohexanone 4-bromophenylhydrazone in 500 mL 3.7 M ethanolic hydrogen chloride was stirred at reflux for 18 hours. The reaction mixture was cooled to room temperature and was then concentrated under reduced pressure. The residue was partitioned between 1 N sodium hydroxide and dichloromethane. The aqueous phase was extracted well with dichloromethane. The organic phases were combined, dried over sodium sulfate and concentrated under reduced pressure. The residue was subjected to silica gel chromatography, eluting with 5% methanol in dichloromethane which contained 1% ammonium hydroxide.

(S)-(−)-N-((R)-(+)-α-methyl-(4-nitrophenyl)ethyl)-6-bromo-3-amino-1,2,3,4-tetrahydro-9H-carbazole The fastest eluting diastereomer was recovered as 9.47 gm (31%) of a reddish-brown oil.

MS(m/e): 415($M^+$)

IR(CHCl$_3$): 3471, 2970, 2926, 2845, 1522, 1471, 1348, 857 cm$^{-1}$ $[\alpha]_D^{20}$(c=10, methanol): −122.3°

Calculated for $C_{20}H_{20}N_3O_2Br$: Theory: C, 57.78; H, 4.87; N, 10.14. Found: C, 58.23; H, 5.03; N, 10.12.

(R)-(+)-N-((R)-(+)-α-methyl-(4-nitrophenyl)ethyl)-6-bromo-3-amino-1,2,3,4-tetrahydro-9H-carbazole The slower eluting diastereomer was recovered as 8.13 gm (27%) of pale green crystals.

MS(m/e): 415($M^+$)

IR(CHCl$_3$): 3471, 3012, 2970, 2952, 2846, 1522, 1471, 1348, 857 cm$^{-1}$ $[\alpha]_D^{20}$(c=10, methanol): +337.9°

Calculated for $C_{20}H_{20}N_3O_2Br$: Theory: C, 57.78; H, 4.87; N, 10.14. Found: C, 58.26; H, 5.03; N, 9.93.

X-Ray crystallography determined that the slower eluting diastereomer was of the S,R absolute configuration.

Example B-111

(R)-(+)-6-bromo-2-(dimethyl)amino-1,2,3,4-tetrahydro-9H-carbazole hydroiodide

Quaternization

To a solution of 5.00 gm (12.1 mMol) (R)-(+)-N-((R)-(+)-α-methyl-(4-nitrophenyl)ethyl)-6-bromo-2-amino-1,2,3,4-tetrahydro-9H-carbazole in 150 mL acetonitrile were added 10.0 mL iodomethane followed by 5.0 gm potassium carbonate. The mixture was stirred for 2 days at room temperature and then for 18 hours at reflux. The reaction mixture was then cooled to room temperature and the resulting yellow precipitate filtered, washed with methanol and dried under reduced pressure to give 3.65 gm (53%) (R)-(+)-N,N-dimethyl-N-((R)-(+)-α-methyl-(4-nitrophenyl)ethyl)-6-bromo-2-amino-1,2,3,4-tetrahydro-9H-carbazole iodide as a yellow solid.

Calculated for $C_{22}H_{25}N_3O_2BrI$: Theory: C, 46.34; H, 4.42; N, 7.37. Found: C, 46.22; H, 4.41; N, 7.30.

Hydrogenolysis

A mixture of 0.70 gm (1.23 mMol) (R)-(+)-N,N-dimethyl-N-((R)-(+)-α-methyl-(4-nitrophenyl)ethyl)-6-bromo-2-amino-1,2,3,4-tetrahydro-9H-carbazole iodide and 0.20 gm sulfided platinum on carbon in 150 mL methanol were hydrogenated at room temperature for 18 hours at an initial hydrogen pressure of 40 p.s.i. The reaction mixture was then degassed and warmed to effect methanolysis. The reaction mixture was filtered and concentrated under reduced pressure to give 0.471 gm (91%) of the title compound as a light yellow solid.

m.p.=252° C.

MS(m/e): 293($M^+$)

IR(KBr): 3271, 3016, 2924, 2842, 2737, 2709, 1469, 1460, 1435, 1308, 793 cm$^{-1}$ $[\alpha]_D^{20}$(c=10, methanol): +54.7°

Calculated for $C_{14}H_{18}N_2BrI$: Theory: C, 39.93; H, 4.31; N, 6.65. Found: C, 39.87; H, 4.19; N, 6.38.

Example B-112

Resolution of Racemic 6-bromo-2-(dimethyl)amino-1,2,3,4-tetrahydro-9H-carbazole

To a solution of 5.0 gm (17.06 mMol) 6-bromo-2-(dimethyl)amino-1,2,3,4-tetrahydro-9H-carbazole in 200 mL of warm ethyl acetate was added a solution of 6.59 gm (17.06 mMol) di-p-toluoyl-D-tartaric acid in 100 mL ethyl acetate with mixing. After standing for 4 hours, the resulting precipitate was filtered and dried to give 12.0 gm of the salt. A suspension of 1.0 gm of this solid was heated to boiling in 10 mL of methanol. This mixture was then cooled to room temperature and allowed to stand for 18 hours. The remaining solid was filtered and dried to give 0.65 gm. This solid was again suspended in 10 mL boiling methanol and allowed to cool and stand for 18 hours to give 0.52 gm of solid after filtration and vacuum drying. This solid was partitioned between dichloromethane and dilute aqueous sodium hydroxide. The phases were separated and the organics were washed with saturated aqueous sodium chloride, dried over sodium sulfate and concentrated under reduced pressure. The residue was dissolved in 7 mL of toluene and allowed to stand at room temperature for 18 hours. The solution was filtered to remove the solid which had formed and the filtrate was concentrated under reduced pressure to give 0.133 gm of an oil which gradually crystallized.

m.p.=131–3° C.

$[\alpha]_D^{20}$(c=10, methanol): −83°

The two methanol filtrates were combined and concentrated under reduced pressure to give 0.33 gm of a glass. The glass was treated as described above to give 0.121 gm of an oil which gradually crystallized.

m.p.=131–4° C.

$[\alpha]_D^{20}$(c=10, methanol): +78°

Example B-113

(R)-(+)-6-(t-butyloxycarbonyl)amino-2-(dimethyl)amino-1,2,3,4-tetrahydro-9H-carbazole Beginning with (R)-(+)-6-bromo-2-(dimethyl)amino-1,2,3,4-tetrahydro-9H-carbazole, the title compound was prepared by the procedure described in Preparation B-III.

$[\alpha]_D^{20}$(c=10, methanol): +73°

Example B-114

(S)-(−)-6-(t-butyloxycarbonyl)amino-2-(dimethyl)amino-1,2,3,4-tetrahydro-9H-carbazole Beginning with (S)-(−)-6-bromo-2-(dimethyl)amino-1,2,3,4-tetrahydro-9H-carbazole, the title compound was prepared by the procedure described in Preparation B-III.

$[\alpha]_D^{20}$(c=10, methanol): −72°

Example B-115

(R)-(+)-6-(4-fluorobenzoyl)amino-2-(dimethyl)amino-1,2,3,4-tetrahydro-9H-carbazole Beginning with (R)-(+)-6-bromo-2-(dimethyl)amino-1,2,3,4-tetrahydro-9H-carbazole, the title compound was prepared by the procedure described in Example B-52.

$[\alpha]_D^{20}$(c=10, methanol): +75°

Example B-116

(S)-(−)-6-(4-fluorobenzoyl)amino-2-(dimethyl)amino-1,2,3,4-tetrahydro-9H-carbazole Beginning with (S)-(−)-6-bromo-2-(dimethyl)amino-1,2,3,4-tetrahydro-9H-carbazole, the title compound was prepared by the procedure described in Example B-52.

$[\alpha]_D^{20}$(c=10, methanol): −70°

A further class of serotonin 5-HT$_{1F}$ receptor agonists are 5-substituted-3-aminoethylindoles of Formula VI:

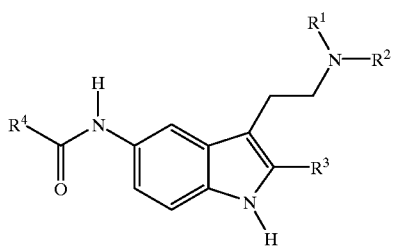

VI in which

R$^1$ is C$_1$–C$_4$ alkyl;

R$^2$ is C$_1$–C$_4$ alkyl, cycloalkyl-(C$_1$–C$_3$ alkylene), aryl-(C$_1$–C$_3$ alkylene), or heteroaryl-(C$_1$–C$_3$ alkylene);

R$^3$ is C$_1$–C$_4$ alkyl or phenyl;

R$^4$ is C$_1$–C$_4$ alkyl, C$_3$–C$_7$ cycloalkyl, phenyl, substituted phenyl, biphenylyl, naphthyl, or a heterocycle; and pharmaceutically acceptable acid addition salts thereof.

The general chemical terms used in the above formula above have their usual meanings. For example, the terms "alkyl, alkoxy and alkylthio" include such groups as methyl, ethyl, n-propyl, isopropyl, n-butyl, isobutyl, sec-butyl, tert-butyl, and the like. The term "cycloalkyl" includes cyclopropyl, cyclobutyl, cyclopentyl, cyclohexyl, and cycloheptyl. The term "acyl" includes formyl, acetyl, propanoyl, butanoyl, and 2-methylpropanoyl. The term "(C$_1$–C$_4$ alkyl) sulfonyl" includes methanesulfonyl, ethanesulfonyl, propanesulfonyl, isopropanesulfonyl, butanesulfonyl and the like. The term "halogen" includes fluoro, chloro, bromo and iodo.

The term "substituted phenyl" is taken to mean a phenyl ring substituted with 1 to 3 substitutents independently selected from the group consisting of halogen, C$_1$–C$_4$ alkoxy, C$_1$–C$_4$ alkylthio, C$_1$–C$_4$ alkyl, C$_1$–C$_4$ alkylsulfonyl, nitro, trifluoromethyl, N-(C$_1$–C$_4$ acyl)amino, N-(C$_1$–C$_4$ alkyl)-N-(C$_1$–C$_4$ acyl)amino, N,N-di(C$_1$–C$_4$ alkyl)amino and C$_1$–C$_4$ alkoxycarbonyl.

The term "heterocycle" is taken to mean a thienyl, benzothienyl, furyl, benzofuryl, isobenzofuryl, pyrrolyl, 1-(C$_1$–C$_3$ alkyl)pyrrolyl, imidazolyl, pyrazolyl, 1-(C$_1$–C$_3$ alkyl)pyrazolyl, pyridyl, pyrazinyl, pyrimidinyl, pyridazinyl, indolyl, indazolyl, quinolinyl, isoquinolinyl, quinoxalinyl, thiazolyl, benzothiazolyl, oxazolyl, benzoxazolyl, 1,3-benzodioxolyl, 1,4-benzodioxanyl, isoxazolyl, benzisoxazolyl, oxadiazolyl or triazolyl. Each of these rings may be substituted with up to two substituents independently selected from the group consisting of halo, hydroxy, C$_1$–C$_4$ alkyl, C$_1$–C$_4$ alkoxy, C$_1$–C$_4$ alkylthio, hydroxy substituted (C$_1$–C$_4$ alkylene), cyano, carboxamido, nitro, amino, or di(C$_1$–C$_4$ alkyl)amino.

The term "cycloalkyl-(C$_1$–C$_3$ alkylene)" is taken to be an alkylene chain of 1–3 carbon atoms to which is bonded a cycloalkyl moiety.

The term "aryl-(C$_1$–C$_3$ alkylene)" is taken to be an alkylene chain of 1–3 carbon atoms which may be monosubstituted with a methyl group and to which is bonded a phenyl or substituted phenyl moiety.

The term "heteroaryl-(C$_1$–C$_3$ alkylene)" is taken to be an alkylene chain of 1–3 carbon atoms optionally monosubstituted with a methyl group and to which is bonded a heterocycle.

The synthetic methodology required to prepare the compounds of Formula VI is well known to those skilled in the art. An appropriate carboxylic acid, or carboxylic acid equivalent, is reacted with 4-nitroaniline to prepare the corresponding amide, which is then hydrogenated to give the corresponding N-(4-aminophenyl)amide. The N-(4-aminophenyl)amide is then diazotized and reduced to give the corresponding hydrazine which is then combined with an appropriate ketone under Fischer indole cyclization conditions to give the compounds of the present invention. This chemistry is illustrated in Synthetic Scheme C-I where X is chloro, bromo, hydroxy or R$^4$C(O) and R$^1$, R$^2$, R$^3$ and R$^4$ are as described supra.

Synthetic Scheme C-I

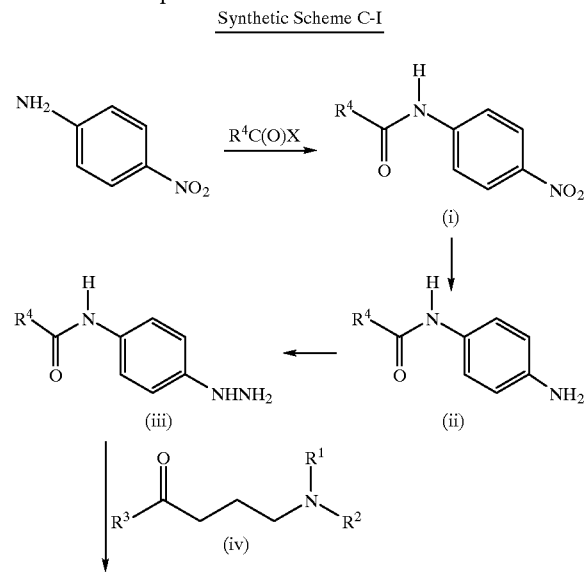

-continued

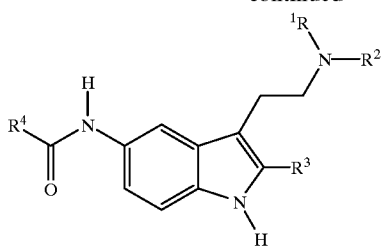

An appropriate carboxylic acid chloride, bromide or anhydride, optionally in the presence of an acylation catalyst such as dimethylaminopyridine, is reacted with 4-nitroaniline in the presence of a suitable base. Suitable bases include amines typically used as acid scavengers, such as pyridine or triethylamine, or commercially available polymer bound bases such as polyvinylpyridine. When an excess of the carboxylic acid chloride, bromide or anhydride is necessary to ensure complete reaction of the amine, a polymer bound primary or secondary amine, such as an aminomethylated polystyrene, may be conveniently added to react with the excess reagent. Isolation of products from reactions where a polymer bound reagent has been used is greatly simplified, requiring only filtration of the reaction mixture to remove the polymer bound constituents, and then concentration of the filtrate under reduced pressure to isolate the desired product. The product from these reactions may be purified chromatographically or recrystallized from a suitable solvent if desired.

Alternatively, the 4-nitroaniline is reacted with an appropriate carboxylic acid in the presence of a typical peptide coupling reagent such as N,N'-carbonyldiimidazole (CDI), N,N'-dicyclohexylcarbodiimide (DCC) and 1-(3-dimethylaminopropyl)-3-ethylcarbodiimide hydrochloride (EDC). Polymer supported forms of carbodiimide peptide coupling reagents are useful for the preparation of compounds of the present invention. A polymer supported form of EDC, for example, has been described (*Tetrahedron Letters*, 34(48), 7685 (1993)).

The carboxylic acid coupling reactions employing these reagents are performed at about ambient to about 45° C., for from about three hours to about three days. Typically, the product may be isolated by washing the reaction with water and concentrating the remaining organics under reduced pressure. As discussed supra, isolation of products from reactions where a polymer bound reagent has been used is greatly simplified, requiring only filtration of the reaction mixture and then concentration of the filtrate under reduced pressure. The N-(4-nitro)phenylamides (i) from these reactions may be used directly in a subsequent step or first purified chromatographically or recrystallized from a suitable solvent prior to further reaction if desired.

The N-(4-nitro)phenylamides (i) are converted to the corresponding N-(4-amino)phenylamides (ii) by catalytic hydrogenation. These hydrogenations are performed using a precious metal catalyst, such as platinum oxide or platinum or palladium on a support such as carbon. The hydrogenation solvent may consist of a lower alkanol, such as methanol or ethanol, tetrahydrofuran, or a mixed solvent system of tetrahydrofuran and ethyl acetate. The hydrogenation may be performed at an initial hydrogen pressure of 20–80 p.s.i., preferably from 50–60 p.s.i., at 0–60° C., preferably at ambient temperature to 40° C., for 1 hour to 3 days. Additional charges of hydrogen may be required to drive the reaction to completion depending on the specific substrate. The N-(4-amino)phenylamides (ii) prepared in this manner are isolated by removal of the catalyst by filtration followed by concentration of the reaction solvent under reduced pressure. The product recovered may be used directly in a subsequent step or further purified by chromatography, or by recrystallization from a suitable solvent.

The N-(4-amino)phenylamides (ii) are then diazotized by suspension in concentrated hydrochloric acid cooled to about 0° C. To this cooled mixture is then added an aqueous solution of sodium or potassium nitrite at such a rate as to maintain the temperature of the reaction mixture at or below 5° C. The reaction is stirred at about 0° C for from about 10 minutes to about an hour. The resulting diazonium salt mixture is reduced directly by dropwise addition to a solution of stannous chloride in concentrated hydrochloric acid at such a rate as to maintain the temperature of the reaction mixture at about 0° C. A solid forms which is recovered by filtration. The solid is partitioned between an aqueous base, such as sodium hydroxide, and a suitable water immiscible solvent, such as diethyl ether or ethyl acetate. The hydrazine (iii) is isolated by separating the water immiscible phase, drying over an appropriate dessicant, such as sodium or magnesium sulfate, and removing the solvent under reduced pressure. The product recovered may be used directly in a subsequent step or further purified by chromatography, or by recrystallization from a suitable solvent.

The hydrazines (iii) are then reacted with an appropriate aminoketone (iv) under standard Fischer indolization conditions as described in Robinson, *The Fischer Indole Synthesis,* Wiley, New York, 1983; Hamel, et al., *Journal of Organic Chemistry,* 59, 6372 (1994); and Russell, et al., *Organic Preparations and Procedures International,* 17, 391 (1985), to provide the compounds of Formula VI.

The aminoketones required for the Fischer indolization step are available by methods well known to the skilled artisan. One method is to react an appropriate haloketone, optionally protected as the corresponding ketal, with an appropriate amine under standard alkylating conditions as described in Synthetic Scheme C-II, where halo is chloro, bromo or iodo and $R^1$, $R^2$ and $R^3$ are as defined supra.

Synthetic Scheme C-II

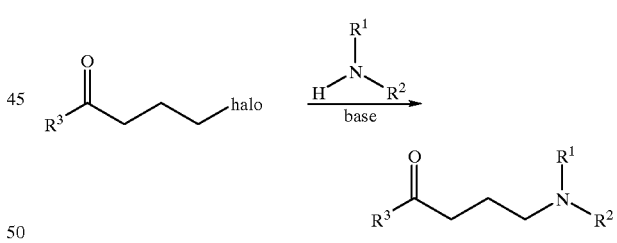

The halo ketone and an appropriate amine are combined in a suitable solvent, such as acetonitrile, dichloromethane, acetone or dimethylformamide, in the presence of a suitable base, such as potassium or sodium carbonate. The resulting mixture is heated to a temperature from about 40° C. to about 120° C. until all reactants are consumed. These reactions typically require about 2 hours to about 2 days to reach completion. The desired aminoketones may be isolated by filtering the reaction mixture to remove any solids which have formed, and concentrating the reaction mixture under reduced pressure. Alternatively, the reaction mixture may be partitioned between water and a water immiscible solvent such as dichloromethane. The water immiscible phase is then concentrated under reduced pressure to provide the desired compound. The aminoketones isolated in this manner may be used directly in a subsequent step or purified by distillation, chromatography, or crystallization from a suitable solvent if desired.

The skilled artisan will appreciate that certain of the compounds of Formula VI, while useful as $5\text{-HT}_{1F}$ agonists in their own right, are also useful intermediates for the preparation of other compounds of Formula VI. The amide moiety, for example, may be hydrolyzed to provide the corresponding 5-amino-3-(2-aminoethyl)-1H-indole. This hydrolysis may be performed by heating a mixture of the amide and 6N hydrochloric acid at reflux for about 4 hours to about 2 days. After cooling, the aqueous phase is extracted with a water immiscible solvent, such as toluene, benzene or hexane. This water immiscible phase is discarded and then the remaining aqueous phase is treated with a base such as sodium, potassium or ammonium hydroxide, until the solution has reached a pH of about 11 or 12. The aqueous phase is then extracted with a water immiscible solvent like dichloromethane. These organic extracts are concentrated under reduced pressure to give the corresponding 5-amino-3-(2-aminoethyl)-1H-indole which may be reacted directly or first purified by chromatography or recrystallization from an appropriate solvent. The 5-amino-3-(2-aminoethyl)-1H-indole may then be treated with appropriate carboxylic acids or derivatives as described supra to provide additional compounds of the invention.

Alternatively, the 2-substituted-5-amino-3-(2-aminoethyl)-1H-indoles may be prepared by the reaction of 4-nitrophenylhydrazine with an appropriate aminoketone (Synthetic Scheme II) under the Fischer indolization conditions described by Robinson, *The Fischer Indole Synthesis*, Wiley, New York, 1983; Hamel, et al., *Journal of Organic Chemistry* 59, 6372 (1994); and Russell, et al., *Organic Preparations and Procedures International*, 17, 391 (1985). The resulting 5-nitroindole may be hydrogenated to give the same 2-substituted-5-amino-3-(2-aminoethyl)-1H-indoles prepared by the hydrolysis described supra.

Additionally, when compounds of Formula VI where $R^2$ is benzyl or 1-phenylethyl are subjected to the hydrogenation conditions described supra, the $R^2$ substituent is removed by hydrogenolysis to give the corresponding secondary amines (III). These secondary amines (III) may then be alkylated with an appropriate alkylating agent under the alkylation conditions described supra, or they may be subjected to reductive alkylation conditions in the presence of an appropriate aldehyde, to provide additional compounds of the invention. This chemistry is illustrated in Synthetic Scheme C-III where $R^{2'}$—CHO represents an aldehyde which, after undergoing the reductive alkylation reaction provides the moiety $R^2$, and $R^1$, $R^2$, $R^3$ and $R^4$ are as defined supra.

Synthetic Scheme C-III

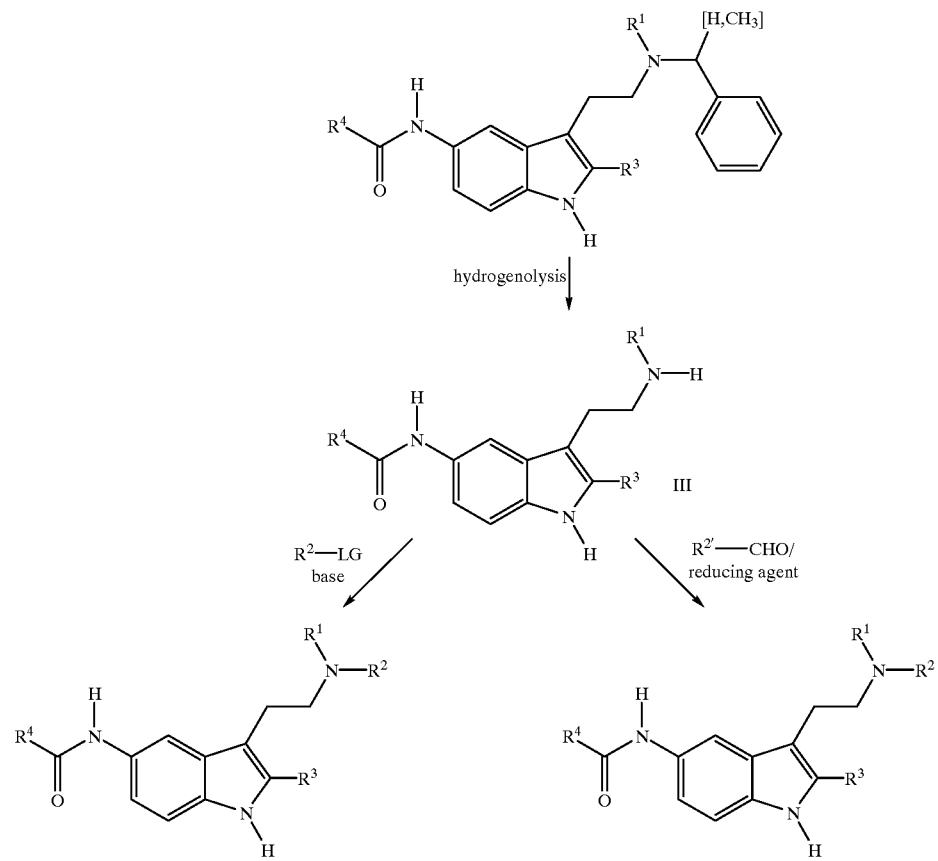

The leaving group (LG) of the alkylating agents may be chloro, bromo, iodo, methanesulfonyloxy, trifluoromethanesulfonyloxy, 2,2,2-trifluoroethanesulfonyloxy, benzenesulfonyloxy, p-bromobenzenesulfonyloxy, p-nitrobenzenesulfonyloxy or p-toluenesulfonyloxy, all of which are useful for the preparation of compounds of Formula VI. The specific alkylating agent employed is determined by its commercial availability or a convenient synthesis from commercially available starting materials. The preferred alkylating agents for synthesis of compounds of this invention are those where the leaving group is chloro, bromo or methanesulfonyloxy.

The reductive alkylation may be performed by combining an appropriate aldehyde, $R^{2'}$—CHO, with the secondary amine (III) in a suitable solvent. Suitable solvents include tetrahydrofuran, dichloromethane, and the lower alkanols such as methanol, ethanol or isopropanol. The preferred solvents for the reductive alkylation include methanol and dichloromethane. The aldehyde and amine are typically combined in the presence of an acid, such as acetic acid or hydrogen chloride, and a hydride reducing agent. Suitable hydride reducing agents include sodium borohydride, sodium cyanoborohydride or sodium triacetoxyborohydride. Preferred hydride reducing agents include sodium cyanoborohydride or sodium triacetoxyborohydride. The combined reagents are allowed to react at a temperature of from about ambient to the reflux temperature of the solvent. The reaction time is typically from about 3 to about 24 hours. The compounds of the invention may then be isolated and purified by standard extractive workups. The compounds may be further purified by chromatography or crystallization from suitable solvents if desired.

The skilled artisan will appreciate that, as an alternative to the reductive alkylation conditions described supra, the aldehyde and amine may be combined in a suitable solvent in the presence of acid. The resulting imine may then be reduced in a separate step by addition of a suitable hydride reducing agent, or by subjecting the reaction mixture to hydrogenation conditions using standard precious metal catalysts. The use of hydrogenation conditions is limited to those compounds of Formula VI which are stable to the reaction conditions.

Alternatively, the compounds of Formula VI may be prepared from the appropriate 2-substituted-5-nitroindoles. These starting indoles may be prepared by reaction of 4-nitrophenylhydrazine and a ketone of formula $R^3$—C(O) $CH_3$, where $R^3$ is as defined supra, under Fischer indolization conditions as described by Robinson, *The Fischer Indole Synthesis*, Wiley, New York, 1983; Hamel, et al., *Journal of Organic Chemistry*, 59, 6372 (1994); and Russell, et al., *Organic Preparations and Procedures International*, 17, 391 (1985). The 3-(2-aminoethyl) functionality may then be introduced by chemistry described by Larsen et al. (U.S. Pat. No. 3,472,870 (Oct. 14, 1969)), Smythies (U.S. Pat. No. 3,915,990 (Oct. 28, 1975)), and Stanley et al. (U.S. Pat. No. 4,803,218 (Feb. 7, 1989)), herein incorporated by reference.

The following preparations and examples further illustrate the synthesis of the compounds of Formula VI. The compounds described below were identified by various standard analytical techniques as stated in the individual preparations and examples.

The aminoketones required for the synthesis of the compounds of the invention are available by the procedures described in Preparations C-I and C-II.

Preparation C-I

N,N-dimethyl-5-amino-2-pentanone

A mixture of 21.77 gm (180.5 mMol) 5-chloro-2-pentanone, 13.40 gm (164.3 mMol) dimethylamine hydrochloride and 50.0 gm (361.8 mMol) potassium carbonate in 150 mL acetonitrile was stirred at room temperature for 2 days and then at reflux for 2 hours. The reaction mixture was then cooled to room temperature and partitioned between water and dichloromethane. The phases were separated and the aqueous phase again extracted with dichloromethane. All organic phases were combined, dried over sodium sulfate and concentrated under reduced pressure. The residue was subjected to silica gel chromatography, eluting with dichloromethane containing 10% methanol and 1% ammonium hydroxide. Fractions shown to contain product were combined and concentrated under reduced pressure. The desired product was then isolated by distillation.

Preparation C-II

N-methyl-N-((S)-1-phenylethyl)-5-amino-2-pentanone

A mixture of 5.85 mL (38.87 mMol) 5-chloro-2-pentanone ethylene glycol ketal, 5.0 gm (37.0 mMol) N-methyl-(S)-1-phenylethylamine, 6.14 gm (37.0 mMol) potassium iodide and 15.33 gm (110.9 mMol) potassium carbonate in 100 mL acetonitrile was stirred at room temperature for 2 days. The reaction mixture was then filtered and the filtrate concentrated under reduced pressure. The residue was dissolved in 50 mL acetone to which was added 50 mL 2N hydrochloric acid. The resulting solution was stirred at room temperature for 3 hours and was then concentrated to half volume under reduced pressure. The residue was extracted diethyl ether (2×50 mL) and the remaining aqueous solution was treated with 5N sodium hydroxide until the pH of the solution was about 13. This aqueous phase was now extracted with dichloromethane (3×60 mL). The organic phases were combined, dried over sodium sulfate and concentrated under reduced pressure. The residue was subjected to silica gel chromatography, eluting with 40% ethyl acetated in hexane. Fractions shown to contain product were combined and concentrated under reduced pressure to give 7.11 gm (88%) of the desired compound.

The phenylhydrazines required are available by the procedure described in Preparation C-III.

Preparation C-III

N-(4-fluorobenzoyl)-4-aminophenylhydrazine

Acylation of 4-nitroaniline

To a stirred suspension of 19.83 gm (143.56 mMol) 4-nitroaniline in 150 mL dichloromethane and 12.9 mL (159.5 mMol) pyridine at 0° C. were slowly added 24.5 gm (154.8 mMol) 4-fluorobenzoyl chloride. The reaction mixture was then stirred for 15 minutes at 0° C., at which time the reaction mixture became homogeneous, and then for an hour at room temperature. To this mixture were then added 100 mL water and the solid which formed was collected by filtration. The filter cake was washed with hexane (80 mL) followed by water (100 mL) and it was then dried under vacuum at 60° C. to give 34.1 gm (91%) N-(4-fluorobenzoyl)-4-nitroaniline.

m.p.=117–118° C.

MS(FD): m/e=260 ($M^+$)

Catalytic Hydrogenation of Nitro Group

A mixture of 32.25 gm (124 mMol) N-(4-fluorobenzoyl)-4-nitroaniline and 3.2 gm platinum on carbon in 500 mL tetrahydrofuran was hydrogenated at room temperature for 18 hours with an initial pressure of 60 p.s.i. The reaction mixture was then filtered and the filtrate concentrated under reduced pressure to give 22.45 gm (79%) of N-(4-fluorobenzoyl)-4-aminoaniline.

Diazotization and Reduction

To a stirred suspension of 5.0 gm (23.9 mMol) N-(4-fluorobenzoyl)-4-aminoaniline in 42 mL concentrated hydrochloric acid at 0° C. was added dropwise a solution of 1.65 gm (23.9 mMol) sodium nitrite in 30 mL water. The mixture was stirred for 10 minutes after the addition was complete and was then added dropwise to a solution of 19.6 gm (86.87 mMol) stannous chloride dihydrate in 40 mL concentrated hydrochloric acid at 0° C. The resultant white paste was stirred vigorously for 1 hour and was then filtered under vacuum. The solid which formed was then partitioned between ethyl acetate and 5N sodium hydroxide, the phases separated and the aqueous phase was extracted again with dichloromethane. The combined organic phases were combined, dried over sodium sulfate and concentrated under reduced pressure to give 3.8 gm (72%) of the title compound as a brown solid which is suitable for use in subsequent reactions without further purification.

Preparation C-IV 2-methyl-5-amino-3-(2-[N',N'-dimethylamino]ethyl)-1H-indole

A mixture of 1.58 gm (4.65 mMol) N-[2-methyl-3-(2-[N',N'-dimethylamino]ethyl)-1H-indol-5-yl]-4-fluorobenzamide and 40 mL 6N hydrochloric acid was heated to reflux for 4 hours. The reaction mixture was then cooled to room temperature and then extracted with benzene (3×70 mL). The remaining aqueous phase was treated with 5N sodium hydroxide until pH of about 11–12. The aqueous phase was then extracted with dichloromethane (4×100 mL) and the combined extracts were dried over sodium sulfate and concentrated under reduced pressure. The resultant residue was subjected to silica gel chromatography, eluting with dichloromethane containing 14% methanol and 1% ammonium hydroxide. Fractions shown to contain product were combined and concentrated under reduced pressure to give 0.71 gm (70%) of the title compound.

MS(FAB): m/e=218 (M+1)

Preparation C-V

N-[2-methyl-3-(2-[N'-methylamino]ethyl)-1H-indol-5-yl]-4-fluorobenzamide

A mixture of 3.74 gm (8.7 mMol) N-[2-methyl-3-(2-[N'-methyl-N'-((S)-1-phenylethyl)amino]ethyl)-1H-indol-5-yl]-4-fluorobenzamide, 5.49 gm (87.1 mMol) ammonium formate and 0.4 gm 5% palladium on carbon in 80 mL methanol was heated at reflux for 45 minutes. The reaction mixture was filtered and the filtrate concentrated under reduced pressure. The resulting residue was subjected to flash chromatography, eluting with dichloromethane containing 20% methanol and 2% ammonium hydroxide. Fractions shown to contain product were combined and concentrated under reduced pressure to give 1.93 gm (68%) of the title compound.

m.p.=82–84° C.

MS: Exact Mass: Calculated for: $C_{19}H_{21}N_3OF=326.1669$ Found: 326.1694.

The Fischer indolization conditions described in detail in Example C-1 are typical of those required to prepare the compounds of Formula VI.

Example C-1

N-[2-methyl-3-(2-[N',N'-dimethylamino]ethyl)-1H-indol-5-yl]-4-fluorobenzamide hydrochloride To a solution of 4.00 gm (30.96 mMol) N,N-dimethyl-5-amino-2-pentanone and 7.74 gm (31.6 mMol) N-(4-fluorobenzoyl)-4-aminohydrazine in 140 mL ethanol were added 1.5 mL concentrated hydrochloric acid and the reaction mixture was heated to reflux for 3 hours. At this point an additional 6.0 mL concentrated hydrochloric acid were added and the reflux was continued for 36 hours. The reaction mixture was concentrated to half volume under reduced pressure and was then diluted with 300 mL dichloromethane followed by 200 mL 1N sodium hydroxide. The organic phase was separated and the aqueous phase extracted dichloromethane (4×150 mL). The organic extracts were combined, dried over sodium sulfate and concentrated under reduced pressure. The resulting residue was subjected to flash chromatography, eluting with dichloromethane containing 10% methanol and 1% ammonium hydroxide. Fractions shown to contain product were combined and concentrated under reduced pressure to give 6.66 gm (63.3%) N-[2-methyl-3-(2-[N',N'-dimethylamino]ethyl)-1H-indol-5-yl]-4-fluorobenzamide. This material was converted to the hydrochloride salt, crystallizing from ethanol/diethyl ether to give the title compound.

m.p.=281–283° C.

MS: m/e=339 (M+)

Calculated for $C_{20}H_{22}N_3OF \cdot HCl$: Theory: C, 63.91; H, 6.17; N, 11.18. Found: C, 64.20; H, 6.29; N, 11.20.

Example C-2

N-[2-methyl-3-(2-[N'-methyl-N'-((S)-1-phenylethyl)amino]-ethyl)-1H-indol-5-yl]-4-fluorobenzamide Following the procedure described in detail in Example 1, 5.32 gm (21.7 mMol) N-(4-fluorobenzoyl)-4-aminohydrazine and 2.95 gm (13.45 mMol) N-methyl-N-((S)-1-phenylethyl)-5-amino-2-pentanone were reacted together to prepare 4.988 gm (86%) of the title compound.

m.p.=65–67° C.

MS: m/e=430 (M+1)

Calculated for $C_{27}H_{28}N_3OF$: Theory: C, 75.50; H, 6.57; N, 9.78. Found: C, 75.28; H, 6.75; N, 9.93.

Example C-3

N-[2-methyl-3-(2-[N'-methyl-N'-ethylamino]ethyl)-1H-indol-5-yl]-4-fluorobenzamide A mixture of 0.125 gm (0.38 mMol) N-[2-methyl-3-(2-(N'-methylamino)ethyl)-1H-indol-5-yl]-4-fluorobenzamide, 0.033 mL (0.41 mMol) ethyl iodide and 0.105 gm (0.76 mMol) potassium carbonate in 4.0 mL acetonitrile was heated at reflux for 6 hours. To the reaction mixture were then added 15.0 mL water and 40 mL dichloromethane. The phases were separated and the aqueous phase was extracted with dichloromethane (2×15 mL). The combined organic phases were dried over sodium sulfate and concentrated under reduced pressure. The resultant residue was subjected to silica gel chromatography, eluting with dichloromethane containing 10% methanol and 1% ammonium hydroxide. Fractions shown to contain product were combined and concentrated under reduced pressure to give 0.040 gm (30%) of the title compound.

m.p.=79–81° C.

MS: m/e=353 (M+)

The compounds of Examples C-4 to C-8 were prepared by the procedure described in detail in Example C-3.

Example C-4

N-(2-methyl-3-(2-(N'-methyl-N'-propylamino)ethyl)-1H-indol-5-yl)-4-fluorobenzamide hydrobromide Beginning with 0.152 gm (0.467 mMol) N-[(2-methyl-3-(2-[N'-methylamino]ethyl)-1H-indol-5-yl]-4- fluorobenzamide and 0.068 mL (0.697 mMol) 1-iodopropane, 0.071 gm (41%) of N-[2-methyl-3-(2-[N'-methyl-N-propylamino]ethyl)-1H-indol-5-yl]-4-fluorobenzamide were prepared. The hydrobromide salt was prepared and crystallized from ethanol/diethyl ether to give the title compound.

m.p.=97–99° C.

MS: Exact Mass: Calculated for: $C_{22}H_{27}N_3OF$=368.2138. Found: 368.2135.

Example C-5

N-[2-methyl-3-(2-[N'-methyl-N'-cyclohexylmethylamino]ethyl)-1H-indol-5-yl]-4-fluorobenzamide hydrobromide Beginning with 0.166 gm (0.51 mMol) N-[2-methyl-3-(2-[N'-methylamino]ethyl-1H-indol-5-yl]-4-fluorobenzamide and 0.085 mL (0.61 mMol) cyclohexylmethyl bromide, 0.170 gm (79%) of N-[2-methyl-3-(2-[N'-methyl-N'-cyclopropylmethylamino]-ethyl)-1H-indol-5-yl]-4-fluorobenzamide were prepared. The hydrobromide salt was prepared and crystallized from ethanol/diethyl ether to give the title compound.

m.p.=195–198° C.

MS: m/e=422 (M+1)

Calculated for $C_{26}H_{33}N_3OF \cdot HBr$: Theory: C, 62.05; H, 6.62; N, 8.36. Found: C, 61.96; H, 6.71; N, 8.25.

Example C-6

N-[2-methyl-3-(2-[N'-methyl-N'-(2-phenylethyl)amino]ethyl)-1H-indol-5-yl]-4-fluorobenzamide hydrochloride Beginning with 0.215 gm (0.66 mMol) N-[(2-methyl-3-(2-[N'-methylamino]ethyl)-1H-indol-5-yl]-4-fluorobenzamide and 0.12 mL (0.88 mMol) 2-phenylethyl bromide, 0.225 gm (80%) of N-[2-methyl-3-(2-[N'-methyl-N'-(2-phenylethyl)amino]ethyl)-1H-indol-5-yl]-4-fluorobenzamide were prepared. The hydrochloride salt was prepared and crystallized from ethanol/diethyl ether to give the title compound.

m.p.=221–223° C.

MS: m/e=429 (M+)

Calculated for $C_{27}H_{28}N_3OF \cdot HCl$: Theory: C, 69.59; H, 6.27; N, 9.02. Found: C, 69.84; H, 6.38; N, 8.87.

Example C-7

N-[2-methyl-3-(2-[N'-methyl-N'-(4-pyridinylmethyl)amino]ethyl)-1H-indol-5-yl]-4-fluorobenzamide Beginning with 0.139 gm (0.43 mMol) N-[2-methyl-3-(2-[N'-methylamino]ethyl)-1H-indol-5-yl]-4-fluorobenzamide and 0.100 gm (0.61 mMol) 4-pyridinylmethyl chloride hydrochloride, 0.145 gm (82%) of the title compound were prepared.

m.p.=77–80° C.

MS: m/e=416 (M+)

MS: Exact Mass: Calculated for $C_{25}H_{26}N_4OF$=417.2091. Found: 417.2082.

Example C-8

N-[2-methyl-3-(2-[N'-methyl-N'-(2-[1-methylpyrazol-4-yl]ethyl)amino]ethyl)-1H-indol-5-yl]-4-fluorobenzamide hydrochloride Beginning with 0.209 gm (0.64 mMol) N-[(2-methyl-3-(2-[N'-methylamino]ethyl)-1H-indol-5-yl]-4-fluorobenzamide and 0.195 gm (0.95 mMol) 2-(1-methyl-1H-pyrazol-3-yl)-1-methanesulfonyloxyethane, 0.204 gm (74%) of N-[2-methyl-3-(2-[N'-methyl-N'-(2-[1-methylpyrazol-4-yl]ethyl)amino]ethyl)-1H-indol-5-yl]-4-fluorobenzamide were recovered. This compound was converted to its hydrochloride salt, crystallizing from ethanol/diethyl ether to give the title compound.

m.p.=84–86° C.

MS: m/e=433 (M+)

MS: Exact Mass: Calculated for $C_{25}H_{29}N_5OF$=434.2356. Found: 434.2363.

Example C-9

N-[2-methyl-3-(2-[N',N'-dimethylamino]ethyl)-1H-indol-5-yl]-4-methylthiobenzamide A mixture of 0.142 gm (0.65 mMol) 2-methyl-5-amino-3-(2-(N',N'-dimethylamino)ethyl)-1H-indole, 0.12 gm (0.71 mMol) 4-methylthiobenzoic acid, 0.096 gm (0.71 mMol) 1-hydroxybenzotriazole, and 0.136 gm (0.71 mMol) 1-(3-dimethylaminopropyl)-3-ethylcarbodiimide hydrochloride (EDC) in 8 mL dimethylformamide and 1 mL tetrahydrofuran was stirred at room temperature under a nitrogen atmosphere for 48 hours. The the mixture were then added 50 mL dichloromethane, 5 mL 2N sodium hydroxide and 50 mL water. The phases were separated and the aqueous layer extracted with dichloromethane (3×30 mL). The combined organic layers were dried over sodium sulfate and concentrated under reduced pressure. The resulting residue was subjected to silica gel chromatography, eluting with dichloromethane containing 10% methanol and 1% ammonium hydroxide. Fractions shown to contain product were combined and concentrated under reduced pressure to give 0.134 gm (56%) of the title compound.

m.p.=87–91° C.

MS: Exact Mass: Calculated for $C_{21}H_{26}N_3OS$=368.1797. Found: 368.1808.

The compounds of Examples C-10 to C-14 were prepared by the procedure described in detail in Example C-9.

Example C-10

N-[2-methyl-3-(2-[N',N'-dimethylamino]ethyl)-1H-indol-5-yl]-4-(N'',N''-dimethylamino)benzamide Beginning with 0.148 gm (0.68 mMol) 2-methyl-5-amino-3-(2-(N',N'-dimethylamino)ethyl)-1H-indole and 0.113 gm (0.68 mMol) 4-(dimethylamino)benzoic acid, 0.080 gm (32%) of the title compound were recovered.

m.p.=100–104° C. (decomp.)

Calculated for $C_{22}H_{28}N_4O$: Theory: C, 72.50; H, 7.74; N, 15.37. Found: C, 72.26; H, 7.56; N, 15.33.

Example C-11

N-[2-methyl-3-(2-[N',N'-dimethylamino]ethyl)-1H-indol-5-yl]-4-acetamidobenzamide Beginning with 0.130 gm (0.598 mMol) 2-methyl-5-amino-3-(2-(N',N'-dimethylamino)ethyl)-1H-indole and 0.107 gm (0.598 mMol) 4-acetamidobenzoic acid, 0.130 gm (32%) of the title compound were recovered.

m.p.=134–138° C.

MS: Exact Mass: Calculated for $C_{22}H_{26}N_4O_2$=379.2134. Found: 379.2142.

Example C-12

N-[2-methyl-3-(2-[N',N'-dimethylamino]ethyl)-1H-indol-5-yl]-4-(2-methyl-4-fluoro)benzamide Beginning with 0.148 gm (0.68 mMol) 2-methyl-5-amino-3-(2-(N',N'-dimethylamino)ethyl)-1H-indole and 0.115 gm (0.75 mMol) 2-methyl-4-fluorobenzoic acid, 0.206 gm (86%) of the title compound were recovered.

m.p.=71–75° C.

MS: Exact Mass: Calculated for $C_{21}H_{25}N_3OF=354.1982$. Found: 354.1993.

Example C-13

N-[2-methyl-3-(2-[N',N'-dimethylamino]ethyl)-1H-indol-5-yl]-2-acetamido-4-fluorobenzamide Beginning with 0.150 gm (0.69 mMol) 2-methyl-5-amino-3-(2-(N',N'-dimethylamino)ethyl)-1H-indole and 0.150 gm (0.76 mMol) 2-acetamido-4-fluorobenzoic acid, 0.150 gm (55%) of the title compound were recovered.

m.p.=183–187° C.

MS(FD): m/e=396 (M$^+$)

Example C-14

N-[2-methyl-3-(2-[N',N'-dimethylamino]ethyl)-1H-indol-5-yl]-6-fluoropyridin-3-ylcarboxamide Beginning with 0.141 gm (0.65 mMol) 2-methyl-5-amino-3-(2-(N',N'-dimethylamino)ethyl)-1H-indole and 0.101 gm (0.71 mMol) 6-fluoro-3-pyridinecarboxylic acid, 0.0935 gm (42%) of the title compound were recovered.

m.p.=165–168° C.

MS: Exact Mass: Calculated for $C_{19}H_{22}N_4OF=341.1778$. Found: 341.1783.

Example C-15

N-[2-methyl-3-(2-[N',N'-dimethylamino]ethyl)-1H-indol-5-yl]-2-chloro-4-fluorobenzamide hydrobromide To a stirred solution of 0.115 gm (0.66 mMol) 2-chloro-4-fluorobenzoic acid in 2 mL dimethylformamide were added 0.107 gm (0.66 mMol) carbonyldiimidazole (CDI) and immediate gas evolution was observed. The reaction mixture was stirred for 5 hours at room temperature and then 0.131 gm (0.60 mMol) 2-methyl-5-amino-3-(2-(N',N'-dimethylamino)ethyl)-1H-indole were added. The resulting mixture was stirred at room temperature for 72 hours. The reaction mixture was then concentrated under reduced pressure and the residue subjected to silica gel chromatography. The material isolated was further purified by silica gel chromatography, eluting with dichloromethane containing 7% methanol and 1% ammonium hydroxide. Fractions shown to contain product were combined and concentrated under reduced pressure to give 0.107 gm (43%) of N-[2-methyl-3-(2-[N',N'-dimethylamino]ethyl)-1H-indol-5-yl]-2-chloro-4-fluorobenzamide. The hydrobromide salt was formed and crystallized from ethanol/diethyl ether to give the title compound.

m.p.=66–68° C.

MS: m/e=373 (M$^+$)

Example C-16

N-[2-methyl-3-(2-[N',N'-dimethylamino]ethyl)-1H-indol-5-yl]-2,4-difluorobenzamide hydrochloride To a stirred solution of 0.135 gm (0.62 mMol) 2-methyl-5-amino-3-(2-(N',N'-dimethylamino)ethyl)-1H-indole in 6 mL dichloromethane and 0.2 mL pyridine at 0° C. were added 0.09 mL (0.73 mMol) 2,4-difluorobenzoyl chloride. The reaction mixture was warmed to room temperature and stirred for 2 hours at room temperature. The reaction mixture was then diluted with 20 mL dichloromethane and washed with 4 mL 2N sodium hydroxide. The organic phase was separated and the aqueous phase extracted again with dichloromethane. The organic phases were combined, dried over sodium sulfate and concentrated under reduced pressure. The residue was subjected to silica gel chromatography, eluting with dichloromethane containing 8% methanol and 1% ammonium hydroxide. Fractions shown to contain product were combined and concentrated under reduced pressure to give 0.110 gm (50%) of N-[2-methyl-3-(2-[N',N'-dimethylamino]ethyl)-1H-indol-5-yl]-2,4-difluorobenzamide. The hydrochloride salt was formed and crystallizing from ethanol/diethyl ether to give the title compound.

m.p.=269–271° C.

MS: m/e=357 (M$^+$)

Calculated for $C_{20}H_{21}N_3OF_2$: Theory: C, 60.99; H, 5.63; N, 10.67. Found: C, 61.24; H, 5.74; N, 10.67.

General Procedure for the Coupling of Carboxylic Acids with 5-amino-3-(2-(N',N'-dimethylamino)ethyl)-1H-indole To a suspension of 0.120 gm (0.11 mMol) of polymer bound 1-ethyl-3-(3-(1-pyrrolidinylpropyl)carbodiimide in 2 mL chloroform are added 6 mg (0.027 mMol) of 5-amino-3-(2-(N',N'-dimethylamino)ethyl)-1H-indole and 0.055 mMol of the desired carboxylic acid. The reaction is agitated for 48 hours at room temperature. The resin is removed by filtration and the product isolated by evaporation of solvent. This procedure is illustrated by Examples C-17 to C-34.

Example C-17

N-[2-methyl-3-(2-[N',N'-dimethylamino]ethyl)-1H-indol-5-yl]-isobutyramide

Beginning with 0.027 mMol of 2-methyl-5-amino-3-(2-(N',N'-dimethylamino)ethyl)-1H-indole and 0.055 mMol of isobutyric acid, the title compound was prepared in 60% yield.

MS: m/e=390 (M$^+$)

Example C-18

N-[2-methyl-3-(2-[N',N'-dimethylamino]ethyl)-1H-indol-5-yl]-cyclopropanecarboxylic amide Beginning with 0.027 mMol of 2-methyl-5-amino-3-(2-(N',N'-dimethylamino)ethyl)-1H-indole and 0.055 mMol of cyclopropanecarboxylic acid, the title compound was prepared in 65% yield.

Example C-19

N-[2-methyl-3-(2-[N',N'-dimethylamino]ethyl)-1H-indol-5-yl]-3-trifluoromethylbenzamide Beginning with 0.027 mMol of 2-methyl-5-amino-3-(2-(N',N'-dimethylamino)ethyl)-1H-indole and 0.055 mMol of 3-trifluoromethylbenzoic acid, the title compound was prepared in 55% yield.

MS: m/e=390 (M$^+$)

Example C-20

N-[2-methyl-3-(2-[N',N'-dimethylamino]ethyl)-1H-indol-5-yl]-3,5-dichlorobenzamide Beginning with 0.027 mMol of 2-methyl-5-amino-3-(2-(N',N'-dimethylamino)ethyl)-1H-indole and 0.055 mMol of 3,5-dichlorobenzoic acid, the title compound was prepared in 55% yield.

Example C-21

N-[2-methyl-3-(2-[N',N'-dimethylamino]ethyl)-1H-indol-5-yl]-2-methoxy-4-chlorobenzamide Beginning with 0.027 mMol of 2-methyl-5-amino-3-(2-(N',N'-dimethylamino)ethyl)-1H-indole and 0.055 mMol of 2-methoxy-4-chlorobenzoic acid, the title compound was prepared in 33% yield.
MS: m/e=386 (M$^+$)

Example C-22

N-[2-methyl-3-(2-[N',N'-dimethylamino]ethyl)-1H-indol-5-yl]-2-chloro-4-nitrobenzamide Beginning with 0.027 mMol of 2-methyl-5-amino-3-(2-(N',N'-dimethylamino)ethyl)-1H-indole and 0.055 mMol of 2-chloro-4-nitrobenzoic acid, the title compound was prepared in 27% yield.
MS: m/e=401 (M$^+$)

Example C-23

N-[2-methyl-3-(2-[N',N'-dimethylamino]ethyl)-1H-indol-5-yl]-2-furylcarboxamide

Beginning with 0.027 mMol of 2-methyl-5-amino-3-(2-(N',N'-dimethylamino)ethyl)-1H-indole and 0.055 mMol of 2-furylcarboxylic acid, the title compound was prepared in 67% yield.

Example C-24

N-[2-methyl-3-(2-[N',N'-dimethylamino]ethyl)-1H-indol-5-yl]-3-furylcarboxamide

Beginning with 0.027 mMol of 2-methyl-5-amino-3-(2-(N',N'-dimethylamino)ethyl)-1H-indole and 0.055 mMol of 3-furylcarboxylic acid, the title compound was prepared in 65% yield.

Example C-25

N-[2-methyl-3-(2-[N',N'-dimethylamino]ethyl)-1H-indol-5-yl]-5-methyl-2-furylcarboxamide Beginning with 0.027 mMol of 2-methyl-5-amino-3-(2-(N',N'-dimethylamino)ethyl)-1H-indole and 0.055 mMol of 5-methyl-2-furylcarboxylic acid, the title compound was prepared in 66% yield.
MS: m/e=326 (M$^+$)

Example C-26

N-[2-methyl-3-(2-[N',N'-dimethylamino]ethyl)-1H-indol-5-yl]-2-methyl-3-furylcarboxamide Beginning with 0.027 mMol of 2-methyl-5-amino-3-(2-(N',N'-dimethylamino)ethyl)-1H-indole and 0.055 mMol of 2-methyl-3-furylcarboxylic acid, the title compound was prepared in 32% yield.
MS: m/e=326 (M$^+$)

Example C-27

N-[2-methyl-3-(2-[N',N'-dimethylamino]ethyl)-1H-indol-5-yl]-5-methyl-3-furylcarboxamide Beginning with 0.027 mmol of 2-methyl-5-amino-3-(2-(N',N'-dimethylamino)ethyl)-1H-indole and 0.055 mMol of 5-methyl-3-furylcarboxylic acid, the title compound was prepared in 32% yield.
MS: m/e=326 (M$^+$)

Example C-28

N-[2-methyl-3-(2-[N',N'-dimethylamino]ethyl)-1H-indol-5-yl]-5-chloro-2-furylcarboxamide Beginning with 0.027 mMol of 2-methyl-5-amino-3-(2-(N',N'-dimethylamino)ethyl)-1H-indole and 0.055 mMol of 5-chloro-2-furylcarboxylic acid, the title compound was prepared in 42% yield.
MS: m/e=346 (M$^+$)

Example C-29

N-[2-methyl-3-(2-[N',N'-dimethylamino]ethyl)-1H-indol-5-yl]-3-thienylcarboxamide Beginning with 0.027 mMol of 2-methyl-5-amino-3-(2-(N',N'-dimethylamino)ethyl)-1H-indole and 0.055 mMol of 3-thienylcarboxylic acid, the title compound was prepared in 32% yield.
MS: m/e=328 (M$^+$)

Example C-30

N-[2-methyl-3-(2-[N',N'-dimethylamino]ethyl)-1H-indol-5-yl]-3-methyl-2-thienylcarboxamide Beginning with 0.027 mMol of 2-methyl-5-amino-3-(2-(N',N'-dimethylamino)ethyl)-1H-indole and 0.055 mMol of 3-methyl-2-thienylcarboxylic acid, the title compound was prepared in 50% yield.
MS: m/e=342 (M$^+$)

Example C-31

N-[2-methyl-3-(2-[N',N'-dimethylamino]ethyl)-1H-indol-5-yl]-5-methyl-2-thienylcarboxamide Beginning with 0.027 mMol of 2-methyl-5-amino-3-(2-(N',N'-dimethylamino)ethyl)-1H-indole and 0.055 mMol of 5-methyl-2-thienylcarboxylic acid, the title compound was prepared in 33% yield.

Example C-32

N-[2-methyl-3-(2-[N',N'-dimethylamino]ethyl)-1H-indol-5-yl]-5-bromo-2-thienylcarboxamide Beginning with 0.027 mMol of 2-methyl-5-amino-3-(2-(N',N'-dimethylamino)ethyl)-1H-indole and 0.055 mMol of 5-bromo-2-thienylcarboxylic acid, the title compound was prepared in 35% yield.

Example C-33

N-[2-methyl-3-(2-[N',N'-dimethylamino]ethyl)-1H-indol-5-yl]-5-chloro-2-thienylcarboxamide Beginning with 0.027 mMol of 2-methyl-5-amino-3-(2-(N',N'-dimethylamino)ethyl)-1H-indole and 0.055 mMol of 5-chloro-2-thienylcarboxylic acid, the title compound was prepared in 25% yield.
MS: m/e=362 (M$^+$)

Example C-34

N-[2-methyl-3-(2-[N',N'-dimethylamino]ethyl)-1H-indol-5-yl]-3-pyridinecarboxamide Beginning with 0.027 mMol of 2-methyl-5-amino-3-(2-(N',N'-dimethylamino)ethyl)-1H-indole and 0.055 mMol of 3-pyridine-carboxylic acid, the title compound was prepared in 33% yield.
MS: m/e=323 (M$^+$)

General Procedure for the Coupling of Carboxylic Acid Halides with 5-amino-3-(2-(N',N'-dimethylamino)ethyl)-1H-indole To a suspension of 0.041 gm (0.056 mMol) of polymer bound 4-(N,N-dimethylamino)pyridine in 2 mL chloroform are added 6 mg (0.027 mMol) of 2-methyl-5-amino-3-(2-(N',N'-dimethylamino)ethyl)-1H-indole and 0.035 mMol of the desired carboxylic acid halide. The reaction is agitated for 24 hours at room temperature. To the reaction mixture are then added 0.07 gm (0.056 mMol) aminomethylated polystyrene and the reaction agitated for an additional 24 hours. The resin is removed by filtration and the product isolated by evaporation of solvent. This procedure is illustrated by Examples C-35 to C-83.

Example C-35

N-[2-methyl-3-(2-[N',N'-dimethylamino]ethyl)-1H-indol-5-yl]acetamide

Beginning with 0.027 mMol of 2-methyl-5-amino-3-(2-(N',N'-dimethylamino)ethyl)-1H-indole and 0.035 mMol of acetyl chloride, the title compound was prepared in 50% yield.

MS: m/e=260 ($M^+$)

Example C-36

N-[2-methyl-3-(2-[N',N'-dimethylamino]ethyl)-1H-indol-5-yl]propanamide

Beginning with 0.027 mMol of 2-methyl-5-amino-3-(2-(N',N'-dimethylamino)ethyl)-1H-indole and 0.035 mMol of propanoyl chloride, the title compound was prepared in 73% yield.

MS: m/e=274 ($M^+$)

Example C-37

N-[2-methyl-3-(2-[N',N'-dimethylamino]ethyl)-1H-indol-5-yl]isobutyramide

Beginning with 0.027 mMol of 2-methyl-5-amino-3-(2-(N',N'-dimethylamino)ethyl)-1H-indole and 0.035 mMol of isobutyryl chloride, the title compound was prepared in 67% yield.

MS: m/e=288 ($M^+$)

Example C-38

N-[2-methyl-3-(2-[N',N'-dimethylamino]ethyl)-1H-indol-5-yl]-4-methylpentanamide

Beginning with 0.027 mMol of 2-methyl-5-amino-3-(2-(N',N'-dimethylamino)ethyl)-1H-indole and 0.035 mMol of 4-methyl-pentanoyl chloride, the title compound was prepared in 70% yield.

MS: m/e=316 ($M^+$)

Example C-39

N-[2-methyl-3-(2-[N',N'-dimethylamino]ethyl)-1H-indol-5-yl]cyclobutanecarboxamide Beginning with 0.027 mMol of 2-methyl-5-amino-3-(2-(N',N'-dimethylamino)ethyl)-1H-indole and 0.035 mMol of cyclobutane-carbonyl chloride, the title compound was prepared in 69% yield.

MS: m/e=300 ($M^+$)

Example C-40

N-[2-methyl-3-(2-[N',N'-dimethylamino]ethyl)-1H-indol-5-yl]cyclopentanecarboxamide Beginning with 0.027 mMol of 2-methyl-5-amino-3-(2-(N',N'-dimethylamino)ethyl)-1H-indole and 0.035 mMol of cyclopentanecarbonyl chloride, the title compound was prepared in 63% yield.

MS: m/e=314 ($M^+$)

Example C-41

N-[2-methyl-3-(2-[N',N'-dimethylamino]ethyl)-1H-indol-5-yl]cyclohexanecarboxamide Beginning with 0.027 mMol of 2-methyl-5-amino-3-(2-(N',N'-dimethylamino)ethyl)-1H-indole and 0.035 mMol of cyclohexane-carbonyl chloride, the title compound was prepared in 80% yield.

MS: m/e=328 ($M^+$)

Example C-42

N-[2-methyl-3-(2-[N',N'-dimethylamino]ethyl)-1H-indol-5-yl]benzamide

Beginning with 0.027 mMol of 2-methyl-5-amino-3-(2-(N',N'-dimethylamino)ethyl)-1H-indole and 0.035 mMol of benzoyl chloride, the title compound was prepared in 83% yield.

MS: m/e=321 ($M^+$)

Example C-43

N-[2-methyl-3-(2-[N',N'-dimethylamino]ethyl)-1H-indol-5-yl]-4-fluorobenzamide

Beginning with 0.027 mMol of 2-methyl-5-amino-3-(2-(N',N'-dimethylamino)ethyl)-1H-indole and 0.035 mMol of 4-fluorobenzoyl chloride, the title compound was prepared in 73% yield.

MS: m/e=339 ($M^+$)

Example C-44

N-[2-methyl-3-(2-[N',N'-dimethylamino]ethyl)-1H-indol-5-yl]-3-fluorobenzamide

Beginning with 0.027 mMol of 2-methyl-5-amino-3-(2-(N',N'-dimethylamino)ethyl)-1H-indole and 0.035 mMol of 3-fluorobenzoyl chloride, the title compound was prepared in 63% yield.

MS: m/e=340 (M+1)

Example C-45

N-[2-methyl-3-(2-[N',N'-dimethylamino]ethyl)-1H-indol-5-yl]-2-fluorobenzamide

Beginning with 0.027 mMol of 2-methyl-5-amino-3-(2-(N',N'-dimethylamino)ethyl)-1H-indole and 0.035 mMol of 2-fluorobenzoyl chloride, the title compound was prepared in 76% yield.

MS: m/e=340 (M+1)

Example C-46

N-[2-methyl-3-(2-[N',N'-dimethylamino]ethyl)-1H-indol-5-yl]-3-chlorobenzamide

Beginning with 0.027 mMol of 2-methyl-5-amino-3-(2-(N',N'-dimethylamino)ethyl)-1H-indole and 0.035 mMol of 3-chlorobenzoyl chloride, the title compound was prepared in 62% yield.

MS: m/e=356 ($M^+$)

Example C-47

N-[2-methyl-3-(2-[N',N'-dimethylamino]ethyl)-1H-indol-5-yl]-4-chlorobenzamide

Beginning with 0.027 mMol of 2-methyl-5-amino-3-(2-(N',N'-dimethylamino)ethyl)-1H-indole and 0.035 mMol of 4-chlorobenzoyl chloride, the title compound was prepared in 66% yield.

Example C-48

N-[2-methyl-3-(2-[N',N'-dimethylamino]ethyl)-1H-indol-5-yl]-4-methylbenzamide

Beginning with 0.027 mMol of 2-methyl-5-amino-3-(2-(N',N'-dimethylamino)ethyl)-1H-indole and 0.035 mMol of 4-methylbenzoyl chloride, the title compound was prepared in 84% yield.

MS: m/e=336 (M$^+$)

Example C-49

N-[2-methyl-3-(2-[N',N'-dimethylamino]ethyl)-1H-indol-5-yl]-2-methylbenzamide

Beginning with 0.027 mMol of 2-methyl-5-amino-3-(2-(N',N'-dimethylamino)ethyl)-1H-indole and 0.035 mMol of 2-methylbenzoyl chloride, the title compound was prepared in 95% yield.

MS: m/e=336 (M$^+$)

Example C-50

N-[2-methyl-3-(2-[N',N'-dimethylamino]ethyl)-1H-indol-5-yl]-4-trifluoromethylbenzamide Beginning with 0.027 mMol of 2-methyl-5-amino-3-(2-(N',N'-dimethylamino)ethyl)-1H-indole and 0.035 mMol of 4-trifluoromethylbenzoyl chloride, the title compound was prepared in 87% yield.

MS: m/e=390 (M$^+$)

Example C-51

N-[2-methyl-3-(2-[N',N'-dimethylamino]ethyl)-1H-indol-5-yl]-2-trifluoromethylbenzamide Beginning with 0.027 mMol of 2-methyl-5-amino-3-(2-(N',N'-dimethylamino)ethyl)-1H-indole and 0.035 mMol of 2-trifluoromethylbenzoyl chloride, the title compound was prepared in 89% yield.

MS: m/e=390 (M$^+$)

Example C-52

N-[2-methyl-3-(2-[N',N'-dimethylamino]ethyl)-1H-indol-5-yl]-4-methoxycarbonylbenzamide Beginning with 0.027 mMol of 2-methyl-5-amino-3-(2-(N',N'-dimethylamino)ethyl)-1H-indole and 0.035 mMol of 4-methoxycarbonylbenzoyl chloride, the title compound was prepared in 78% yield.

MS: m/e=380 (M$^+$)

Example C-53

N-[2-methyl-3-(2-[N',N'-dimethylamino]ethyl)-1H-indol-5-yl]-4-methoxybenzamide

Beginning with 0.027 mMol of 2-methyl-5-amino-3-(2-(N',N'-dimethylamino)ethyl)-1H-indole and 0.035 mMol of 4-methoxybenzoyl chloride, the title compound was prepared in 64% yield.

MS: m/e =351 (M$^+$)

Example C-54

N-[2-methyl-3-(2-[N',N'-dimethylamino]ethyl)-1H-indol-5-yl]-4-phenylbenzamide

Beginning with 0.027 mMol of 2-methyl-5-amino-3-(2-(N',N'-dimethylamino)ethyl)-1H-indole and 0.035 mMol of 4-phenylbenzoyl chloride, the title compound was prepared in 91% yield.

MS: m/e=398 (M$^+$)

Example C-55

N-[2-methyl-3-(2-[N',N'-dimethylamino]ethyl)-1H-indol-5-yl]-2,3-difluorobenzamide Beginning with 0.027 mMol of 2-methyl-5-amino-3-(2-(N',N'-dimethylamino)ethyl)-1H-indole and 0.035 mMol of 2,3-difluorobenzoyl chloride, the title compound was prepared in 76% yield.

MS: m/e=358 (M$^+$)

Example C-56

N-[2-methyl-3-(2-[N',N'-dimethylamino]ethyl)-1H-indol-5-yl]-2,6-difluorobenzamide Beginning with 0.027 mMol of 2-methyl-5-amino-3-(2-(N',N'-dimethylamino)ethyl)-1H-indole and 0.035 mMol of 2,6-difluorobenzoyl chloride, the title compound was prepared in 65% yield.

Example C-57

N-[2-methyl-3-(2-[N',N'-dimethylamino]ethyl)-1H-indol-5-yl]-3,5-difluorobenzamide Beginning with 0.027 mMol of 2-methyl-5-amino-3-(2-(N',N'-dimethylamino)ethyl)-1H-indole and 0.035 mMol of 3,5-difluorobenzoyl chloride, the title compound was prepared in 85% yield.

Example C-58

N-[2-methyl-3-(2-[N',N'-dimethylamino]ethyl)-1H-indol-5-yl]-3,4-difluorobenzamide Beginning with 0.027 mMol of 2-methyl-5-amino-3-(2-(N',N'-dimethylamino)ethyl)-1H-indole and 0.035 mMol of 3,4-difluorobenzoyl chloride, the title compound was prepared in 75% yield.

Example C-59

N-[2-methyl-3-(2-[N',N'-dimethylamino]ethyl)-1H-indol-5-yl]-2,5-difluorobenzamide Beginning with 0.027 mMol of 2-methyl-5-amino-3-(2-(N',N'-dimethylamino)ethyl)-1H-indole and 0.035 mMol of 2,5-difluorobenzoyl chloride, the title compound was prepared in 86% yield.

MS: m/e=358 (M$^+$)

Example C-60

N-[2-methyl-3-(2-[N',N'-dimethylamino]ethyl)-1H-indol-5-yl]-3,4-dichlorobenzamide Beginning with 0.027 mMol of 2-methyl-5-amino-3-(2-(N',N'-dimethylamino)ethyl)-1H-indole and 0.035 mMol of 3,4-dichlorobenzoyl chloride, the title compound was prepared in 69% yield.

Example C-61

N-[2-methyl-3-(2-[N',N'-dimethylamino]ethyl)-1H-indol-5-yl]-2,6-dichlorobenzamide Beginning with 0.027 mMol of 2-methyl-5-amino-3-(2-(N',N'-dimethylamino)ethyl)-1H-indole and 0.035 mMol of 2,6-dichlorobenzoyl chloride, the title compound was prepared in 69% yield.

Example C-62

N-[2-methyl-3-(2-[N',N'-dimethylamino]ethyl)-1H-indol-5-yl]-2,4-dichlorobenzamide Beginning with 0.027 mMol of 2-methyl-5-amino-3-(2-(N',N'-dimethylamino)ethyl)-1H-indole and 0.035 mMol of 2,4-dichlorobenzoyl chloride, the title compound was prepared in 64% yield.

MS: m/e=392 (M+1)

Example C-63

N-[2-methyl-3-(2-[N',N'-dimethylamino]ethyl)-1H-indol-5-yl]-2,3-dichlorobenzamide Beginning with 0.027 mMol of 2-methyl-5-amino-3-(2-(N',N'-dimethylamino)ethyl)-1H-indole and 0.035 mMol of 2,3-dichlorobenzoyl chloride, the title compound was prepared in 61% yield.

MS: m/e=392 (M−1)

Example C-64

N-[2-methyl-3-(2-[N',N'-dimethylamino]ethyl)-1H-indol-5-yl]-2,3,6-trifluorobenzamide Beginning with 0.027 mMol of 2-methyl-5-amino-3-(2-(N',N'-dimethylamino)ethyl)-1H-indole and 0.035 mMol of 2,3,6-trifluorobenzoyl chloride, the title compound was prepared in 86% yield.

MS: m/e=376 (M+)

Example C-65

N-[2-methyl-3-(2-[N',N'-dimethylamino]ethyl)-1H-indol-5-yl]-2,3,4-trifluorobenzamide Beginning with 0.027 mMol of 2-methyl-5-amino-3-(2-(N',N'-dimethylamino)ethyl)-1H-indole and 0.035 mMol of 2,3,4-trifluorobenzoyl chloride, the title compound was prepared in 70% yield.

Example C-66

N-[2-methyl-3-(2-[N',N'-dimethylamino]ethyl)-1H-indol-5-yl]-2,4,5-trifluorobenzamide Beginning with 0.027 mMol of 2-methyl-5-amino-3-(2-(N',N'-dimethylamino)ethyl)-1H-indole and 0.035 mMol of 2,4,5-trifluorobenzoyl chloride, the title compound was prepared in 81% yield.

Example C-67

N-[2-methyl-3-(2-[N',N'-dimethylamino]ethyl)-1H-indol-5-yl]-2,4,6-trifluorobenzamide Beginning with 0.027 mMol of 2-methyl-5-amino-3-(2-(N',N'-dimethylamino)ethyl)-1H-indole and 0.035 mMol of 2,4,6-trifluorobenzoyl chloride, the title compound was prepared in 76% yield.

Example C-68

N-[2-methyl-3-(2-[N',N'-dimethylamino]ethyl)-1H-indol-5-yl]-2,4,6-trichlorobenzamide Beginning with 0.027 mMol of 2-methyl-5-amino-3-(2-(N',N'-dimethylamino)ethyl)-1H-indole and 0.035 mMol of 2,4,6-trichlorobenzoyl chloride, the title compound was prepared in 59% yield.

Example C-69

N-[2-methyl-3-(2-[N',N'-dimethylamino]ethyl)-1H-indol-5-yl]-2-trifluoromethyl-4-fluorobenzamide Beginning with 0.027 mMol of 2-methyl-5-amino-3-(2-(N',N'-dimethylamino)ethyl)-1H-indole and 0.035 mMol of 2-trifluoromethyl-4-fluorobenzoyl chloride, the title compound was prepared in 49% yield.

Example C-70

N-[2-methyl-3-(2-[N',N'-dimethylamino]ethyl)-1H-indol-5-yl]-4-trifluoromethyl-2-fluorobenzamide Beginning with 0.027 mMol of 2-methyl-5-amino-3-(2-(N',N'-dimethylamino)ethyl)-1H-indole and 0.035 mMol of 4-trifluoromethyl-2-fluorobenzoyl chloride, the title compound was prepared in 71% yield.

Example C-71

N-[2-methyl-3-(2-[N',N'-dimethylamino]ethyl)-1H-indol-5-yl]-2-trifluoromethyl-6-fluorobenzamide Beginning with 0.027 mMol of 2-methyl-5-amino-3-(2-(N',N'-dimethylamino)ethyl)-1H-indole and 0.035 mMol of 2-trifluoromethyl-6-fluorobenzoyl chloride, the title compound was prepared in 66% yield.

Example C-72

N-[2-methyl-3-(2-[N',N'-dimethylamino]ethyl)-1H-indol-5-yl]-3-trifluoromethyl-4-fluorobenzamide Beginning with 0.027 mMol of 2-methyl-5-amino-3-(2-(N',N'-dimethylamino)ethyl)-1H-indole and 0.035 mMol of 3-trifluoromethyl-4-fluorobenzoyl chloride, the title compound was prepared in 75% yield.

Example C-73

N-[2-methyl-3-(2-[N',N'-dimethylamino]ethyl)-1H-indol-5-yl]-2,4-dichloro-5-fluorobenzamide Beginning with 0.027 mMol of 2-methyl-5-amino-3-(2-(N',N'-dimethylamino)ethyl)-1H-indole and 0.035 mMol of 2,4-dichloro-5-fluorobenzoyl chloride, the title compound was prepared in 75% yield.

Example C-74

N-[2-methyl-3-(2-[N',N'-dimethylamino]ethyl)-1H-indol-5-yl]-thiophene-2-carboxamide Beginning with 0.027 mMol of 2-methyl-5-amino-3-(2-(N',N'-dimethylamino)ethyl)-1H-indole and 0.035 mMol of thiophene-2-carbonyl chloride, the title compound was prepared in 63% yield.

MS: m/e=328 (M+)

Example C-75

N-[2-methyl-3-(2-[N',N'-dimethylamino]ethyl)-1H-indol-5-yl]-isoxazole-5-carboxamide Beginning with 0.027 mMol of 2-methyl-5-amino-3-(2-(N',N'-dimethylamino)ethyl)-1H-indole and 0.035 mMol of isoxazole-5-carbonyl chloride, the title compound was prepared in 63% yield.

Example C-76

N-[2-methyl-3-(2-[N',N'-dimethylamino]ethyl)-1H-indol-5-yl]-2-chloropyridine-3-carboxamide Beginning with 0.027 mMol of 2-methyl-5-amino-3-(2-(N',N'-dimethylamino)ethyl)-1H-indole and 0.035 mMol of 2-chloropyridine-3-carbonyl chloride, the title compound was prepared in 60% yield.

Example C-77

N-[2-methyl-3-(2-[N',N'-dimethylamino]ethyl)-1H-indol-5-yl]-6-chloropyridine-3-carboxamide Beginning with 0.027 mMol of 2-methyl-5-amino-3-(2-(N',N'-dimethylamino)ethyl)-1H-indole and 0.035 mMol of 6-chloropyridine-3-carbonyl chloride, the title compound was prepared in 68% yield.

Example C-78

N-[2-methyl-3-(2-[N',N'-dimethylamino]ethyl)-1H-indol-5-yl]-3-chlorothiophene-2-carboxamide Beginning with 0.027 mmol of 2-methyl-5-amino-3-(2-(N',N'-dimethylamino)ethyl)-1H-indole and 0.035 mMol of 3-chlorothiophene-2-carbonyl chloride, the title compound was prepared in 77% yield.

MS: m/e=362 (M$^+$)

Example C-79

N-[2-methyl-3-(2-[N',N'-dimethylamino]ethyl)-1H-indol-5-yl]naphthalene-2-carboxamide Beginning with 0.027 mMol of 2-methyl-5-amino-3-(2-(N',N'-dimethylamino)ethyl)-1H-indole and 0.035 mMol of naphthalene-2-carbonyl chloride, the title compound was prepared in 67% yield.

MS: m/e=372 (M$^+$)

Example C-80

N-[2-methyl-3-(2-[N',N'-dimethylamino]ethyl)-1H-indol-5-yl]naphthalene-1-carboxamide Beginning with 0.027 mMol of 2-methyl-5-amino-3-(2-(N',N'-dimethylamino)ethyl)-1H-indole and 0.035 mMol of naphthalene-1-carbonyl chloride, the title compound was prepared in 77% yield.

MS: m/e=372 (M$^+$)

Example C-81

N-[2-methyl-3-(2-[N',N'-dimethylamino]ethyl)-1H-indol-5-yl]benzothiophene-2-carboxamide Beginning with 0.027 mMol of 2-methyl-5-amino-3-(2-(N',N'-dimethylamino)ethyl)-1H-indole and 0.035 mMol of benzothiophene-2-carbonyl chloride, the title compound was prepared in 53% yield.

MS: m/e=378 (M$^+$)

Example C-82

N-[2-methyl-3-(2-[N',N'-dimethylamino]ethyl)-1H-indol-5-yl]quinoxaline-2-carboxamide Beginning with 0.027 mMol of 2-methyl-5-amino-3-(2-(N',N'-dimethylamino)ethyl)-1H-indole and 0.035 mMol of quinoxaline-2-carbonyl chloride, the title compound was prepared in 67% yield.

MS: m/e=374 (M$^+$)

Example C-83

N-[2-methyl-3-(2-[N',N'-dimethylamino]ethyl)-1H-indol-5-yl]quinoline-2-carboxamide Beginning with 0.027 mMol of 2-methyl-5-amino-3-(2-(N',N'-dimethylamino)ethyl)-1H-indole and 0.035 mMol of quinoline-2-carbonyl chloride, the title compound was prepared in 86% yield.

MS: m/e=372 (M$^+$)

General Procedures for the Reductive Alkylation of Secondary Amines of Formula III

Procedure A

A solution of 1 equivalent amine (III), 2–3 equivalents of aldehyde, and 2 molar equivalents of sodium cyanoborohydride in 4:1 methanol:acetic acid is mixed well and allowed to stand for 24 hours at room temperature for from 3 to 24 hours. The reaction mixture is then loaded onto a VARIAN BOND ELUT SCX™ (Varian, Harbor City, Calif., U.S.A.) ion exchange column. The column is eluted with several volumes of methanol and is then eluted with either saturated methanolic hydrogen chloride or 2M ammonia in methanol. Fractions from the column containing product are concentrated under reduced pressure. Compounds eluted with methanolic hydrogen chloride provide the hydrochloride salts, and compounds eluted with ammonia in methanol provide the free bases, of compounds of the invention.

Procedure B

A solution of 1 equivalent of secondary amine (III), 1.2 equivalents of aldehyde, 12 equivalents of sodium triacetoxyborohydride, and 0.3 equivalents of acetic acid in dichloromethane is mixed for 24 hours at room temperature. The compounds of the invention are isolated as described in PROCEDURE A.

The compounds of Examples C-84 to C-89 were prepared by PROCEDURE A.

Example C-84

N-[2-methyl-3-(2-[N'-methyl-N'-(2-thienyl)methylamino]ethyl)-1H-indol-5-yl]-4-fluorobenzamide Beginning with 0.025 mmol of N-[2-methyl-3-(2-[N'-methylamino]ethyl)-1H-indol-5-yl]-4-fluorobenzamide (Preparation V) and 0.075 mMol of thiophene-2-carboxaldehyde, the title compound was prepared in 91% yield.

Example C-85

N-[2-methyl-3-(2-[N'-methyl-N'-(3-thienyl)methylamino]ethyl)-1H-indol-5-yl]-4-fluorobenzamide Beginning with 0.025 mMol of N-[2-methyl-3-(2-[N'-methylamino]ethyl)-1H-indol-5-yl]-4-fluorobenzamide (Preparation V) and 0.075 mMol of thiophene-3-carboxaldehyde, the title compound was prepared in 80% yield.

Example C-86

N-[2-methyl-3-(2-[N'-methyl-N'-(2-furyl)methylamino]ethyl)-1H-indol-5-yl]-4-fluorobenzamide Beginning with 0.025 mMol of N-[2-methyl-3-(2-[N'-methylamino]ethyl)-1H-indol-5-yl]-4-fluorobenzamide (Preparation V) and 0.075 mMol of 2-furaldehyde, the title compound was prepared in 83% yield.

Example C-87

N-[2-methyl-3-(2-[N'-methyl-N'-(2-pyridyl)methylamino]ethyl)-1H-indol-5-yl]-4-fluorobenzamide Beginning with 0.025 mMol of N-[2-methyl-3-(2-[N'-methylamino]ethyl)-1H-indol-5-yl]-4-fluorobenzamide (Preparation V) and 0.075 mMol of pyridine-2-carboxaldehyde, the title compound was prepared in 94% yield.

Example C-88

N-[2-methyl-3-(2-[N'-methyl-N'-(3-pyridyl)methylamino]ethyl)-1H-indol-5-yl]-4-fluorobenzamide Beginning with 0.025 mMol of N-[2-methyl-3-(2-[N'-methylamino]ethyl)-1H-indol-5-yl]-4-fluorobenzamide (Preparation V) and 0.075 mMol of pyridine-3-carboxaldehyde, the title compound was prepared in 84% yield.

Example C-89

N-[2-methyl-3-(2-[N'-methyl-N'-(3-indolyl)methylamino]ethyl)-1H-indol-5-yl]-4-fluorobenzamide Beginning with 0.025 mMol of N-[2-methyl-3-(2-[N'-methylamino]ethyl)-1H-indol-5-yl]-4-fluorobenzamide (Preparation V) and 0.075 mMol of indole-3-carboxaldehyde, the title compound was prepared in 100% yield.

The compounds of Examples C-90 to C-94 were prepared by PROCEDURE B.

Example C-90

N-[2-methyl-3-(2-[N'-methyl-N'-(1-methylpyrrol-2-yl)methylamino]ethyl)-1H-indol-5-yl]-4-fluorobenzamide Beginning with 0.017 mMol of N-[2-methyl-3-(2-[N'-methylamino]ethyl)-1H-indol-5-yl]-4-fluorobenzamide (Preparation V) and 0.021 mMol of 1-methylpyrrole-2-carboxaldehyde, the title compound was prepared.

Example C-91

N-[2-methyl-3-(2-[N'-methyl-N'-(5-methylthien-2-yl)methylamino]ethyl)-1H-indol-5-yl]-4-fluorobenzamide Beginning with 0.017 mMol of N-[2-methyl-3-(2-[N'-methylamino]ethyl)-1H-indol-5-yl]-4-fluorobenzamide (Preparation V) and 0.021 mMol of 5-methylthiophene-2-carboxaldehyde, the title compound was prepared.

Example C-92

N-[2-methyl-3-(2-[N'-methyl-N'-(5-hydroxymethylfur-2-yl)methylamino]ethyl)-1H-indol-5-yl]-4-fluorobenzamide Beginning with 0.017 mMol of N-[2-methyl-3-(2-[N'-methylamino]ethyl)-1H-indol-5-yl]-4-fluorobenzamide (Preparation V) and 0.021 mMol of 5-hydroxymethylfuran-2-carboxaldehyde, the title compound was prepared.

Example C-93

N-[2-methyl-3-(2-[N'-methyl-N'-(3-methylbenzothiophen-2-yl)methylamino]ethyl)-1H-indol-5-yl]-4-fluorobenzamide Beginning with 0.017 mMol of N-[2-methyl-3-(2-[N'-methylamino]ethyl)-1H-indol-5-yl]-4-fluorobenzamide (Preparation V) and 0.021 mMol of 3-methylbenzothiophene-2-carboxaldehyde, the title compound was prepared.

Example C-94

N-[2-methyl-3-(2-[N'-methyl-N'-(5-chloro-1,3-benzodioxol-4-yl)methylamino]ethyl)-1H-indol-5-yl]-4-fluorobenzamide Beginning with 0.017 mMol of N-[2-methyl-3-(2-[N'-methylamino]ethyl)-1H-indol-5-yl]-4-fluorobenzamide (Preparation V) and 0.021 mMol of 5-chloro-1,3-benzodioxole-4-carboxaldehyde, the title compound was prepared.

The above groups of compounds are only illustrative of the serotonin 5-HT$_{1F}$ receptor agonists which are currently under development. This listing of groups of compounds is not meant to be comprehensive. The method of the present invention may employ any serotonin 5-HT$_{1F}$ receptor agonist and is not limited to any particular class of compounds.

While all compounds exhibiting serotonin 5-HT$_{1F}$ receptor agonist activity are useful for the method of the present invention, compounds which are selective for the serotonin 5-HT$_{1F}$ receptor relative to other receptors are preferred. Particularly preferred serotonin 5-HT$_{1F}$ receptor agonists are those of Formula IV, supra. Especially preferred is the compound of Formula IV which is N-(4-fluorobenzoyl)-5-amino-3-(1-methylpiperidin-4-yl)-1H-indole. It is also preferred that the mammal treated by the method of the present invention is a human.

Human clinical models demonstrating the effectiveness of the methods of the present invention are well known to those skilled in the art. For example, in evaluating the methods of the present invention in treating or ameliorating the symptoms of the common cold or allergic rhinitis, it is especially preferred to ultimately employ clinical studies. Clinical studies for evaluating the effectiveness of a treatment of either of these disorders are described in U.S. Pat. No. 5,240,694, issued Aug. 31, 1993, and U.S. Pat. No. 5,252,602, issued Oct. 12, 1993, the entirety of which are herein incorporated by reference.

While it is possible to administer a compound employed in the methods of this invention directly without any formulation, the compounds are usually administered in the form of pharmaceutical compositions comprising a pharmaceutically acceptable excipient and at least one active ingredient. These compositions can be administered by a variety of routes including oral, rectal, transdermal, subcutaneous, intravenous, intramuscular, and intranasal. Many of the compounds employed in the methods of this invention are effective as both injectable and oral compositions. Such compositions are prepared in a manner well known in the pharmaceutical art and comprise at least one active compound. See, e.g., Remington's Pharmaceutical Sciences, (16th ed. 1980).

In making the compositions employed in the present invention the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 0.05 to about 100 mg, more usually about 1.0 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The active compounds are generally effective over a wide dosage range. For examples, dosages per day normally fall within the range of about 0.01 to about 30 mg/kg of body weight. In the treatment of adult humans, the range of about 0.1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

Formulation Preparation 1

Hard gelatin capsules containing the following ingredients are prepared:

| Ingredient | Quantity (mg/capsule) |
| --- | --- |
| N-(4-fluorobenzoyl)-5-amino-3-(1-methylpiperidin-4-yl)-1H-indole | 30.0 |
| Starch | 305.0 |
| Magnesium stearate | 5.0 |

The above ingredients are mixed and filled into hard gelatin capsules in 340 mg quantities.

Formulation Preparation 2

A tablet formula is prepared using the ingredients below:

| Ingredient | Quantity (mg/tablet) |
| --- | --- |
| N-(4-fluorobenzoyl)-5-amino-3-(1-methylpiperidin-4-yl)-1H-indole | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Preparation 3

A dry powder inhaler formulation is prepared containing the following components:

| Ingredient | Weight % |
| --- | --- |
| N-(4-fluorobenzoyl)-5-amino-3-(1-methylpiperidin-4-yl)-1H-indole | 5 |
| Lactose | 95 |

The active mixture is mixed with the lactose and the mixture is added to a dry powder inhaling appliance.

Formulation Preparation 4

Tablets, each containing 30 mg of active ingredient, are prepared as follows:

| Ingredient | Quantity (mg/tablet) |
| --- | --- |
| N-(4-fluorobenzoyl)-5-amino-3-(1-methylpiperidin-4-yl)-1H-indole | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50–60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Preparation 5

Capsules, each containing 40 mg of medicament are made as follows:

| Ingredient | Quantity (mg/capsule) |
| --- | --- |
| N-(4-fluorobenzoyl)-5-amino-3-(1-methylpiperidin-4-yl)-1H-indole | 40.0 mg |
| Starch | 109.0 mg |
| Magnesium stearate | 1.0 mg |
| Total | 150.0 mg |

The active ingredient, cellulose, starch, and magnesium stearate are blended, passed through a No. 20 mesh U.S. sieve, and filled into hard gelatin capsules in 150 mg quantities.

Formulation Preparation 6

Suppositories, each containing 25 mg of active ingredient are made as follows:

| Ingredient | Amount |
| --- | --- |
| N-(4-fluorobenzoyl)-5-amino-3-(1-methylpiperidin-4-yl)-1H-indole | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Preparation 7

Suspensions, each containing 50 mg of medicament per 5.0 ml dose are made as follows:

| Ingredient | Amount |
| --- | --- |
| N-(4-fluorobenzoyl)-5-amino-3-(1-methylpiperidin-4-yl)-1H-indole | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Preparation 8

Capsules, each containing 15 mg of medicament, are made as follows:

| Ingredient | Quantity (mg/capsule) |
| --- | --- |
| N-(4-fluorobenzoyl)-5-amino-3-(1-methylpiperidin-4-yl)-1H-indole | 15.0 mg |
| Starch | 407.0 mg |
| Magnesium Stearate | 3.0 mg |
| Total | 425.0 mg |

The active ingredient, cellulose, starch, and magnesium stearate are blended, passed through a No. 20 mesh U.S. sieve, and filled into hard gelatin capsules in 425 mg quantities.

Formulation Preparation 9

An intravenous formulation may be prepared as follows:

| Ingredient | Quantity |
| --- | --- |
| N-(4-fluorobenzoyl)-5-amino-3-(1-methylpiperidin-4-yl)-1H-indole | 250.0 mg |
| Isotonic saline | 1000 ml |

Formulation Preparation 10

A topical formulation may be prepared as follows:

| Ingredient | Quantity |
| --- | --- |
| N-(4-fluorobenzoyl)-5-amino-3-(1-methylpiperidin-4-yl)-1H-indole | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Formulation Preparation 11

Sublingual or buccal tablets, each containing 10 mg of active ingredient, may be prepared as follows:

| Ingredient | Quantity Per Tablet |
|---|---|
| N-(4-fluorobenzoyl)-5-amino-3-(1-methylpiperidin-4-yl)-1H-indole | 10.0 mg |
| Glycerol | 210.5 mg |
| Water | 143.0 mg |
| Sodium Citrate | 4.5 mg |
| Polyvinyl Alcohol | 26.5 mg |
| Polyvinylpyrrolidone | 15.5 mg |
| Total | 410.0 mg |

The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50–55° C. and the medicament is slowly admixed. The homogenous mixture is poured into forms made of an inert material to produce a drug-containing diffusion matrix having a thickness of about 2–4 mm. This diffusion matrix is then cut to form individual tablets having the appropriate size.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

The type of formulation employed for the administration of the compounds employed in the methods of the present invention may be dictated by the particular compounds employed, the type of pharmacokinetic profile desired from the route of administration and the compound, and the state of the patient.

We claim:

1. A method for the treatment or amelioration of the symptoms of the common cold or allergic rhinitis in a mammal which comprises administering to a mammal in need thereof an effective amount of a serotonin 5-HT$_{1F}$ agonist.

2. A method of claim 1 where the serotonin 5-HT$_{1F}$ is selective for the 5-HT$_{1F}$ receptor relative to other receptors.

3. A method of claim 1 wherein the mammal is a human.

* * * * *